US011155628B2

(12) United States Patent
Swanson et al.

(10) Patent No.: US 11,155,628 B2
(45) Date of Patent: Oct. 26, 2021

(54) ANTIGEN BINDING PROTEINS THAT BIND C-MET

(71) Applicant: Sorrento Therapeutics, Inc., San Diego, CA (US)

(72) Inventors: Barbara A. Swanson, Encinitas, CA (US); Heyue Zhou, San Diego, CA (US); Yan-Liang Zhang, San Diego, CA (US); Randy Gastwirt, San Diego, CA (US); John Dixon Gray, San Diego, CA (US)

(73) Assignee: Sorrento Therapeutics, Inc., San Diego, CA (US)

( * ) Notice: Subject to any disclaimer, the term of this patent is extended or adjusted under 35 U.S.C. 154(b) by 302 days.

(21) Appl. No.: 16/451,511

(22) Filed: Jun. 25, 2019

(65) Prior Publication Data
US 2019/0359719 A1 Nov. 28, 2019

Related U.S. Application Data

(62) Division of application No. 13/924,492, filed on Jun. 21, 2013, now Pat. No. 10,377,827.

(60) Provisional application No. 61/662,910, filed on Jun. 21, 2012.

(51) Int. Cl.
| *A61K 39/00* | (2006.01) |
| *C07K 16/28* | (2006.01) |
| *C07K 16/30* | (2006.01) |

(52) U.S. Cl.
CPC .......... *C07K 16/2863* (2013.01); *C07K 16/30* (2013.01); *A61K 2039/505* (2013.01); *C07K 2317/21* (2013.01); *C07K 2317/55* (2013.01); *C07K 2317/56* (2013.01); *C07K 2317/622* (2013.01); *C07K 2317/73* (2013.01); *C07K 2317/732* (2013.01); *C07K 2317/76* (2013.01); *C07K 2317/92* (2013.01)

(58) Field of Classification Search
CPC ................................ A61K 2039/505
See application file for complete search history.

(56) References Cited

U.S. PATENT DOCUMENTS

| 7,498,420 | B2 | 3/2009 | Michaud |
| 10,377,827 | B2 | 8/2019 | Swanson |
| 2007/0179086 | A1 | 8/2007 | Gliniak |
| 2013/0109844 | A1 | 5/2013 | Goetsch |
| 2013/0344070 | A1 | 12/2013 | Huang et al. |

FOREIGN PATENT DOCUMENTS

| EP | 2014681 | 6/2009 |
| EP | 2078732 | 7/2009 |
| GB | 2404660 | 2/2005 |
| JP | 2007501013 | 1/2007 |
| JP | 2008508880 | 3/2008 |
| JP | 2012510280 | 5/2012 |
| WO | 2004072117 | 8/2004 |
| WO | 2005016382 | 2/2005 |
| WO | 2006015371 | 2/2006 |
| WO | 2008007648 | 1/2008 |
| WO | 201069765 | 6/2010 |
| WO | 2012030842 | 3/2012 |

OTHER PUBLICATIONS

International Preliminary Report on Patentability and Written Opinion of the International Searching Authority relating to Counter-part International Application No. PCT/US2013/047190, completed on Jan. 21, 2014 and dated Dec. 23, 2014.
International Search Report relating to Counter-part International Application No. PCT/US2013/047190, completed on Jan. 21, 2014 and dated Feb. 6, 2014.
Extended European Search Report relating to Counter-part International Application No. PCT/US2013/047190 completed on Feb. 29, 2016 and dated Mar. 14, 2016.
Gheradi et al., "Targeting MET in Cancer: Rationale and Progress" Nature Reviews/Cancer 12:89-103, 2012.
Herrera et al. "The HGF Receptor c-MET is Overexpressed Esophageal Adenocarcinoma" Neoplasia, 7:75-84, 2005.
Jin et al. "MetMab, the One-Armed 5D5 anti-c-Met antibody Inhibits Orthotopic Pancreatic Tumor Growth and Improves Survival" Cancer Res. 68:4360-4368, 2008.
Martens et al., "A Novel One=Armed anti-c-Met Antibody Inhibits Glioblastoma Growth in vivo" Clin. Cancer Res. 12:6144-6152, 2006.
Merchant et al. "Monovalent antibody design and mechanism of action of Onertuzumab, a MET agonist with anti-tumor activity as a therapeutic agent" PNAS published online Jul. 23, 2013.
Sierra et al. "c-Met as a potential therapeutic target and biomarker in cancer" Ther. Adv. Med. Oncol. 3(S1):S21-S35, 2011.
Rodrigues et al., "Alternative Splicing Generates Isoforms of the met Receptor Tyrosine Kinase Which Undergo Differential Processing" (Mol. Cell. Biol. Jun. 1991; 11 (6): 2962-70).
Rudikoff et al., "Single Amino Acid Substitution Altering Antigen-Binding Specificity" (Proc. Natl. Acad. Sci. USA. 1982; 79: 1979-1983).

(Continued)

*Primary Examiner* — Stephen L Rawlings
(74) *Attorney, Agent, or Firm* — McNeill Baur PLLC

(57) ABSTRACT

There is disclosed compositions and methods relating to or derived from anti-c-Met antibodies. More specifically, there is disclosed fully human antibodies that bind c-Met, c-Met-binding fragments and derivatives of such antibodies, and c-Met-binding polypeptides comprising such fragments. Further still, there is disclosed nucleic acids encoding such antibodies, antibody fragments and derivatives and polypeptides, cells comprising such polynucleotides, methods of making such antibodies, antibody fragments and derivatives and polypeptides, and methods of using such antibodies, antibody fragments and derivatives and polypeptides, including methods of treating or diagnosing subjects having c-Met related disorders or conditions, including various inflammatory disorders and various cancers.

18 Claims, 23 Drawing Sheets

Specification includes a Sequence Listing.

(56) References Cited

OTHER PUBLICATIONS

Mariuzza et al., "The Structural Basis of Antigen-Antibody Recognition" (Annu. Rev. Biophys. Biophys. Chem. 1987; 16: 139-159).
Gussow et al., "Humanization of Monoclonal Antibodies" (Methods in Enzymology. 1991; 203: 99-121).
Winkler et al., "Changing the Antigen Binding Specificity by Single Point Mutations of an Anti-p24 (HIV-1) Antibody" (J. Immunol. Oct. 15, 2000; 165 (8): 4505-4514).
Giusti et al., "Somatic Diversification of S107 from an Antiphosphocholine to an Anti-DNA Autoantibody is Due to a Single Base Change in its Heavy Chain Variable Region" (Proc. Natl. Acad. Sci. USA. May 1987; 84 (9): 2926-2930).
Chien et al., "Significant Structural and Functional Change of an Antigen-Binding Site by a Distant Amino Acid Substitution: Proposal of a Structural Mechanism" (Proc. Natl. Acad. Sci. USA. Jul. 1989; 86 (14): 5532-5536).
Caldas et al., "Humanization of the Anti-CD18 Antibody 6.7: An Unexpected Effect of a Framework Residue in Binding to Antigen" (Mol. Immunol. May 2003; 39 (15): 941-952).
Vajdos et al., "Comprehensive Functional Maps of the Antigen-Binding Site of an Anti-ErbB2 Antibody Obtained with Shotgun Scanning Mutagenesis" (J. Mol. Biol. Jul. 5, 2002; 320 (2): 415-428).
De Pascalis et al., "Grafting of "Abbreviated" Complementarity-Determining Regions Containing Specificity-Determining Residues Essential for Ligand Contact to Engineer a Less Immunogenic Humanized Monoclonal Antibody" (J. Immunol. 2002; 169 (6): 3076-3084).
Wu et al., "Humanization of a Murine Monoclonal Antibody by Simultaneous Optimization of Framework and CDR Residues" (J. Mol. Biol. Nov. 19, 1999; 294 (1): 151-162).
Casset et al., "A Peptide Mimetic of an Anti-CD4 Monoclonal Antibody by Rational Design" (Biochem. Biophys. Res. Commun. Jul. 18, 2003; 307 (1): 198-205).
MacCallum et al., "Antibody-Antigen Interactions: Contact Analysis and Binding Site Topography" (J. Mol. Biol. Oct. 11, 1996; 262 (5): 732-745).
Holm et al., "Functional Mapping and Single Chain Construction of the Anti-Cytokeratin 8 Monoclonal Antibody TS1" (Mol. Immunol. Feb. 2007; 44 (6): 1075-1084).
Yu et al., "Rationalization and Design of the Complementarity Determining Region Sequences in an Antibody-Antigen Recognition Interface" (PLoS One. 2012; 7 (3): e33340; pp. 1-15).
Chang et al., "Loop-Sequence Features and Stability Determinants in Antibody Variable Domains by High-Throughput Experiments" (Structure. Jan. 7, 2014; 22 (1): 9-21).

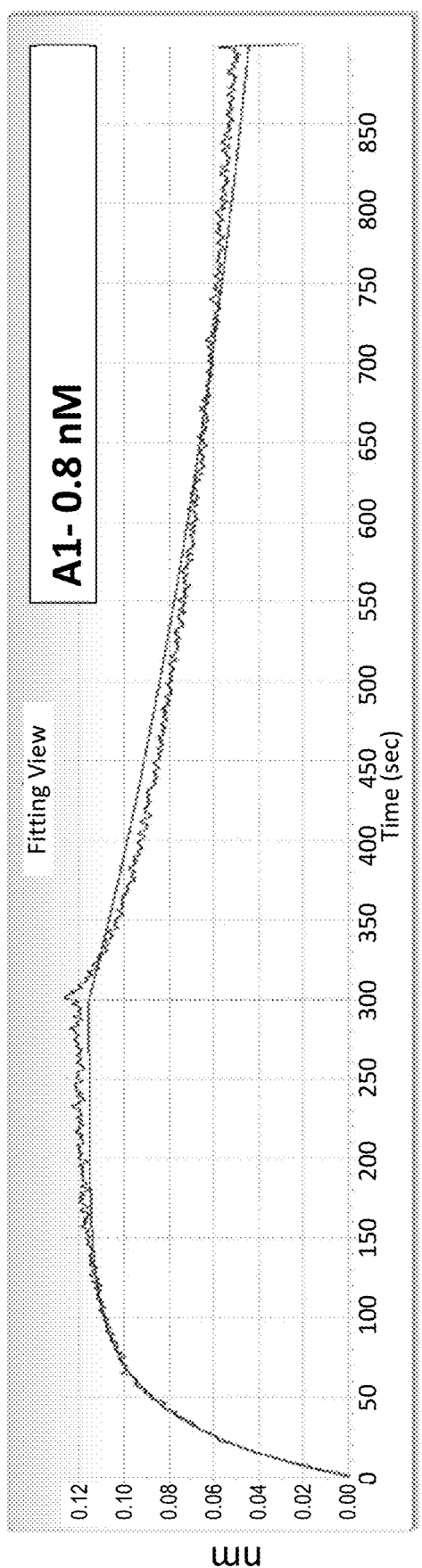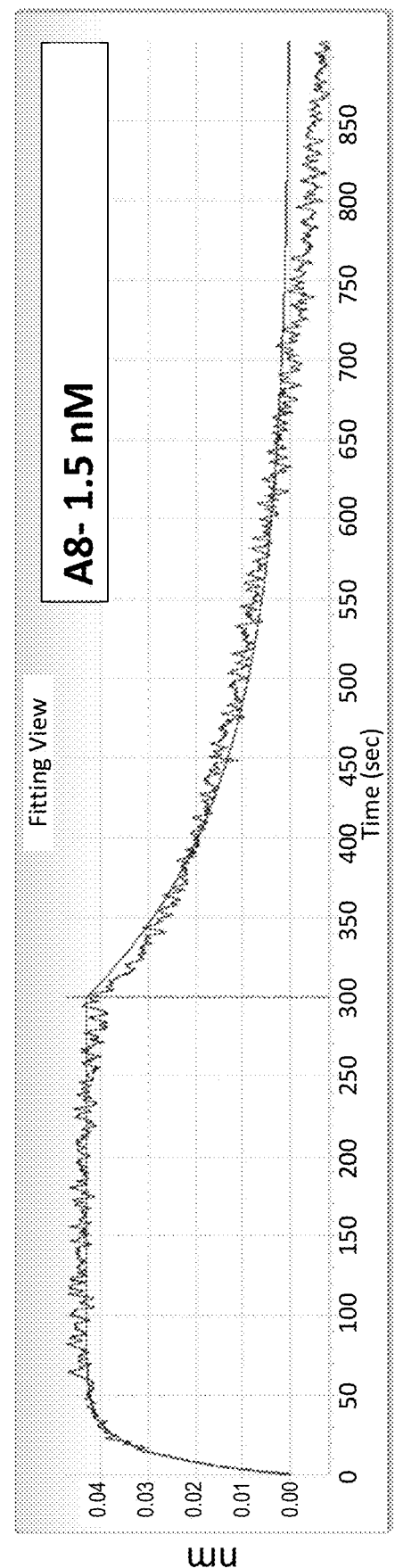
Fig. 1A
Fig. 1B

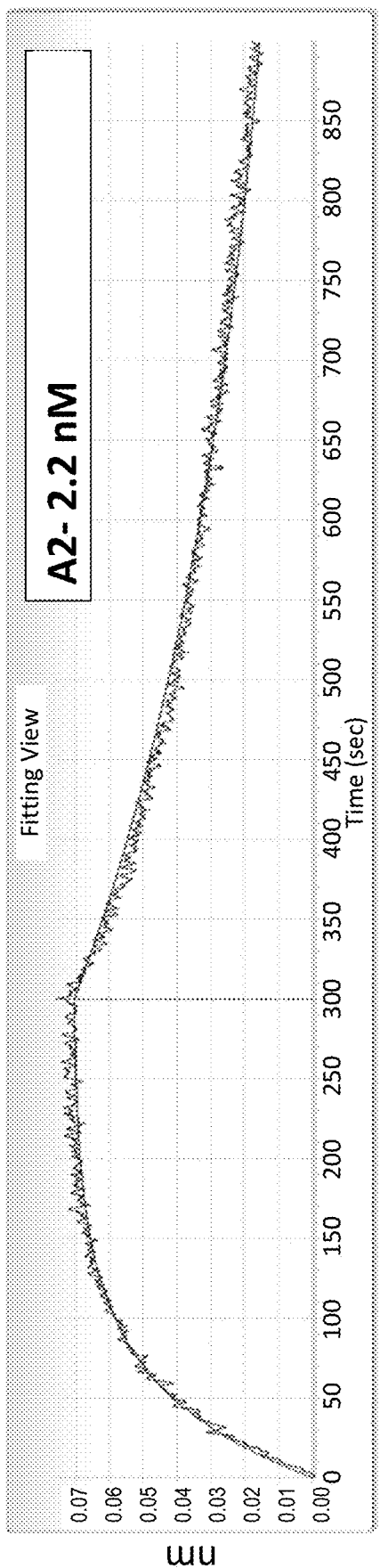
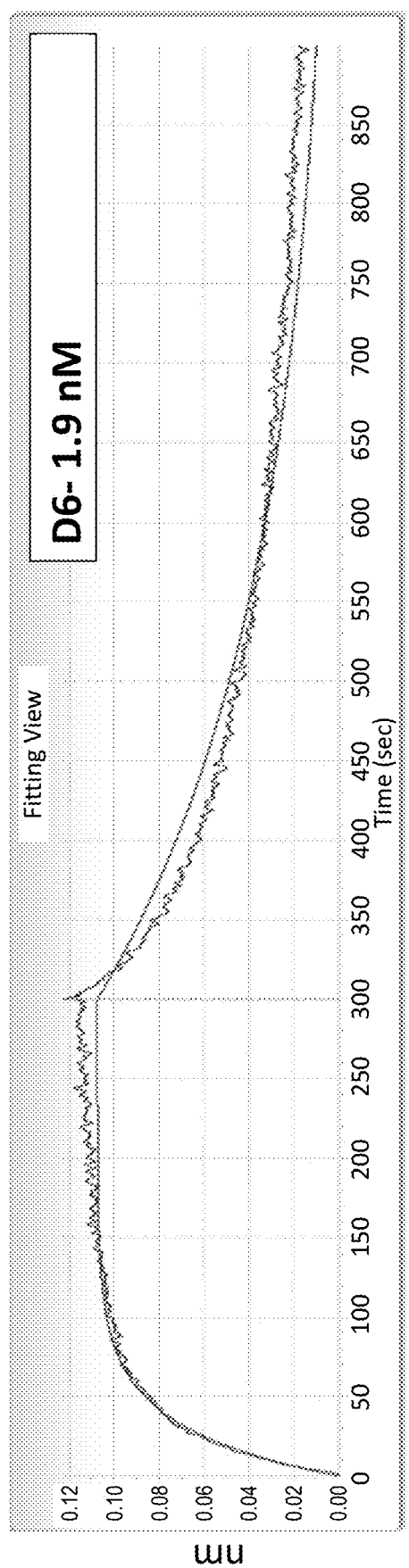
Fig. 1G
Fig. 1H

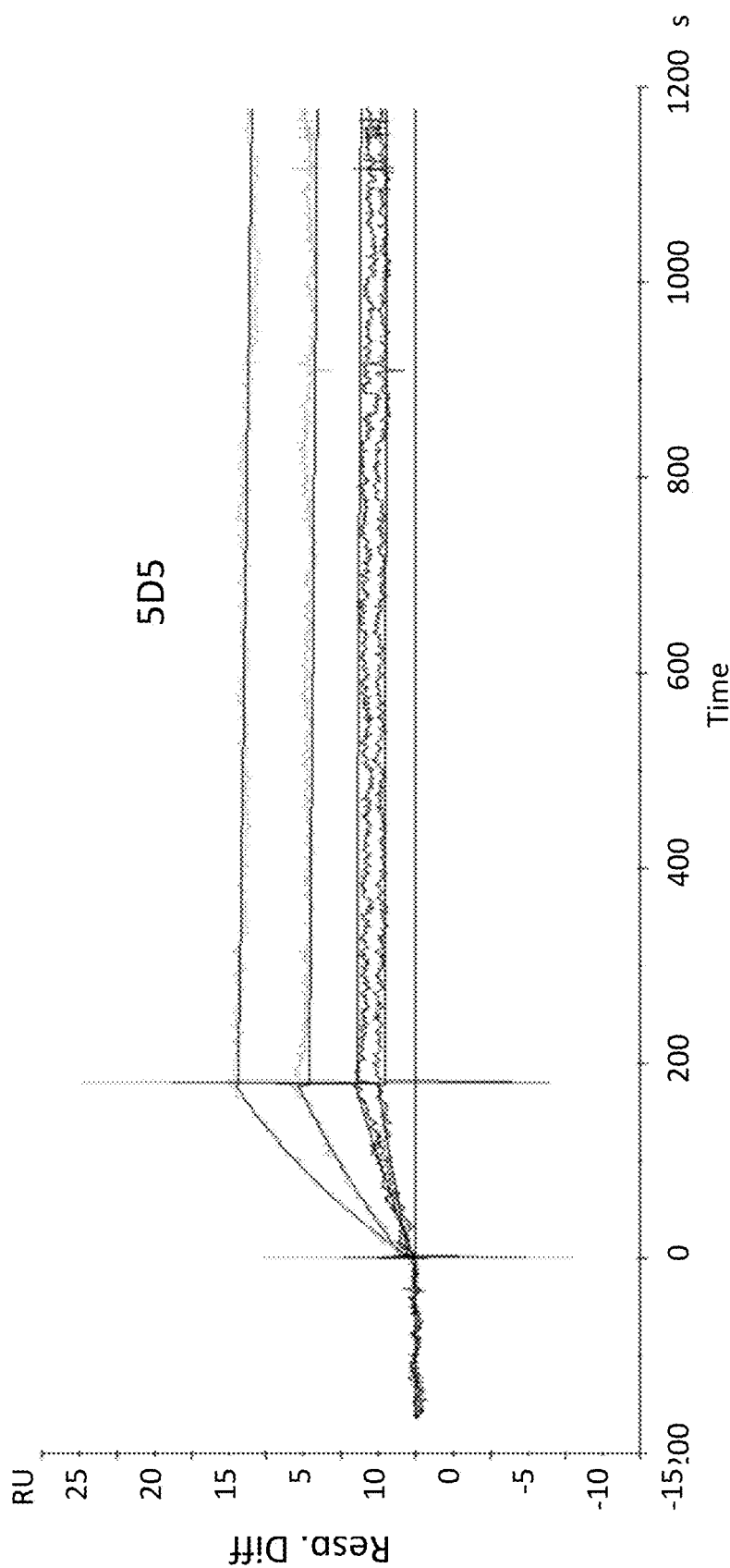

ANTIGEN BINDING PROTEINS THAT BIND C-MET

CROSS REFERENCE TO RELATED APPLICATIONS

This patent application is a divisional application of U.S. application Ser. No. 13/924,492, filed Jun. 21, 2013, now U.S. Pat. No. 10,377,827, which is incorporated herein by reference in its entirety for all purposes, and which claims priority to U.S. provisional application 61/662,910 filed Jun. 21, 2012.

SEQUENCE LISTING

The instant application contains a Sequence Listing which has been submitted in ASCII format via EFS-Web and is hereby incorporated by reference in its entirety. Said ASCII copy, created on Jun. 24, 2019, is named 2019-06-24_01223-0023-01US_Sequence_Listing.txt and is 96.2 kilobytes in size.

TECHNICAL FIELD

The present disclosure provides compositions and methods relating to or derived from anti-c-Met antibodies. More specifically, the present disclosure provides human antibodies that bind c-Met, c-Met-binding fragments and derivatives of such antibodies, and C-Met-binding polypeptides comprising such fragments. Further still, the present disclosure provides nucleic acids encoding such antibodies, antibody fragments and derivatives and polypeptides, cells comprising such polynucleotides, methods of making such antibodies, antibody fragments and derivatives and polypeptides, and methods of using such antibodies, antibody fragments and derivatives and polypeptides, including methods of treating or diagnosing subjects having C-Met related disorders or conditions, including various inflammatory disorders and various cancers.

BACKGROUND

HGF is a mesenchyme-derived pleiotrophic factor with mitogenic, motogenic and morphogenic activities on a number of different cell types. HGF effects are mediated through a specific tyrosine kinase, c-Met, and aberrant HGF and c-Met expression are frequently observed in a variety of tumors. (Maulik et al., *Cytokine & Growth Factor Reviews* (2002), 13:41-59; Danilkovitch-Miagkova & Zbar, *J. Clin. Invest.* (2002), 109(7):863-867). Regulation of the HGF/c-Met signaling pathway is implicated in tumor progression and metastasis. (Trusolino & Comoglio, *Nature Rev.* (2002), 2:289-300).

HGF binds the extracellular domain of the Met receptor tyrosine kinase (RTK) and regulates diverse biological processes such as cell scattering, proliferation, and survival. HGF-Met signaling is essential for normal embryonic development especially in migration of muscle progenitor cells and development of the liver and nervous system (Bladt et al., *Nature* 376, 768-771. 1995; Hamanoue et al. *J. Neurosci. Res.* 43, 554-564. 1996; Schmidt et al., *Proc. Natl. Acad. Sci. USA* 94, 11445-11450, 1995; Uehara et al., *Nature* 373, 702-705, 1995). Developmental phenotypes of Met and HGF knockout mice are very similar suggesting that HGF is the cognate ligand for the Met receptor (Schmidt et al., *Proc. Natl. Acad. Sci. USA* 94, 11445-11450, 1995; Uehara et al., *Nature* 373, 702-705, 1995). HGF-Met also plays a role in liver regeneration, angiogenesis, and wound healing (Bussolino et al., *J. Cell Biol.* 119, 629-641 1992; Nusrat et al., *J. Clin. Invest.* 93, 2056-2065 1994). The precursor Met receptor undergoes proteolytic cleavage into an extracellular subunit and membrane spanning subunit linked by disulfide bonds (Tempest et al., *Br. J. Cancer* 58, 3-7 1988). The subunit contains the cytoplasmic kinase domain and harbors a multi-substrate docking site at the C-terminus where adapter proteins bind and initiate signaling. Upon HGF binding, activation of Met leads to tyrosine phosphorylation and downstream signaling through Gab1 and Grb2/Sos mediated PI3-kinase and Ras/MAPK activation respectively, which drives cell motility and proliferation (Furge et al., *Oncogene* 19, 5582-5589 2000; Hartmann et al., *J. Biol. Chem.* 269, 21936-21939 1994; Ponzetto et al., *Cell* 87, 531-542 1996; and Royal and Park, *J. Biol. Chem.* 270, 27780-27787 1995).

Met overexpression or gene-amplification has been observed in a variety of human cancers. For example, Met protein is overexpressed at least 5-fold in colorectal cancers and reported to be gene-amplified in liver metastasis (Di Renzo et al., *Clin. Cancer Res.* 1, 147-154, 1995; Liu et al., *Oncogene* 7, 181-185 1992). Met protein is also reported to be overexpressed in oral squamous cell carcinoma, hepatocellular carcinoma, renal cell carcinoma, breast carcinoma, and lung carcinoma (Jin et al., *Cancer* 79, 749-760 1997; Morello et al., *J. Cell Physiol.* 189, 285-290 2001; Natali et al., *Int. J. Cancer* 69, 212-217. 1996; Olivero et al., *Br. J. Cancer* 74, 1862-1868 1996; Suzuki et al., *Hepatology* 20, 1231-1236 1994). In addition, overexpression of mRNA has been observed in hepatocellular carcinoma, gastric carcinoma, and colorectal carcinoma (Boix et al., *Hepatology* 19, 88-91 1994; Kuniyasu et al., *Int. J. Cancer* 55, 72-75 1993; Liu et al., *Oncogene* 7, 181-185 1992).

A number of mutations in the kinase domain of Met have been found in renal papillary carcinoma which leads to constitutive receptor activation (Olivero et al., *Int. J. Cancer* 82, 640-643 1999; Schmidt et al., *Nat. Genet.* 16, 68-73 1997; Schmidt et al., *Oncogene* 18, 2343-2350 1999). These activating mutations confer constitutive Met tyrosine phosphorylation and result in MAPK activation, focus formation, and tumorigenesis (Jeffers et al., *Proc. Natl. Acad. Sci. USA* 94, 11445-11450 1997). In addition, these mutations enhance cell motility and invasion (Giordano et al., 2000; Lorenzato et al., *Cancer Res.* 62, 7025-7030 2002). HGF-dependent Met activation in transformed cells mediates increased motility, scattering, and migration which eventually leads to invasive tumor growth and metastasis (Jeffers et al., *Mol. Cell Biol.* 16, 1115-1125 1996; Meiners et al., *Oncogene* 16, 9-20 1998).

Met is a member of the subfamily of RTKs which include Ron and Sea (Maulik et al., *Cytokine Growth Factor Rev.* 13, 41-59 2002). Prediction of the extracellular domain structure of Met suggests shared homology with the semaphorins and plexins. The N-terminus of Met contains a Sema domain of approximately 500 amino acids that is conserved in all semaphorins and plexins. The semaphorins and plexins belong to a large family of secreted and membrane-bound proteins first described for their role in neural development (Van Vactor and Lorenz, *Curr. Biol.* 9, R201-204 1999). However, semaphorin overexpression has been correlated with tumor invasion and metastasis. A cysteine-rich PSI domain (also referred to as a Met Related Sequence domain) found in plexins, semaphorins, and integrins lies adjacent to the Sema domain followed by four IPT repeats that are immunoglobulin-like regions found in plexins and transcription factors. A recent study suggests that the Met Sema domain is sufficient for HGF and heparin binding (Gherardi et al., (2003). Functional map and domain structure of Met, the product of the c-Met protooncogene and receptor for hepatocyte growth factor/scatter factor. *Proc. Natl. Acad. Sci. USA* 2003). Furthermore, Kong-Beltran et al. (*Cancer Cell* (2004), 6:61-73) have reported that the Sema domain of Met is necessary for receptor dimerization and activation.

Numerous molecules targeted at the HGF/c-Met pathway have been reported. These molecules include antibodies such as those described in U.S. Pat. No. 5,686,292. A portion of the extracellular domain of c-Met has also been shown to be capable of antagonistic effects against the HGF/c-Met pathway. In view of the important role that this pathway plays in the etiology of various pathological conditions, however, it is clear that there continues to be a need for agents that have clinical attributes that are optimal for development as therapeutic agents.

SUMMARY

The present disclosure provides a fully human antibody of an IgG class that binds to a c-Met epitope with a binding affinity of at least $10^{-6}$M, which has a heavy chain variable domain sequence that is at least 95% identical to the amino acid sequences selected from the group consisting of SEQ ID NO. 1, SEQ ID NO. 3, SEQ ID NO. 5, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 24, SEQ ID NO. 25, SEQ ID NO. 27, SEQ ID NO. 29, SEQ ID NO. 31, SEQ ID NO. 32, SEQ ID NO. 33, SEQ ID NO. 34, SEQ ID NO. 36, SEQ ID NO. 37, SEQ ID NO. 40, SEQ ID NO. 42, SEQ ID NO. 44, SEQ ID NO. 45, SEQ ID NO. 47, SEQ ID NO. 49, SEQ ID NO. 51, SEQ ID NO. 53, SEQ ID NO. 56, SEQ ID NO. 58, SEQ ID NO. 59, SEQ ID NO. 61, SEQ ID NO. 63, SEQ ID NO. 65, SEQ ID NO. 69, SEQ ID NO. 71, SEQ ID NO. 74, SEQ ID NO. 75, SEQ ID NO. 76, SEQ ID NO. 79, SEQ ID NO. 80, SEQ ID NO. 82, SEQ ID NO. 84, SEQ ID NO. 86, SEQ ID NO. 88, SEQ ID NO. 90, SEQ ID NO. 92, and combinations thereof, and that has a light chain variable domain sequence that is at least 95% identical to the amino acid sequences selected from the group consisting of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 18, SEQ ID NO. 20, SEQ ID NO. 22, SEQ ID NO. 23, SEQ ID NO. 26, SEQ ID NO. 28, SEQ ID NO. 30, SEQ ID NO. 35, SEQ ID NO. 38, SEQ ID NO. 39, SEQ ID NO. 41, SEQ ID NO. 43, SEQ ID NO. 46, SEQ ID NO. 48, SEQ ID NO. 50, SEQ ID NO. 52, SEQ ID NO. 54, SEQ ID NO. 55, SEQ ID NO. 57, SEQ ID NO. 60, SEQ ID NO. 62, SEQ ID NO. 64, SEQ ID NO. 66, SEQ ID NO. 67, SEQ ID NO. 68, SEQ ID NO. 70, SEQ ID NO. 72, SEQ ID NO. 73, SEQ ID NO. 77, SEQ ID NO. 78, SEQ ID NO. 81, SEQ ID NO. 83, SEQ ID NO. 85, SEQ ID NO. 87, SEQ ID NO. 89, SEQ ID NO. 91, SEQ ID NO. 93, and combinations thereof. Preferably, the fully human antibody has both a heavy chain and a light chain wherein the antibody has a heavy chain/light chain variable domain sequence selected from the group consisting of SEQ ID NO. 1/SEQ ID NO. 2 (called A1 herein), SEQ ID NO. 3/SEQ ID NO. 4 (called A2 herein), SEQ ID NO. 5/SEQ ID NO. 6 (called A8 herein), SEQ ID NO. 7/SEQ ID NO. 8 (called B12 herein), SEQ ID NO. 9/SEQ ID NO. 10 (called D6 herein), SEQ ID NO. 11/SEQ ID NO. 12 (called E1 herein), SEQ ID NO. 13/SEQ ID NO. 14 (called E6 herein), SEQ ID NO. 15/SEQ ID NO. 16 (called F3 herein), SEQ ID NO. 17/SEQ ID NO. 18 (called H6 herein), SEQ ID NO. 19/SEQ ID NO. 20 (called H8 herein), SEQ ID NO. 21/SEQ ID NO. 22 (called H8-9 herein), SEQ ID NO. 21/SEQ ID NO. 23 (called H8-9EE8L3 herein), SEQ ID NO. 24/SEQ ID NO. 22 (called H8-G3S herein), SEQ ID NO. 25/SEQ ID NO. 26 (called H8-A2 herein), SEQ ID NO. 27/SEQ ID NO. 28 (called H8-B6 herein), SEQ ID NO. 29/SEQ ID NO. 23 (called H8-C1 herein), SEQ ID NO. 24/SEQ ID NO. 30 (called H8-D4 herein), SEQ ID NO. 31/SEQ ID NO. 23 (called H8-D5 herein), SEQ ID NO. 24/SEQ ID NO. 23 (called H8-D6 herein), SEQ ID NO. 32/SEQ ID NO. 23 (called H8-D10 herein), SEQ ID NO. 33/SEQ ID NO. 22 (called H8-E5 herein), SEQ ID NO. 34/SEQ ID NO. 22 (called H8-G7 herein), SEQ ID NO. 24/SEQ ID NO. 35 (called H8-G9 herein), SEQ ID NO. 36/SEQ ID NO. 26 (called H8-H6 herein), SEQ ID NO. 29/SEQ ID NO. 22 (called H8-2A2 herein), SEQ ID NO. 37/SEQ ID NO. 38 (called H8-2B1 herein), SEQ ID NO. 34/SEQ ID NO. 23 (called H8-2B2 herein), SEQ ID NO. 37/SEQ ID NO. 23 (called H8-2B4 herein), SEQ ID NO. 32/SEQ ID NO. 39 (called H8-2B7 herein), SEQ ID NO. 32/SEQ ID NO. 22 (called H8-A7P herein), SEQ ID NO. 40/SEQ ID NO. 41 (called GCE-A10 herein), SEQ ID NO. 42/SEQ ID NO. 43 (called GCE-A11 herein), SEQ ID NO. 44/SEQ ID NO. 41 (called GCE-A13 herein), SEQ ID NO. 45/SEQ ID NO. 46 (called GCE-A14 herein), SEQ ID NO. 47/SEQ ID NO. 48 (called GCE-A16 herein), SEQ ID NO. 49/SEQ ID NO. 50 (called GCE-A18 herein), SEQ ID NO. 51/SEQ ID NO. 52 (called GCE-B2 herein), SEQ ID NO. 53/SEQ ID NO. 54 (called GCE-B9 herein), SEQ ID NO. 45/SEQ ID NO. 55 (called GCE-B11 herein), SEQ ID NO. 56/SEQ ID NO. 57 (called GCE-B13 herein), SEQ ID NO. 58/SEQ ID NO. 57 (called GCE-B19 herein), SEQ ID NO. 59/SEQ ID NO. 60 (called GCE-BR1 herein), SEQ ID NO. 61/SEQ ID NO. 62 (called GCE-B20 herein), SEQ ID NO. 63/SEQ ID NO. 64 (called GCE-A19 herein), SEQ ID NO. 65/SEQ ID NO. 66 (called GCE-B10 herein), SEQ ID NO. 58/SEQ ID NO. 67 (called GCE-B5 herein), SEQ ID NO. 61/SEQ ID NO. 68 (called GCE-B4 herein), SEQ ID NO. 69/SEQ ID NO. 70 (called GCE-A26 herein), SEQ ID NO. 71/SEQ ID NO. 72 (called GCE-L1A-9 herein), SEQ ID NO. 49/SEQ ID NO. 73 (called GCE-H34-36 herein), SEQ ID NO. 74/SEQ ID NO. 73 (called GCE-H13-1 herein), SEQ ID NO. 61/SEQ ID NO. 73 (called GCE-H13-2 herein), SEQ ID NO. 44/SEQ ID NO. 73 (called GCE-H13-3 herein), SEQ ID NO. 40/SEQ ID NO. 73 (called GCE-H13-4 herein), SEQ ID NO. 75/SEQ ID NO. 73 (called GCE-H13-5 herein), SEQ ID NO. 69/SEQ ID NO. 73 (called GCE-H13-6 herein), SEQ ID NO. 76/SEQ ID NO. 73 (called GCE-H13-8 herein), SEQ ID NO. 21/SEQ ID NO. 77 (called H8-9EH11L herein), SEQ ID NO. 21/SEQ ID NO. 78 (called H8-9EG11L herein), SEQ ID NO. 79/SEQ ID NO. 20 (called H8-6AG2H3 herein), SEQ ID NO. 80/SEQ ID NO. 81 (called A1-2 herein), SEQ ID NO. 82/SEQ ID NO. 83 (called A1-4 herein), SEQ ID NO. 84/SEQ ID NO. 85 (called A1-6 herein), SEQ ID NO. 86/SEQ ID NO. 87 (called A1-8 herein), SEQ ID NO. 88/SEQ ID NO. 89 (called A1-9 herein), SEQ ID NO. 90/SEQ ID NO. 91 (called A1-24 herein), SEQ ID NO. 92/SEQ ID NO. 93 (called A1-32 herein), and combinations thereof.

The present disclosure provides a fully human antibody Fab fragment, having a variable domain region from a heavy chain and a variable domain region from a light chain, wherein the heavy chain variable domain sequence that is at least 95% identical to the amino acid sequences selected from the group consisting of SEQ ID NO. 1, SEQ ID NO. 3, SEQ ID NO. 5, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 24, SEQ ID NO. 25, SEQ ID NO. 27, SEQ ID NO. 29, SEQ ID NO. 31, SEQ ID NO. 32, SEQ ID NO. 33, SEQ ID NO. 34, SEQ ID NO. 36, SEQ ID NO. 37, SEQ ID NO. 40, SEQ ID NO. 42, SEQ ID NO. 44, SEQ ID NO. 45, SEQ ID NO. 47, SEQ ID NO. 49, SEQ ID NO. 51, SEQ ID NO. 53, SEQ ID NO. 56, SEQ ID NO. 58, SEQ ID NO. 59, SEQ ID NO. 61, SEQ ID NO. 63, SEQ ID NO. 65, SEQ ID NO. 69, SEQ ID NO. 71, SEQ ID NO. 74, SEQ ID NO. 75, SEQ ID NO. 76, SEQ ID NO. 79, SEQ ID NO. 80, SEQ ID NO. 82, SEQ ID NO. 84, SEQ ID NO. 86, SEQ ID NO. 88, SEQ ID NO. 90, SEQ ID NO. 92, and combinations thereof, and that has a light chain variable domain sequence that is at least 95% identical to the amino acid sequences selected from the group consisting of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 18, SEQ ID NO. 20, SEQ ID NO. 22, SEQ ID NO. 23, SEQ ID NO. 26, SEQ ID NO. 28, SEQ ID NO. 30, SEQ ID NO. 35, SEQ ID NO. 38, SEQ ID NO. 39, SEQ ID NO. 41, SEQ ID NO. 43, SEQ ID NO. 46, SEQ ID NO. 48, SEQ ID NO. 50, SEQ ID NO. 52, SEQ ID NO. 54, SEQ ID NO. 55, SEQ ID NO. 57, SEQ ID NO. 60, SEQ ID NO. 62, SEQ ID NO. 64, SEQ ID NO. 66, SEQ ID NO. 67, SEQ ID NO. 68, SEQ ID NO. 70, SEQ ID NO. 72, SEQ ID NO. 73, SEQ ID NO. 77, SEQ ID NO. 78, SEQ ID NO. 81, SEQ ID NO. 83, SEQ ID NO. 85, SEQ ID NO. 87, SEQ ID NO. 89, SEQ ID NO. 91, SEQ ID NO. 93, and combinations thereof. Preferably, the fully human antibody Fab fragment has both a heavy chain variable domain region and a light chain variable domain region wherein the antibody has a heavy chain/light chain variable domain sequence selected from the group consisting of SEQ ID NO. 1/SEQ ID NO. 2, SEQ ID NO. 3/SEQ ID NO. 4, SEQ ID NO. 5/SEQ ID NO. 6, SEQ ID NO. 7/SEQ ID NO. 8, SEQ ID NO. 9/SEQ ID NO. 10, SEQ ID NO. 11/SEQ ID NO. 12, SEQ ID NO. 13/SEQ ID NO. 14, SEQ ID NO. 15/SEQ ID NO. 16, SEQ ID NO. 17/SEQ ID NO. 18, SEQ ID NO. 19/SEQ ID NO. 20, SEQ ID NO. 21/SEQ ID NO. 22, SEQ ID NO. 21/SEQ ID NO. 23, SEQ ID NO. 24/SEQ ID NO. 22, SEQ ID NO. 25/SEQ ID NO. 26, SEQ ID NO. 27/SEQ ID NO. 28, SEQ ID NO. 29/SEQ ID NO. 23, SEQ ID NO. 24/SEQ ID NO. 30, SEQ ID NO. 31/SEQ ID NO. 23, SEQ ID NO. 24/SEQ ID NO. 23, SEQ ID NO. 32/SEQ ID NO. 23, SEQ ID NO. 33/SEQ ID NO. 22, SEQ ID NO. 34/SEQ ID NO. 22, SEQ ID NO. 24/SEQ ID NO. 35, SEQ ID NO. 36/SEQ ID NO. 26, SEQ ID NO. 29/SEQ ID NO. 22, SEQ ID NO. 37/SEQ ID NO. 38, SEQ ID NO. 34/SEQ ID NO. 23, SEQ ID NO. 37/SEQ ID NO. 23, SEQ ID NO. 32/SEQ ID NO. 39, SEQ ID NO. 32/SEQ ID NO. 22, SEQ ID NO. 40/SEQ ID NO. 41, SEQ ID NO. 42/SEQ ID NO. 43, SEQ ID NO. 44/SEQ ID NO. 41, SEQ ID NO. 45/SEQ ID NO. 46, SEQ ID NO. 47/SEQ ID NO. 48, SEQ ID NO. 49/SEQ ID NO. 50, SEQ ID NO. 51/SEQ ID NO. 52, SEQ ID NO. 53/SEQ ID NO. 54, SEQ ID NO. 45/SEQ ID NO. 55, SEQ ID NO. 56/SEQ ID NO. 57, SEQ ID NO. 58/SEQ ID NO. 57, SEQ ID NO. 59/SEQ ID NO. 60, SEQ ID NO. 61/SEQ ID NO. 62, SEQ ID NO. 63/SEQ ID NO. 64, SEQ ID NO. 65/SEQ ID NO. 66, SEQ ID NO. 58/SEQ ID NO. 67, SEQ ID NO. 61/SEQ ID NO. 68, SEQ ID NO. 69/SEQ ID NO. 70, SEQ ID NO. 71/SEQ ID NO. 72, SEQ ID NO. 49/SEQ ID NO. 73, SEQ ID NO. 74/SEQ ID NO. 73, SEQ ID NO. 61/SEQ ID NO. 73, SEQ ID NO. 44/SEQ ID NO. 73, SEQ ID NO. 40/SEQ ID NO. 73, SEQ ID NO. 75/SEQ ID NO. 73, SEQ ID NO. 69/SEQ ID NO. 73, SEQ ID NO. 76/SEQ ID NO. 73, SEQ ID NO. 21/SEQ ID NO. 77, SEQ ID NO. 21/SEQ ID NO. 78, SEQ ID NO. 79/SEQ ID NO. 20, SEQ ID NO. 80/SEQ ID NO. 81, SEQ ID NO. 82/SEQ ID NO. 83, SEQ ID NO. 84/SEQ ID NO. 85, SEQ ID NO. 86/SEQ ID NO. 87, SEQ ID NO. 88/SEQ ID NO. 89, SEQ ID NO. 90/SEQ ID NO. 91, SEQ ID NO. 92/SEQ ID NO. 93, and combinations thereof.

The present disclosure provides a single chain human antibody, having a variable domain region from a heavy chain and a variable domain region from a light chain and a peptide linker connection the heavy chain and light chain variable domain regions, wherein the heavy chain variable domain sequence that is at least 95% identical to the amino acid sequences selected from the group consisting of SEQ ID NO. 1, SEQ ID NO. 3, SEQ ID NO. 5, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 24, SEQ ID NO. 25, SEQ ID NO. 27, SEQ ID NO. 29, SEQ ID NO. 31, SEQ ID NO. 32, SEQ ID NO. 33, SEQ ID NO. 34, SEQ ID NO. 36, SEQ ID NO. 37, SEQ ID NO. 40, SEQ ID NO. 42, SEQ ID NO. 44, SEQ ID NO. 45, SEQ ID NO. 47, SEQ ID NO. 49, SEQ ID NO. 51, SEQ ID NO. 53, SEQ ID NO. 56, SEQ ID NO. 58, SEQ ID NO. 59, SEQ ID NO. 61, SEQ ID NO. 63, SEQ ID NO. 65, SEQ ID NO. 69, SEQ ID NO. 71, SEQ ID NO. 74, SEQ ID NO. 75, SEQ ID NO. 76, SEQ ID NO. 79, SEQ ID NO. 80, SEQ ID NO. 82, SEQ ID NO. 84, SEQ ID NO. 86, SEQ ID NO. 88, SEQ ID NO. 90, SEQ ID NO. 92, and combinations thereof, and that has a light chain variable domain sequence that is at least 95% identical to the amino acid sequences selected from the group consisting of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 18, SEQ ID NO. 20, SEQ ID NO. 22, SEQ ID NO. 23, SEQ ID NO. 26, SEQ ID NO. 28, SEQ ID NO. 30, SEQ ID NO. 35, SEQ ID NO. 38, SEQ ID NO. 39, SEQ ID NO. 41, SEQ ID NO. 43, SEQ ID NO. 46, SEQ ID NO. 48, SEQ ID NO. 50, SEQ ID NO. 52, SEQ ID NO. 54, SEQ ID NO. 55, SEQ ID NO. 57, SEQ ID NO. 60, SEQ ID NO. 62, SEQ ID NO. 64, SEQ ID NO. 66, SEQ ID NO. 67, SEQ ID NO. 68, SEQ ID NO. 70, SEQ ID NO. 72, SEQ ID NO. 73, SEQ ID NO. 77, SEQ ID NO. 78, SEQ ID NO. 81, SEQ ID NO. 83, SEQ ID NO. 85, SEQ ID NO. 87, SEQ ID NO. 89, SEQ ID NO. 91, SEQ ID NO. 93, and combinations thereof. Preferably, the fully human single chain antibody has both a heavy chain variable domain region and a light chain variable domain region, wherein the single chain fully human antibody has a heavy chain/light chain variable domain sequence selected from the group consisting of SEQ ID NO. 1/SEQ ID NO. 2, SEQ ID NO. 3/SEQ ID NO. 4, SEQ ID NO. 5/SEQ ID NO. 6, SEQ ID NO. 7/SEQ ID NO. 8, SEQ ID NO. 9/SEQ ID NO. 10, SEQ ID NO. 11/SEQ ID NO. 12, SEQ ID NO. 13/SEQ ID NO. 14, SEQ ID NO. 15/SEQ ID NO. 16, SEQ ID NO. 17/SEQ ID NO. 18, SEQ ID NO. 19/SEQ ID NO. 20, SEQ ID NO. 21/SEQ ID NO. 22, SEQ ID NO. 21/SEQ ID NO. 23, SEQ ID NO. 24/SEQ ID NO. 22, SEQ ID NO. 25/SEQ ID NO. 26, SEQ ID NO. 27/SEQ ID NO. 28, SEQ ID NO. 29/SEQ ID NO. 23, SEQ ID NO. 24/SEQ ID NO. 30, SEQ ID NO. 31/SEQ ID NO. 23, SEQ ID NO. 24/SEQ ID NO. 23, SEQ ID NO. 32/SEQ ID NO. 23, SEQ ID NO. 33/SEQ ID NO. 22, SEQ ID NO. 34/SEQ ID NO. 22, SEQ ID NO. 24/SEQ ID NO. 35, SEQ ID NO. 36/SEQ ID NO. 26, SEQ ID NO. 29/SEQ ID NO. 22, SEQ ID NO. 37/SEQ ID NO. 38, SEQ ID NO. 34/SEQ ID NO. 23, SEQ ID NO. 37/SEQ ID NO. 23, SEQ ID NO. 32/SEQ ID NO. 39, SEQ ID NO. 32/SEQ ID NO. 22, SEQ ID NO. 40/SEQ ID NO. 41, SEQ ID NO. 42/SEQ ID NO. 43, SEQ ID NO. 44/SEQ ID NO. 41, SEQ ID NO. 45/SEQ ID NO. 46, SEQ ID NO. 47/SEQ ID NO. 48, SEQ ID NO. 49/SEQ ID NO. 50, SEQ ID NO. 51/SEQ ID NO. 52, SEQ ID NO. 53/SEQ ID NO.

54, SEQ ID NO. 45/SEQ ID NO. 55, SEQ ID NO. 56/SEQ ID NO. 57, SEQ ID NO. 58/SEQ ID NO. 57, SEQ ID NO. 59/SEQ ID NO. 60, SEQ ID NO. 61/SEQ ID NO. 62, SEQ ID NO. 63/SEQ ID NO. 64, SEQ ID NO. 65/SEQ ID NO. 66, SEQ ID NO. 58/SEQ ID NO. 67, SEQ ID NO. 61/SEQ ID NO. 68, SEQ ID NO. 69/SEQ ID NO. 70, SEQ ID NO. 71/SEQ ID NO. 72, SEQ ID NO. 49/SEQ ID NO. 73, SEQ ID NO. 74/SEQ ID NO. 73, SEQ ID NO. 61/SEQ ID NO. 73, SEQ ID NO. 44/SEQ ID NO. 73, SEQ ID NO. 40/SEQ ID NO. 73, SEQ ID NO. 75/SEQ ID NO. 73, SEQ ID NO. 69/SEQ ID NO. 73, SEQ ID NO. 76/SEQ ID NO. 73, SEQ ID NO. 21/SEQ ID NO. 77, SEQ ID NO. 21/SEQ ID NO. 78, SEQ ID NO. 79/SEQ ID NO. 20, SEQ ID NO. 80/SEQ ID NO. 81, SEQ ID NO. 82/SEQ ID NO. 83, SEQ ID NO. 84/SEQ ID NO. 85, SEQ ID NO. 86/SEQ ID NO. 87, SEQ ID NO. 88/SEQ ID NO. 89, SEQ ID NO. 90/SEQ ID NO. 91, SEQ ID NO. 92/SEQ ID NO. 93, and combinations thereof.

The present disclosure further provides a method for treating a broad spectrum of mammalian cancers or a broad-spectrum of inflammatory diseases and autoimmune diseases, comprising administering an effective amount of an anti-c-Met polypeptide, wherein the anti-c-Met polypeptide is selected from the group consisting of a fully human antibody of an IgG class that binds to a c-Met epitope with a binding affinity of at least $10^{-6}$M, a fully human antibody Fab fragment, having a variable domain region from a heavy chain and a variable domain region from a light chain, a single chain human antibody, having a variable domain region from a heavy chain and a variable domain region from a light chain and a peptide linker connection the heavy chain and light chain variable domain regions, and combinations thereof;

wherein the fully human antibody has a heavy chain variable domain sequence that is at least 95% identical to the amino acid sequences selected from the group consisting of SEQ ID NO. 1, SEQ ID NO. 3, SEQ ID NO. 5, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 24, SEQ ID NO. 25, SEQ ID NO. 27, SEQ ID NO. 29, SEQ ID NO. 31, SEQ ID NO. 32, SEQ ID NO. 33, SEQ ID NO. 34, SEQ ID NO. 36, SEQ ID NO. 37, SEQ ID NO. 40, SEQ ID NO. 42, SEQ ID NO. 44, SEQ ID NO. 45, SEQ ID NO. 47, SEQ ID NO. 49, SEQ ID NO. 51, SEQ ID NO. 53, SEQ ID NO. 56, SEQ ID NO. 58, SEQ ID NO. 59, SEQ ID NO. 61, SEQ ID NO. 63, SEQ ID NO. 65, SEQ ID NO. 69, SEQ ID NO. 71, SEQ ID NO. 74, SEQ ID NO. 75, SEQ ID NO. 76, SEQ ID NO. 79, SEQ ID NO. 80, SEQ ID NO. 82, SEQ ID NO. 84, SEQ ID NO. 86, SEQ ID NO. 88, SEQ ID NO. 90, SEQ ID NO. 92, and combinations thereof, and that has a light chain variable domain sequence that is at least 95% identical to the amino acid sequences selected from the group consisting of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 18, SEQ ID NO. 20, SEQ ID NO. 22, SEQ ID NO. 23, SEQ ID NO. 26, SEQ ID NO. 28, SEQ ID NO. 30, SEQ ID NO. 35, SEQ ID NO. 38, SEQ ID NO. 39, SEQ ID NO. 41, SEQ ID NO. 43, SEQ ID NO. 46, SEQ ID NO. 48, SEQ ID NO. 50, SEQ ID NO. 52, SEQ ID NO. 54, SEQ ID NO. 55, SEQ ID NO. 57, SEQ ID NO. 60, SEQ ID NO. 62, SEQ ID NO. 64, SEQ ID NO. 66, SEQ ID NO. 67, SEQ ID NO. 68, SEQ ID NO. 70, SEQ ID NO. 72, SEQ ID NO. 73, SEQ ID NO. 77, SEQ ID NO. 78, SEQ ID NO. 81, SEQ ID NO. 83, SEQ ID NO. 85, SEQ ID NO. 87, SEQ ID NO. 89, SEQ ID NO. 91, SEQ ID NO. 93, and combinations thereof;

wherein the fully human antibody Fab fragment has the heavy chain variable domain sequence that is at least 95% identical to the amino acid sequences selected from the group consisting of SEQ ID NO. 1, SEQ ID NO. 3, SEQ ID NO. 5, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 24, SEQ ID NO. 25, SEQ ID NO. 27, SEQ ID NO. 29, SEQ ID NO. 31, SEQ ID NO. 32, SEQ ID NO. 33, SEQ ID NO. 34, SEQ ID NO. 36, SEQ ID NO. 37, SEQ ID NO. 40, SEQ ID NO. 42, SEQ ID NO. 44, SEQ ID NO. 45, SEQ ID NO. 47, SEQ ID NO. 49, SEQ ID NO. 51, SEQ ID NO. 53, SEQ ID NO. 56, SEQ ID NO. 58, SEQ ID NO. 59, SEQ ID NO. 61, SEQ ID NO. 63, SEQ ID NO. 65, SEQ ID NO. 69, SEQ ID NO. 71, SEQ ID NO. 74, SEQ ID NO. 75, SEQ ID NO. 76, SEQ ID NO. 79, SEQ ID NO. 80, SEQ ID NO. 82, SEQ ID NO. 84, SEQ ID NO. 86, SEQ ID NO. 88, SEQ ID NO. 90, SEQ ID NO. 92, and combinations thereof, and that has the light chain variable domain sequence that is at least 95% identical to the amino acid sequences selected from the group consisting of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 18, SEQ ID NO. 20, SEQ ID NO. 22, SEQ ID NO. 23, SEQ ID NO. 26, SEQ ID NO. 28, SEQ ID NO. 30, SEQ ID NO. 35, SEQ ID NO. 38, SEQ ID NO. 39, SEQ ID NO. 41, SEQ ID NO. 43, SEQ ID NO. 46, SEQ ID NO. 48, SEQ ID NO. 50, SEQ ID NO. 52, SEQ ID NO. 54, SEQ ID NO. 55, SEQ ID NO. 57, SEQ ID NO. 60, SEQ ID NO. 62, SEQ ID NO. 64, SEQ ID NO. 66, SEQ ID NO. 67, SEQ ID NO. 68, SEQ ID NO. 70, SEQ ID NO. 72, SEQ ID NO. 73, SEQ ID NO. 77, SEQ ID NO. 78, SEQ ID NO. 81, SEQ ID NO. 83, SEQ ID NO. 85, SEQ ID NO. 87, SEQ ID NO. 89, SEQ ID NO. 91, SEQ ID NO. 93, and combinations thereof; and wherein the single chain human antibody has the heavy chain variable domain sequence that is at least 95% identical to the amino acid sequences selected from the group consisting of SEQ ID NO. 1, SEQ ID NO. 3, SEQ ID NO. 5, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 24, SEQ ID NO. 25, SEQ ID NO. 27, SEQ ID NO. 29, SEQ ID NO. 31, SEQ ID NO. 32, SEQ ID NO. 33, SEQ ID NO. 34, SEQ ID NO. 36, SEQ ID NO. 37, SEQ ID NO. 40, SEQ ID NO. 42, SEQ ID NO. 44, SEQ ID NO. 45, SEQ ID NO. 47, SEQ ID NO. 49, SEQ ID NO. 51, SEQ ID NO. 53, SEQ ID NO. 56, SEQ ID NO. 58, SEQ ID NO. 59, SEQ ID NO. 61, SEQ ID NO. 63, SEQ ID NO. 65, SEQ ID NO. 69, SEQ ID NO. 71, SEQ ID NO. 74, SEQ ID NO. 75, SEQ ID NO. 76, SEQ ID NO. 79, SEQ ID NO. 80, SEQ ID NO. 82, SEQ ID NO. 84, SEQ ID NO. 86, SEQ ID NO. 88, SEQ ID NO. 90, SEQ ID NO. 92, and combinations thereof, and that has the light chain variable domain sequence that is at least 95% identical to the amino acid sequences selected from the group consisting of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 18, SEQ ID NO. 20, SEQ ID NO. 22, SEQ ID NO. 23, SEQ ID NO. 26, SEQ ID NO. 28, SEQ ID NO. 30, SEQ ID NO. 35, SEQ ID NO. 38, SEQ ID NO. 39, SEQ ID NO. 41, SEQ ID NO. 43, SEQ ID NO. 46, SEQ ID NO. 48, SEQ ID NO. 50, SEQ ID NO. 52, SEQ ID NO. 54, SEQ ID NO. 55, SEQ ID NO. 57, SEQ ID NO. 60, SEQ ID NO. 62, SEQ ID NO. 64, SEQ ID NO. 66, SEQ ID NO. 67, SEQ ID NO. 68, SEQ ID NO. 70, SEQ ID NO. 72, SEQ ID NO. 73, SEQ ID NO. 77, SEQ ID NO. 78, SEQ ID NO. 81, SEQ ID NO. 83, SEQ ID NO. 85, SEQ ID NO. 87, SEQ ID NO. 89, SEQ ID NO. 91, SEQ ID NO. 93, and combinations thereof.

Preferably, the fully human antibody has both a heavy chain and a light chain wherein the antibody has a heavy chain/light chain variable domain sequence selected from the group consisting of SEQ ID NO. 1/SEQ ID NO. 2 (called A1 herein), SEQ ID NO. 3/SEQ ID NO. 4 (called A2 herein), SEQ ID NO. 5/SEQ ID NO. 6 (called A8 herein), SEQ ID NO. 7/SEQ ID NO. 8 (called B12 herein), SEQ ID NO. 9/SEQ ID NO. 10 (called D6 herein), SEQ ID NO. 11/SEQ ID NO. 12 (called E1 herein), SEQ ID NO. 13/SEQ ID NO. 14 (called E6 herein), SEQ ID NO. 15/SEQ ID NO. 16 (called F3 herein), SEQ ID NO. 17/SEQ ID NO. 18 (called H6 herein), SEQ ID NO. 19/SEQ ID NO. 20 (called H8 herein), SEQ ID NO. 21/SEQ ID NO. 22 (called H8-9 herein), SEQ ID NO. 21/SEQ ID NO. 23 (called H8-9EE8L3 herein), SEQ ID NO. 24/SEQ ID NO. 22 (called H8-G3S herein), SEQ ID NO. 25/SEQ ID NO. 26 (called H8-A2 herein), SEQ ID NO. 27/SEQ ID NO. 28 (called H8-B6 herein), SEQ ID NO. 29/SEQ ID NO. 23 (called H8-C1 herein), SEQ ID NO. 24/SEQ ID NO. 30 (called H8-D4 herein), SEQ ID NO. 31/SEQ ID NO. 23 (called H8-D5 herein), SEQ ID NO. 24/SEQ ID NO. 23 (called H8-D6 herein), SEQ ID NO. 32/SEQ ID NO. 23 (called H8-D10 herein), SEQ ID NO. 33/SEQ ID NO. 22 (called H8-E5 herein), SEQ ID NO. 34/SEQ ID NO. 22 (called H8-G7 herein), SEQ ID NO. 24/SEQ ID NO. 35 (called H8-G9 herein), SEQ ID NO. 36/SEQ ID NO. 26 (called H8-H6 herein), SEQ ID NO. 29/SEQ ID NO. 22 (called H8-2A2 herein), SEQ ID NO. 37/SEQ ID NO. 38 (called H8-2B1 herein), SEQ ID NO. 34/SEQ ID NO. 23 (called H8-2B2 herein), SEQ ID NO. 37/SEQ ID NO. 23 (called H8-2B4 herein), SEQ ID NO. 32/SEQ ID NO. 39 (called H8-2B7 herein), SEQ ID NO. 32/SEQ ID NO. 22 (called H8-A7P herein), SEQ ID NO. 40/SEQ ID NO. 41 (called GCE-A10 herein), SEQ ID NO. 42/SEQ ID NO. 43 (called GCE-A11 herein), SEQ ID NO. 44/SEQ ID NO. 41 (called GCE-A13 herein), SEQ ID NO. 45/SEQ ID NO. 46 (called GCE-A14 herein), SEQ ID NO. 47/SEQ ID NO. 48 (called GCE-A16 herein), SEQ ID NO. 49/SEQ ID NO. 50 (called GCE-A18 herein), SEQ ID NO. 51/SEQ ID NO. 52 (called GCE-B2 herein), SEQ ID NO. 53/SEQ ID NO. 54 (called GCE-B9 herein), SEQ ID NO. 45/SEQ ID NO. 55 (called GCE-B11 herein), SEQ ID NO. 56/SEQ ID NO. 57 (called GCE-B13 herein), SEQ ID NO. 58/SEQ ID NO. 57 (called GCE-B19 herein), SEQ ID NO. 59/SEQ ID NO. 60 (called GCE-BR1 herein), SEQ ID NO. 61/SEQ ID NO. 62 (called GCE-B20 herein), SEQ ID NO. 63/SEQ ID NO. 64 (called GCE-A19 herein), SEQ ID NO. 65/SEQ ID NO. 66 (called GCE-B10 herein), SEQ ID NO. 58/SEQ ID NO. 67 (called GCE-B5 herein), SEQ ID NO. 61/SEQ ID NO. 68 (called GCE-B4 herein), SEQ ID NO. 69/SEQ ID NO. 70 (called GCE-A26 herein), SEQ ID NO. 71/SEQ ID NO. 72 (called GCE-L1A-9 herein), SEQ ID NO. 49/SEQ ID NO. 73 (called GCE-H34-36 herein), SEQ ID NO. 74/SEQ ID NO. 73 (called GCE-H13-1 herein), SEQ ID NO. 61/SEQ ID NO. 73 (called GCE-H13-2 herein), SEQ ID NO. 44/SEQ ID NO. 73 (called GCE-H13-3 herein), SEQ ID NO. 40/SEQ ID NO. 73 (called GCE-H13-4 herein), SEQ ID NO. 75/SEQ ID NO. 73 (called GCE-H13-5 herein), SEQ ID NO. 69/SEQ ID NO. 73 (called GCE-H13-6 herein), SEQ ID NO. 76/SEQ ID NO. 73 (called GCE-H13-8 herein), SEQ ID NO. 21/SEQ ID NO. 77 (called H8-9EH11L herein), SEQ ID NO. 21/SEQ ID NO. 78 (called H8-9EG11L herein), SEQ ID NO. 79/SEQ ID NO. 20 (called H8-6AG2H3 herein), SEQ ID NO. 80/SEQ ID NO. 81 (called A1-2 herein), SEQ ID NO. 82/SEQ ID NO. 83 (called A1-4 herein), SEQ ID NO. 84/SEQ ID NO. 85 (called A1-6 herein), SEQ ID NO. 86/SEQ ID NO. 87 (called A1-8 herein), SEQ ID NO. 88/SEQ ID NO. 89 (called A1-9 herein), SEQ ID NO. 90/SEQ ID NO. 91 (called A1-24 herein), SEQ ID NO. 92/SEQ ID NO. 93 (called A1-32 herein), and combinations thereof. Preferably, the fully human antibody Fab fragment has both a heavy chain variable domain region and a light chain variable domain region wherein the antibody has a heavy chain/light chain variable domain sequence selected from the group consisting of SEQ ID NO. 1/SEQ ID NO. 2 (called A1 herein), SEQ ID NO. 3/SEQ ID NO. 4 (called A2 herein), SEQ ID NO. 5/SEQ ID NO. 6 (called A8 herein), SEQ ID NO. 7/SEQ ID NO. 8 (called B12 herein), SEQ ID NO. 9/SEQ ID NO. 10 (called D6 herein), SEQ ID NO. 11/SEQ ID NO. 12 (called E1 herein), SEQ ID NO. 13/SEQ ID NO. 14 (called E6 herein), SEQ ID NO. 15/SEQ ID NO. 16 (called F3 herein), SEQ ID NO. 17/SEQ ID NO. 18 (called H6 herein), SEQ ID NO. 19/SEQ ID NO. 20 (called H8 herein), SEQ ID NO. 21/SEQ ID NO. 22 (called H8-9 herein), SEQ ID NO. 21/SEQ ID NO. 23 (called H8-9EE8L3 herein), SEQ ID NO. 24/SEQ ID NO. 22 (called H8-G3S herein), SEQ ID NO. 25/SEQ ID NO. 26 (called H8-A2 herein), SEQ ID NO. 27/SEQ ID NO. 28 (called H8-B6 herein), SEQ ID NO. 29/SEQ ID NO. 23 (called H8-C1 herein), SEQ ID NO. 24/SEQ ID NO. 30 (called H8-D4 herein), SEQ ID NO. 31/SEQ ID NO. 23 (called H8-D5 herein), SEQ ID NO. 24/SEQ ID NO. 23 (called H8-D6 herein), SEQ ID NO. 32/SEQ ID NO. 23 (called H8-D10 herein), SEQ ID NO. 33/SEQ ID NO. 22 (called H8-E5 herein), SEQ ID NO. 34/SEQ ID NO. 22 (called H8-G7 herein), SEQ ID NO. 24/SEQ ID NO. 35 (called H8-G9 herein), SEQ ID NO. 36/SEQ ID NO. 26 (called H8-H6 herein), SEQ ID NO. 29/SEQ ID NO. 22 (called H8-2A2 herein), SEQ ID NO. 37/SEQ ID NO. 38 (called H8-2B1 herein), SEQ ID NO. 34/SEQ ID NO. 23 (called H8-2B2 herein), SEQ ID NO. 37/SEQ ID NO. 23 (called H8-2B4 herein), SEQ ID NO. 32/SEQ ID NO. 39 (called H8-2B7 herein), SEQ ID NO. 32/SEQ ID NO. 22 (called H8-A7P herein), SEQ ID NO. 40/SEQ ID NO. 41 (called GCE-A10 herein), SEQ ID NO. 42/SEQ ID NO. 43 (called GCE-A11 herein), SEQ ID NO. 44/SEQ ID NO. 41 (called GCE-A13 herein), SEQ ID NO. 45/SEQ ID NO. 46 (called GCE-A14 herein), SEQ ID NO. 47/SEQ ID NO. 48 (called GCE-A16 herein), SEQ ID NO. 49/SEQ ID NO. 50 (called GCE-A18 herein), SEQ ID NO. 51/SEQ ID NO. 52 (called GCE-B2 herein), SEQ ID NO. 53/SEQ ID NO. 54 (called GCE-B9 herein), SEQ ID NO. 45/SEQ ID NO. 55 (called GCE-B11 herein), SEQ ID NO. 56/SEQ ID NO. 57 (called GCE-B13 herein), SEQ ID NO. 58/SEQ ID NO. 57 (called GCE-B19 herein), SEQ ID NO. 59/SEQ ID NO. 60 (called GCE-BR1 herein), SEQ ID NO. 61/SEQ ID NO. 62 (called GCE-B20 herein), SEQ ID NO. 63/SEQ ID NO. 64 (called GCE-A19 herein), SEQ ID NO. 65/SEQ ID NO. 66 (called GCE-B10 herein), SEQ ID NO. 58/SEQ ID NO. 67 (called GCE-B5 herein), SEQ ID NO. 61/SEQ ID NO. 68 (called GCE-B4 herein), SEQ ID NO. 69/SEQ ID NO. 70 (called GCE-A26 herein), SEQ ID NO. 71/SEQ ID NO. 72 (called GCE-L1A-9 herein), SEQ ID NO. 49/SEQ ID NO. 73 (called GCE-H34-36 herein), SEQ ID NO. 74/SEQ ID NO. 73 (called GCE-H13-1 herein), SEQ ID NO. 61/SEQ ID NO. 73 (called GCE-H13-2 herein), SEQ ID NO. 44/SEQ ID NO. 73 (called GCE-H13-3 herein), SEQ ID NO. 40/SEQ ID NO. 73 (called GCE-H13-4 herein), SEQ ID NO. 75/SEQ ID NO. 73 (called GCE-H13-5 herein), SEQ ID NO. 69/SEQ ID NO. 73 (called GCE-H13-6 herein), SEQ ID NO. 76/SEQ ID NO. 73 (called GCE-H13-8 herein), SEQ ID NO. 21/SEQ ID NO. 77 (called H8-9EH11L herein), SEQ ID NO. 21/SEQ ID NO. 78 (called H8-9EG11L herein), SEQ ID NO. 79/SEQ ID NO. 20 (called H8-6AG2H3 herein), SEQ ID NO. 80/SEQ ID NO. 81 (called A1-2 herein), SEQ ID NO. 82/SEQ ID NO. 83 (called A1-4 herein), SEQ ID NO. 84/SEQ ID NO. 85 (called A1-6 herein), SEQ ID NO. 86/SEQ ID NO. 87 (called A1-8 herein), SEQ ID NO. 88/SEQ ID NO. 89 (called A1-9 herein), SEQ ID NO. 90/SEQ ID NO. 91 (called A1-24 herein), SEQ ID NO. 92/SEQ ID NO. 93 (called A1-32 herein), and combinations thereof. Preferably, the fully human single chain antibody has both a heavy chain variable domain region and a light chain variable domain region, wherein the single chain fully human antibody has a heavy chain/light chain variable domain sequence selected from the group consisting of SEQ ID NO. 1/SEQ ID NO. 2, SEQ ID NO. 3/SEQ ID NO. 4, SEQ ID NO. 5/SEQ ID NO. 6, SEQ ID NO. 7/SEQ ID NO. 8, SEQ ID NO. 9/SEQ ID NO. 10, SEQ ID NO. 11/SEQ ID NO. 12, SEQ ID NO. 13/SEQ ID NO. 14, SEQ ID NO. 15/SEQ ID NO. 16, SEQ ID NO. 17/SEQ ID NO. 18, SEQ ID NO. 19/SEQ ID NO. 20, SEQ ID NO. 21/SEQ ID NO. 22, SEQ ID NO. 21/SEQ ID NO. 23, SEQ ID NO. 24/SEQ ID NO. 22, SEQ ID NO. 25/SEQ ID NO. 26, SEQ ID NO. 27/SEQ ID NO. 28, SEQ ID NO. 29/SEQ ID NO. 23, SEQ ID NO. 24/SEQ ID NO. 30, SEQ ID NO. 31/SEQ ID NO. 23, SEQ ID NO. 24/SEQ ID NO. 23, SEQ ID NO. 32/SEQ ID NO. 23, SEQ ID NO. 33/SEQ ID NO. 22, SEQ ID NO. 34/SEQ ID NO. 22, SEQ ID NO. 24/SEQ ID NO. 35, SEQ ID NO. 36/SEQ ID NO. 26, SEQ ID NO. 29/SEQ ID NO. 22, SEQ ID NO. 37/SEQ ID NO. 38, SEQ ID NO. 34/SEQ ID NO. 23, SEQ ID NO. 37/SEQ ID NO. 23, SEQ ID NO. 32/SEQ ID NO. 39, SEQ ID NO. 32/SEQ ID NO. 22, SEQ ID NO. 40/SEQ ID NO. 41, SEQ ID NO. 42/SEQ ID NO. 43, SEQ ID NO. 44/SEQ ID NO. 41, SEQ ID NO. 45/SEQ ID NO. 46, SEQ ID NO. 47/SEQ ID NO. 48, SEQ ID NO. 49/SEQ ID NO. 50, SEQ ID NO. 51/SEQ ID NO. 52, SEQ ID NO. 53/SEQ ID NO. 54, SEQ ID NO. 45/SEQ ID NO. 55, SEQ ID NO. 56/SEQ ID NO. 57, SEQ ID NO. 58/SEQ ID NO. 57, SEQ ID NO. 59/SEQ ID NO. 60, SEQ ID NO. 61/SEQ ID NO. 62, SEQ ID NO. 63/SEQ ID NO. 64, SEQ ID NO. 65/SEQ ID NO. 66, SEQ ID NO. 58/SEQ ID NO. 67, SEQ ID NO. 61/SEQ ID NO. 68, SEQ ID NO. 69/SEQ ID NO. 70, SEQ ID NO. 71/SEQ ID NO. 72, SEQ ID NO. 49/SEQ ID NO. 73, SEQ ID NO. 74/SEQ ID NO. 73, SEQ ID NO. 61/SEQ ID NO. 73, SEQ ID NO. 44/SEQ ID NO. 73, SEQ ID NO. 40/SEQ ID NO. 73, SEQ ID NO. 75/SEQ ID NO. 73, SEQ ID NO. 69/SEQ ID NO. 73, SEQ ID NO. 76/SEQ ID NO. 73, SEQ ID NO. 21/SEQ ID NO. 77, SEQ ID NO. 21/SEQ ID NO. 78, SEQ ID NO. 79/SEQ ID NO. 20, SEQ ID NO. 80/SEQ ID NO. 81, SEQ ID NO. 82/SEQ ID NO. 83, SEQ ID NO. 84/SEQ ID NO. 85, SEQ ID NO. 86/SEQ ID NO. 87, SEQ ID NO. 88/SEQ ID NO. 89, SEQ ID NO. 90/SEQ ID NO. 91, SEQ ID NO. 92/SEQ ID NO. 93, and combinations thereof.

Preferably, the broad spectrum of mammalian cancers to be treated the cancer is a c-Met-activation-related cancer, chosen from c-Met-activation-related cancers that are HGF-dependent, HGF-independent, or both. Preferably, the broad spectrum of mammalian cancers to be treated is selected from the group consisting of prostate cancer, osteosarcoma, lung cancer, breast cancer, endometrial cancer, glyoblastoma, and colon cancer.

BRIEF DESCRIPTION OF THE FIGURES

FIG. 1A shows the affinity of the A1 anti-c-Met antibody in IgG format obtained by the Octet® Red method (Forte Bio) where this data is part of an antibody affinity ranking. FIG. 1B shows the affinity of the A8 anti-c-Met antibody in IgG format obtained by the Octet® Red method (Forte Bio) where this data is part of an antibody affinity ranking. FIG. 1G shows the affinity of the A2 anti-c-Met antibody in IgG format obtained by the Octet® Red method (Forte Bio) where this data is part of an antibody affinity ranking. FIG. 1H shows the affinity of the D6 anti-c-Met antibody in IgG format obtained by the Octet® Red method (Forte Bio) where this data is part of an antibody affinity ranking.

FIG. 2C shows the affinity kinetics of Genentech 5D5 IgG constructed and expressed in house. FIG. 2D is a table listing Biacore™ affinity kinetics of anti-c-Met antibodies.

FIG. 11 shows ADCC induced by anti-c-Met antibodies using a cell based reporter assay (Promega). As shown in FIG. 11, the EC50 value for E1 and E1 optimized clones for the induction of ADCC ranged from 23 0 pM to 1.1 nM.

As shown in FIG. 12, 5 ng/ml HGF induced cell migration and the described anti-c-Met mAbs inhibited this migration to varying degrees. Data are shown as the cell index normalized to the untreated control (+/−SD) at 8 hrs after the beginning of the experiment.

DETAILED DESCRIPTION

Figure 1C:
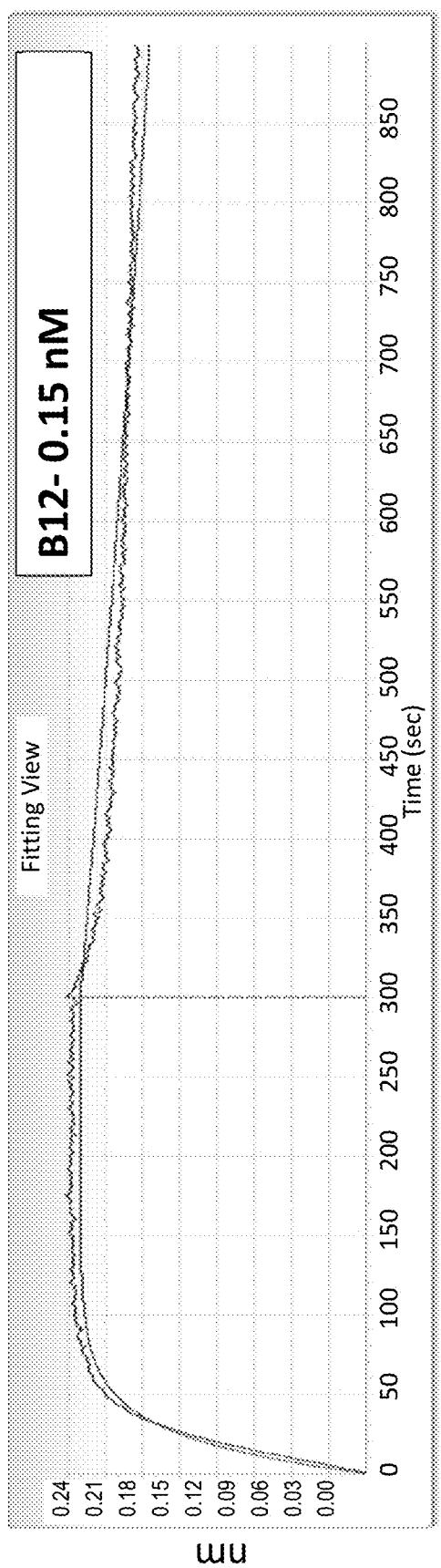
FIG. 1C shows the affinity of the B12 anti-c-Met antibody in IgG format obtained by the Octet® Red method (Forte Bio) where this data is part of an antibody affinity ranking.
Figure 1D:
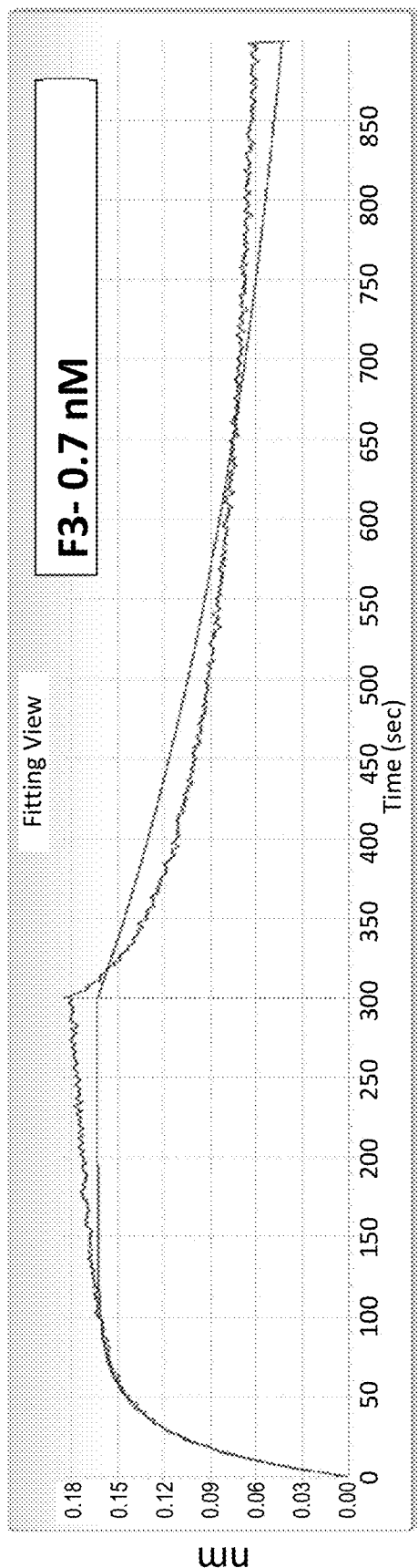
FIG. 1D shows the affinity of the F3 anti-c-Met antibody in IgG format obtained by the Octet® Red method (Forte Bio) where this data is part of an antibody affinity ranking.
Figure 1E:
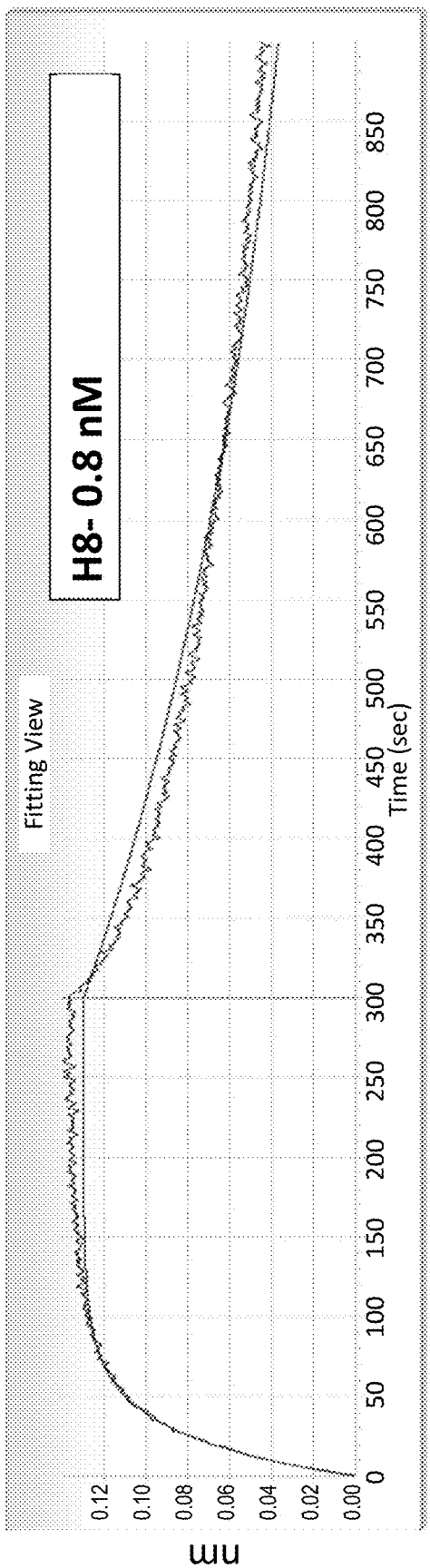
FIG. 1E shows the affinity of the H8 anti-c-Met antibody in IgG format obtained by the Octet® Red method (Forte Bio) where this data is part of an antibody affinity ranking.
Figure 1F:
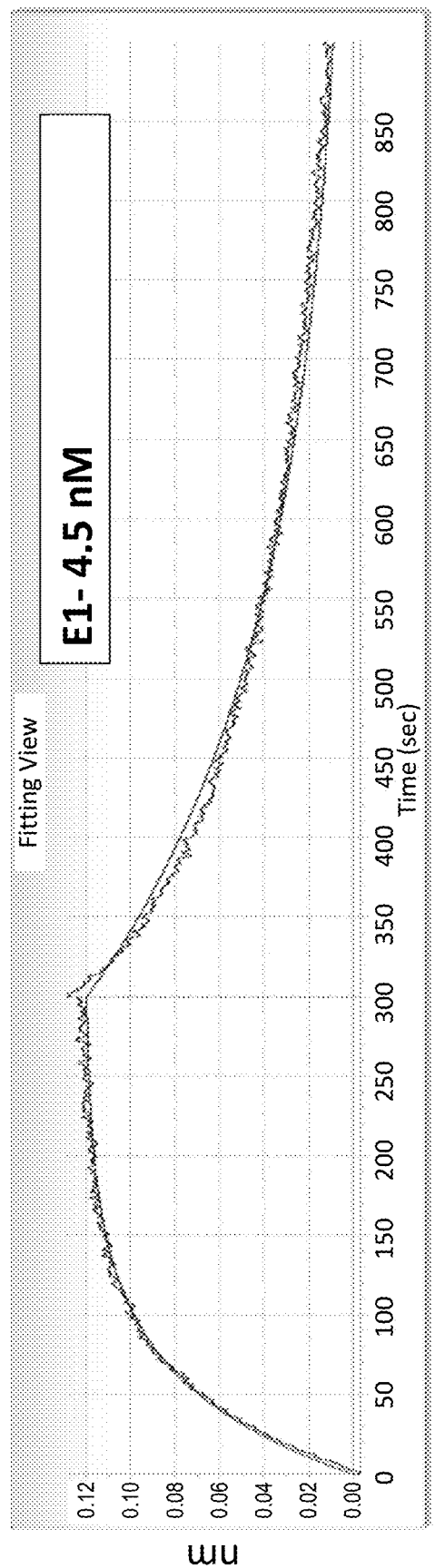
FIG. 1F shows the affinity of the E1 anti-c-Met antibody in IgG format obtained by the Octet® Red method (Forte Bio) where this data is part of an antibody affinity ranking.
Figure 2A:
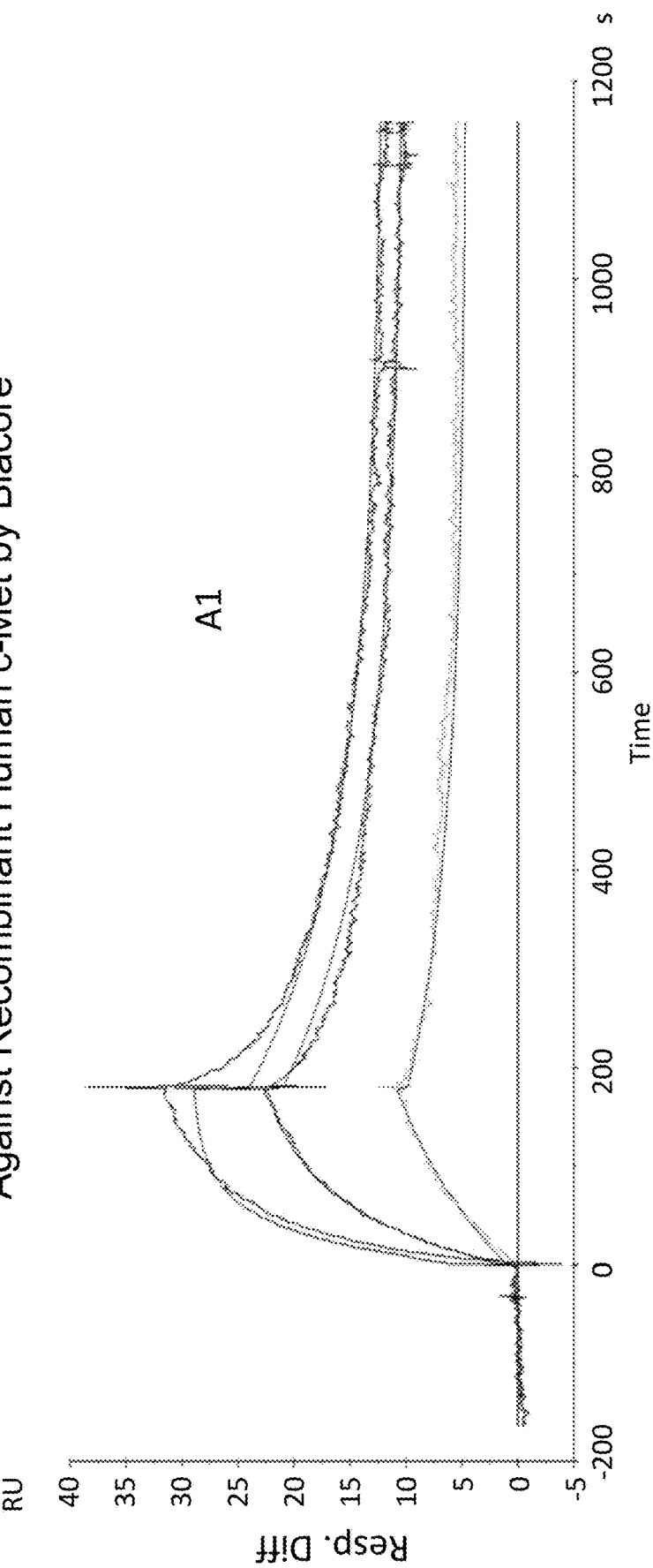
FIG. 2A shows the affinity kinetics of a preferred anti-c-Met antibody A1 in IgG format where this data is part of a comparison to Genentech 5D5 IgG constructed and expressed in house.
Figure 2B:
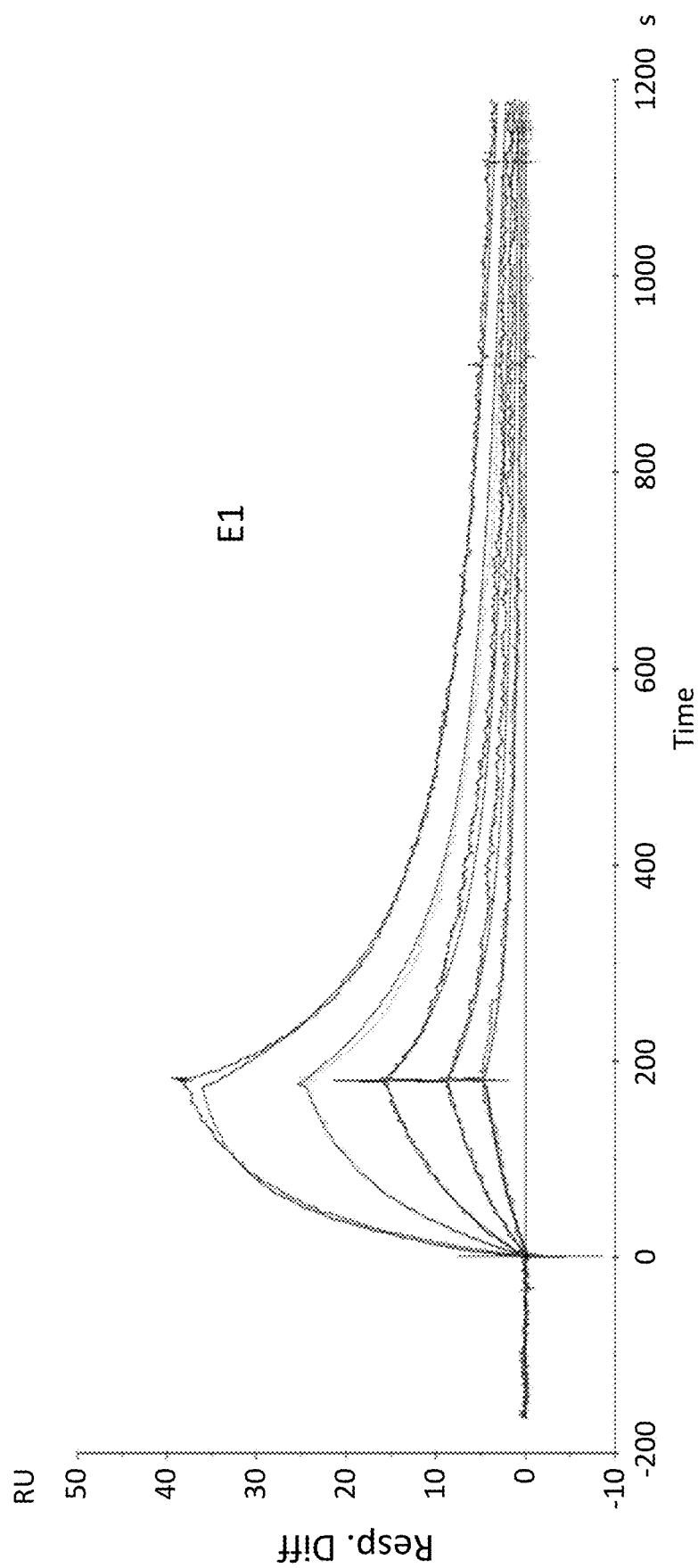
FIG. 2B shows the affinity kinetics of a preferred anti-c-Met antibody E1 in IgG format where this data is part of a comparison to Genentech 5D5 IgG constructed and expressed in house.
Figure 3A:
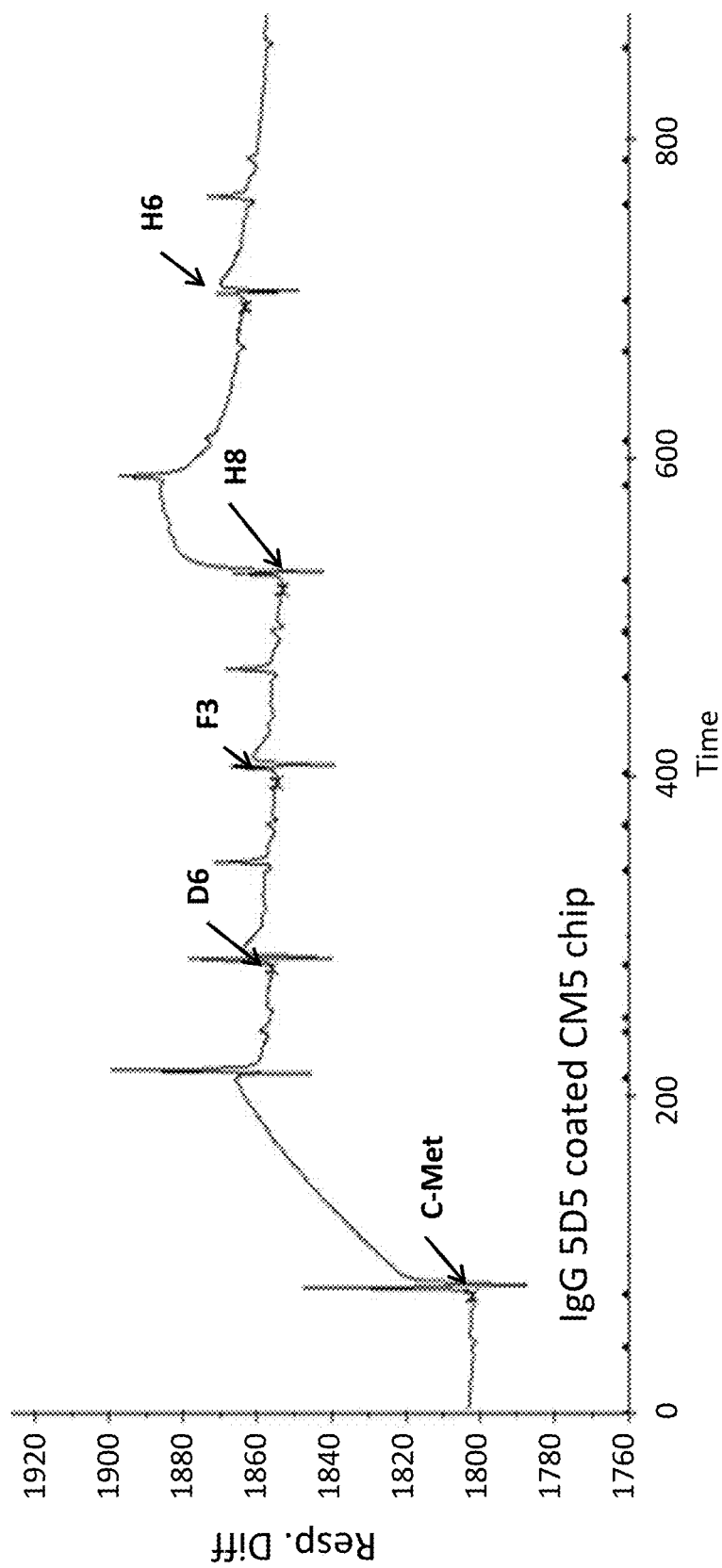
FIG. 3A shows crude epitope mapping of c-Met antibodies in IgG format in relation to Genentech 5D5 IgG. Genetech 5D5 IgG was immobilized on a CM5 chip using standard NHS/EDC coupling methodology. Then recombinant human c-Met was loaded. The anti-c-Met antibodies were then added and any additional binding was detected. Additional binding registered by Biacore™ would indicate that this antibody binds to an epitope of c-Met that is not occupied by 5D5.
Figure 3B:
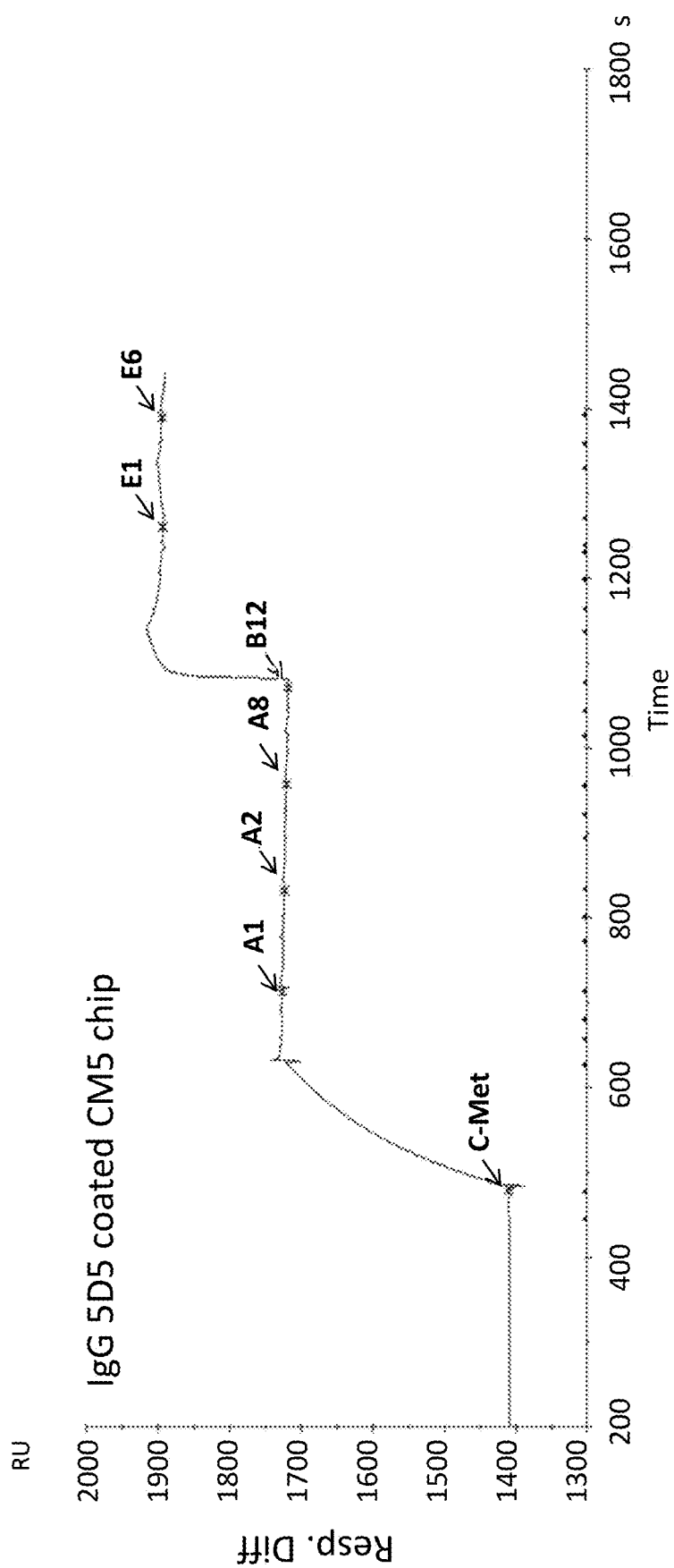
FIG. 3B shows crude epitope mapping of c-Met antibodies in IgG format in relation to Genentech 5D5 IgG.
Figures 3C, 3D:
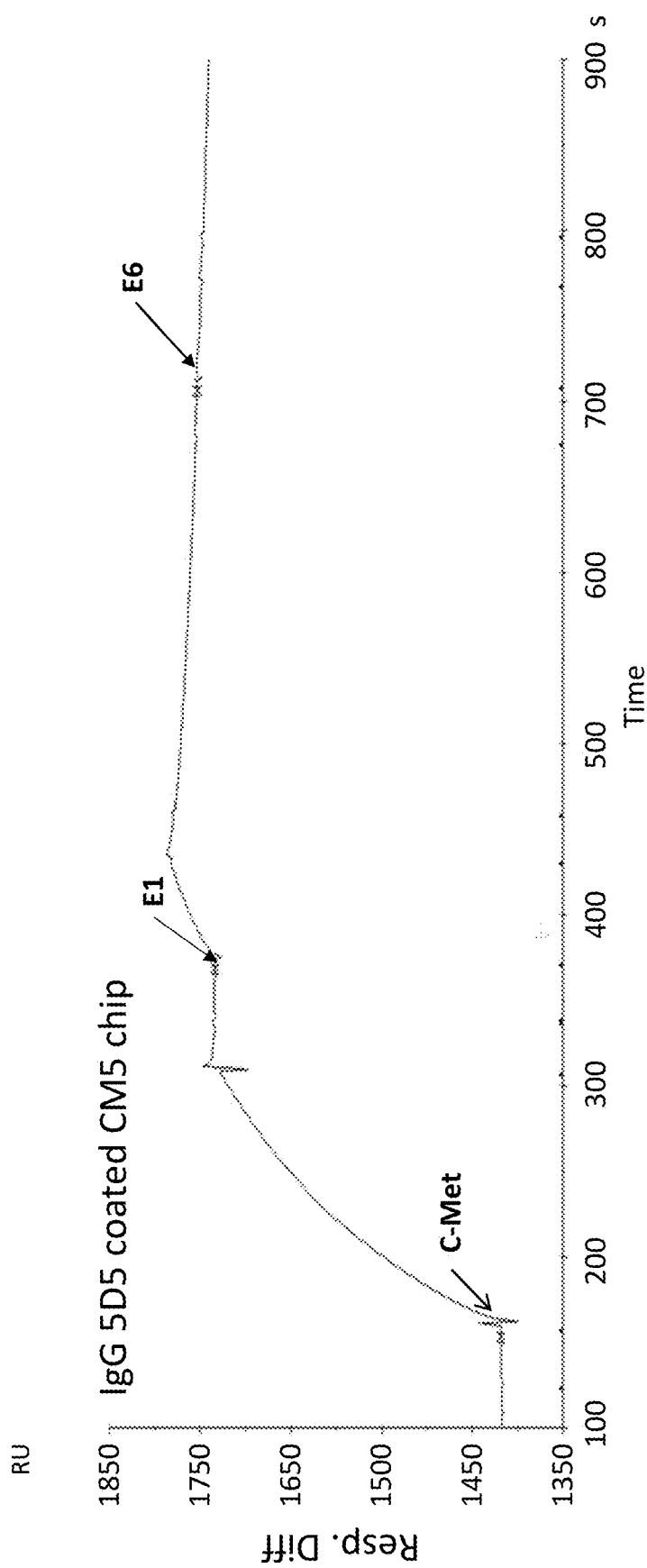
FIG. 3C shows crude epitope mapping of c-Met antibodies in IgG format in relation to Genentech 5D5 IgG.
FIG. 3D is a table listing the epitope mapping results.

The present disclosure provides a fully human antibody of an IgG class that binds to a c-Met epitope with a binding affinity of $10^{-6}$M or less, that has a heavy chain variable domain sequence that is at least 95% identical to the amino acid sequences selected from the group consisting of SEQ ID NO. 1, SEQ ID NO. 3, SEQ ID NO. 5, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 24, SEQ ID NO. 25, SEQ ID NO. 27, SEQ ID NO. 29, SEQ ID NO. 31, SEQ ID NO. 32, SEQ ID NO. 33, SEQ ID NO. 34, SEQ ID NO. 36, SEQ ID NO. 37, SEQ ID NO. 40, SEQ ID NO. 42, SEQ ID NO. 44, SEQ ID NO. 45, SEQ ID NO. 47, SEQ ID NO. 49, SEQ ID NO. 51, SEQ ID NO. 53, SEQ ID NO. 56, SEQ ID NO. 58, SEQ ID NO. 59, SEQ ID NO. 61, SEQ ID NO. 63, SEQ ID NO. 65, SEQ ID NO. 69, SEQ ID NO. 71, SEQ ID NO. 74, SEQ ID NO. 75, SEQ ID NO. 76, SEQ ID NO. 79, SEQ ID NO. 80, SEQ ID NO. 82, SEQ ID NO. 84, SEQ ID NO. 86, SEQ ID NO. 88, SEQ ID NO. 90, SEQ ID NO. 92, and combinations thereof, and that has a light chain variable domain sequence that is at least 95% identical to the amino acid sequences selected from the group consisting of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 18, SEQ ID NO. 20, SEQ ID NO. 22, SEQ ID NO. 23, SEQ ID NO. 26, SEQ ID NO. 28, SEQ ID NO. 30, SEQ ID NO. 35, SEQ ID NO. 38, SEQ ID NO. 39, SEQ ID NO. 41, SEQ ID NO. 43, SEQ ID NO. 46, SEQ ID NO. 48, SEQ ID NO. 50, SEQ ID NO. 52, SEQ ID NO. 54, SEQ ID NO. 55, SEQ ID NO. 57, SEQ ID NO. 60, SEQ ID NO. 62, SEQ ID NO. 64, SEQ ID NO. 66, SEQ ID NO. 67, SEQ ID NO. 68, SEQ ID NO. 70, SEQ ID NO. 72, SEQ ID NO. 73, SEQ ID NO. 77, SEQ ID NO. 78, SEQ ID NO. 81, SEQ ID NO. 83, SEQ ID NO. 85, SEQ ID NO. 87, SEQ ID NO. 89, SEQ ID NO. 91, SEQ ID NO. 93, and combinations thereof. Preferably, the fully human antibody has both a heavy chain and a light chain wherein the antibody has a heavy chain/light chain variable domain sequence selected from the group consisting of SEQ ID NO. 1/SEQ ID NO. 2 (called A1 herein), SEQ ID NO. 3/SEQ ID NO. 4 (called A2 herein), SEQ ID NO. 5/SEQ ID NO. 6 (called A8 herein), SEQ ID NO. 7/SEQ ID NO. 8 (called B12 herein), SEQ ID NO. 9/SEQ ID NO. 10 (called D6 herein), SEQ ID NO. 11/SEQ ID NO. 12 (called E1 herein), SEQ ID NO. 13/SEQ ID NO. 14 (called E6 herein), SEQ ID NO. 15/SEQ ID NO. 16 (called F3 herein), SEQ ID NO. 17/SEQ ID NO. 18 (called H6 herein), SEQ ID NO. 19/SEQ ID NO. 20 (called H8 herein), SEQ ID NO. 21/SEQ ID NO. 22 (called H8-9 herein), SEQ ID NO. 21/SEQ ID NO. 23 (called H8-9EE8L3 herein), SEQ ID NO. 24/SEQ ID NO. 22 (called H8-G3S herein), SEQ ID NO. 25/SEQ ID NO. 26 (called H8-A2 herein), SEQ ID NO. 27/SEQ ID NO. 28 (called H8-B6 herein), SEQ ID NO. 29/SEQ ID NO. 23 (called H8-C1 herein), SEQ ID NO. 24/SEQ ID NO. 30 (called H8-D4 herein), SEQ ID NO. 31/SEQ ID NO. 23 (called H8-D5 herein), SEQ ID NO. 24/SEQ ID NO. 23 (called H8-D6 herein), SEQ ID NO. 32/SEQ ID NO. 23 (called H8-D10 herein), SEQ ID NO. 33/SEQ ID NO. 22 (called H8-E5 herein), SEQ ID NO. 34/SEQ ID NO. 22 (called H8-G7 herein), SEQ ID NO. 24/SEQ ID NO. 35 (called H8-G9 herein), SEQ ID NO. 36/SEQ ID NO. 26 (called H8-H6 herein), SEQ ID NO. 29/SEQ ID NO. 22 (called H8-2A2 herein), SEQ ID NO. 37/SEQ ID NO. 38 (called H8-2B1 herein), SEQ ID NO. 34/SEQ ID NO. 23 (called H8-2B2 herein), SEQ ID NO. 37/SEQ ID NO. 23 (called H8-2B4 herein), SEQ ID NO. 32/SEQ ID NO. 39 (called H8-2B7 herein), SEQ ID NO. 32/SEQ ID NO. 22 (called H8-A7P herein), SEQ ID NO. 40/SEQ ID NO. 41 (called GCE-A10 herein), SEQ ID NO. 42/SEQ ID NO. 43 (called GCE-A11 herein), SEQ ID NO. 44/SEQ ID NO. 41 (called GCE-A13 herein), SEQ ID NO. 45/SEQ ID NO. 46 (called GCE-A14 herein), SEQ ID NO. 47/SEQ ID NO. 48 (called GCE-A16 herein), SEQ ID NO. 49/SEQ ID NO. 50 (called GCE-A18 herein), SEQ ID NO. 51/SEQ ID NO. 52 (called GCE-B2 herein), SEQ ID NO. 53/SEQ ID NO. 54 (called GCE-B9 herein), SEQ ID NO. 45/SEQ ID NO. 55 (called GCE-B11 herein), SEQ ID NO. 56/SEQ ID NO. 57 (called GCE-B13 herein), SEQ ID NO. 58/SEQ ID NO. 57 (called GCE-B19 herein), SEQ ID NO. 59/SEQ ID NO. 60 (called GCE-BR1 herein), SEQ ID NO. 61/SEQ ID NO. 62 (called GCE-B20 herein), SEQ ID NO. 63/SEQ ID NO. 64 (called GCE-A19 herein), SEQ ID NO. 65/SEQ ID NO. 66 (called GCE-B10 herein), SEQ ID NO. 58/SEQ ID NO. 67 (called GCE-B5 herein), SEQ ID NO. 61/SEQ ID NO. 68 (called GCE-B4 herein), SEQ ID NO. 69/SEQ ID NO. 70 (called GCE-A26 herein), SEQ ID NO. 71/SEQ ID NO. 72 (called GCE-L1A-9 herein), SEQ ID NO. 49/SEQ ID NO. 73 (called GCE-H34-36 herein), SEQ ID NO. 74/SEQ ID NO. 73 (called GCE-H13-1 herein), SEQ ID NO. 61/SEQ ID NO. 73 (called GCE-H13-2 herein), SEQ ID NO. 44/SEQ ID NO. 73 (called GCE-H13-3 herein), SEQ ID NO. 40/SEQ ID NO. 73 (called GCE-H13-4 herein), SEQ ID NO. 75/SEQ ID NO. 73 (called GCE-H13-5 herein), SEQ ID NO. 69/SEQ ID NO. 73 (called GCE-H13-6 herein), SEQ ID NO. 76/SEQ ID NO. 73 (called GCE-H13-8 herein), SEQ ID NO. 21/SEQ ID NO. 77 (called H8-9EH11L herein), SEQ ID NO. 21/SEQ ID NO. 78 (called H8-9EG11L herein), SEQ ID NO. 79/SEQ ID NO. 20 (called H8-6AG2H3 herein), SEQ ID NO. 80/SEQ ID NO. 81 (called A1-2 herein), SEQ ID NO. 82/SEQ ID NO. 83 (called A1-4 herein), SEQ ID NO. 84/SEQ ID NO. 85 (called A1-6 herein), SEQ ID NO. 86/SEQ ID NO. 87 (called A1-8 herein), SEQ ID NO. 88/SEQ ID NO. 89 (called A1-9 herein), SEQ ID NO. 90/SEQ ID NO. 91 (called A1-24 herein), SEQ ID NO. 92/SEQ ID NO. 93 (called A1-32 herein), and combinations thereof.

The present disclosure provides a fully human antibody Fab fragment, having a variable domain region from a heavy chain and a variable domain region from a light chain, wherein the heavy chain variable domain sequence that is at least 95% identical to the amino acid sequences selected from the group consisting of SEQ ID NO. 1, SEQ ID NO. 3, SEQ ID NO. 5, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 24, SEQ ID NO. 25, SEQ ID NO. 27, SEQ ID NO. 29, SEQ ID NO. 31, SEQ ID NO. 32, SEQ ID NO. 33, SEQ ID NO. 34, SEQ ID NO. 36, SEQ ID NO. 37, SEQ ID NO. 40, SEQ ID NO. 42, SEQ ID NO. 44, SEQ ID NO. 45, SEQ ID NO. 47, SEQ ID NO. 49, SEQ ID NO. 51, SEQ ID NO. 53, SEQ ID NO. 56, SEQ ID NO. 58, SEQ ID NO. 59, SEQ ID NO. 61, SEQ ID NO. 63, SEQ ID NO. 65, SEQ ID NO. 69, SEQ ID NO. 71, SEQ ID NO. 74, SEQ ID NO. 75, SEQ ID NO. 76, SEQ ID NO. 79, SEQ ID NO. 80, SEQ ID NO. 82, SEQ ID NO. 84, SEQ ID NO. 86, SEQ ID NO. 88, SEQ ID NO. 90, SEQ ID NO. 92, and combinations thereof, and that has a light chain variable domain sequence that is at least 95% identical to the amino acid sequences selected from the group consisting of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 18, SEQ ID NO. 20, SEQ ID NO. 22, SEQ ID NO. 23, SEQ ID NO. 26, SEQ ID NO. 28, SEQ ID NO. 30, SEQ ID NO. 35, SEQ ID NO. 38, SEQ ID NO. 39, SEQ ID NO. 41, SEQ ID NO. 43, SEQ ID NO. 46, SEQ ID NO. 48, SEQ ID NO. 50, SEQ ID NO. 52, SEQ ID NO. 54, SEQ ID NO. 55, SEQ ID NO. 57, SEQ ID NO. 60, SEQ ID NO. 62, SEQ ID NO. 64, SEQ ID NO. 66, SEQ ID NO. 67, SEQ ID NO. 68, SEQ ID NO. 70, SEQ ID NO. 72, SEQ ID NO. 73, SEQ ID NO. 77, SEQ ID NO. 78, SEQ ID NO. 81, SEQ ID NO. 83, SEQ ID NO. 85, SEQ ID NO. 87, SEQ ID NO. 89, SEQ ID NO. 91, SEQ ID NO. 93, and combinations thereof. Preferably, the fully human antibody Fab fragment has both a heavy chain variable domain region and a light chain variable domain region wherein the antibody has a heavy chain/light chain variable domain sequence selected from the group consisting of SEQ ID NO. 1/SEQ ID NO. 2, SEQ ID NO. 3/SEQ ID NO. 4, SEQ ID NO. 5/SEQ ID NO. 6, SEQ ID NO. 7/SEQ ID NO. 8, SEQ ID NO. 9/SEQ ID NO. 10, SEQ ID NO. 11/SEQ ID NO. 12, SEQ ID NO. 13/SEQ ID NO. 14, SEQ ID NO. 15/SEQ ID NO. 16, SEQ ID NO. 17/SEQ ID NO. 18, SEQ ID NO. 19/SEQ ID NO. 20, SEQ ID NO. 21/SEQ ID NO. 22, SEQ ID NO. 21/SEQ ID NO. 23, SEQ ID NO. 24/SEQ ID NO. 22, SEQ ID NO. 25/SEQ ID NO. 26, SEQ ID NO. 27/SEQ ID NO. 28, SEQ ID NO. 29/SEQ ID NO. 23, SEQ ID NO. 24/SEQ ID NO. 30, SEQ ID NO. 31/SEQ ID NO. 23, SEQ ID NO. 24/SEQ ID NO. 23, SEQ ID NO. 32/SEQ ID NO. 23, SEQ ID NO. 33/SEQ ID NO. 22, SEQ ID NO. 34/SEQ ID NO. 22, SEQ ID NO. 24/SEQ ID NO. 35, SEQ ID NO. 36/SEQ ID NO. 26, SEQ ID NO. 29/SEQ ID NO. 22, SEQ ID NO. 37/SEQ ID NO. 38, SEQ ID NO. 34/SEQ ID NO. 23, SEQ ID NO. 37/SEQ ID NO. 23, SEQ ID NO. 32/SEQ ID NO. 39, SEQ ID NO. 32/SEQ ID NO. 22, SEQ ID NO. 40/SEQ ID NO. 41, SEQ ID NO. 42/SEQ ID NO. 43, SEQ ID NO. 44/SEQ ID NO. 41, SEQ ID NO. 45/SEQ ID NO. 46, SEQ ID NO. 47/SEQ ID NO. 48, SEQ ID NO. 49/SEQ ID NO. 50, SEQ ID NO. 51/SEQ ID NO. 52, SEQ ID NO. 53/SEQ ID NO. 54, SEQ ID NO. 45/SEQ ID NO. 55, SEQ ID NO. 56/SEQ ID NO. 57, SEQ ID NO. 58/SEQ ID NO. 57, SEQ ID NO. 59/SEQ ID NO. 60, SEQ ID NO. 61/SEQ ID NO. 62, SEQ ID NO. 63/SEQ ID NO. 64, SEQ ID NO. 65/SEQ ID NO. 66, SEQ ID NO. 58/SEQ ID NO. 67, SEQ ID NO. 61/SEQ ID NO. 68, SEQ ID NO. 69/SEQ ID NO. 70, SEQ ID NO. 71/SEQ ID NO. 72, SEQ ID NO. 49/SEQ ID NO. 73, SEQ ID NO. 74/SEQ ID NO. 73, SEQ ID NO. 61/SEQ ID NO. 73, SEQ ID NO. 44/SEQ ID NO. 73, SEQ ID NO. 40/SEQ ID NO. 73, SEQ ID NO. 75/SEQ ID NO. 73, SEQ ID NO. 69/SEQ ID NO. 73, SEQ ID NO. 76/SEQ ID NO. 73, SEQ ID NO. 21/SEQ ID NO. 77, SEQ ID NO. 21/SEQ ID NO. 78, SEQ ID NO. 79/SEQ ID NO. 20, SEQ ID NO. 80/SEQ ID NO. 81, SEQ ID NO. 82/SEQ ID NO. 83, SEQ ID NO. 84/SEQ ID NO. 85, SEQ ID NO. 86/SEQ ID NO. 87, SEQ ID NO. 88/SEQ ID NO. 89, SEQ ID NO. 90/SEQ ID NO. 91, SEQ ID NO. 92/SEQ ID NO. 93, and combinations thereof.

The present disclosure provides a single chain human antibody, having a variable domain region from a heavy chain and a variable domain region from a light chain and a peptide linker connection the heavy chain and light chain variable domain regions, wherein the heavy chain variable domain sequence that is at least 95% identical to the amino acid sequences selected from the group consisting of SEQ ID NO. 1, SEQ ID NO. 3, SEQ ID NO. 5, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 24, SEQ ID NO. 25, SEQ ID NO. 27, SEQ ID NO. 29, SEQ ID NO. 31, SEQ ID NO. 32, SEQ ID NO. 33, SEQ ID NO. 34, SEQ ID NO. 36, SEQ ID NO. 37, SEQ ID NO. 40, SEQ ID NO. 42, SEQ ID NO. 44, SEQ ID NO. 45, SEQ ID NO. 47, SEQ ID NO. 49, SEQ ID NO. 51, SEQ ID NO. 53, SEQ ID NO. 56, SEQ ID NO. 58, SEQ ID NO. 59, SEQ ID NO. 61, SEQ ID NO. 63, SEQ ID NO. 65, SEQ ID NO. 69, SEQ ID NO. 71, SEQ ID NO. 74, SEQ ID NO. 75, SEQ ID NO. 76, SEQ ID NO. 79, SEQ ID NO. 80, SEQ ID NO. 82, SEQ ID NO. 84, SEQ ID NO. 86, SEQ ID NO. 88, SEQ ID NO. 90, SEQ ID NO. 92, and combinations thereof, and that has a light chain variable domain sequence that is at least 95% identical to the amino acid sequences selected from the group consisting of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 18, SEQ ID NO. 20, SEQ ID NO. 22, SEQ ID NO. 23, SEQ ID NO. 26, SEQ ID NO. 28, SEQ ID NO. 30, SEQ ID NO. 35, SEQ ID NO. 38, SEQ ID NO. 39, SEQ ID NO. 41, SEQ ID NO. 43, SEQ ID NO. 46, SEQ ID NO. 48, SEQ ID NO. 50, SEQ ID NO. 52, SEQ ID NO. 54, SEQ ID NO. 55, SEQ ID NO. 57, SEQ ID NO. 60, SEQ ID NO. 62, SEQ ID NO. 64, SEQ ID NO. 66, SEQ ID NO. 67, SEQ ID NO. 68, SEQ ID NO. 70, SEQ ID NO. 72, SEQ ID NO. 73, SEQ ID NO. 77, SEQ ID NO. 78, SEQ ID NO. 81, SEQ ID NO. 83, SEQ ID NO. 85, SEQ ID NO. 87, SEQ ID NO. 89, SEQ ID NO. 91, SEQ ID NO. 93, and combinations thereof. Preferably, the fully human single chain antibody has both a heavy chain variable domain region and a light chain variable domain region, wherein the single chain fully human antibody has a heavy chain/light chain variable domain sequence selected from the group consisting of SEQ ID NO. 1/SEQ ID NO. 2, SEQ ID NO. 3/SEQ ID NO. 4, SEQ ID NO. 5/SEQ ID NO. 6, SEQ ID NO. 7/SEQ ID NO. 8, SEQ ID NO. 9/SEQ ID NO. 10, SEQ ID NO. 11/SEQ ID NO. 12, SEQ ID NO. 13/SEQ ID NO. 14, SEQ ID NO. 15/SEQ ID NO. 16, SEQ ID NO. 17/SEQ ID NO. 18, SEQ ID NO. 19/SEQ ID NO. 20, SEQ ID NO. 21/SEQ ID NO. 22, SEQ ID NO. 21/SEQ ID NO. 23, SEQ ID NO. 24/SEQ ID NO. 22, SEQ ID NO. 25/SEQ ID NO. 26, SEQ ID NO. 27/SEQ ID NO. 28, SEQ ID NO. 29/SEQ ID NO. 23, SEQ ID NO. 24/SEQ ID NO. 30, SEQ ID NO. 31/SEQ ID NO. 23, SEQ ID NO. 24/SEQ ID NO. 23, SEQ ID NO. 32/SEQ ID NO. 23, SEQ ID NO. 33/SEQ ID NO. 22, SEQ ID NO. 34/SEQ ID NO. 22, SEQ ID NO. 24/SEQ ID NO. 35, SEQ ID NO. 36/SEQ ID NO. 26, SEQ ID NO. 29/SEQ ID NO. 22, SEQ ID NO. 37/SEQ ID NO. 38, SEQ ID NO. 34/SEQ ID NO. 23, SEQ ID NO. 37/SEQ ID NO. 23, SEQ ID NO. 32/SEQ ID NO. 39, SEQ ID NO. 32/SEQ ID NO. 22, SEQ ID NO. 40/SEQ ID NO. 41, SEQ ID NO. 42/SEQ ID NO. 43, SEQ ID NO. 44/SEQ ID NO. 41, SEQ ID NO. 45/SEQ ID NO. 46, SEQ ID NO. 47/SEQ ID NO. 48, SEQ ID NO. 49/SEQ ID NO. 50, SEQ ID NO. 51/SEQ ID NO. 52, SEQ ID NO. 53/SEQ ID NO. 54, SEQ ID NO. 45/SEQ ID NO. 55, SEQ ID NO. 56/SEQ ID NO. 57, SEQ ID NO. 58/SEQ ID NO. 57, SEQ ID NO. 59/SEQ ID NO. 60, SEQ ID NO. 61/SEQ ID NO. 62, SEQ ID NO. 63/SEQ ID NO. 64, SEQ ID NO. 65/SEQ ID NO. 66, SEQ ID NO. 58/SEQ ID NO. 67, SEQ ID NO. 61/SEQ ID NO. 68, SEQ ID NO. 69/SEQ ID NO. 70, SEQ ID NO. 71/SEQ ID NO. 72, SEQ ID NO. 49/SEQ ID NO. 73, SEQ ID NO. 74/SEQ ID NO. 73, SEQ ID NO. 61/SEQ ID NO. 73, SEQ ID NO. 44/SEQ ID NO. 73, SEQ ID NO. 40/SEQ ID NO. 73, SEQ ID NO. 75/SEQ ID NO. 73, SEQ ID NO. 69/SEQ ID NO. 73, SEQ ID NO. 76/SEQ ID NO. 73, SEQ ID NO. 21/SEQ ID NO. 77, SEQ ID NO. 21/SEQ ID NO. 78, SEQ ID NO. 79/SEQ ID NO. 20, SEQ ID NO. 80/SEQ ID NO. 81, SEQ ID NO. 82/SEQ ID NO. 83, SEQ ID NO. 84/SEQ ID NO. 85, SEQ ID NO. 86/SEQ ID NO. 87, SEQ ID NO. 88/SEQ ID NO. 89, SEQ ID NO. 90/SEQ ID NO. 91, SEQ ID NO. 92/SEQ ID NO. 93, and combinations thereof.

The present disclosure further provides a method for treating a broad spectrum of mammalian cancers or inflammatory diseases or autoimmune diseases, comprising administering an effective amount of an anti-c-Met polypeptide, wherein the anti-c-Met polypeptide is selected from the group consisting of a fully human antibody of an IgG class that binds to a c-Met epitope with a binding affinity of at least $10^{-6}$M, a fully human antibody Fab fragment, having a variable domain region from a heavy chain and a variable domain region from a light chain, a single chain human antibody, having a variable domain region from a heavy chain and a variable domain region from a light chain and a peptide linker connection the heavy chain and light chain variable domain regions, and combinations thereof;

wherein the fully human antibody has a heavy chain variable domain sequence that is at least 95% identical to the amino acid sequences selected from the group consisting of SEQ ID NO. 1, SEQ ID NO. 3, SEQ ID NO. 5, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 24, SEQ ID NO. 25, SEQ ID NO. 27, SEQ ID NO. 29, SEQ ID NO. 31, SEQ ID NO. 32, SEQ ID NO. 33, SEQ ID NO. 34, SEQ ID NO. 36, SEQ ID NO. 37, SEQ ID NO. 40, SEQ ID NO. 42, SEQ ID NO. 44, SEQ ID NO. 45, SEQ ID NO. 47, SEQ ID NO. 49, SEQ ID NO. 51, SEQ ID NO. 53, SEQ ID NO. 56, SEQ ID NO. 58, SEQ ID NO. 59, SEQ ID NO. 61, SEQ ID NO. 63, SEQ ID NO. 65, SEQ ID NO. 69, SEQ ID NO. 71, SEQ ID NO. 74, SEQ ID NO. 75, SEQ ID NO. 76, SEQ ID NO. 79, SEQ ID NO. 80, SEQ ID NO. 82, SEQ ID NO. 84, SEQ ID NO. 86, SEQ ID NO. 88, SEQ ID NO. 90, SEQ ID NO. 92, and combinations thereof, and that has a light chain variable domain sequence that is at least 95% identical to the amino acid sequences selected from the group consisting of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 18, SEQ ID NO. 20, SEQ ID NO. 22, SEQ ID NO. 23, SEQ ID NO. 26, SEQ ID NO. 28, SEQ ID NO. 30, SEQ ID NO. 35, SEQ ID NO. 38, SEQ ID NO. 39, SEQ ID NO. 41, SEQ ID NO. 43, SEQ ID NO. 46, SEQ ID NO. 48, SEQ ID NO. 50, SEQ ID NO. 52, SEQ ID NO. 54, SEQ ID NO. 55, SEQ ID NO. 57, SEQ ID NO. 60, SEQ ID NO. 62, SEQ ID NO. 64, SEQ ID NO. 66, SEQ ID NO. 67, SEQ ID NO. 68, SEQ ID NO. 70, SEQ ID NO. 72, SEQ ID NO. 73, SEQ ID NO. 77, SEQ ID NO. 78, SEQ ID NO. 81, SEQ ID NO. 83, SEQ ID NO. 85, SEQ ID NO. 87, SEQ ID NO. 89, SEQ ID NO. 91, SEQ ID NO. 93, and combinations thereof;

wherein the fully human antibody Fab fragment has the heavy chain variable domain sequence that is at least 95% identical to the amino acid sequences selected from the group consisting of SEQ ID NO. 1, SEQ ID NO. 3, SEQ ID NO. 5, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 24, SEQ ID NO. 25, SEQ ID NO. 27, SEQ ID NO. 29, SEQ ID NO. 31, SEQ ID NO. 32, SEQ ID NO. 33, SEQ ID NO. 34, SEQ ID NO. 36, SEQ ID NO. 37, SEQ ID NO. 40, SEQ ID NO. 42, SEQ ID NO. 44, SEQ ID NO. 45, SEQ ID NO. 47, SEQ ID NO. 49, SEQ ID NO. 51, SEQ ID NO. 53, SEQ ID NO. 56, SEQ ID NO. 58, SEQ ID NO. 59, SEQ ID NO. 61, SEQ ID NO. 63, SEQ ID NO. 65, SEQ ID NO. 69, SEQ ID NO. 71, SEQ ID NO. 74, SEQ ID NO. 75, SEQ ID NO. 76, SEQ ID NO. 79, SEQ ID NO. 80, SEQ ID NO. 82, SEQ ID NO. 84, SEQ ID NO. 86, SEQ ID NO. 88, SEQ ID NO. 90, SEQ ID NO. 92, and combinations thereof, and that has the light chain variable domain sequence that is at least 95% identical to the amino acid sequences selected from the group consisting of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 18, SEQ ID NO. 20, SEQ ID NO. 22, SEQ ID NO. 23, SEQ ID NO. 26, SEQ ID NO. 28, SEQ ID NO. 30, SEQ ID NO. 35, SEQ ID NO. 38, SEQ ID NO. 39, SEQ ID NO. 41, SEQ ID NO. 43, SEQ ID NO. 46, SEQ ID NO. 48, SEQ ID NO. 50, SEQ ID NO. 52, SEQ ID NO. 54, SEQ ID NO. 55, SEQ ID NO. 57, SEQ ID NO. 60, SEQ ID NO. 62, SEQ ID NO. 64, SEQ ID NO. 66, SEQ ID NO. 67, SEQ ID NO. 68, SEQ ID NO. 70, SEQ ID NO. 72, SEQ ID NO. 73, SEQ ID NO. 77, SEQ ID NO. 78, SEQ ID NO. 81, SEQ ID NO. 83, SEQ ID NO. 85, SEQ ID NO. 87, SEQ ID NO. 89, SEQ ID NO. 91, SEQ ID NO. 93, and combinations thereof; and wherein the single chain human antibody has the heavy chain variable domain sequence that is at least 95% identical to the amino acid sequences selected from the group consisting of SEQ ID NO. 1, SEQ ID NO. 3, SEQ ID NO. 5, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 24, SEQ ID NO. 25, SEQ ID NO. 27, SEQ ID NO. 29, SEQ ID NO. 31, SEQ ID NO. 32, SEQ ID NO. 33, SEQ ID NO. 34, SEQ ID NO. 36, SEQ ID NO. 37, SEQ ID NO. 40, SEQ ID NO. 42, SEQ ID NO. 44, SEQ ID NO. 45, SEQ ID NO. 47, SEQ ID NO. 49, SEQ ID NO. 51, SEQ ID NO. 53, SEQ ID NO. 56, SEQ ID NO. 58, SEQ ID NO. 59, SEQ ID NO. 61, SEQ ID NO. 63, SEQ ID NO. 65, SEQ ID NO. 69, SEQ ID NO. 71, SEQ ID NO. 74, SEQ ID NO. 75, SEQ ID NO. 76, SEQ ID NO. 79, SEQ ID NO. 80, SEQ ID NO. 82, SEQ ID NO. 84, SEQ ID NO. 86, SEQ ID NO. 88, SEQ ID NO. 90, SEQ ID NO. 92, and combinations thereof, and that has the light chain variable domain sequence that is at least 95% identical to the amino acid sequences selected from the group consisting of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 18, SEQ ID NO. 20, SEQ ID NO. 22, SEQ ID NO. 23, SEQ ID NO. 26, SEQ ID NO. 28, SEQ ID NO. 30, SEQ ID NO. 35, SEQ ID NO. 38, SEQ ID NO. 39, SEQ ID NO. 41, SEQ ID NO. 43, SEQ ID NO. 46, SEQ ID NO. 48, SEQ ID NO. 50, SEQ ID NO. 52, SEQ ID NO. 54, SEQ ID NO. 55, SEQ ID NO. 57, SEQ ID NO. 60, SEQ ID NO. 62, SEQ ID NO. 64, SEQ ID NO. 66, SEQ ID NO. 67, SEQ ID NO. 68, SEQ ID NO. 70, SEQ ID NO. 72, SEQ ID NO. 73, SEQ ID NO. 77, SEQ ID NO. 78, SEQ ID NO. 81, SEQ ID NO. 83, SEQ ID NO. 85, SEQ ID NO. 87, SEQ ID NO. 89, SEQ ID NO. 91, SEQ ID NO. 93, and combinations thereof.

Preferably, the fully human antibody has both a heavy chain and a light chain wherein the antibody has a heavy chain/light chain variable domain sequence selected from the group consisting of SEQ ID NO. 1/SEQ ID NO. 2, SEQ ID NO. 3/SEQ ID NO. 4, SEQ ID NO. 5/SEQ ID NO. 6, SEQ ID NO. 7/SEQ ID NO. 8, SEQ ID NO. 9/SEQ ID NO. 10, SEQ ID NO. 11/SEQ ID NO. 12, SEQ ID NO. 13/SEQ ID NO. 14, SEQ ID NO. 15/SEQ ID NO. 16, SEQ ID NO. 17/SEQ ID NO. 18, SEQ ID NO. 19/SEQ ID NO. 20, SEQ ID NO. 21/SEQ ID NO. 22, SEQ ID NO. 21/SEQ ID NO. 23, SEQ ID NO. 24/SEQ ID NO. 22, SEQ ID NO. 25/SEQ ID NO. 26, SEQ ID NO. 27/SEQ ID NO. 28, SEQ ID NO. 29/SEQ ID NO. 23, SEQ ID NO. 24/SEQ ID NO. 30, SEQ ID NO. 31/SEQ ID NO. 23, SEQ ID NO. 24/SEQ ID NO. 23, SEQ ID NO. 32/SEQ ID NO. 23, SEQ ID NO. 33/SEQ ID NO. 22, SEQ ID NO. 34/SEQ ID NO. 22, SEQ ID NO. 24/SEQ ID NO. 35, SEQ ID NO. 36/SEQ ID NO. 26, SEQ ID NO. 29/SEQ ID NO. 22, SEQ ID NO. 37/SEQ ID NO. 38, SEQ ID NO. 34/SEQ ID NO. 23, SEQ ID NO. 37/SEQ ID NO. 23, SEQ ID NO. 32/SEQ ID NO. 39, SEQ ID NO. 32/SEQ ID NO. 22, SEQ ID NO. 40/SEQ ID NO. 41, SEQ ID NO. 42/SEQ ID NO. 43, SEQ ID NO. 44/SEQ ID NO. 41, SEQ ID NO. 45/SEQ ID NO. 46, SEQ ID NO. 47/SEQ ID NO. 48, SEQ ID NO. 49/SEQ ID NO. 50, SEQ ID NO. 51/SEQ ID NO. 52, SEQ ID NO. 53/SEQ ID NO. 54, SEQ ID NO. 45/SEQ ID NO. 55, SEQ ID NO. 56/SEQ ID NO. 57, SEQ ID NO. 58/SEQ ID NO. 57, SEQ ID NO. 59/SEQ ID NO. 60, SEQ ID NO. 61/SEQ ID NO. 62, SEQ ID NO. 63/SEQ ID NO. 64, SEQ ID NO. 65/SEQ ID NO. 66, SEQ ID NO. 58/SEQ ID NO. 67, SEQ ID NO. 61/SEQ ID NO. 68, SEQ ID NO. 69/SEQ ID NO. 70, SEQ ID NO. 71/SEQ ID NO. 72, SEQ ID NO. 49/SEQ ID NO. 73, SEQ ID NO. 74/SEQ ID NO. 73, SEQ ID NO. 61/SEQ ID NO. 73, SEQ ID NO. 44/SEQ ID NO. 73, SEQ ID NO. 40/SEQ ID NO. 73, SEQ ID NO. 75/SEQ ID NO. 73, SEQ ID NO. 69/SEQ ID NO. 73, SEQ ID NO. 76/SEQ ID NO. 73, SEQ ID NO. 21/SEQ ID NO. 77, SEQ ID NO. 21/SEQ ID NO. 78, SEQ ID NO. 79/SEQ ID NO. 20, SEQ ID NO. 80/SEQ ID NO. 81, SEQ ID NO. 82/SEQ ID NO. 83, SEQ ID NO. 84/SEQ ID NO. 85, SEQ ID NO. 86/SEQ ID NO. 87, SEQ ID NO. 88/SEQ ID NO. 89, SEQ ID NO. 90/SEQ ID NO. 91, SEQ ID NO. 92/SEQ ID NO. 93, and combinations thereof.

Preferably, the fully human antibody Fab fragment has both a heavy chain variable domain region and a light chain variable domain region wherein the antibody has a heavy chain/light chain variable domain sequence selected from the group consisting of SEQ ID NO. 1/SEQ ID NO. 2, SEQ ID NO. 3/SEQ ID NO. 4, SEQ ID NO. 5/SEQ ID NO. 6, SEQ ID NO. 7/SEQ ID NO. 8, SEQ ID NO. 9/SEQ ID NO. 10, SEQ ID NO. 11/SEQ ID NO. 12, SEQ ID NO. 13/SEQ ID NO. 14, SEQ ID NO. 15/SEQ ID NO. 16, SEQ ID NO. 17/SEQ ID NO. 18, SEQ ID NO. 19/SEQ ID NO. 20, SEQ ID NO. 21/SEQ ID NO. 22, SEQ ID NO. 21/SEQ ID NO. 23, SEQ ID NO. 24/SEQ ID NO. 22, SEQ ID NO. 25/SEQ ID NO. 26, SEQ ID NO. 27/SEQ ID NO. 28, SEQ ID NO. 29/SEQ ID NO. 23, SEQ ID NO. 24/SEQ ID NO. 30, SEQ ID NO. 31/SEQ ID NO. 23, SEQ ID NO. 24/SEQ ID NO. 23, SEQ ID NO. 32/SEQ ID NO. 23, SEQ ID NO. 33/SEQ ID NO. 22, SEQ ID NO. 34/SEQ ID NO. 22, SEQ ID NO. 24/SEQ ID NO. 35, SEQ ID NO. 36/SEQ ID NO. 26, SEQ ID NO. 29/SEQ ID NO. 22, SEQ ID NO. 37/SEQ ID NO. 38, SEQ ID NO. 34/SEQ ID NO. 23, SEQ ID NO. 37/SEQ ID NO. 23, SEQ ID NO. 32/SEQ ID NO. 39, SEQ ID NO. 32/SEQ ID NO. 22, SEQ ID NO. 40/SEQ ID NO. 41, SEQ ID NO. 42/SEQ ID NO. 43, SEQ ID NO. 44/SEQ ID NO. 41, SEQ ID NO. 45/SEQ ID NO. 46, SEQ ID NO. 47/SEQ ID NO. 48, SEQ ID NO. 49/SEQ ID NO. 50, SEQ ID NO. 51/SEQ ID NO. 52, SEQ ID NO. 53/SEQ ID NO. 54, SEQ ID NO. 45/SEQ ID NO. 55, SEQ ID NO. 56/SEQ ID NO. 57, SEQ ID NO. 58/SEQ ID NO. 57, SEQ ID NO. 59/SEQ ID NO. 60, SEQ ID NO. 61/SEQ ID NO. 62, SEQ ID NO. 63/SEQ ID NO. 64, SEQ ID NO. 65/SEQ ID NO. 66, SEQ ID NO. 58/SEQ ID NO. 67, SEQ ID NO. 61/SEQ ID NO. 68, SEQ ID NO. 69/SEQ ID NO. 70, SEQ ID NO. 71/SEQ ID NO. 72, SEQ ID NO.
49/SEQ ID NO. 73, SEQ ID NO. 74/SEQ ID NO. 73, SEQ ID NO. 61/SEQ ID NO. 73, SEQ ID NO. 44/SEQ ID NO. 73, SEQ ID NO. 40/SEQ ID NO. 73, SEQ ID NO. 75/SEQ ID NO. 73, SEQ ID NO. 69/SEQ ID NO. 73, SEQ ID NO. 76/SEQ ID NO. 73, SEQ ID NO. 21/SEQ ID NO. 77, SEQ ID NO. 21/SEQ ID NO. 78, SEQ ID NO. 79/SEQ ID NO. 20, SEQ ID NO. 80/SEQ ID NO. 81, SEQ ID NO. 82/SEQ ID NO. 83, SEQ ID NO. 84/SEQ ID NO. 85, SEQ ID NO. 86/SEQ ID NO. 87, SEQ ID NO. 88/SEQ ID NO. 89, SEQ ID NO. 90/SEQ ID NO. 91, SEQ ID NO. 92/SEQ ID NO. 93, and combinations thereof.

Preferably, the fully human single chain antibody has both a heavy chain variable domain region and a light chain variable domain region, wherein the single chain fully human antibody has a heavy chain/light chain variable domain sequence selected from the group consisting of SEQ ID NO. 1/SEQ ID NO. 2, SEQ ID NO. 3/SEQ ID NO. 4, SEQ ID NO. 5/SEQ ID NO. 6, SEQ ID NO. 7/SEQ ID NO. 8, SEQ ID NO. 9/SEQ ID NO. 10, SEQ ID NO. 11/SEQ ID NO. 12, SEQ ID NO. 13/SEQ ID NO. 14, SEQ ID NO. 15/SEQ ID NO. 16, SEQ ID NO. 17/SEQ ID NO. 18, SEQ ID NO. 19/SEQ ID NO. 20, SEQ ID NO. 21/SEQ ID NO. 22, SEQ ID NO. 21/SEQ ID NO. 23, SEQ ID NO. 24/SEQ ID NO. 22, SEQ ID NO. 25/SEQ ID NO. 26, SEQ ID NO. 27/SEQ ID NO. 28, SEQ ID NO. 29/SEQ ID NO. 23, SEQ ID NO. 24/SEQ ID NO. 30, SEQ ID NO. 31/SEQ ID NO. 23, SEQ ID NO. 24/SEQ ID NO. 23, SEQ ID NO. 32/SEQ ID NO. 23, SEQ ID NO. 33/SEQ ID NO. 22, SEQ ID NO. 34/SEQ ID NO. 22, SEQ ID NO. 24/SEQ ID NO. 35, SEQ ID NO. 36/SEQ ID NO. 26, SEQ ID NO. 29/SEQ ID NO. 22, SEQ ID NO. 37/SEQ ID NO. 38, SEQ ID NO. 34/SEQ ID NO. 23, SEQ ID NO. 37/SEQ ID NO. 23, SEQ ID NO. 32/SEQ ID NO. 39, SEQ ID NO. 32/SEQ ID NO. 22, SEQ ID NO. 40/SEQ ID NO. 41, SEQ ID NO. 42/SEQ ID NO. 43, SEQ ID NO. 44/SEQ ID NO. 41, SEQ ID NO. 45/SEQ ID NO. 46, SEQ ID NO. 47/SEQ ID NO. 48, SEQ ID NO. 49/SEQ ID NO. 50, SEQ ID NO. 51/SEQ ID NO. 52, SEQ ID NO. 53/SEQ ID NO. 54, SEQ ID NO. 45/SEQ ID NO. 55, SEQ ID NO. 56/SEQ ID NO. 57, SEQ ID NO. 58/SEQ ID NO. 57, SEQ ID NO. 59/SEQ ID NO. 60, SEQ ID NO. 61/SEQ ID NO. 62, SEQ ID NO. 63/SEQ ID NO. 64, SEQ ID NO. 65/SEQ ID NO. 66, SEQ ID NO. 58/SEQ ID NO. 67, SEQ ID NO. 61/SEQ ID NO. 68, SEQ ID NO. 69/SEQ ID NO. 70, SEQ ID NO. 71/SEQ ID NO. 72, SEQ ID NO.

49/SEQ ID NO. 73, SEQ ID NO. 74/SEQ ID NO. 73, SEQ ID NO. 61/SEQ ID NO. 73, SEQ ID NO. 44/SEQ ID NO. 73, SEQ ID NO. 40/SEQ ID NO. 73, SEQ ID NO. 75/SEQ ID NO. 73, SEQ ID NO. 69/SEQ ID NO. 73, SEQ ID NO. 76/SEQ ID NO. 73, SEQ ID NO. 21/SEQ ID NO. 77, SEQ ID NO. 21/SEQ ID NO. 78, SEQ ID NO. 79/SEQ ID NO. 20, SEQ ID NO. 80/SEQ ID NO. 81, SEQ ID NO. 82/SEQ ID NO. 83, SEQ ID NO. 84/SEQ ID NO. 85, SEQ ID NO. 86/SEQ ID NO. 87, SEQ ID NO. 88/SEQ ID NO. 89, SEQ ID NO. 90/SEQ ID NO. 91, SEQ ID NO. 92/SEQ ID NO. 93, and combinations thereof.

Preferably, the broad spectrum of mammalian cancers to be treated the cancer is a c-Met-activation-related cancer, chosen from c-Met-activation-related cancers that are HGF-dependent, HGF-independent, or both. Preferably, the broad spectrum of mammalian cancers to be treated is selected from the group consisting of prostate cancer, osteosarcoma, lung cancer, breast cancer, endometrial cancer, glyoblastoma, and colon cancer.

An "antigen binding protein" is a protein comprising a portion that binds to an antigen and, optionally, a scaffold or framework portion that allows the antigen binding portion to adopt a conformation that promotes binding of the antigen binding protein to the antigen. Examples of antigen binding proteins include antibodies, antibody fragments (e.g., an antigen binding portion of an antibody), antibody derivatives, and antibody analogs. The antigen binding protein can comprise, for example, an alternative protein scaffold or artificial scaffold with grafted CDRs or CDR derivatives. Such scaffolds include, but are not limited to, antibody-derived scaffolds comprising mutations introduced to, for example, stabilize the three-dimensional structure of the antigen binding protein as well as wholly synthetic scaffolds comprising, for example, a biocompatible polymer. See, for example, Korndorfer et al., 2003, *Proteins: Structure, Function, and Bioinformatics*, Volume 53, Issue 1:121-129; Roque et al., 2004, *Biotechnol. Prog.* 20:639-654. In addition, peptide antibody mimetics ("PAMs") can be used, as well as scaffolds based on antibody mimetics utilizing fibronection components as a scaffold.

An antigen binding protein can have, for example, the structure of a naturally occurring immunoglobulin. An "immunoglobulin" is a tetrameric molecule. In a naturally occurring immunoglobulin, each tetramer is composed of two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function. Human light chains are classified as kappa or lambda light chains. Heavy chains are classified as mu, delta, gamma, alpha, or epsilon, and define the antibody's isotype as IgM, IgD, IgG, IgA, and IgE, respectively. Within light and heavy chains, the variable and constant regions are joined by a "J" region of about 12 or more amino acids, with the heavy chain also including a "D" region of about 10 more amino acids. See generally, Fundamental Immunology Ch. 7 (Paul, W., ed., 2nd ed. Raven Press, N.Y. (1989)) (incorporated by reference in its entirety for all purposes). The variable regions of each light/heavy chain pair form the antibody binding site such that an intact immunoglobulin has two binding sites.

The variable regions of naturally occurring immunoglobulin chains exhibit the same general structure of relatively conserved framework regions (FR) joined by three hypervariable regions, also called complementarity determining regions or CDRs. From N-terminus to C-terminus, both light and heavy chains comprise the domains FR1, CDR1, FR2, CDR2, FR3, CDR3 and FR4. The assignment of amino acids to each domain is in accordance with the definitions of Kabat et al. in Sequences of Proteins of Immunological Interest, 5$^{th}$ Ed., US Dept. of Health and Human Services, PHS, NIH, NIH Publication no. 91-3242, 1991. Other numbering systems for the amino acids in immunoglobulin chains include IMGT® (international ImMunoGeneTics information system; Lefranc et al, *Dev. Comp. Immunol.* 29:185-203; 2005) and AHo (Honegger and Pluckthun, *J. Mol. Biol.* 309(3):657-670; 2001).

Antibodies can be obtained from sources such as serum or plasma that contain immunoglobulins having varied antigenic specificity. If such antibodies are subjected to affinity purification, they can be enriched for a particular antigenic specificity. Such enriched preparations of antibodies usually are made of less than about 10% antibody having specific binding activity for the particular antigen. Subjecting these preparations to several rounds of affinity purification can increase the proportion of antibody having specific binding activity for the antigen. Antibodies prepared in this manner are often referred to as "monospecific." Monospecfic antibody preparations can be made up of about 10%, 20%, 30%, 40%, 50%, 60%, 70%, 75%, 80%, 85%, 90%, 95%, 97%, 99%, or 99.9% antibody having specific binding activity for the particular antigen.

An "antibody" refers to an intact immunoglobulin or to an antigen binding portion thereof that competes with the intact antibody for specific binding, unless otherwise specified. Antigen binding portions may be produced by recombinant DNA techniques or by enzymatic or chemical cleavage of intact antibodies. Antigen binding portions include, inter alia, Fab, Fab', F(ab')2, Fv, domain antibodies (dAbs), and complementarity determining region (CDR) fragments, single-chain antibodies (scFv), chimeric antibodies, diabodies, triabodies, tetrabodies, and polypeptides that contain at least a portion of an immunoglobulin that is sufficient to confer specific antigen binding to the polypeptide.

A Fab fragment is a monovalent fragment having the $V_L$, $V_H$, $C_L$ and $C_{H1}$ domains; a F(ab')2 fragment is a bivalent fragment having two Fab fragments linked by a disulfide bridge at the hinge region; a Fd fragment has the $V_H$ and $C_{H1}$ domains; an Fv fragment has the $V_L$ and $V_H$ domains of a single arm of an antibody; and a dAb fragment has a $V_H$ domain, a $V_L$ domain, or an antigen-binding fragment of a $V_H$ or $V_L$ domain (U.S. Pat. Nos. 6,846,634; 6,696,245, US Patent Applications 2002/02512; 2004/0202995; 2004/0038291; 2004/0009507; 2003/0039958, and Ward et al., *Nature* 341:544-546, 1989).

A single-chain antibody (scFv) is an antibody in which a $V_L$ and a $V_H$ region are joined via a linker (e.g., a synthetic sequence of amino acid residues) to form a continuous protein chain wherein the linker is long enough to allow the protein chain to fold back on itself and form a monovalent antigen binding site (Bird et al., 1988, *Science* 242:423-26 and Huston et al., 1988, *Proc. Natl. Acad. Sci. USA* 85:5879-83). Diabodies are bivalent antibodies comprising two polypeptide chains, wherein each polypeptide chain comprises $V_H$ and $V_L$ domains joined by a linker that is too short to allow for pairing between two domains on the same chain, thus allowing each domain to pair with a complementary domain on another polypeptide chain (Holliger et al., 1993, *Proc. Natl. Acad. Sci. USA* 90:6444-48, and Poljak et al., 1994, Structure 2:1121-23). If the two polypeptide chains of a diabody are identical, then a diabody resulting from their pairing will have two identical antigen binding sites. Polypeptide chains having different sequences can be used to make a diabody with two different antigen binding sites. Similarly, tribodies and tetrabodies are antibodies comprising three and four polypeptide chains, respectively, and forming three and four antigen binding sites, respectively, which can be the same or different.

Complementarity determining regions (CDRs) and framework regions (FR) of a given antibody may be identified using the system described by Kabat et al. supra; Lefranc et al., supra and/or Honegger and Pluckthun, supra. One or more CDRs may be incorporated into a molecule either covalently or noncovalently to make it an antigen binding protein. An antigen binding protein may incorporate the CDR(s) as part of a larger polypeptide chain, may covalently link the CDR(s) to another polypeptide chain, or may incorporate the CDR(s) noncovalently. The CDRs permit the antigen binding protein to specifically bind to a particular antigen of interest.

An antigen binding protein may have one or more binding sites. If there is more than one binding site, the binding sites may be identical to one another or may be different. For example, a naturally occurring human immunoglobulin typically has two identical binding sites, while a "bispecific" or "bifunctional" antibody has two different binding sites.

The term "human antibody" includes all antibodies that have one or more variable and constant regions derived from human immunoglobulin sequences. In one embodiment, all of the variable and constant domains are derived from human immunoglobulin sequences (a fully human antibody). These antibodies may be prepared in a variety of ways, examples of which are described below, including through the immunization with an antigen of interest of a mouse that is genetically modified to express antibodies derived from human heavy and/or light chain-encoding genes.

A humanized antibody has a sequence that differs from the sequence of an antibody derived from a non-human species by one or more amino acid substitutions, deletions, and/or additions, such that the humanized antibody is less likely to induce an immune response, and/or induces a less severe immune response, as compared to the non-human species antibody, when it is administered to a human subject. In one embodiment, certain amino acids in the framework and constant domains of the heavy and/or light chains of the non-human species antibody are mutated to produce the humanized antibody. In another embodiment, the constant domain(s) from a human antibody are fused to the variable domain(s) of a non-human species. In another embodiment, one or more amino acid residues in one or more CDR sequences of a non-human antibody are changed to reduce the likely immunogenicity of the non-human antibody when it is administered to a human subject, wherein the changed amino acid residues either are not critical for immunospecific binding of the antibody to its antigen, or the changes to the amino acid sequence that are made are conservative changes, such that the binding of the humanized antibody to the antigen is not significantly worse than the binding of the non-human antibody to the antigen. Examples of how to make humanized antibodies may be found in U.S. Pat. Nos. 6,054,297, 5,886,152 and 5,877,293.

The term "chimeric antibody" refers to an antibody that contains one or more regions from one antibody and one or more regions from one or more other antibodies. In one embodiment, one or more of the CDRs are derived from a human anti-c-Met antibody. In another embodiment, all of the CDRs are derived from a human anti-c-Met antibody. In another embodiment, the CDRs from more than one human anti-c-Met antibodies are mixed and matched in a chimeric antibody. For instance, a chimeric antibody may comprise a CDR1 from the light chain of a first human anti-PAR-2 antibody, a CDR2 and a CDR3 from the light chain of a second human anti-c-Met antibody, and the CDRs from the heavy chain from a third anti-c-Met antibody. Other combinations are possible.

Further, the framework regions may be derived from one of the same anti-c-Met antibodies, from one or more different antibodies, such as a human antibody, or from a humanized antibody. In one example of a chimeric antibody, a portion of the heavy and/or light chain is identical with, homologous to, or derived from an antibody from a particular species or belonging to a particular antibody class or subclass, while the remainder of the chain(s) is/are identical with, homologous to, or derived from an antibody (-ies) from another species or belonging to another antibody class or subclass. Also included are fragments of such antibodies that exhibit the desired biological activity (i.e., the ability to specifically bind c-Met).

A "neutralizing antibody" or an "inhibitory antibody" is an antibody that inhibits the proteolytic activation of c-Met when an excess of the anti-c-Met antibody reduces the amount of activation by at least about 20% using an assay such as those described herein in the Examples. In various embodiments, the antigen binding protein reduces the amount of amount of proteolytic activation of c-Met by at least 30%, 40%, 50%, 60%, 70%, 75%, 80%, 85%, 90%, 95%, 97%, 99%, and 99.9%.

Fragments or analogs of antibodies can be readily prepared by those of ordinary skill in the art following the teachings of this specification and using techniques known in the art. Preferred amino- and carboxy-termini of fragments or analogs occur near boundaries of functional domains. Structural and functional domains can be identified by comparison of the nucleotide and/or amino acid sequence data to public or proprietary sequence databases. Computerized comparison methods can be used to identify sequence motifs or predicted protein conformation domains that occur in other proteins of known structure and/or function. Methods to identify protein sequences that fold into a known three-dimensional structure are known. See, Bowie et al., 1991, *Science* 253:164.

A "CDR grafted antibody" is an antibody comprising one or more CDRs derived from an antibody of a particular species or isotype and the framework of another antibody of the same or different species or isotype.

A "multi-specific antibody" is an antibody that recognizes more than one epitope on one or more antigens. A subclass of this type of antibody is a "bi-specific antibody" which recognizes two distinct epitopes on the same or different antigens.

An antigen binding protein "specifically binds" to an antigen (e.g., human c-Met) if it binds to the antigen with a dissociation constant of 1 nanomolar or less.

An "antigen binding domain," "antigen binding region," or "antigen binding site" is a portion of an antigen binding protein that contains amino acid residues (or other moieties) that interact with an antigen and contribute to the antigen binding protein's specificity and affinity for the antigen. For an antibody that specifically binds to its antigen, this will include at least part of at least one of its CDR domains.

An "epitope" is the portion of a molecule that is bound by an antigen binding protein (e.g., by an antibody). An epitope can comprise non-contiguous portions of the molecule (e.g., in a polypeptide, amino acid residues that are not contiguous in the polypeptide's primary sequence but that, in the context of the polypeptide's tertiary and quaternary structure, are near enough to each other to be bound by an antigen binding protein).

The "percent identity" of two polynucleotide or two polypeptide sequences is determined by comparing the sequences using the GAP computer program (a part of the GCG Wisconsin Package, version 10.3 (Accelrys, San Diego, Calif.)) using its default parameters.

The terms "polynucleotide," "oligonucleotide" and "nucleic acid" are used interchangeably throughout and include DNA molecules (e.g., cDNA or genomic DNA), RNA molecules (e.g., mRNA), analogs of the DNA or RNA generated using nucleotide analogs (e.g., peptide nucleic acids and non-naturally occurring nucleotide analogs), and hybrids thereof. The nucleic acid molecule can be single-stranded or double-stranded. In one embodiment, the nucleic acid molecules of the invention comprise a contiguous open reading frame encoding an antibody, or a fragment, derivative, mutein, or variant thereof.

Two single-stranded polynucleotides are "the complement" of each other if their sequences can be aligned in an anti-parallel orientation such that every nucleotide in one polynucleotide is opposite its complementary nucleotide in the other polynucleotide, without the introduction of gaps, and without unpaired nucleotides at the 5' or the 3' end of either sequence. A polynucleotide is "complementary" to another polynucleotide if the two polynucleotides can hybridize to one another under moderately stringent conditions. Thus, a polynucleotide can be complementary to another polynucleotide without being its complement.

A "vector" is a nucleic acid that can be used to introduce another nucleic acid linked to it into a cell. One type of vector is a "plasmid," which refers to a linear or circular double stranded DNA molecule into which additional nucleic acid segments can be ligated. Another type of vector is a viral vector (e.g., replication defective retroviruses, adenoviruses and adeno-associated viruses), wherein additional DNA segments can be introduced into the viral genome. Certain vectors are capable of autonomous replication in a host cell into which they are introduced (e.g., bacterial vectors comprising a bacterial origin of replication and episomal mammalian vectors). Other vectors (e.g., non-episomal mammalian vectors) are integrated into the genome of a host cell upon introduction into the host cell, and thereby are replicated along with the host genome. An "expression vector" is a type of vector that can direct the expression of a chosen polynucleotide.

A nucleotide sequence is "operably linked" to a regulatory sequence if the regulatory sequence affects the expression (e.g., the level, timing, or location of expression) of the nucleotide sequence. A "regulatory sequence" is a nucleic acid that affects the expression (e.g., the level, timing, or location of expression) of a nucleic acid to which it is operably linked. The regulatory sequence can, for example, exert its effects directly on the regulated nucleic acid, or through the action of one or more other molecules (e.g., polypeptides that bind to the regulatory sequence and/or the nucleic acid). Examples of regulatory sequences include promoters, enhancers and other expression control elements (e.g., polyadenylation signals). Further examples of regulatory sequences are described in, for example, Goeddel, 1990, Gene Expression Technology: *Methods in Enzymology* 185, Academic Press, San Diego, Calif. and Baron et al., 1995, *Nucleic Acids Res.* 23:3605-06.

A "host cell" is a cell that can be used to express a nucleic acid, e.g., a nucleic acid of the invention. A host cell can be a prokaryote, for example, *E. coli*, or it can be a eukaryote, for example, a single-celled eukaryote (e.g., a yeast or other fungus), a plant cell (e.g., a tobacco or tomato plant cell), an animal cell (e.g., a human cell, a monkey cell, a hamster cell, a rat cell, a mouse cell, or an insect cell) or a hybridoma. Examples of host cells include the COS-7 line of monkey kidney cells (ATCC CRL 1651) (see Gluzman et al., 1981, Cell 23:175), L cells, C127 cells, 3T3 cells (ATCC CCL 163), Chinese hamster ovary (CHO) cells or their derivatives such as Veggie CHO and related cell lines which grow in serum-free media (see Rasmussen et al., 1998, *Cytotechnology* 28:31) or CHO strain DX-B11, which is deficient in DHFR (see Urlaub et al., 1980, *Proc. Natl. Acad. Sci. USA* 77:4216-20), HeLa cells, BHK (ATCC CRL 10) cell lines, the CV1/EBNA cell line derived from the African green monkey kidney cell line CV1 (ATCC CCL 70) (see McMahan et al., 1991, *EMBO J.* 10:2821), human embryonic kidney cells such as 293,293 EBNA or MSR 293, human epidermal A431 cells, human Colo205 cells, other transformed primate cell lines, normal diploid cells, cell strains derived from in vitro culture of primary tissue, primary explants, HL-60, U937, HaK or Jurkat cells. Typically, a host cell is a cultured cell that can be transformed or transfected with a polypeptide-encoding nucleic acid, which can then be expressed in the host cell. The phrase "recombinant host cell" can be used to denote a host cell that has been transformed or transfected with a nucleic acid to be expressed. A host cell also can be a cell that comprises the nucleic acid but does not express it at a desired level unless a regulatory sequence is introduced into the host cell such that it becomes operably linked with the nucleic acid. It is understood that the term host cell refers not only to the particular subject cell but also to the progeny or potential progeny of such a cell. Because certain modifications may occur in succeeding generations due to, e.g., mutation or environmental influence, such progeny may not, in fact, be identical to the parent cell, but are still included within the scope of the term as used herein.

Preferably, the mammalian cancer to be treated is selected from the group consisting of ovarian, colon, breast or hepatic carcinoma cell lines, myelomas, neuroblastic-derived CNS tumors, monocytic leukemias, B-cell derived leukemia's, T-cell derived leukemias, B-cell derived lymphomas, T-cell derived lymphomas, mast cell derived tumors, and combinations thereof.

Polypeptides of the present disclosure can be produced using any standard methods known in the art. In one example, the polypeptides are produced by recombinant DNA methods by inserting a nucleic acid sequence (e.g., a cDNA) encoding the polypeptide into a recombinant expression vector and expressing the DNA sequence under conditions promoting expression.

Nucleic acids encoding any of the various polypeptides disclosed herein may be synthesized chemically. Codon usage may be selected so as to improve expression in a cell. Such codon usage will depend on the cell type selected. Specialized codon usage patterns have been developed for *E. coli* and other bacteria, as well as mammalian cells, plant cells, yeast cells and insect cells.

The DNA encoding the polypeptide is operably linked to suitable transcriptional or translational regulatory elements derived from mammalian, viral, or insect genes. Such regulatory elements include a transcriptional promoter, an optional operator sequence to control transcription, a sequence encoding suitable mRNA ribosomal binding sites, and sequences that control the termination of transcription and translation. The ability to replicate in a host, usually conferred by an origin of replication, and a selection gene to facilitate recognition of transformants is additionally incorporated.

The recombinant DNA can also include any type of protein tag sequence that may be useful for purifying the protein. Examples of protein tags include but are not limited to a histidine tag, a FLAG tag, a myc tag, an HA tag, or a GST tag.

The expression construct is introduced into the host cell using a method appropriate to the host cell. A variety of methods for introducing nucleic acids into host cells are known in the art, including, but not limited to, electroporation; transfection employing calcium chloride, rubidium chloride, calcium phosphate, DEAE-dextran, or other substances; microprojectile bombardment; lipofection; and infection (where the vector is an infectious agent). Suitable host cells include prokaryotes, yeast, mammalian cells, or bacterial cells.

Suitable bacteria include gram negative or gram positive organisms, for example, *E. coli* or *Bacillus* spp. Yeast, preferably from the *Saccharomyces* species, such as *S. cerevisiae*, may also be used for production of polypeptides. Various mammalian or insect cell culture systems can also be employed to express recombinant proteins. Baculovirus systems for production of heterologous proteins in insect cells are reviewed by Luckow and Summers, (*Bio/Technology*, 6:47, 1988). Examples of suitable mammalian host cell lines include endothelial cells, COS-7 monkey kidney cells, CV-1, L cells, C127, 3T3, Chinese hamster ovary (CHO), human embryonic kidney cells, HeLa, 293, 293T, and BHK cell lines. Purified polypeptides are prepared by culturing suitable host/vector systems to express the recombinant proteins. For many applications, the small size of many of the polypeptides disclosed herein would make expression in *E. coli* as the preferred method for expression. The protein is then purified from culture media or cell extracts.

Proteins disclosed herein can also be produced using cell-translation systems. For such purposes the nucleic acids encoding the polypeptide must be modified to allow in vitro transcription to produce mRNA and to allow cell-free translation of the mRNA in the particular cell-free system being utilized (eukaryotic such as a mammalian or yeast cell-free translation system or prokaryotic such as a bacterial cell-free translation system.

The polypeptides of the present disclosure can be purified by isolation/purification methods for proteins generally known in the field of protein chemistry. Non-limiting examples include extraction, recrystallization, salting out (e.g., with ammonium sulfate or sodium sulfate), centrifugation, dialysis, ultrafiltration, adsorption chromatography, ion exchange chromatography, hydrophobic chromatography, normal phase chromatography, reversed-phase chromatography, gel filtration, gel permeation chromatography, affinity chromatography, electrophoresis, countercurrent distribution or any combinations of these. After purification, polypeptides may be exchanged into different buffers and/or concentrated by any of a variety of methods known to the art, including, but not limited to, filtration and dialysis.

The purified polypeptide is preferably at least 85% pure, more preferably at least 95% pure, and most preferably at least 98% pure. Regardless of the exact numerical value of the purity, the polypeptide is sufficiently pure for use as a pharmaceutical product.

Post-Translational Modifications of Polypeptides

In certain embodiments, the binding polypeptides of the invention may further comprise post-translational modifications. Exemplary post-translational protein modifications include phosphorylation, acetylation, methylation, ADP-ribosylation, ubiquitination, glycosylation, carbonylation, sumoylation, biotinylation or addition of a polypeptide side chain or of a hydrophobic group. As a result, the modified soluble polypeptides may contain non-amino acid elements, such as lipids, poly- or mono-saccharide, and phosphates. A preferred form of glycosylation is sialylation, which conjugates one or more sialic acid moieties to the polypeptide. Sialic acid moieties improve solubility and serum half-life while also reducing the possible immunogeneticity of the protein. See Raju et al. *Biochemistry*. 2001 31; 40(30):8868-76.

In one specific embodiment, modified forms of the subject soluble polypeptides comprise linking the subject soluble polypeptides to nonproteinaceous polymers. In one specific embodiment, the polymer is polyethylene glycol ("PEG"), polypropylene glycol, or polyoxyalkylenes, in the manner as set forth in U.S. Pat. No. 4,640,835; 4,496,689; 4,301,144; 4,670,417; 4,791,192 or 4,179,337.

PEG is a water soluble polymer that is commercially available or can be prepared by ring-opening polymerization of ethylene glycol according to methods well known in the art (Sandler and Karo, Polymer Synthesis, Academic Press, New York, Vol. 3, pages 138-161). The term "PEG" is used broadly to encompass any polyethylene glycol molecule, without regard to size or to modification at an end of the PEG, and can be represented by the formula: X—O(CH$_2$CH$_2$O)$_n$-1CH$_2$CH$_2$OH (1), where n is 20 to 2300 and X is H or a terminal modification, e.g., a C$_{1-4}$ alkyl. In one embodiment, the PEG of the invention terminates on one end with hydroxy or methoxy, i.e., X is H or CH$_3$ ("methoxy PEG"). A PEG can contain further chemical groups which are necessary for binding reactions; which results from the chemical synthesis of the molecule; or which is a spacer for optimal distance of parts of the molecule. In addition, such a PEG can consist of one or more PEG side-chains which are linked together. PEGs with more than one PEG chain are called multiarmed or branched PEGs. Branched PEGs can be prepared, for example, by the addition of polyethylene oxide to various polyols, including glycerol, pentaerythriol, and sorbitol. For example, a four-armed branched PEG can be prepared from pentaerythriol and ethylene oxide. Branched PEG are described in, for example, EP-A 0 473 084 and U.S. Pat. No. 5,932,462. One form of PEGs includes two PEG side-chains (PEG2) linked via the primary amino groups of a lysine (Monfardini et al., *Bioconjugate Chem*. 6 (1995) 62-69).

In a preferred embodiment, the pegylater $^{10F}$n3 polypeptide is produced by site-directed pegylation, particularly by conjugation of PEG to a cysteine moiety at the N- or C-terminus. Accordingly, the present disclosure provides a target-binding $^{10F}$n3 polypeptide with improved pharmacokinetic properties, the polypeptide comprising: a $^{10F}$n3 domain having from about 80 to about 150 amino acids, wherein at least one of the loops of said $^{10F}$n3 domain participate in target binding; and a covalently bound PEG moiety, wherein said $^{10F}$n3 polypeptide binds to the target with a K$_D$ of less than 100 nM and has a clearance rate of less than 30 mL/hr/kg in a mammal. The PEG moiety may be attached to the $^{10F}$n3 polypeptide by site directed pegylation, such as by attachment to a Cys residue, where the Cys residue may be positioned at the N-terminus of the $^{0F}$n3 polypeptide or between the N-terminus and the most N-terminal beta or beta-like strand or at the C-terminus of the $^{10F}$n3 polypeptide or between the C-terminus and the most C-terminal beta or beta-like strand. A Cys residue may be situated at other positions as well, particularly any of the loops that do not participate in target binding. A PEG moiety may also be attached by other chemistry, including by conjugation to amines.

A variety of molecular mass forms of PEG can be selected, e.g., from about 1,000 Daltons (Da) to 100,000 Da (n is 20 to 2300), for conjugating to c-Met-binding polypeptides. The number of repeating units "n" in the PEG is approximated for the molecular mass described in Daltons. It is preferred that the combined molecular mass of PEG on an activated linker is suitable for pharmaceutical use. Thus, in one embodiment, the molecular mass of the PEG molecules does not exceed 100,000 Da. For example, if three PEG molecules are attached to a linker, where each PEG molecule has the same molecular mass of 12,000 Da (each n is about 270), then the total molecular mass of PEG on the linker is about 36,000 Da (total n is about 820). The molecular masses of the PEG attached to the linker can also be different, e.g., of three molecules on a linker two PEG molecules can be 5,000 Da each (each n is about 110) and one PEG molecule can be 12,000 Da (n is about 270).

In a specific embodiment of the disclosure a c-Met binding polypeptide is covalently linked to one poly(ethylene glycol) group of the formula: —CO—$(CH_2)_x$—$(OCH_2CH_2)_m$—OR, with the —CO (i.e. carbonyl) of the poly(ethylene glycol) group forming an amide bond with one of the amino groups of the binding polypeptide; R being lower alkyl; x being 2 or 3; m being from about 450 to about 950; and n and m being chosen so that the molecular weight of the conjugate minus the binding polypeptide is from about 10 to 40 kDa. In one embodiment, a binding polypeptide's ϵ-amino group of a lysine is the available (free) amino group.

The above conjugates may be more specifically presented by formula (II): P—NHCO—$(CH_2)_x$—$(OCH_2CH_2)_m$—OR (II), wherein P is the group of a binding polypeptide as described herein, (i.e. without the amino group or amino groups which form an amide linkage with the carbonyl shown in formula (II); and wherein R is lower alkyl; x is 2 or 3; m is from about 450 to about 950 and is chosen so that the molecular weight of the conjugate minus the binding polypeptide is from about 10 to about 40 kDa. As used herein, the given ranges of "m" have an orientational meaning. The ranges of "m" are determined in any case, and exactly, by the molecular weight of the PEG group.

In one embodiment, PEG molecules may be activated to react with amino groups on a binding polypeptide, such as with lysines.

In one specific embodiment, carbonate esters of PEG are used to form the PEG-binding polypeptide conjugates. N,N'-disuccinimidylcarbonate (DSC) may be used in the reaction with PEG to form active mixed PEG-succinimidyl carbonate that may be subsequently reacted with a nucleophilic group of a linker or an amino group of a binding polypeptide (U.S. Pat. Nos. 5,281,698 and 5,932,462). In a similar type of reaction, 1,1'-(dibenzotriazolyl)carbonate and di-(2-pyridyl) carbonate may be reacted with PEG to form PEG-benzotriazolyl and PEG-pyridyl mixed carbonate (U.S. Pat. No. 5,382,657), respectively.

Pegylation of a $^{10F}$n3 polypeptide can be performed according to the methods of the state of the art, for example by reaction of the binding polypeptide with electrophilically active PEGs (supplier: Shearwater Corp., USA, www.shearwatercorp.com). Preferred PEG reagents of the present invention are, e.g., N-hydroxysuccinimidyl propionates (PEG-SPA), butanoates (PEG-SBA), PEG-succinimidyl propionate or branched N-hydroxysuccinimides such as mPEG2-NHS (Monfardini et al., *Bioconjugate Chem.* 6 (1995) 62-69). Such methods may used to pegylated at an f-amino group of a binding polypeptide lysine or the N-terminal amino group of the binding polypeptide.

In another embodiment, PEG molecules may be coupled to sulfhydryl groups on a binding polypeptide (Sartore et al., *Appl. Biochem. Biotechnol.*, 27, 45 (1991); Morpurgo et al., *Biocon. Chem.*, 7, 363-368 (1996); Goodson et al., *Bio/Technology* (1990) 8, 343; U.S. Pat. No. 5,766,897). U.S. Pat. Nos. 6,610,281 and 5,766,897 describes exemplary reactive PEG species that may be coupled to sulfhydryl groups.

In some embodiments where PEG molecules are conjugated to cysteine residues on a binding polypeptide, the cysteine residues are native to the binding polypeptide, whereas in other embodiments, one or more cysteine residues are engineered into the binding polypeptide. Mutations may be introduced into a binding polypeptide coding sequence to generate cysteine residues. This might be achieved, for example, by mutating one or more amino acid residues to cysteine. Preferred amino acids for mutating to a cysteine residue include serine, threonine, alanine and other hydrophilic residues. Preferably, the residue to be mutated to cysteine is a surface-exposed residue. Alternatively, surface residues may be predicted by comparing the amino acid sequences of binding polypeptides, given that the crystal structure of the framework based on which binding polypeptides are designed and evolved has been solved (Himanen et al., *Nature.* (2001) 20-27; 414(6866): 933-8) and thus the surface-exposed residues identified. In one embodiment, cysteine residues are introduced into binding polypeptides at or near the N- and/or C-terminus, or within loop regions.

In some embodiments, the pegylated binding polypeptide comprises a PEG molecule covalently attached to the alpha amino group of the N-terminal amino acid. The use of a PEG-aldehyde for the reductive amination of a protein utilizing other available nucleophilic amino groups is described in U.S. Pat. No. 4,002,531, in Wieder et al., (1979) *J. Biol. Chem.* 254, 12579, and in Chamow et al., (1994) *Bioconjugate Chem.* 5, 133.

In another embodiment, pegylated binding polypeptide comprises one or more PEG molecules covalently attached to a linker, which in turn is attached to the alpha amino group of the amino acid residue at the N-terminus of the binding polypeptide. Such an approach is disclosed in U.S. Patent Publication 2002/0044921 and in WO094/01451.

In one embodiment, a binding polypeptide is pegylated at the C-terminus. In a specific embodiment, a protein is pegylated at the C-terminus by the introduction of C-terminal azido-methionine and the subsequent conjugation of a methyl-PEG-triarylphosphine compound via the Staudinger reaction. This C-terminal conjugation method is described in Cazalis et al., *Bioconjug. Chem.* 2004; 15(5):1005-1009.

Monopegylation of a binding polypeptide can also be produced according to the general methods described in WO 94/01451. WO 94/01451 describes a method for preparing a recombinant polypeptide with a modified terminal amino acid alpha-carbon reactive group. The steps of the method involve forming the recombinant polypeptide and protecting it with one or more biologically added protecting groups at the N-terminal alpha-amine and C-terminal alpha-carboxyl. The polypeptide can then be reacted with chemical protecting agents to selectively protect reactive side chain groups and thereby prevent side chain groups from being modified. The polypeptide is then cleaved with a cleavage reagent specific for the biological protecting group to form an unprotected terminal amino acid alpha-carbon reactive group. The unprotected terminal amino acid alpha-carbon reactive group is modified with a chemical modifying agent. The side chain protected terminally modified single copy polypeptide is then deprotected at the side chain groups to form a terminally modified recombinant single copy polypeptide. The number and sequence of steps in the method can be varied to achieve selective modification at the N- and/or C-terminal amino acid of the polypeptide.

The ratio of a binding polypeptide to activated PEG in the conjugation reaction can be from about 1:0.5 to 1:50, between from about 1:1 to 1:30, or from about 1:5 to 1:15. Various aqueous buffers can be used in the present method to catalyze the covalent addition of PEG to the binding polypeptide. In one embodiment, the pH of a buffer used is from about 7.0 to 9.0. In another embodiment, the pH is in a slightly basic range, e.g., from about 7.5 to 8.5. Buffers having a pKa close to neutral pH range may be used, e.g., phosphate buffer.

Conventional separation and purification techniques known in the art can be used to purify PEGylated binding polypeptide, such as size exclusion (e.g. gel filtration) and ion exchange chromatography. Products may also be separated using SDS-PAGE. Products that may be separated include mono-, di-, tri-poly- and un-pegylated binding polypeptide, as well as free PEG. The percentage of mono-PEG conjugates can be controlled by pooling broader fractions around the elution peak to increase the percentage of mono-PEG in the composition. About ninety percent mono-PEG conjugates represents a good balance of yield and activity. Compositions in which, for example, at least ninety-two percent or at least ninety-six percent of the conjugates are mono-PEG species may be desired. In an embodiment of this invention the percentage of mono-PEG conjugates is from ninety percent to ninety-six percent.

In another embodiment, the pegylated binding polypeptides will preferably retain at least 25%, 50%, 60%, 70%, 80%, 85%, 90%, 95% or 100% of the biological activity associated with the unmodified protein. In one embodiment, biological activity refers to its ability to bind to c-Met, as assessed by $K_D$, $k_{on}$ or $k_{off}$. In one specific embodiment, the pegylated binding polypeptide protein shows an increase in binding to c-Met relative to unpegylated binding polypeptide.

The serum clearance rate of PEG-modified polypeptide may be decreased by about 10%, 20%, 30%, 40%, 50%, 60%, 70%, 80%, or even 90%, relative to the clearance rate of the unmodified binding polypeptide. The PEG-modified polypeptide may have a half-life ($t_{1/2}$) which is enhanced relative to the half-life of the unmodified protein. The half-life of PEG-binding polypeptide may be enhanced by at least 10%, 20%, 30%, 40%, 50%, 60%, 70%, 80%, 90%, 100%, 125%, 150%, 175%, 200%, 250%, 300%, 400% or 500%, or even by 1000% relative to the half-life of the unmodified binding polypeptide. In some embodiments, the protein half-life is determined in vitro, such as in a buffered saline solution or in serum. In other embodiments, the protein half-life is an in vivo half life, such as the half-life of the protein in the serum or other bodily fluid of an animal.

Therapeutic Formulations and Modes of Administration

The present disclosure features methods for treating conditions or preventing pre-conditions which respond to an inhibition of c-Met biological activity. Preferred examples are conditions that are characterized by inflammation or cellular hyperproliferation. Techniques and dosages for administration vary depending on the type of specific polypeptide and the specific condition being treated but can be readily determined by the skilled artisan. In general, regulatory agencies require that a protein reagent to be used as a therapeutic is formulated so as to have acceptably low levels of pyrogens. Accordingly, therapeutic formulations will generally be distinguished from other formulations in that they are substantially pyrogen free, or at least contain no more than acceptable levels of pyrogen as determined by the appropriate regulatory agency (e.g., FDA).

Therapeutic compositions of the present disclosure may be administered with a pharmaceutically acceptable diluent, carrier, or excipient, in unit dosage form. Administration may be parenteral (e.g., intravenous, subcutaneous), oral, or topical, as non-limiting examples. In addition, any gene therapy technique, using nucleic acids encoding the polypeptides of the invention, may be employed, such as naked DNA delivery, recombinant genes and vectors, cell-based delivery, including ex vivo manipulation of patients' cells, and the like.

The polypeptide may be optionally administered as a pharmaceutically acceptable salt, such as non-toxic acid addition salts or metal complexes that are commonly used in the pharmaceutical industry. Examples of acid addition salts include organic acids such as acetic, lactic, pamoic, maleic, citric, malic, ascorbic, succinic, benzoic, palmitic, suberic, salicylic, tartaric, methanesulfonic, toluenesulfonic, or trifluoroacetic acids or the like; polymeric acids such as tannic acid, carboxymethyl cellulose, or the like; and inorganic acid such as hydrochloric acid, hydrobromic acid, sulfuric acid phosphoric acid, or the like. Metal complexes include zinc, iron, and the like. In one example, the polypeptide is formulated in the presence of sodium acetate to increase thermal stability.

A therapeutically effective dose refers to a dose that produces the therapeutic effects for which it is administered. The exact dose will depend on the disorder to be treated, and may be ascertained by one skilled in the art using known techniques. In general, the polypeptide is administered at about 0.01 µg/kg to about 50 mg/kg per day, preferably 0.01 mg/kg to about 30 mg/kg per day, most preferably 0.1 mg/kg to about 20 mg/kg per day. The polypeptide may be given daily (e.g., once, twice, three times, or four times daily) or preferably less frequently (e.g., weekly, every two weeks, every three weeks, monthly, or quarterly). In addition, as is known in the art, adjustments for age as well as the body weight, general health, sex, diet, time of administration, drug interaction, and the severity of the disease may be necessary, and will be ascertainable with routine experimentation by those skilled in the art.

Exemplary Uses

The c-Met binding proteins described herein and their related variants are useful in a number of therapeutic and diagnostic applications. These include the inhibition of the biological activity of c-Met by competing for or blocking the binding to a c-Met as well as the delivery of cytotoxic or imaging moieties to cells, preferably cells expressing c-Met. The small size and stable structure of these molecules can be particularly valuable with respect to manufacturing of the drug, rapid clearance from the body for certain applications where rapid clearance is desired or formulation into novel delivery systems that are suitable or improved using a molecule with such characteristics.

On the basis of their efficacy as inhibitors of c-Met biological activity, the polypeptides of this disclosure are effective against a number of cancer conditions as well as complications arising from cancer, such as pleural effusion and ascites. Preferably, the c-Met-binding polypeptides of the disclosure can be used for the treatment of prevention of hyperproliferative diseases or cancer and the metastatic spread of cancers. Preferred indications for the disclosed anti-c-Met antibodies include colorectal cancers, head and neck cancers, small cell lung cancer, non-small cell lung cancer (NSCLC) and pancreatic cancer. Non-limiting examples of cancers include bladder, blood, bone, brain, breast, cartilage, colon kidney, liver, lung, lymph node, nervous tissue, ovary, pancreatic, prostate, skeletal muscle, skin, spinal cord, spleen, stomach, testes, thymus, thyroid, trachea, urogenital tract, ureter, urethra, uterus, or vaginal cancer.

A c-Met binding polypeptide can be administered alone or in combination with one or more additional therapies such as chemotherapy radiotherapy, immunotherapy, surgical intervention, or any combination of these. Long-term therapy is equally possible as is adjuvant therapy in the context of other treatment strategies, as described above.

In certain embodiments of such methods, one or more polypeptide therapeutic agents can be administered, together (simultaneously) or at different times (sequentially). In addition, polypeptide therapeutic agents can be administered with another type of compounds for treating cancer or for inhibiting angiogenesis.

In certain embodiments, the subject anti-c-Met antibodies agents of the invention can be used alone. Alternatively, the subject agents may be used in combination with other conventional anti-cancer therapeutic approaches directed to treatment or prevention of proliferative disorders (e.g., tumor). For example, such methods can be used in prophylactic cancer prevention, prevention of cancer recurrence and metastases after surgery, and as an adjuvant of other conventional cancer therapy. The present disclosure recognizes that the effectiveness of conventional cancer therapies (e.g., chemotherapy, radiation therapy, phototherapy, immunotherapy, and surgery) can be enhanced through the use of a subject polypeptide therapeutic agent.

A wide array of conventional compounds have been shown to have anti-neoplastic activities. These compounds have been used as pharmaceutical agents in chemotherapy to shrink solid tumors, prevent metastases and further growth, or decrease the number of malignant cells in leukemic or bone marrow malignancies. Although chemotherapy has been effective in treating various types of malignancies, many anti-neoplastic compounds induce undesirable side effects. It has been shown that when two or more different treatments are combined, the treatments may work synergistically and allow reduction of dosage of each of the treatments, thereby reducing the detrimental side effects exerted by each compound at higher dosages. In other instances, malignancies that are refractory to a treatment may respond to a combination therapy of two or more different treatments.

When a polypeptide therapeutic agent of the present invention is administered in combination with another conventional anti-neoplastic agent, either concomitantly or sequentially, such therapeutic agent may be found to enhance the therapeutic effect of the anti-neoplastic agent or overcome cellular resistance to such anti-neoplastic agent. This allows decrease of dosage of an anti-neoplastic agent, thereby reducing the undesirable side effects, or restores the effectiveness of an anti-neoplastic agent in resistant cells.

Pharmaceutical compounds that may be used for combinatory anti-tumor therapy include, merely to illustrate: aminoglutethimide, amsacrine, anastrozole, asparaginase, bcg, bicalutamide, bleomycin, buserelin, busulfan, campothecin, capecitabine, carboplatin, carmustine, chlorambucil, cisplatin, cladribine, clodronate, colchicine, cyclophosphamide, cyproterone, cytarabine, dacarbazine, dactinomycin, daunorubicin, dienestrol, diethylstilbestrol, docetaxel, doxorubicin, epirubicin, estradiol, estramustine, etoposide, exemestane, filgrastim, fludarabine, fludrocortisone, fluorouracil, fluoxymesterone, flutamide, gemcitabine, genistein, goserelin, hydroxyurea, idarubicin, ifosfamide, imatinib, interferon, irinotecan, ironotecan, letrozole, leucovorin, leuprolide, levami sole, lomustine, mechlorethamine, medroxyprogesterone, megestrol, melphalan, mercaptopurine, mesna, methotrexate, mitomycin, mitotane, mitoxantrone, nilutamide, nocodazole, octreotide, oxaliplatin, paclitaxel, pamidronate, pentostatin, plicamycin, porfimer, procarbazine, raltitrexed, rituximab, streptozocin, suramin, tamoxifen, temozolomide, teniposide, testosterone, thioguanine, thiotepa, titanocene dichloride, topotecan, trastuzumab, tretinoin, vinblastine, vincristine, vindesine, and vinorelbine.

Certain chemotherapeutic anti-tumor compounds may be categorized by their mechanism of action into, for example, following groups: anti-metabolites/anti-cancer agents, such as pyrimidine analogs (5-fluorouracil, floxuridine, capecitabine, gemcitabine and cytarabine) and purine analogs, folate antagonists and related inhibitors (mercaptopurine, thioguanine, pentostatin and 2-chlorodeoxyadenosine (cladribine)); antiproliferative/antimitotic agents including natural products such as vinca alkaloids (vinblastine, vincristine, and vinorelbine), microtubule disruptors such as taxane (paclitaxel, docetaxel), vincristin, vinblastin, nocodazole, epothilones and navelbine, epidipodophyllotoxins (etoposide, teniposide), DNA damaging agents (actinomycin, amsacrine, anthracyclines, bleomycin, busulfan, campothecin, carboplatin, chlorambucil, cisplatin, cyclophosphamide, cytoxan, dactinomycin, daunorubicin, doxorubicin, epirubicin, hexamethylmelamineoxaliplatin, iphosphamide, melphalan, merchlorehtamine, mitomycin, mitoxantrone, nitrosourea, plicamycin, procarbazine, taxotere, teniposide, triethylenethiophosphoramide and etoposide (VP16)); antibiotics such as dactinomycin (actinomycin D), daunorubicin, doxorubicin (Adriamycin®), idarubicin, anthracyclines, mitoxantrone, bleomycins, plicamycin (Mithramycin®) and mitomycin; enzymes (L-asparaginase which systemically metabolizes L-asparagine and deprives cells which do not have the capacity to synthesize their own asparagine); antiplatelet agents; antiproliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nitrosoureas (carmustine (BCNU) and analogs, streptozocin), trazenes-dacarbazinine (DTIC); antiproliferative/antimitotic antimetabolites such as folic acid analogs (methotrexate); platinum coordination complexes (cisplatin, carboplatin), procarbazine, hydroxyurea, mitotane, aminoglutethimide; hormones, hormone analogs (estrogen, tamoxifen, goserelin, bicalutamide, nilutamide) and aromatase inhibitors (letrozole, anastrozole); anticoagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory agents; antisecretory agents (breveldin); immunosuppressives (cyclosporine, tacrolimus (FK-506), sirolimus (rapamycin), azathioprine, mycophenolate mofetil); anti-angiogenic compounds (TNP-470, genistein) and growth factor inhibitors (e.g., VEGF inhibitors, fibroblast growth factor (FGF) inhibitors); angiotensin receptor blocker; nitric oxide donors; anti-sense oligonucleotides; antibodies (trastuzumab); cell cycle inhibitors and differentiation inducers (tretinoin); mTOR inhibitors, topoisomerase inhibitors (doxorubicin (Adriamycin®), amsacrine, camptothecin, daunorubicin, dactinomycin, eniposide, epirubicin, etoposide, idarubicin and mitoxantrone, topotecan, irinotecan), corticosteroids (cortisone, dexamethasone, hydrocortisone, methylpednisolone, prednisone, and prenisolone); growth factor signal transduction kinase inhibitors; mitochondrial dysfunction inducers and caspase activators; and chromatin disruptors.

Depending on the nature of the combinatory therapy, administration of the polypeptide therapeutic agents may be continued while the other therapy is being administered and/or thereafter. Administration of the polypeptide therapeutic agents may be made in a single dose, or in multiple doses. In some instances, administration of the polypeptide therapeutic agents is commenced at least several days prior to the conventional therapy, while in other instances, administration is begun either immediately before or at the time of the administration of the conventional therapy.

In one example of a diagnostic application, a biological sample, such as serum or a tissue biopsy, from a patient suspected of having a condition characterized by inappropriate angiogenesis is contacted with a detectably labeled polypeptide of the disclosure to detect levels of c-Met. The levels of c-Met detected are then compared to levels of c-Met detected in a normal sample also contacted with the labeled polypeptide. An increase of at least 10%, 20%, 30%, 40%, 50%, 60%, 70%, 80%, or 90% in the levels of the c-Met may be considered a diagnostic indicator.

In certain embodiments, the c-Met binding polypeptides are further attached to a label that is able to be detected (e.g., the label can be a radioisotope, fluorescent compound, enzyme or enzyme co-factor). The active moiety may be a radioactive agent, such as: radioactive heavy metals such as iron chelates, radioactive chelates of gadolinium or manganese, positron emitters of oxygen, nitrogen, iron, carbon, or gallium, $^{43}K$, $^{52}Fe$, $^{57}Co$, $^{67}Cu$, $^{67}Ga$, $^{68}Ga$, $^{123}I$, $^{125}I$, $^{131}I$, $^{132}I$, or $^{99}Tc$. A binding agent affixed to such a moiety may be used as an imaging agent and is administered in an amount effective for diagnostic use in a mammal such as a human and the localization and accumulation of the imaging agent is then detected. The localization and accumulation of the imaging agent may be detected by radioscintigraphy, nuclear magnetic resonance imaging, computed tomography or positron emission tomography. Immunoscintigraphy using c-Met binding polypeptides directed at c-Met may be used to detect and/or diagnose cancers and vasculature. For example, any of the binding polypeptide against a c-Met marker labeled with $^{99}$Technetium, $^{111}$Indium, or $^{125}$Iodine may be effectively used for such imaging. As will be evident to the skilled artisan, the amount of radioisotope to be administered is dependent upon the radioisotope. Those having ordinary skill in the art can readily formulate the amount of the imaging agent to be administered based upon the specific activity and energy of a given radionuclide used as the active moiety. Typically 0.1-100 millicuries per dose of imaging agent, preferably 1-10 millicuries, most often 2-5 millicuries are administered. Thus, compositions according to the present invention useful as imaging agents comprising a targeting moiety conjugated to a radioactive moiety comprise 0.1-100 millicuries, in some embodiments preferably 1-10 millicuries, in some embodiments preferably 2-5 millicuries, in some embodiments more preferably 1-5 millicuries.

The c-Met binding polypeptides can also be used to deliver additional therapeutic agents (including but not limited to drug compounds, chemotherapeutic compounds, and radiotherapeutic compounds) to a cell or tissue expressing c-Met. In one example, the c-Met binding polypeptide is fused to a chemotherapeutic agent for targeted delivery of the chemotherapeutic agent to a tumor cell or tissue expressing c-Met.

The c-Met binding polypeptides are useful in a variety of applications, including research, diagnostic and therapeutic applications. For instance, they can be used to isolate and/or purify receptor or portions thereof, and to study receptor structure (e.g., conformation) and function.

In certain aspects, the various binding polypeptides can be used to detect or measure the expression of c-Met, for example, on endothelial cells (e.g., venous endothelial cells), or on cells transfected with a c-Met gene. Thus, they also have utility in applications such as cell sorting and imaging (e.g., flow cytometry, and fluorescence activated cell sorting), for diagnostic or research purposes.

In certain embodiments, the binding polypeptides of fragments thereof can be labeled or unlabeled for diagnostic purposes. Typically, diagnostic assays entail detecting the formation of a complex resulting from the binding of a binding polypeptide to c-Met. The binding polypeptides or fragments can be directly labeled, similar to antibodies. A variety of labels can be employed, including, but not limited to, radionuclides, fluorescers, enzymes, enzyme substrates, enzyme cofactors, enzyme inhibitors and ligands (e.g., biotin, haptens). Numerous appropriate immunoassays are known to the skilled artisan (see, for example, U.S. Pat. Nos. 3,817,827; 3,850,752; 3,901,654; and 4,098,876). When unlabeled, the binding polypeptides can be used in assays, such as agglutination assays. Unlabeled binding polypeptides can also be used in combination with another (one or more) suitable reagent which can be used to detect the binding polypeptide, such as a labeled antibody reactive with the binding polypeptide or other suitable reagent (e.g., labeled protein A).

In one embodiment, the binding polypeptides of the present invention can be utilized in enzyme immunoassays, wherein the subject polypeptides are conjugated to an enzyme. When a biological sample comprising a c-Met protein is combined with the subject binding polypeptides, binding occurs between the binding polypeptides and the c-Met protein. In one embodiment, a sample containing cells expressing a c-Met protein (e.g., endothelial cells) is combined with the subject antibodies, and binding occurs between the binding polypeptides and cells bearing a c-Met protein recognized by the binding polypeptide. These bound cells can be separated from unbound reagents and the presence of the binding polypeptide-enzyme conjugate specifically bound to the cells can be determined, for example, by contacting the sample with a substrate of the enzyme which produces a color or other detectable change when acted on by the enzyme. In another embodiment, the subject binding polypeptides can be unlabeled, and a second, labeled polypeptide (e.g., an antibody) can be added which recognizes the subject binding polypeptide.

In certain aspects, kits for use in detecting the presence of a c-Met protein in a biological sample can also be prepared. Such kits will include a c-Met binding polypeptide which binds to a c-Met protein or portion of said receptor, as well as one or more ancillary reagents suitable for detecting the presence of a complex between the binding polypeptide and the receptor protein or portions thereof. The polypeptide compositions of the present invention can be provided in lyophilized form, either alone or in combination with additional antibodies specific for other epitopes. The binding polypeptides and/or antibodies, which can be labeled or unlabeled, can be included in the kits with adjunct ingredients (e.g., buffers, such as Tris, phosphate and carbonate, stabilizers, excipients, biocides and/or inert proteins, e.g., bovine serum albumin). For example, the binding polypeptides and/or antibodies can be provided as a lyophilized mixture with the adjunct ingredients, or the adjunct ingredients can be separately provided for combination by the user. Generally these adjunct materials will be present in less than about 5% weight based on the amount of active binding polypeptide or antibody, and usually will be present in a total amount of at least about 0.001% weight based on polypeptide or antibody concentration. Where a second antibody capable of binding to the binding polypeptide is employed, such antibody can be provided in the kit, for instance in a separate vial or container. The second antibody, if present, is typically labeled, and can be formulated in an analogous manner with the antibody formulations described above.

Similarly, the present disclosure also provides a method of detecting and/or quantitating expression of c-Met, wherein a composition comprising a cell or fraction thereof (e.g., membrane fraction) is contacted with a binding polypeptide which binds to a c-Met or portion of the receptor under conditions appropriate for binding thereto, and the binding is monitored. Detection of the binding polypeptide, indicative of the formation of a complex between binding polypeptide and c-Met or a portion thereof, indicates the presence of the receptor. Binding of a polypeptide to the cell can be determined by standard methods, such as those described in the working examples. The method can be used to detect expression of c-Met on cells from an individual. Optionally, a quantitative expression of c-Met on the surface of endothelial cells can be evaluated, for instance, by flow cytometry, and the staining intensity can be correlated with disease susceptibility, progression or risk.

The present disclosure also provides a method of detecting the susceptibility of a mammal to certain diseases. To illustrate, the method can be used to detect the susceptibility of a mammal to diseases which progress based on the amount of c-Met present on cells and/or the number of c-Met-positive cells in a mammal.

Polypeptide sequences are indicated using standard one- or three-letter abbreviations. Unless otherwise indicated, each polypeptide sequence has amino termini at the left and a carboxy termini at the right; each single-stranded nucleic acid sequence, and the top strand of each double-stranded nucleic acid sequence, has a 5' termini at the left and a 3' termini at the right. A particular polypeptide sequence also can be described by explaining how it differs from a reference sequence.

The terms "c-Met inhibitor" and "c-Met antagonist" are used interchangeably. Each is a molecule that detectably inhibits at least one function of c-Met. Conversely, a "c-Met agonist" is a molecule that detectably increases at least one function of c-Met. The inhibition caused by a c-Met inhibitor need not be complete so long as it is detectable using an assay. Any assay of a function of c-Met can be used, examples of which are provided herein. Examples of functions of c-Met that can be inhibited by a c-Met inhibitor, or increased by a c-Met agonist, include cancer cell growth or apoptosis (programmed cell death), and so on. Examples of types of c-Met inhibitors and c-Met agonists include, but are not limited to, c-Met binding polypeptides such as antigen binding proteins (e.g., c-Met inhibiting antigen binding proteins), antibodies, antibody fragments, and antibody derivatives.

The terms "peptide," "polypeptide" and "protein" each refers to a molecule comprising two or more amino acid residues joined to each other by peptide bonds. These terms encompass, e.g., native and artificial proteins, protein fragments and polypeptide analogs (such as muteins, variants, and fusion proteins) of a protein sequence as well as post-translationally, or otherwise covalently or non-covalently, modified proteins. A peptide, polypeptide, or protein may be monomeric or polymeric.

A "variant" of a polypeptide (for example, an antibody) comprises an amino acid sequence wherein one or more amino acid residues are inserted into, deleted from and/or substituted into the amino acid sequence relative to another polypeptide sequence. Disclosed variants include, for example, fusion proteins.

A "derivative" of a polypeptide is a polypeptide (e.g., an antibody) that has been chemically modified, e.g., via conjugation to another chemical moiety (such as, for example, polyethylene glycol or albumin, e.g., human serum albumin), phosphorylation, and glycosylation. Unless otherwise indicated, the term "antibody" includes, in addition to antibodies comprising two full-length heavy chains and two full-length light chains, derivatives, variants, fragments, and muteins thereof, examples of which are described below.

An "antigen binding protein" is a protein comprising a portion that binds to an antigen and, optionally, a scaffold or framework portion that allows the antigen binding portion to adopt a conformation that promotes binding of the antigen binding protein to the antigen. Examples of antigen binding proteins include antibodies, antibody fragments (e.g., an antigen binding portion of an antibody), antibody derivatives, and antibody analogs. The antigen binding protein can comprise, for example, an alternative protein scaffold or artificial scaffold with grafted CDRs or CDR derivatives. Such scaffolds include, but are not limited to, antibody-derived scaffolds comprising mutations introduced to, for example, stabilize the three-dimensional structure of the antigen binding protein as well as wholly synthetic scaffolds comprising, for example, a biocompatible polymer. See, for example, Korndorfer et al., 2003, *Proteins: Structure, Function, and Bioinformatics*, Volume 53, Issue 1:121-129; Roque et al., 2004, *Biotechnol. Prog.* 20:639-654. In addition, peptide antibody mimetics ("PAMs") can be used, as well as scaffolds based on antibody mimetics utilizing fibronection components as a scaffold.

An antigen binding protein can have, for example, the structure of a naturally occurring immunoglobulin. An "immunoglobulin" is a tetrameric molecule. In a naturally occurring immunoglobulin, each tetramer is composed of two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function. Human light chains are classified as kappa or lambda light chains. Heavy chains are classified as mu, delta, gamma, alpha, or epsilon, and define the antibody's isotype as IgM, IgD, IgG, IgA, and IgE, respectively. Preferably, the anti-c-Met antibodies disclosed herein are characterized by their variable domain region sequences in the heavy $V_H$ and light $V_L$ amino acid sequences. The preferred antibody is A6 which is a kappa IgG antibody. Within light and heavy chains, the variable and constant regions are joined by a "J" region of about 12 or more amino acids, with the heavy chain also including a "D" region of about 10 more amino acids. The variable regions of each light/heavy chain pair form the antibody binding site such that an intact immunoglobulin has two binding sites.

A "multi-specific antibody" is an antibody that recognizes more than one epitope on one or more antigens. A subclass of this type of antibody is a "bi-specific antibody" which recognizes two distinct epitopes on the same or different antigens.

An antigen binding protein "specifically binds" to an antigen (e.g., human c-Met) if it binds to the antigen with a dissociation constant of 1 nanomolar or less.

An "antigen binding domain," "antigen binding region," or "antigen binding site" is a portion of an antigen binding protein that contains amino acid residues (or other moieties) that interact with an antigen and contribute to the antigen binding protein's specificity and affinity for the antigen. For an antibody that specifically binds to its antigen, this will include at least part of at least one of its CDR domains.

An "epitope" is the portion of a molecule that is bound by an antigen binding protein (e.g., by an antibody). An epitope can comprise non-contiguous portions of the molecule (e.g., in a polypeptide, amino acid residues that are not contiguous in the polypeptide's primary sequence but that, in the context of the polypeptide's tertiary and quaternary structure, are near enough to each other to be bound by an antigen binding protein).

The "percent homology" of two polynucleotide or two polypeptide sequences is determined by comparing the sequences using the GAP computer program (a part of the GCG Wisconsin Package, version 10.3 (Accelrys, San Diego, Calif.)) using its default parameters.

A "host cell" is a cell that can be used to express a nucleic acid. A host cell can be a prokaryote, for example, *E. coli*, or it can be a eukaryote, for example, a single-celled eukaryote (e.g., a yeast or other fungus), a plant cell (e.g., a tobacco or tomato plant cell), an animal cell (e.g., a human cell, a monkey cell, a hamster cell, a rat cell, a mouse cell, or an insect cell) or a hybridoma. Examples of host cells include the COS-7 line of monkey kidney cells (ATCC CRL 1651) (Gluzman et al., 1981, *Cell* 23:175), L cells, C127 cells, 3T3 cells (ATCC CCL 163), Chinese hamster ovary (CHO) cells or their derivatives such as Veggie CHO and related cell lines which grow in serum-free media (Rasmussen et al., 1998, *Cytotechnology* 28:31) or CHO strain DX-B11, which is deficient in DHFR (Urlaub et al., 1980, *Proc. Natl. Acad. Sci. USA* 77:4216-20), HeLa cells, BHK (ATCC CRL 10) cell lines, the CV1/EBNA cell line derived from the African green monkey kidney cell line CV1 (ATCC CCL 70) (McMahan et al., 1991, *EMBO J.* 10:2821), human embryonic kidney cells such as 293,293 EBNA or MSR 293, human epidermal A431 cells, human Colo205 cells, other transformed primate cell lines, normal diploid cells, cell strains derived from in vitro culture of primary tissue, primary explants, HL-60, U937, HaK or Jurkat cells. Typically, a host cell is a cultured cell that can be transformed or transfected with a polypeptide-encoding nucleic acid, which can then be expressed in the host cell. The phrase "recombinant host cell" can be used to denote a host cell that has been transformed or transfected with a nucleic acid to be expressed. A host cell also can be a cell that comprises the nucleic acid but does not express it at a desired level unless a regulatory sequence is introduced into the host cell such that it becomes operably linked with the nucleic acid. It is understood that the term host cell refers not only to the particular subject cell but also to the progeny or potential progeny of such a cell. Because certain modifications may occur in succeeding generations due to, e.g., mutation or environmental influence, such progeny may not, in fact, be identical to the parent cell, but are still included within the scope of the term as used herein.

Antigen Binding Proteins

Antigen binding proteins (e.g., antibodies, antibody fragments, antibody derivatives, antibody muteins, and antibody variants) are polypeptides that bind to c-Met, (preferably, human c-Met). Antigen binding proteins include antigen binding proteins that inhibit a biological activity of c-Met.

Oligomers that contain one or more antigen binding proteins may be employed as c-Met antagonists. Oligomers may be in the form of covalently-linked or non-covalently-linked dimers, trimers, or higher oligomers. Oligomers comprising two or more antigen binding protein are contemplated for use, with one example being a homodimer. Other oligomers include heterodimers, homotrimers, heterotrimers, homotetramers, heterotetramers, etc.

One embodiment is directed to oligomers comprising multiple antigen binding proteins joined via covalent or non-covalent interactions between peptide moieties fused to the antigen binding proteins. Such peptides may be peptide linkers (spacers), or peptides that have the property of promoting oligomerization. Leucine zippers and certain polypeptides derived from antibodies are among the peptides that can promote oligomerization of antigen binding proteins attached thereto, as described in more detail below.

In particular embodiments, the oligomers comprise from two to four antigen binding proteins. The antigen binding proteins of the oligomer may be in any form, such as any of the forms described above, e.g., variants or fragments. Preferably, the oligomers comprise antigen binding proteins that have c-Met binding activity.

One embodiment is directed to a dimer comprising two fusion proteins created by fusing a c-Met binding fragment of an anti-c-Met antibody to the Fc region of an antibody. The dimer can be made by, for example, inserting a gene fusion encoding the fusion protein into an appropriate expression vector, expressing the gene fusion in host cells transformed with the recombinant expression vector, and allowing the expressed fusion protein to assemble much like antibody molecules, whereupon interchain disulfide bonds form between the Fc moieties to yield the dimer.

The term "Fc polypeptide" includes native and mutein forms of polypeptides derived from the Fc region of an antibody. Truncated forms of such polypeptides containing the hinge region that promotes dimerization also are included. Fusion proteins comprising Fc moieties (and oligomers formed therefrom) offer the advantage of facile purification by affinity chromatography over Protein A or Protein G columns.

Another method for preparing oligomeric antigen binding proteins involves use of a leucine zipper. Leucine zipper domains are peptides that promote oligomerization of the proteins in which they are found. Leucine zippers were originally identified in several DNA-binding proteins (Landschulz et al., 1988, *Science* 240:1759), and have since been found in a variety of different proteins. Among the known leucine zippers are naturally occurring peptides and derivatives thereof that dimerize or trimerize. Examples of leucine zipper domains suitable for producing soluble oligomeric proteins are described in WO 94/10308, and the leucine zipper derived from lung surfactant protein D (SPD) described in Hoppe et al., 1994, *FEBS Letters* 344:191. The use of a modified leucine zipper that allows for stable trimerization of a heterologous protein fused thereto is described in Fanslow et al., 1994, *Semin. Immunol.* 6:267-78. In one approach, recombinant fusion proteins comprising an anti-c-Met antibody fragment or derivative fused to a leucine zipper peptide are expressed in suitable host cells, and the soluble oligomeric anti-c-Met antibody fragments or derivatives that form are recovered from the culture supernatant.

Antigen-binding fragments of antigen binding proteins of the invention may be produced by conventional techniques. Examples of such fragments include, but are not limited to, Fab and F(ab)$_2$ fragments.

The present disclosure provides monoclonal antibodies that bind to c-Met. Monoclonal antibodies may be produced using any technique known in the art, e.g., by immortalizing spleen cells harvested from the transgenic animal after completion of the immunization schedule. The spleen cells can be immortalized using any technique known in the art, e.g., by fusing them with myeloma cells to produce hybridomas. Myeloma cells for use in hybridoma-producing fusion procedures preferably are non-antibody-producing, have high fusion efficiency, and enzyme deficiencies that render them incapable of growing in certain selective media which support the growth of only the desired fused cells (hybridomas). Examples of suitable cell lines for use in mouse fusions include Sp-20, P3-X63/Ag8, P3-X63-Ag8.653, NS1/1.Ag 4 1, Sp210-Ag14, FO, NSO/U, MPC-11, MPC11-X45-GTG 1.7 and S194/5XX0 Bul; examples of cell lines used in rat fusions include R210.RCY3, Y3-Ag 1.2.3, IR983F and 48210. Other cell lines useful for cell fusions are U-266, GM1500-GRG2, LICR-LON-HMy2 and UC729-6.

Antigen binding proteins directed against c-Met can be used, for example, in assays to detect the presence of c-Met polypeptides, either in vitro or in vivo. The antigen binding proteins also may be employed in purifying c-Met proteins by immunoaffinity chromatography. Blocking antigen binding proteins can be used in the methods disclosed herein. Such antigen binding proteins that function as c-Met antagonists may be employed in treating any c-Met-induced condition, including but not limited to various cancers.

Antigen binding proteins may be employed in an in vitro procedure, or administered in vivo to inhibit c-Met-induced biological activity. Disorders caused or exacerbated (directly or indirectly) by the proteolytic activation of c-Met, examples of which are provided herein, thus may be treated. In one embodiment, the present invention provides a therapeutic method comprising in vivo administration of a c-Met blocking antigen binding protein to a mammal in need thereof in an amount effective for reducing a c-Met-induced biological activity.

Antigen binding proteins include fully human monoclonal antibodies that inhibit a biological activity of c-Met.

Antigen binding proteins may be prepared by any of a number of conventional techniques. For example, they may be purified from cells that naturally express them (e.g., an antibody can be purified from a hybridoma that produces it), or produced in recombinant expression systems, using any technique known in the art. See, for example, Monoclonal Antibodies, Hybridomas: A New Dimension in Biological Analyses, Kennet et al. (eds.), Plenum Press, New York (1980); and Antibodies: A Laboratory Manual, Harlow and Land (eds.), Cold Spring Harbor Laboratory Press, Cold Spring Harbor, N.Y., (1988).

Any expression system known in the art can be used to make the recombinant polypeptides of the invention. In general, host cells are transformed with a recombinant expression vector that comprises DNA encoding a desired polypeptide. Among the host cells that may be employed are prokaryotes, yeast or higher eukaryotic cells. Prokaryotes include gram negative or gram positive organisms, for example E. coli or bacilli. Higher eukaryotic cells include insect cells and established cell lines of mammalian origin. Examples of suitable mammalian host cell lines include the COS-7 line of monkey kidney cells (ATCC CRL 1651) (Gluzman et al., 1981, Cell 23:175), L cells, 293 cells, C127 cells, 3T3 cells (ATCC CCL 163), Chinese hamster ovary (CHO) cells, HeLa cells, BHK (ATCC CRL 10) cell lines, and the CV1/EBNA cell line derived from the African green monkey kidney cell line CV1 (ATCC CCL 70) as described by McMahan et al., 1991, EMBO J. 10: 2821. Appropriate cloning and expression vectors for use with bacterial, fungal, yeast, and mammalian cellular hosts are described by Pouwels et al. (Cloning Vectors: A Laboratory Manual, Elsevier, N.Y., 1985).

The transformed cells can be cultured under conditions that promote expression of the polypeptide, and the polypeptide recovered by conventional protein purification procedures. One such purification procedure includes the use of affinity chromatography, e.g., over a matrix having all or a portion (e.g., the extracellular domain) of c-Met bound thereto. Polypeptides contemplated for use herein include substantially homogeneous recombinant mammalian anti-c-Met antibody polypeptides substantially free of contaminating endogenous materials.

Antigen binding proteins may be prepared, and screened for desired properties, by any of a number of known techniques. Certain of the techniques involve isolating a nucleic acid encoding a polypeptide chain (or portion thereof) of an antigen binding protein of interest (e.g., an anti-c-Met antibody), and manipulating the nucleic acid through recombinant DNA technology. The nucleic acid may be fused to another nucleic acid of interest, or altered (e.g., by mutagenesis or other conventional techniques) to add, delete, or substitute one or more amino acid residues, for example.

Single chain antibodies may be formed by linking heavy and light chain variable domain (Fv region) fragments via an amino acid bridge (short peptide linker), resulting in a single polypeptide chain. Such single-chain Fvs (scFvs) have been prepared by fusing DNA encoding a peptide linker between DNAs encoding the two variable domain polypeptides ($V_L$ and $V_H$). The resulting polypeptides can fold back on themselves to form antigen-binding monomers, or they can form multimers (e.g., dimers, trimers, or tetramers), depending on the length of a flexible linker between the two variable domains (Kortt et al., 1997, Prot. Eng. 10:423; Kortt et al., 2001, Biomol. Eng. 18:95-108). By combining different $V_L$ and $V_H$-comprising polypeptides, one can form multimeric scFvs that bind to different epitopes (Kriangkum et al., 2001, Biomol. Eng. 18:31-40). Techniques developed for the production of single chain antibodies include those described in U.S. Pat. No. 4,946,778; Bird, 1988, Science 242:423; Huston et al., 1988, Proc. Natl. Acad. Sci. USA 85:5879; Ward et al., 1989, Nature 334:544, de Graaf et al., 2002, Methods Mol. Biol. 178:379-87.

Techniques are known for deriving an antibody of a different subclass or isotype from an antibody of interest, i.e., subclass switching. Thus, IgG antibodies may be derived from an IgM antibody, for example, and vice versa. Such techniques allow the preparation of new antibodies that possess the antigen-binding properties of a given antibody (the parent antibody), but also exhibit biological properties associated with an antibody isotype or subclass different from that of the parent antibody. Recombinant DNA techniques may be employed. Cloned DNA encoding particular antibody polypeptides may be employed in such procedures, e.g., DNA encoding the constant domain of an antibody of the desired isotype (Lantto et al., 2002, Methods Mol. Biol.

178:303-16). Moreover, if an IgG4 is desired, it may also be desired to introduce a point mutation (CPSCP→CPPCP) in the hinge region (Bloom et al., 1997, *Protein Science* 6:407) to alleviate a tendency to form intra-H chain disulfide bonds that can lead to heterogeneity in the IgG4 antibodies.

In particular embodiments, antigen binding proteins of the present invention have a binding affinity ($K_a$) for c-Met of at least $10^6$. In other embodiments, the antigen binding proteins exhibit a $K_a$ of at least $10^7$, at least $10^8$, at least $10^9$, or at least $10^{10}$. In another embodiment, the antigen binding protein exhibits a $K_a$ substantially the same as that of an antibody described herein in the Examples.

In another embodiment, the present disclosure provides an antigen binding protein that has a low dissociation rate from c-Met. In one embodiment, the antigen binding protein has a $K_{off}$ of $1\times10^{-4}$ to $^{-1}$ or lower. In another embodiment, the $K_{off}$ is $5\times10^{-5}$ to $^{-1}$ or lower. In another embodiment, the $K_{off}$ is substantially the same as an antibody described herein. In another embodiment, the antigen binding protein binds to c-Met with substantially the same $K_{off}$ as an antibody described herein.

In another aspect, the present disclosure provides an antigen binding protein that inhibits an activity of c-Met. In one embodiment, the antigen binding protein has an $IC_{50}$ of 1000 nM or lower. In another embodiment, the $IC_{50}$ is 100 nM or lower; in another embodiment, the $IC_{50}$ is 10 nM or lower. In another embodiment, the $IC_{50}$ is substantially the same as that of an antibody described herein in the Examples. In another embodiment, the antigen binding protein inhibits an activity of c-Met with substantially the same $IC_{50}$ as an antibody described herein.

In another aspect, the present disclosure provides an antigen binding protein that binds to human c-Met expressed on the surface of a cell and, when so bound, inhibits c-Met signaling activity in the cell without causing a significant reduction in the amount of c-Met on the surface of the cell. Any method for determining or estimating the amount of c-Met on the surface and/or in the interior of the cell can be used. In other embodiments, binding of the antigen binding protein to the c-Met-expressing cell causes less than about 75%, 50%, 40%, 30%, 20%, 15%, 10%, 5%, 1%, or 0.1% of the cell-surface c-Met to be internalized.

In another aspect, the present disclosure provides an antigen binding protein having a half-life of at least one day in vitro or in vivo (e.g., when administered to a human subject). In one embodiment, the antigen binding protein has a half-life of at least three days. In another embodiment, the antigen binding protein has a half-life of four days or longer. In another embodiment, the antigen binding protein has a half-life of eight days or longer. In another embodiment, the antigen binding protein is derivatized or modified such that it has a longer half-life as compared to the underivatized or unmodified antigen binding protein. In another embodiment, the antigen binding protein contains one or more point mutations to increase serum half life, such as described in WO00/09560, incorporated by reference herein.

The present disclosure further provides multi-specific antigen binding proteins, for example, bispecific antigen binding protein, e.g., antigen binding protein that bind to two different epitopes of c-Met, or to an epitope of c-Met and an epitope of another molecule, via two different antigen binding sites or regions. Moreover, bispecific antigen binding protein as disclosed herein can comprise a c-Met binding site from one of the herein-described antibodies and a second c-Met binding region from another of the herein-described antibodies, including those described herein by reference to other publications. Alternatively, a bispecific antigen binding protein may comprise an antigen binding site from one of the herein described antibodies and a second antigen binding site from another c-Met antibody that is known in the art, or from an antibody that is prepared by known methods or the methods described herein.

Numerous methods of preparing bispecific antibodies are known in the art. Such methods include the use of hybrid-hybridomas as described by Milstein et al., 1983, *Nature* 305:537, and chemical coupling of antibody fragments (Brennan et al., 1985, *Science* 229:81; Glennie et al., 1987, *J. Immunol.* 139:2367; U.S. Pat. No. 6,010,902). Moreover, bispecific antibodies can be produced via recombinant means, for example by using leucine zipper moieties (i.e., from the Fos and Jun proteins, which preferentially form heterodimers; Kostelny et al., 1992, *J. Immunol.* 148:1547) or other lock and key interactive domain structures as described in U.S. Pat. No. 5,582,996. Additional useful techniques include those described in U.S. Pat. Nos. 5,959,083; and 5,807,706.

In another aspect, the antigen binding protein comprises a derivative of an antibody. The derivatized antibody can comprise any molecule or substance that imparts a desired property to the antibody, such as increased half-life in a particular use. The derivatized antibody can comprise, for example, a detectable (or labeling) moiety (e.g., a radioactive, colorimetric, antigenic or enzymatic molecule, a detectable bead (such as a magnetic or electrodense (e.g., gold) bead), or a molecule that binds to another molecule (e.g., biotin or streptavidin), a therapeutic or diagnostic moiety (e.g., a radioactive, cytotoxic, or pharmaceutically active moiety), or a molecule that increases the suitability of the antibody for a particular use (e.g., administration to a subject, such as a human subject, or other in vivo or in vitro uses). Examples of molecules that can be used to derivatize an antibody include albumin (e.g., human serum albumin) and polyethylene glycol (PEG). Albumin-linked and PEGylated derivatives of antibodies can be prepared using techniques well known in the art. In one embodiment, the antibody is conjugated or otherwise linked to transthyretin (TTR) or a TTR variant. The TTR or TTR variant can be chemically modified with, for example, a chemical selected from the group consisting of dextran, poly(n-vinyl pyurrolidone), polyethylene glycols, propropylene glycol homopolymers, polypropylene oxide/ethylene oxide co-polymers, polyoxyethylated polyols and polyvinyl alcohols.

Indications

In one aspect, the present disclosure provides methods of treating a subject. The method can, for example, have a generally salubrious effect on the subject, e.g., it can increase the subject's expected longevity. Alternatively, the method can, for example, treat, prevent, cure, relieve, or ameliorate ("treat") a disease, disorder, condition, or illness ("a condition"). Among the conditions to be treated are conditions characterized by inappropriate expression or activity of c-Met. In some such conditions, the expression or activity level is too high, and the treatment comprises administering a c-Met antagonist as described herein. The disorders or conditions are cancer-related. In particular, those cancers include, but are not limited to, lung, ovarian and colon carcinoma and various myelomas.

Specific medical conditions and diseases that are treatable or preventable with the antigen binding proteins of this disclosure include various cancers.

Therapeutic Methods and Administration of Antigen Binding Proteins

Certain methods provided herein comprise administering a c-Met binding antigen binding protein to a subject, thereby reducing a c-Met-induced biological response that plays a role in a particular condition. In particular embodiments, methods of the invention involve contacting endogenous c-Met with a c-Met binding antigen binding protein, e.g., via administration to a subject or in an ex vivo procedure.

The term "treatment" encompasses alleviation or prevention of at least one symptom or other aspect of a disorder, or reduction of disease severity, and the like. An antigen binding protein need not effect a complete cure, or eradicate every symptom or manifestation of a disease, to constitute a viable therapeutic agent. As is recognized in the pertinent field, drugs employed as therapeutic agents may reduce the severity of a given disease state, but need not abolish every manifestation of the disease to be regarded as useful therapeutic agents. Similarly, a prophylactically administered treatment need not be completely effective in preventing the onset of a condition in order to constitute a viable prophylactic agent. Simply reducing the impact of a disease (for example, by reducing the number or severity of its symptoms, or by increasing the effectiveness of another treatment, or by producing another beneficial effect), or reducing the likelihood that the disease will occur or worsen in a subject, is sufficient. One embodiment of the invention is directed to a method comprising administering to a patient a c-Met antagonist in an amount and for a time sufficient to induce a sustained improvement over baseline of an indicator that reflects the severity of the particular disorder.

As is understood in the pertinent field, pharmaceutical compositions comprising the antibodies and fragments thereof of the disclosure are administered to a subject in a manner appropriate to the indication. Pharmaceutical compositions may be administered by any suitable technique, including but not limited to, parenterally, topically, or by inhalation. If injected, the pharmaceutical composition can be administered, for example, via intra-articular, intravenous, intramuscular, intralesional, intraperitoneal or subcutaneous routes, by bolus injection, or continuous infusion. Localized administration, e.g. at a site of disease or injury is contemplated, as are transdermal delivery and sustained release from implants. Delivery by inhalation includes, for example, nasal or oral inhalation, use of a nebulizer, inhalation of the antagonist in aerosol form, and the like. Other alternatives include eyedrops; oral preparations including pills, syrups, lozenges or chewing gum; and topical preparations such as lotions, gels, sprays, and ointments.

Use of antigen binding proteins in ex vivo procedures also is contemplated. For example, a patient's blood or other bodily fluid may be contacted with an antigen binding protein that binds c-Met ex vivo. The antigen binding protein may be bound to a suitable insoluble matrix or solid support material.

Advantageously, antigen binding proteins are administered in the form of a composition comprising one or more additional components such as a physiologically acceptable carrier, excipient or diluent. Optionally, the composition additionally comprises one or more physiologically active agents, for example, a second inflammation- or immune-inhibiting substance, an anti-angiogenic substance, an analgesic substance, etc., non-exclusive examples of which are provided herein. In various particular embodiments, the composition comprises one, two, three, four, five, or six physiologically active agents in addition to a c-Met binding antigen binding protein Combination Therapy In another aspect, the present disclosure provides a method of treating a subject with a c-Met inhibiting antigen binding protein and one or more other treatments. In one embodiment, such a combination therapy achieves synergy or an additive effect by, for example, attacking multiple sites or molecular targets in a tumor. Types of combination therapies that can be used in connection with the present invention include inhibiting or activating (as appropriate) multiple nodes in a single disease-related pathway, multiple pathways in a target cell, and multiple cell types within a target tissue.

In another embodiment, a combination therapy method comprises administering to the subject two, three, four, five, six, or more of the c-Met agonists or antagonists described herein. In another embodiment, the method comprises administering to the subject two or more treatments that together inhibit or activate (directly or indirectly) c-Met-mediated signal transduction. Examples of such methods include using combinations of two or more c-Met inhibiting antigen binding proteins, of a c-Met inhibiting antigen binding protein and one or more other therapeutic moiety having anti-cancer properties (for example, cytotoxic agents, and/or immunomodulators), or of a c-Met inhibiting antigen binding protein and one or more other treatments (e.g., surgery, or radiation). Furthermore, one or more anti-c-Met antibodies or antibody derivatives can be used in combination with one or more molecules or other treatments, wherein the other molecule(s) and/or treatment(s) do not directly bind to or affect c-Met, but which combination is effective for treating or preventing the condition being treated. In one embodiment, one or more of the molecule(s) and/or treatment(s) treats or prevents a condition that is caused by one or more of the other molecule(s) or treatment(s) in the course of therapy, e.g., nausea, fatigue, alopecia, cachexia, insomnia, etc. In every case where a combination of molecules and/or other treatments is used, the individual molecule(s) and/or treatment(s) can be administered in any order, over any length of time, which is effective, e.g., simultaneously, consecutively, or alternately. In one embodiment, the method of treatment comprises completing a first course of treatment with one molecule or other treatment before beginning a second course of treatment. The length of time between the end of the first course of treatment and beginning of the second course of treatment can be any length of time that allows the total course of therapy to be effective, e.g., seconds, minutes, hours, days, weeks, months, or even years.

In another embodiment, the method comprises administering one or more of the c-Met antagonists described herein and one or more other treatments (e.g., a therapeutic or palliative treatment). Where a method comprises administering more than one treatment to a subject, it is to be understood that the order, timing, number, concentration, and volume of the administrations is limited only by the medical requirements and limitations of the treatment, i.e., two treatments can be administered to the subject, e.g., simultaneously, consecutively, alternately, or according to any other regimen.

Example 1

Figure 4A:
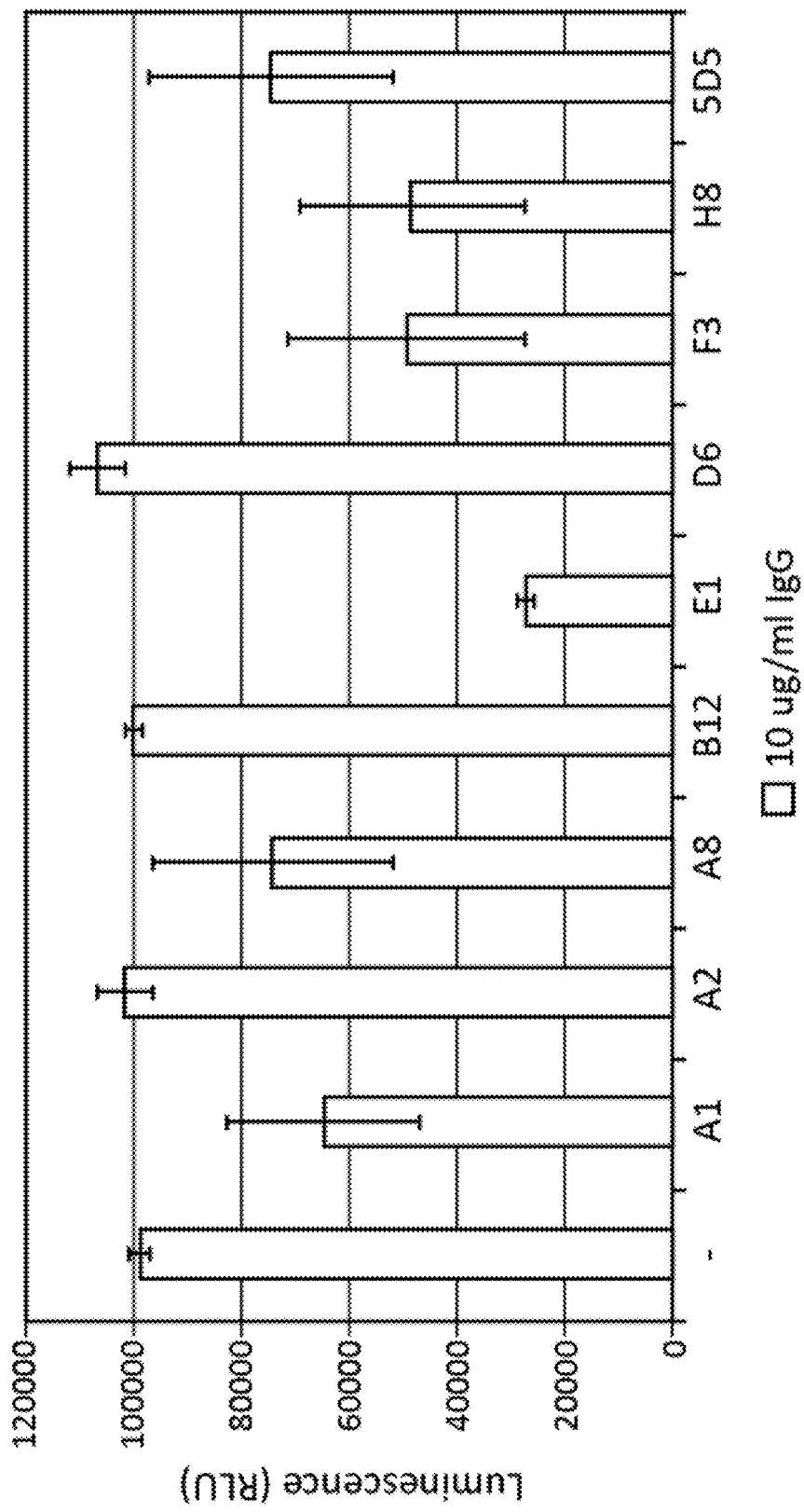
FIG. 4A shows the antagonistic effects of anti-c-Met antibodies in IgG format on the proliferation of U87 glioblastoma cells.
Figure 4B:
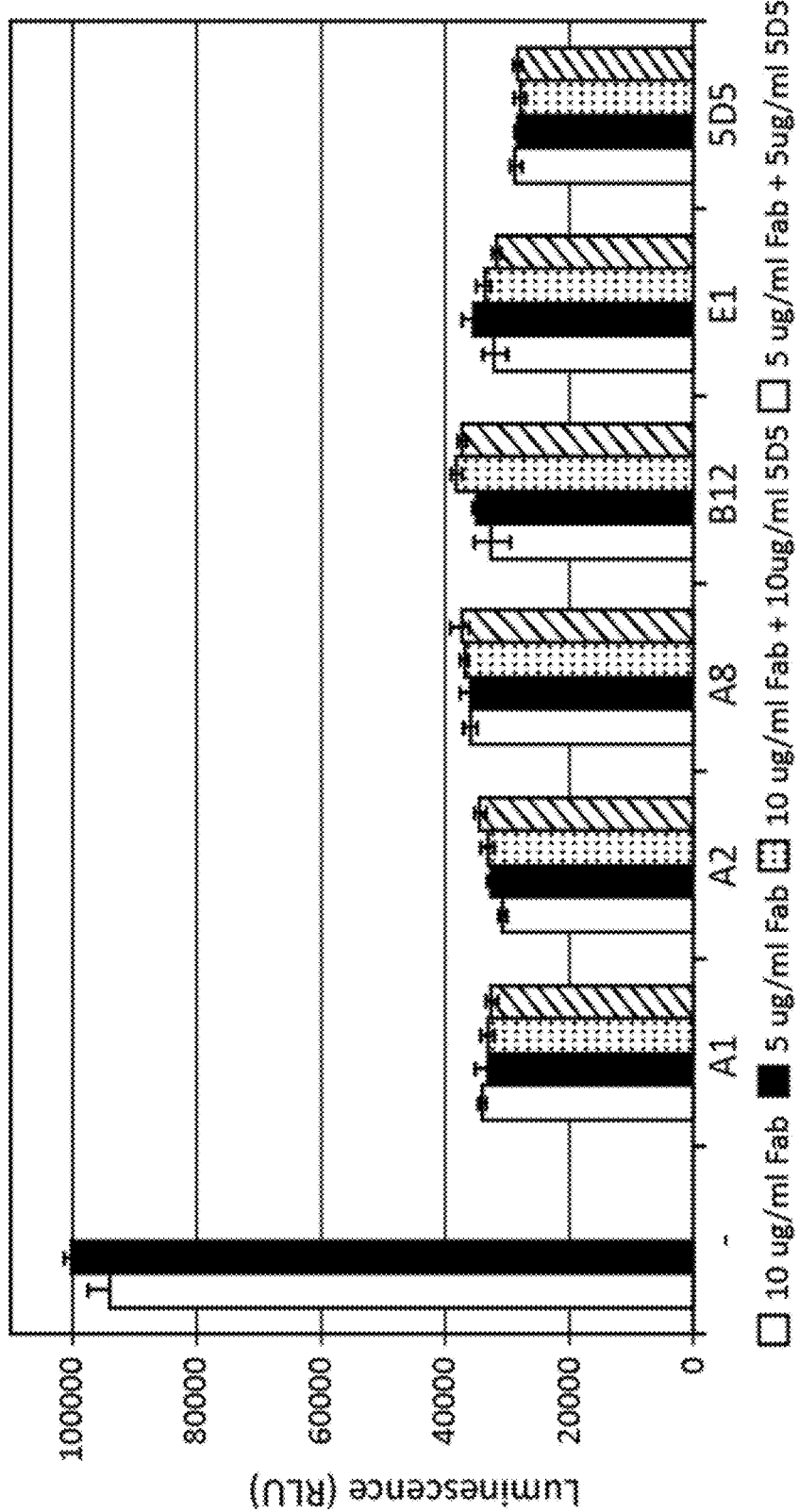
FIG. 4B shows the antagonistic effects of anti-c-Met antibodies in Fab format on the proliferation of U87 glioblastoma cells.

This example illustrates in vitro data showing the inhibition of Met-mediated cell proliferation by anti-c-Met antibodies in IgG (FIG. 4A) and Fab (FIG. 4B) form compared with the IgG and Fab forms of Genetech 5D5 (derivatized from Met Mab). Uncontrolled cell proliferation is a hallmark of cancer and the ability to inhibit proliferation in c-Met positive cancer cells with anti-c-Met antibodies is requisite for a therapeutic compound. In this example, 5000 U87 glioblastoma cells were plated into the wells of a 96-well white opaque cell culture cluster in 100 μl DMEM media supplemented with 10% FBS, in triplicate. 24 hr later, media was removed, cells washed 1× with PBS, and then starved for 18 hr in 100 μl media without FBS (starvation media). Antibodies were diluted to the desired treatment concentration (IgG=10 ng/μl; Fab=5 or 10 ng/μl) in 100 ul starvation media, and added to the cells. U87 cells express the c-Met ligand, HGF, therefore stimulation of these cells with additional HGF is not required. Cells were incubated for 48 hr, after which the Promega CellTiter-Glo® kit was used to evaluate proliferation. Luminescence output is directly proportional to cell number.

Results: The anti-c-Met antibodies A1, E1 and H8 in IgG form (FIG. 4A) and all of the anti-c-Met antibodies in Fab form (FIG. 4B) inhibited U87 cell proliferation. Proliferation inhibition by the E1 IgG was greater than the Genentech 5D5 IgG and the A1 and H8 IgGs showed similar inhibition at the same dose. All tested anti-c-Met antibody Fabs showed complete inhibition of proliferation at both treatment concentrations. Data shown is the mean relative light units of triplicate samples+/− Std Error.

Example 2

This example illustrates in vitro data showing HGF stimulated auto-phosphorylation of the c-Met receptor in PC3 prostate cancer cells. This example demonstrates the ability of antibodies to block the activation of and therefore the function of c-Met in cancer cells. Protocol: 10,000 PC3 prostate cancer cells were plated in the wells of the 96-well cell culture cluster provided in the Human Phospho-HGF-R/c-Met (Y1234/Y1235) Immunoassay Cell Based ELISA Kit (R&D Systems cat #KCB2480) in 100 ul DMEM media supplemented with 10% FBS. 24 hr later, media were removed and the cells washed 1× with PBS, and then starved for 18 hr in 100 μl starvation media (DMEM+2% FBS). Cells were treated with 10 μg/ml anti-c-Met antibody in IgG (FIG. 5A) or Fab (FIG. 5B) form in serum-free media. After 1 hr incubation, HGF was added to a final concentration of 50 ng/ml. Cells were further incubated for 7 min. Cells were then processed according to the manufacturer's protocol. Following stimulation, cells were fixed and permeabilized in the wells. The c-Met phosphorylation was measured using a double immunoenzymatic labeling procedure. The cells were simultaneously incubated with two p ma antibodies: a phospho-specific c-Met antibody and a normalization antibody that recognizes the pan-protein regardless of phosphorylation status. The primary antibodies were derived from different species. Two secondary antibodies recognizing the different species were labeled with either horseradish-peroxidase (HRP) or alkaline phosphatase (AP), and two spectrally distinct fluorogenic substrates for either HRP or AP were used for detection. The fluorescence of the phosphorylated protein was normalized to that of the pan-protein in each well for the correction of well-to-well variations.

Figure 5A:
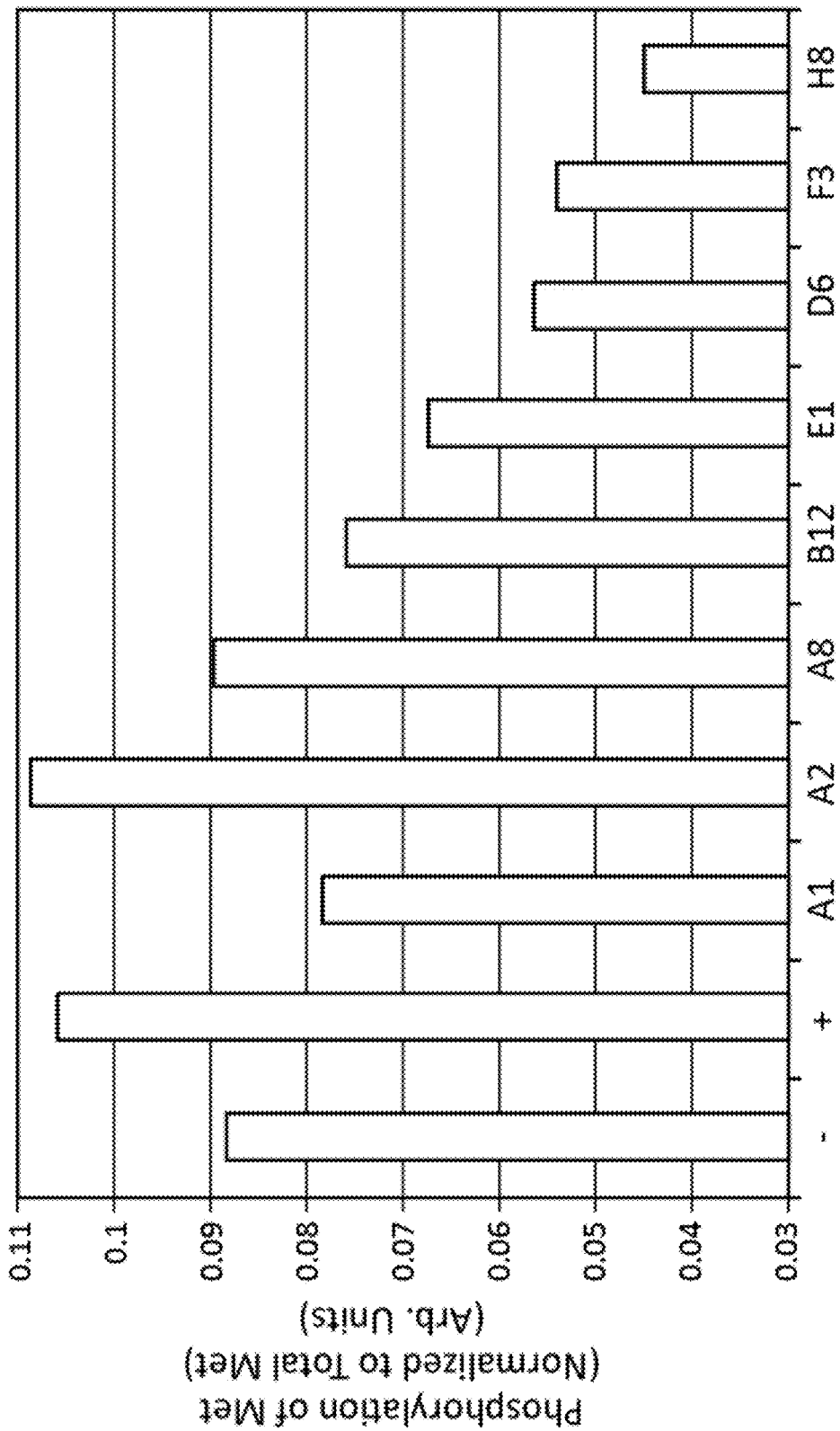
FIG. 5A shows the inhibition of HGF-stimulated c-Met auto-phosphorylation by anti-c-Met antibodies in IgG format.
Figure 5B:
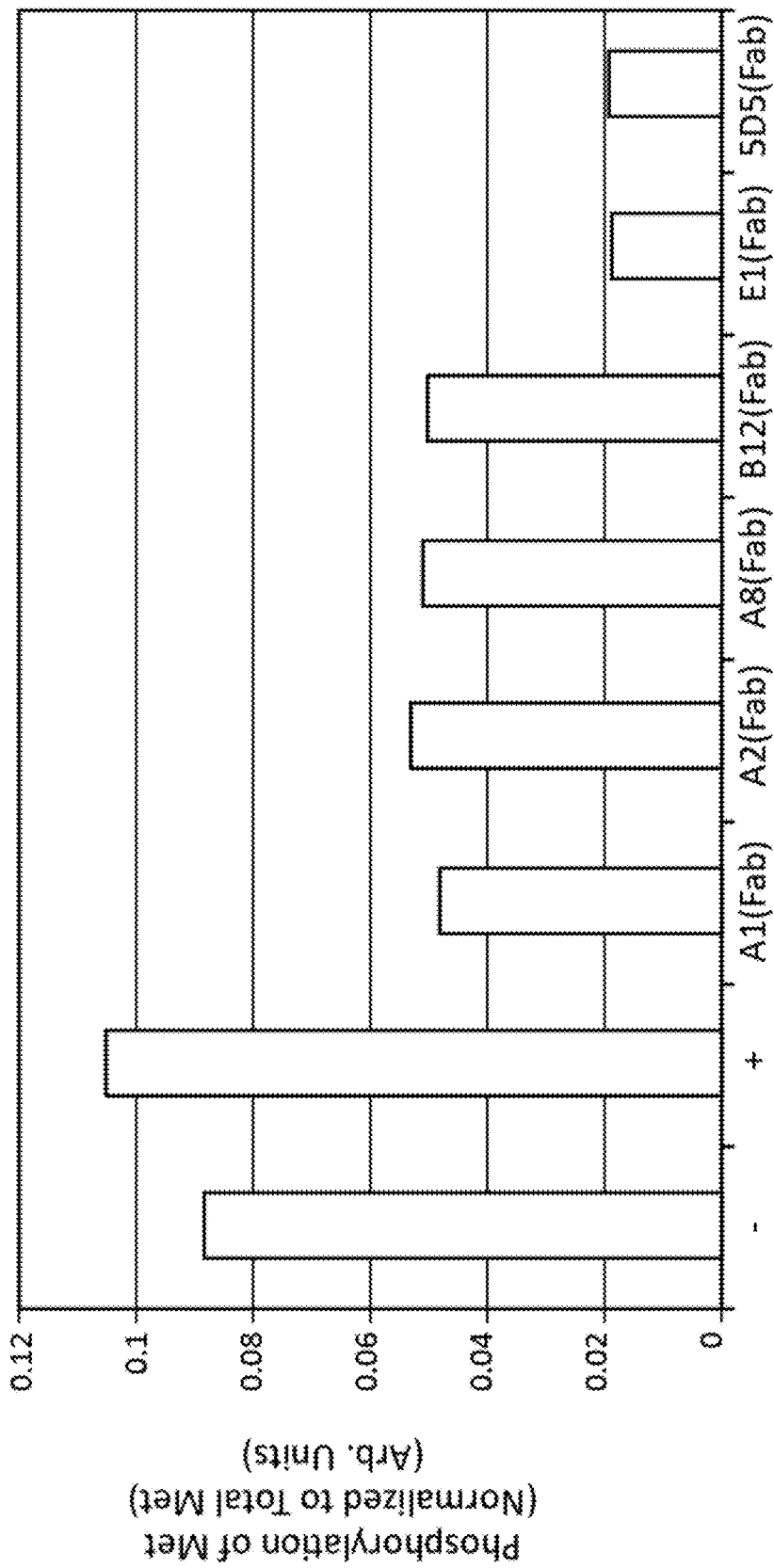
FIG. 5B shows the inhibition of HGF-stimulated c-Met auto-phosphorylation by anti-c-Met antibodies in Fab format.

Results: As shown in FIG. 5A-B, pre-treatment of cells with anti-c-Met antibodies variably blocked the activation of c-Met by auto-phosphorylation. Specifically, the IgG forms of A1, E1, D6, F3, and H8 had strong inhibitory effects on c-Met auto-phosphorylation (FIG. 5A), while all Fab forms tested showed strong antagonism (FIG. 5B). Data shown is representative of multiple experiments and is shown as the normalization of the fluorescence intensity output of the phosphorylated c-Met to the fluorescence intensity output of the pan-protein.

Example 3

This example illustrates in vitro data showing HGF-stimulated, c-Met-mediated cell migration. In this example, a wound healing assay investigated the migration of cells into a denuded area of a cell culture. Stimulation of c-Met by HGF would trigger cells to migrate into the denuded area, therefore exemplary anti-c-Met antibodies will inhibit this migration. In cancer, cell migration away from the local tumor environment allows for metastasis. Inhibition of migration may decrease the potential of metastasis. To evaluate the effect of anti-c-Met antibodies in IgG and Fab forms on cell migration, PC3 prostate cancer cells were used as a model. In this example, cells were grown to confluence on 6-well plates creating a tight monolayer of cells. After 24 hr starvation with serum free media, the cell monolayer was scratched with a 200 μl pipette tip. This created a denuded area for cells to migrate into. Immediately following the disruption of the cell monolayer, cells were incubated with 10 μg/ml antibody in IgG or Fab form for 1 hr. HGF was added to the cultures at a final concentration of 50 ng/ml and cell migration into denuded areas was scored 24 hrs later. To score for migration, 5 fields of view at 40× magnification were examined and the number of cells migrating into the denuded area was counted.

Figure 6:
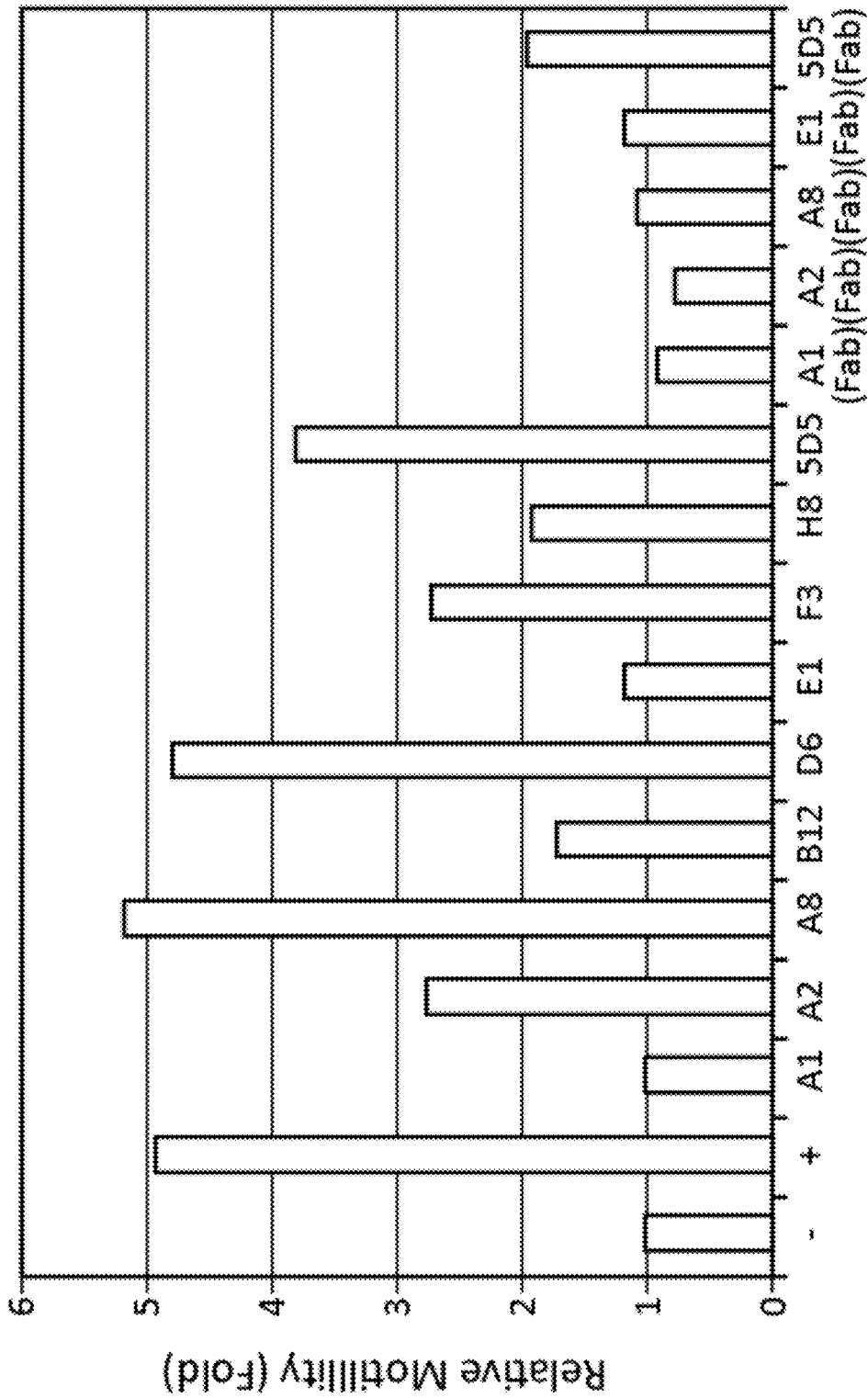
FIG. 6 shows the inhibition of HGF-stimulated, c-Met-mediated cell migration by anti-c-Met antibodies (IgG and Fab format) in a cellular wound healing assay.

Results: As shown in FIG. 6, anti-c-Met antibodies A1, B12, E1 and H8 in the IgG format and all tested antibodies in the Fab format inhibit PC3 cell migration into the denuded area when stimulated with HGF. Data shown as fold increase in Relative Motility calculated by dividing the number of cells migrated in the HGF-treated sample by the number of cells in the untreated control. Data is representative of multiple experiments.

Example 4

This example illustrates in vitro data showing HGF-stimulated, c-Met-mediated cell motility. HGF is also known as Scatter Factor, as it has the ability to trigger dispersion or scattering of cells. This scatter is mediated through c-Met-dependent cell motility. This type of cell motility can be associated with metastasis of tumor cells. In this example, a colony scatter assay is used to demonstrate the ability of anti-c-Met antibodies to inhibit c-Met-dependent cell motility. DU145 prostate cancer cells were seeded in a 10 cm plate at a density of $2 \times 10^3$ cells and cultured for 7 days until colonies formed. Cell colonies were incubated with serum free medium overnight and pre-treated with 10 ug/ml anti-c-Met antibodies in IgG or Fab format for 1 hour before stimulating with HGF (25 ng/mL). Cells were stained with crystal violet (0.1%) 24 hours after treatment. Scattered colonies were visualized at 40× magnification and photographed.

Figure 7:
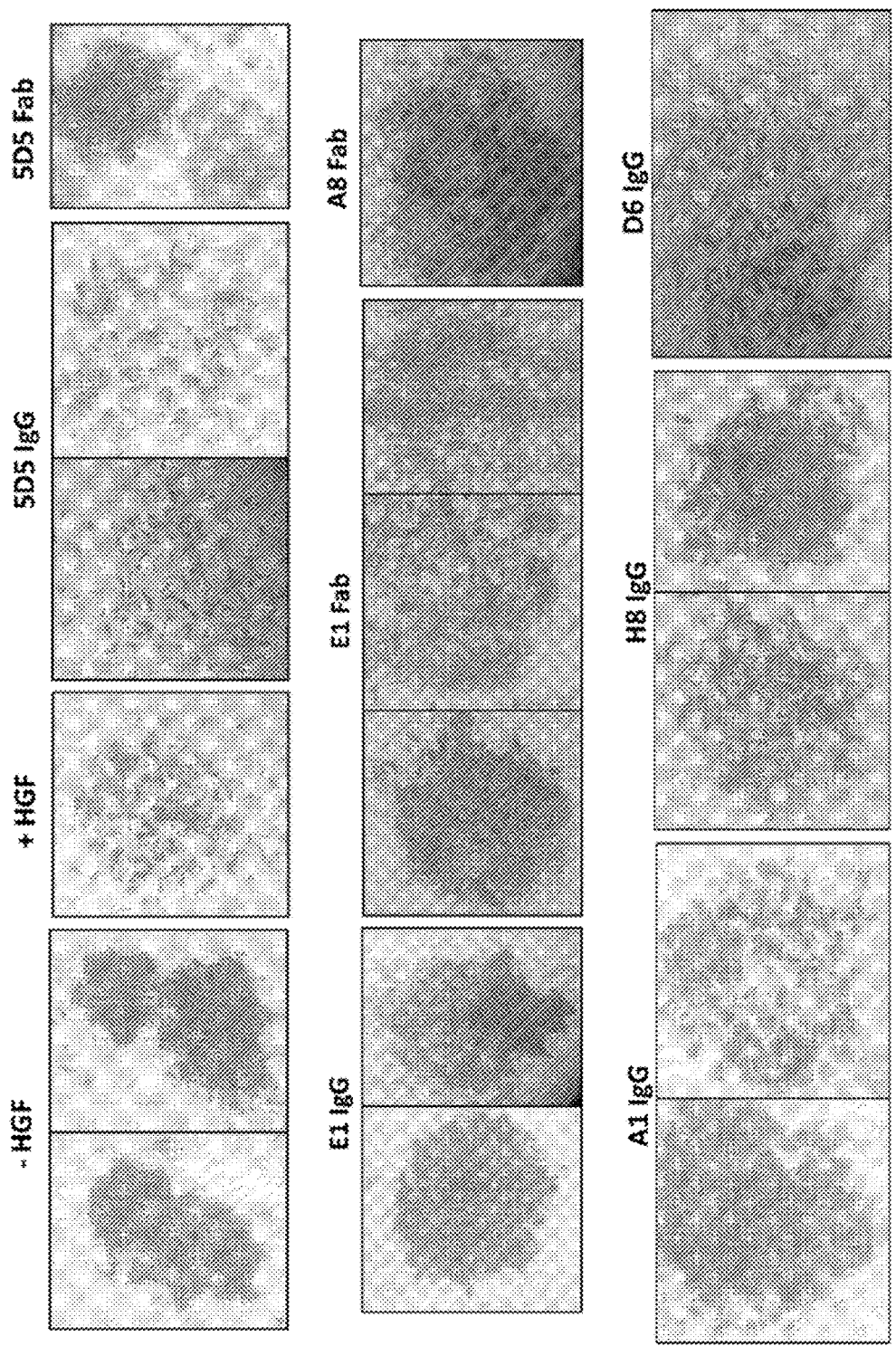
FIG. 7 shows the results of an HGF/c-Met scatter assay indicating that anti-c-Met Antibodies in IgG (A1, E1, and H8) and Fab (E1 and A8) format can inhibit HGF-stimulated, c-Met-mediated cell motility.

Results: As shown in FIG. 7, HGF (+HGF) stimulates cell motility depicted as spreading or scattering of the cells of the colony. Pre-treatment of cells with anti-C-Met antibodies in IgG and Fab format prevented this scatter to a variable extent. Clones E1 (both IgG and Fab format), A1 (IgG format), A8 (Fab format), and H8 (IgG format) antagonized HGF-stimulated, c-Met-mediated cell motility to the same extent as Genentech 5D5 (Fab format), while D6 (IgG format) and the IgG format of Genentech 5D5 have no antagonistic effects on cell motility. These pictures are representative of multiple colonies from multiple experiments. Multiple views for some samples are from the same experiment.

Example 5

This example provides an effect of antibodies reactive with c-Met on tumor growth in vivo. The ability of anti-c-

Figure 8:
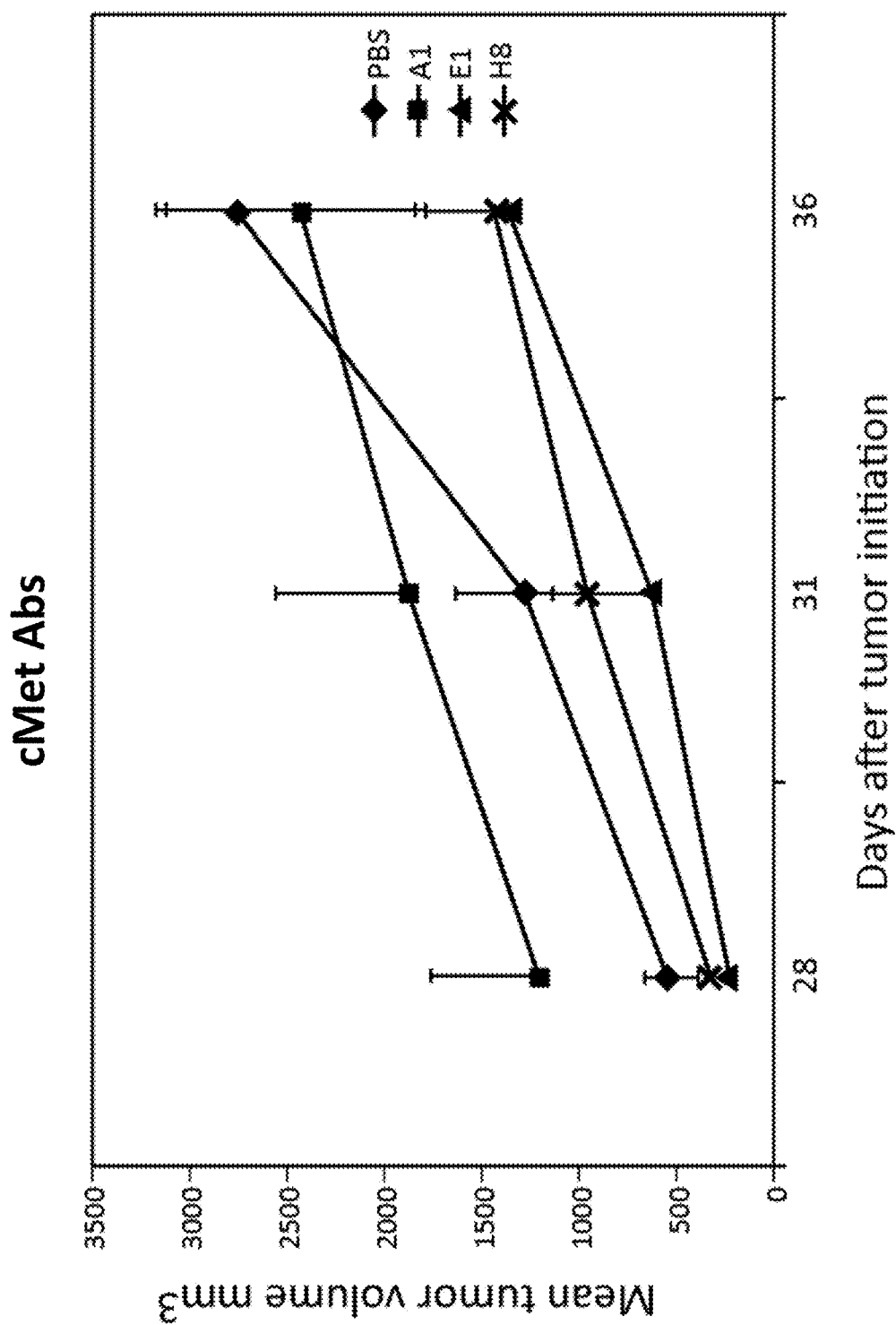
FIG. 8 shows that anti-c-Met antibodies E1 (triangles), A1 (squares), and H8 (X) reduce the growth of xenogeneic tumor cells implanted into nude mice compared to control.
Figure 14:
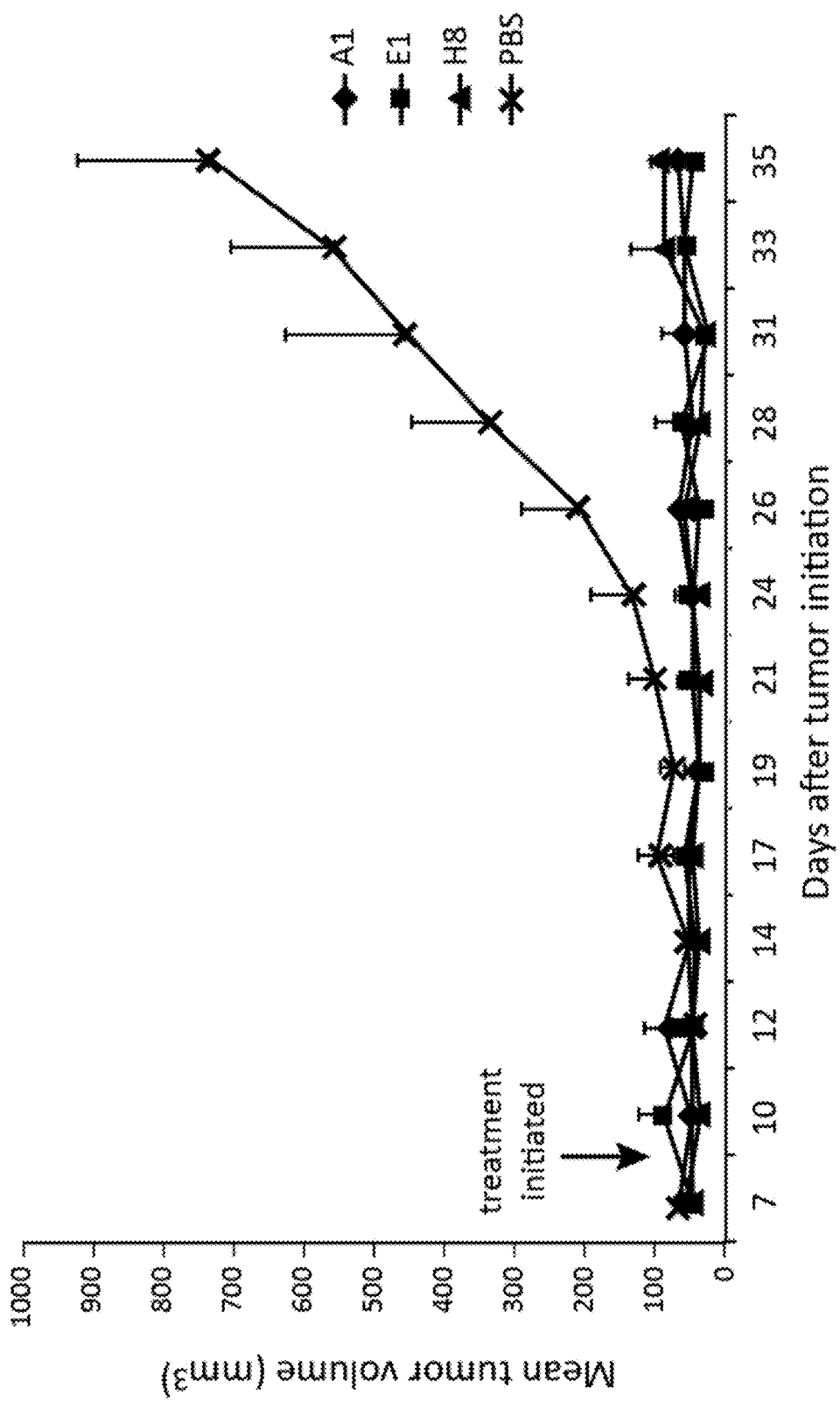
FIG. 14 shows the effect of antibodies A1, E1, and H8 on tumor volume.

Met antibodies to modulate tumor growth was assessed using an athymic murine model. Groups of five mice were injected subcutaneously in the flank with 5×10⁶ U118 human primary glioblastoma cells. Ten days after implantation of cells, mice were treated intraperitoneally with 100 ml of i) PBS, ii) antibody A1 (0.15 mg), iii) antibody E1 (0.15 mg), or iv) antibody H8 (0.15 mg). Treatments were performed three times per week until the termination of the experiment. As shown in FIGS. 8 and 14, E1, A1, and H8 antibodies reduced the growth of the xenogeneic tumor cells compared to PBS alone.

Example 6

This example illustrates in vitro data for anti-c-Met antibody cellular binding $EC_{50}$ measurements. This example shows the binding characteristic for these antibodies in terms of the maximal cell binding and the concentration at which 50% binding saturation ($EC_{50}$) is reached. In this example, DU-145 prostate cancer cells, SK-O-V3 ovarian cancer cells, or human umbilical vein endothelial cells (HUVEC) were aliquoted into the wells of a 96-well, v-bottom plate in FACS Buffer (PBS+2% FBS). A 16-point, 2 fold serial dilution curve of antibodies made in FACS Buffer was used to stain the cells. After 1 hr incubation, cells were washed 2× with FACS Buffer and resuspended in PE-conjugated, goat anti-human IgG (γ-chain specific) secondary antibody (Southern Biotech Cat #2040-09). Cells were further incubated for 0.5 hr and then washed 1× with FACS Buffer. Cells were resuspended in FACS Buffer and the median fluorescence intensity in the FL2-A channel was determined using the Intellicyt® HTFC flow cytometer. The cell binding $EC_{50}$ for these anti-c-Met antibodies on DU-145, SK-O-V3, and HUVEC cells are shown in Table 1. Data was collected and analyzed on the Intellicyt® HTFC flow cytometer using the ForeCyt® software. ND=Not Determined.

Table 1 shows EC50 values for E1 derived anti-c-Met antibodies on DU-145 prostrate cancer cells and SK-O-V3 ovarian cancer cells

| clone  | EC50 nM on DU-145 cells | EC50 nM on SK-O-V3 cells | EC50 nM on HUVEC cells |
|--------|-------------------------|--------------------------|------------------------|
| E1-A10 | 0.2                     | 0.153                    | 0.148                  |
| E1-A11 | 0.26                    | 0.2                      | ND                     |
| E1-A13 | 0.362                   | 0.159                    | ND                     |
| E1-A14 | 0.212                   | 0.12                     | 0.132                  |
| E1-A18 | ND                      | 1.15                     | 0.606                  |
| E1-B11 | 0.34                    | 0.41                     | ND                     |
| E1-B13 | 0.251                   | 0.191                    | 0.190                  |
| E1-B19 | 3.35                    | 0.852                    | ND                     |
| E1-BR1 | 3.36                    | 0.467                    | 0.376                  |

Example 7

This example illustrates in vitro data for anti-c-Met antibody cellular binding $EC_{50}$ measurements. This example shows the binding characteristic for these antibodies in terms of the maximal cell binding and the concentration at which 50% binding saturation ($EC_{50}$) is reached. In this example, DU-145 prostate cancer cells or SK-O-V3 ovarian cancer cells were aliquoted into the wells of a 96-well, v-bottom plate in FACS Buffer (PBS+2% FBS). A 16-point, 2 fold serial dilution curve of antibodies made in FACS Buffer was used to stain the cells. After 1 hr incubation, cells were washed 2× with FACS Buffer and resuspended in PE-conjugated, goat anti-human IgG (γ-chain specific) secondary antibody (Southern Biotech Cat #2040-09). Cells were further incubated for 0.5 hr and then washed 1× with FACS Buffer. Cells were resuspended in FACS Buffer and the median fluorescence intensity in the FL2-A channel was determined using the Intellicyt® HTFC flow cytometer. The cell binding $EC_{50}$ for these anti-c-Met antibodies on DU-145 and SK-O-V3 cells are shown in Table 2. Data was collected and analyzed on the Intellicyt® HTFC flow cytometer using the ForeCyt® software. ND=Not Determined

TABLE 2

| Clone  | EC50 nM on DU-145 Cells | EC50 nM on SK-O-V3 Cells |
|--------|-------------------------|--------------------------|
| A1-2   | ND                      | 0.223                    |
| A1-4   | 0.017                   | 0.054                    |
| A1-6   | ND                      | 0.053                    |
| A1-9   | 0.058                   | 0.076                    |
| A1-24  | 0.003                   | 0.135                    |
| A1-32  | 0.064                   | 0.109                    |

Example 8

Figure 9:
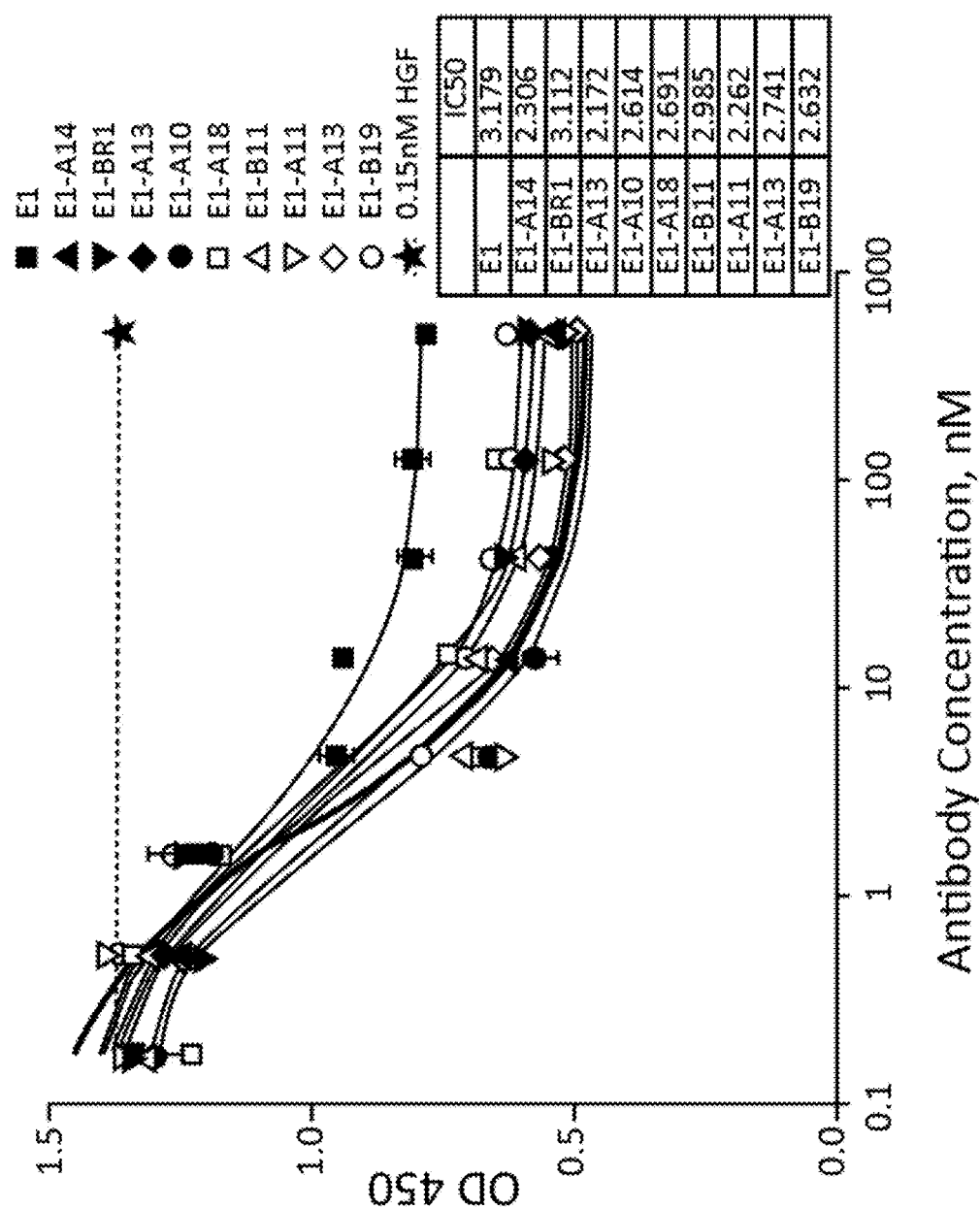
FIG. 9 shows a graph comparing the blocking of the interaction between recombinant HGF and various anti-c-Met antibodies that are E1 and various optimized versions of E1. The IC50 numbers show a comparison of inhibiting ligand binding to its receptor.

This example shows the blocking of the interaction between recombinant HGF and recombinant c-Met by anti-c-Met antibody E1 and its optimized versions. Inhibition of ligand binding to its receptor prevents activation. In this example, an ELISA was used to determine the concentration at which 50% of the ligand/receptor binding was blocked by the antibodies (IC50). Here, recombinant c-Met extracellular domain (R&D Sytems cat #358-MT-100/CF) was immobilized to the ELISA plate followed by blocking with SuperBlock (Scytek, Cat #AAA500). The antibodies were then added to the plate in an 8-point, 4-fold serial dilution. After incubation for 1 hr and washes, HGF (R&D Systems cat #294-HG-005/CF) was added to the plates at a final concentration of 0.15 nM. HGF binding to c-Met was detected using a biotinylated anti-HGF antibody (R&D cat #BAF294) followed by Streptavidin-HRP (Fitzgerald cat #65R-510PHRP). OD450 was plotted against antibody concentration and non-linear regression (GraphPad Prism) was used to determine the IC50 for each antibody (FIG. 9). The data is shown as mean OD450+/−SEM and the IC50 values shown are in nM.

Example 9

Figure 10:
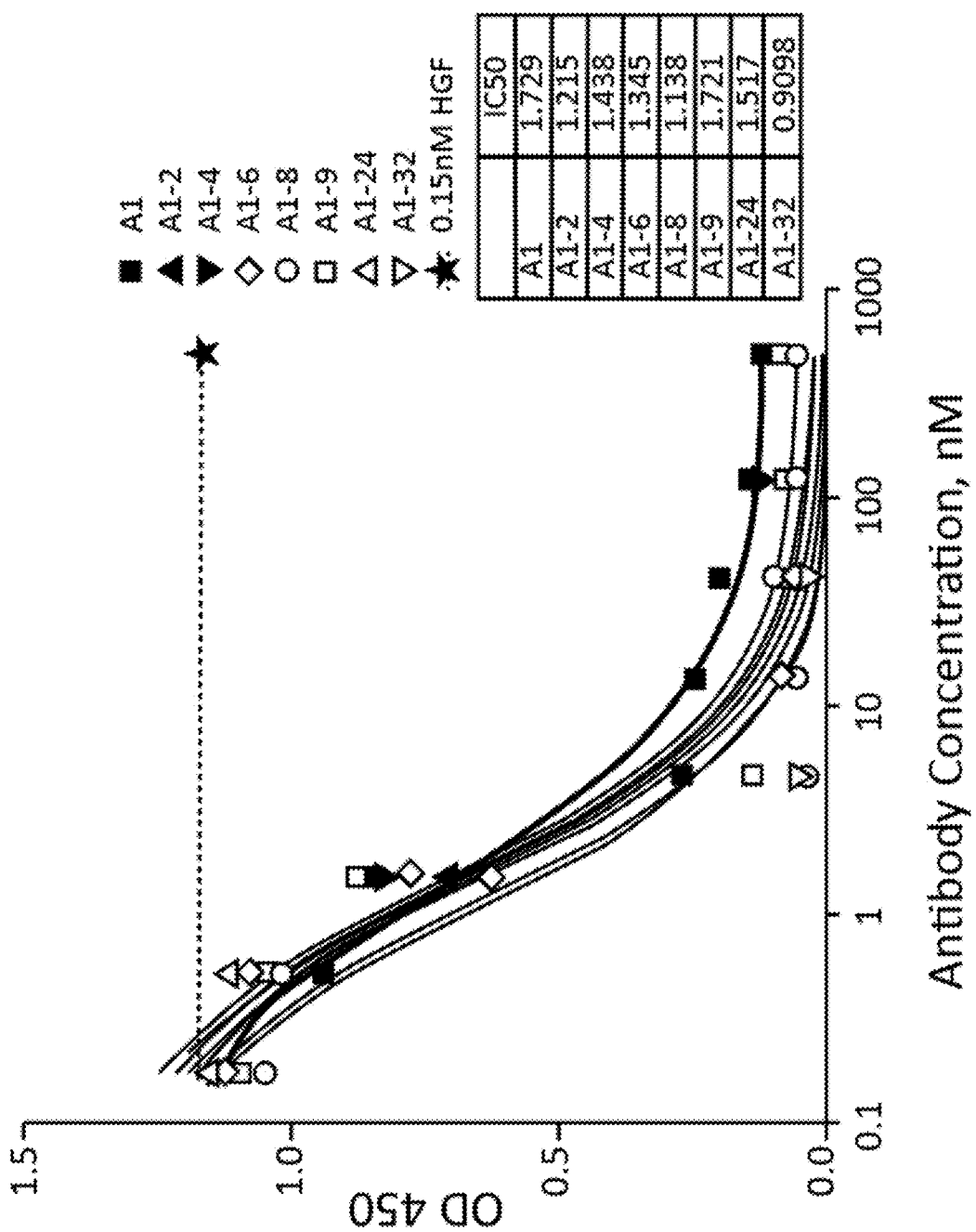
FIG. 10 shows the blocking of the interaction between recombinant HGF and recombinant c-Met by anti-c-Met antibody A1 and its optimized versions. Inhibition of ligand binding to its receptor prevents activation.

This example shows the blocking of the interaction between recombinant HGF and recombinant c-Met by anti-c-Met antibody A1 and its optimized versions. Inhibition of ligand binding to its receptor prevents activation. In this example, an ELISA was used to determine the concentration at which 50% of the ligand/receptor binding was blocked by the antibodies (IC50). Here, recombinant c-Met extracellular domain (R&D Sytems cat #358-MT-100/CF) was immobilized to the ELISA plate followed by blocking with SuperBlock (Scytek, Cat #AAA500). The antibodies were then added to the plate in an 8-point, 4-fold serial dilution. After incubation for 1 hr and washes, HGF (R&D Systems cat #294-HG-005/CF) was added to the plates at a final concentration of 0.15 nM. HGF binding to c-Met is detected using a biotinylated anti-HGF antibody (R&D cat #BAF294) followed by Streptavidin-HRP (Fitzgerald cat #65R-510PHRP). OD450 was plotted against antibody concentration and non-linear regression (GraphPad Prism) is used to determine the IC50 for each antibody (FIG. 10). The data is shown as mean OD450+/−SEM and the IC50 values shown are in nM.

Example 10

Figure 11:
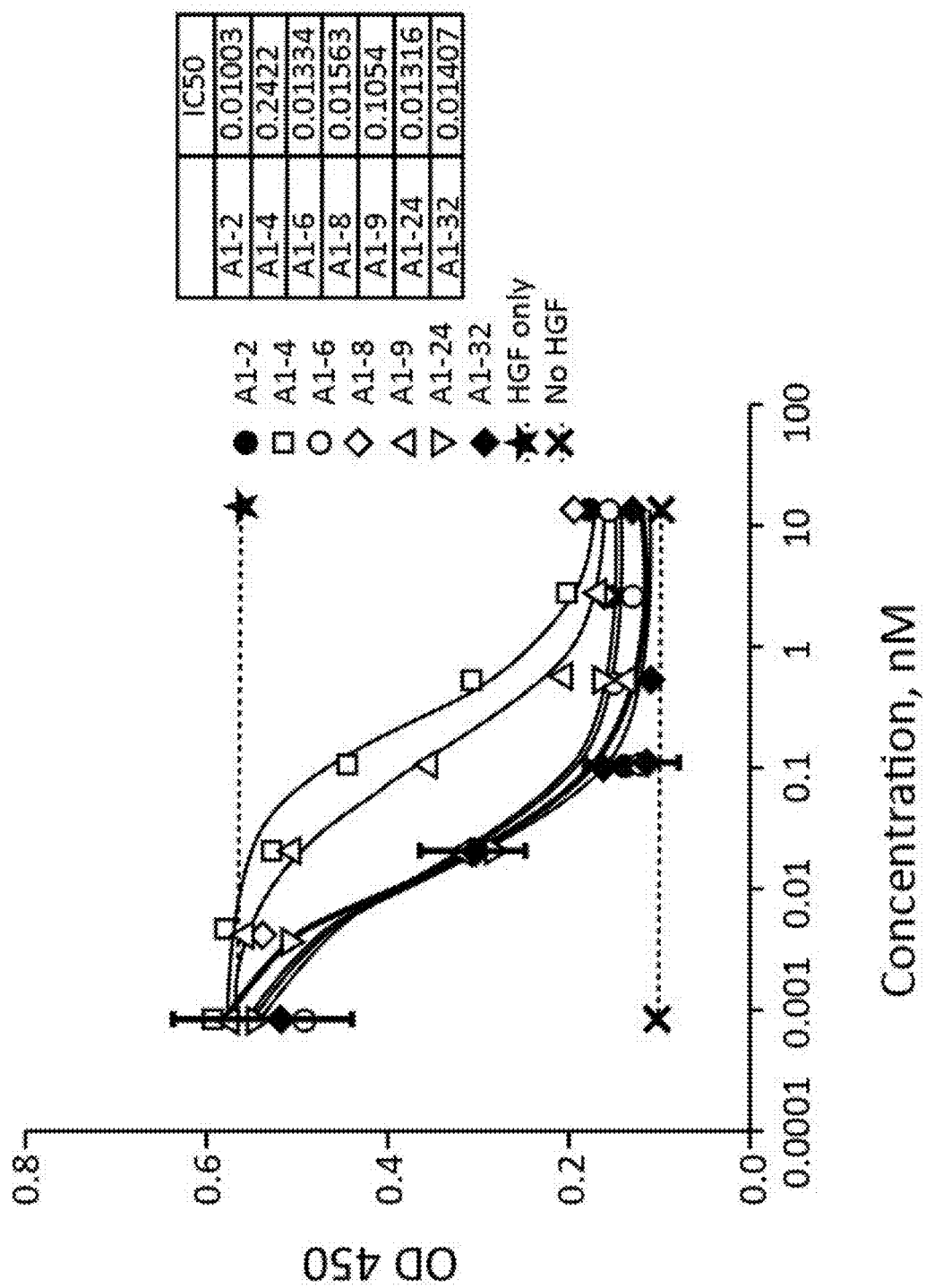
FIG. 11 shows in vitro data of HGF-stimulated phosphorylation of c-Met in A549 NSCLC (Non-small Cell Lung Cancer) cells. These data demonstrates the ability of anti-c-Met A1 optimized clones to block the activation of and therefore the function of c-Met in cancer cells.

This example illustrates in vitro data showing HGF-stimulated phosphorylation of c-Met in A549 NSCLC (Non-small Cell Lung Cancer) cells. This example demonstrates the ability of anti-c-Met A1 optimized clones to block the activation of and therefore the function of c-Met in cancer cells. Here, A549 cells grown for 24 hr in the wells of a 96-well cell culture cluster were treated with an 8-point, 5-fold serial dilution of the listed antibodies. After incubation for 4 hours, 40 ng/ml HGF (R&D Systems cat #294-HG-005/CF) was added to the cells. Cells were then incubated for 15 min. Cells were washed with PBS plus sodium orthovanadate (1:2000) and lysed in cell lysis buffer plus inhibitors. Phosphorylation of c-Met was detected by ELISA (R&D Systems cat #DYC2480-2) according to the manufacturer's protocol adjusted for half area ELISA plates. The OD450 was measured as an indicator of c-Met phosphorylation and was plotted against antibody concentration to yield the curves shown in FIG. 11 (data shown as the mean OD450+/−SEM). The IC50 values for the inhibition of c-Met phosphorylation by these antibody clones were determined using non-linear regression and are listed in FIG. 11 (values shown in nM).

Example 11

Figure 12:
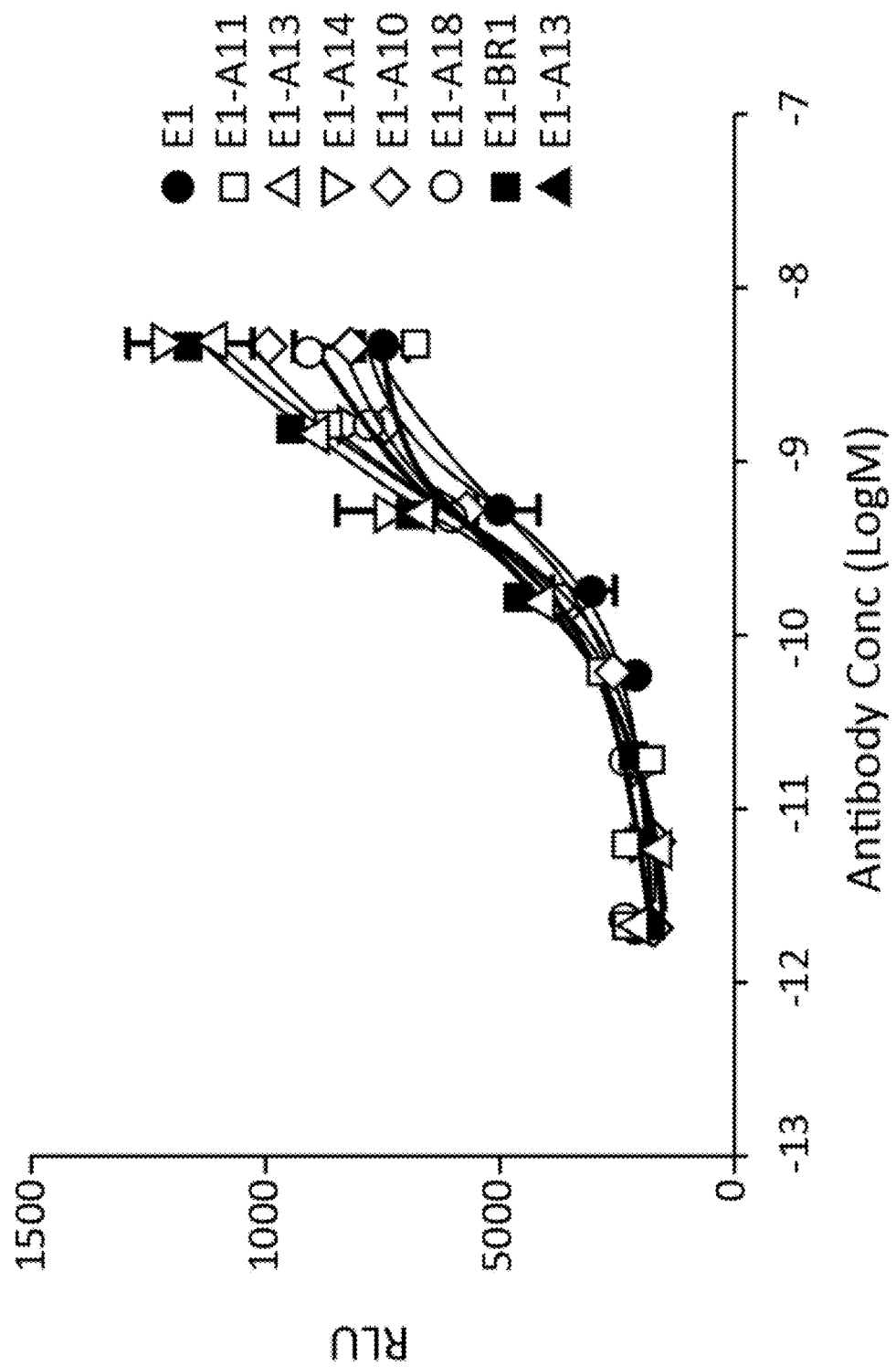
FIG. 12 shows the potential of anti-c-Met antibodies to induce ADCC (Antibody Dependent Cell Cytotoxicity. ADCC is triggered when the Fc region of an antibody which is bound to a target cell, interacts with an Fc receptor on the surface of an effector immune cell leading to the killing of the target cell.

This example illustrates the potential of anti-c-Met antibodies to induce ADCC (Antibody Dependent Cell Cytotoxicity. ADCC is triggered when the Fc region of an antibody which is bound to a target cell, interacts with an Fc receptor on the surface of an effector immune cell leading to the killing of the target cell. Here we measure ADCC induced by anti-c-Met antibodies using a cell based reporter assay (Promega). In brief, 625 A431 cells were seeded into the inner 320 wells of a white 384-well cell culture plate in 100 μl of media. Cells were allowed to attach overnight and in the morning, media was removed and replaced with 7 ul ADCC Assay Buffer (RPMI+4% Low IgG Fetal Bovine Serum) per well (outer unused wells get 21 ul). A 9-point, 3-fold serial dilution curve of anti-c-Met mABs was made at 3× final concentration in ADCC Assay Buffer. 7 μl of the antibody dilution was added to wells in triplicate distributed across the rows to avoid spatial effects. ADCC Effector cells are thawed according to manufacturer's protocol and 7 μl added to each well. The plate was incubated for 6 hr at 37° C. and then removed to the lab bench to reach room temperature. 21 μl of Bio-Glo™ Luciferase Assay Reagent was added to each well and allowed to incubate for 30 min. The plate was then read using the FlexStation® III (Molecular Devices) detecting luminescence. The RLU (relative light units; mean of triplicate values+/−SEM) was plotted against antibody concentration to determine the EC50 for the effect. As shown in FIG. 12, the EC50 value for E1 and E1 optimized clones for the induction of ADCC ranged from 230 pM to 1.1 nM.

Example 12

Figure 13:
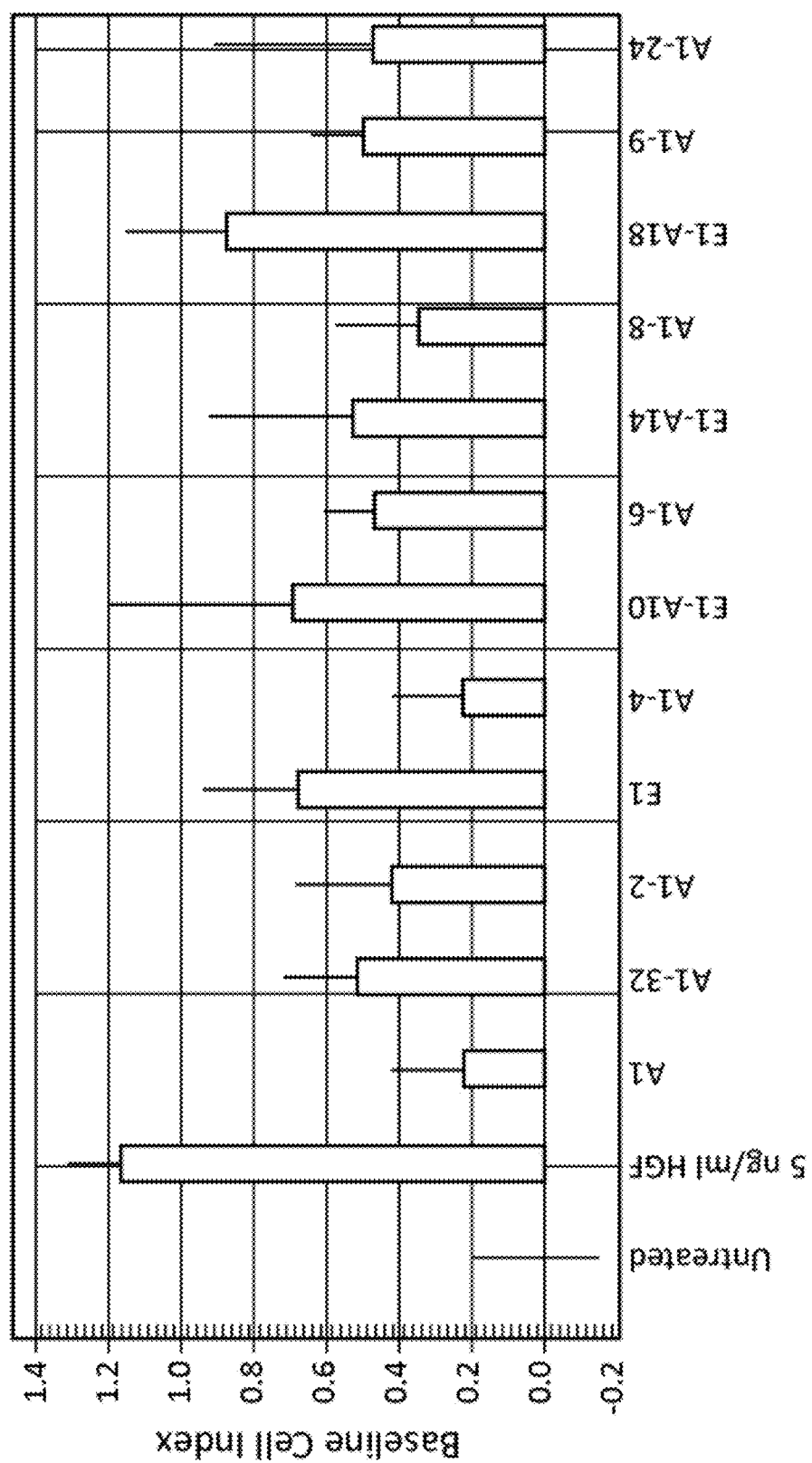
FIG. 13 shows the effects on cell migration of anti-c-Met mAbs, using a modified Boyden Chamber setup utilizing the xCelligence® system (ACEA).

This example illustrates the effects on cell migration of anti-c-Met mAbs, using a modified Boyden Chamber setup utilizing the xCelligence® system (ACEA). Here, both sides of the 8 membrane contained in the upper chamber of the CIM-16 plate were coated with 30 μl of 1 mg/ml Fibronectin for 30 mins. A solution of 50 ng/ml HGF (R&D Systems cat #294-HG-005/CF) to serve as the chemoattractant was made in Migration Basal Media (MBM; fully supplemented media diluted 1:125 in Serum Free Media, SFM). The lower chamber of the CIM-16 plate was filled with 170 μl of the chemoattractant dilution. The upper chamber was then assembled onto the lower chamber and the wells of the upper chamber were filled with 40 μl of SFM. The setup was incubated in the RTCA-DP unit for 1 hr and then a background measurement was taken. Target cells were then lifted non-enzymatically and resuspended in SFM at a concentration of 800,000 cells/ml. Fifty μl of the cell suspension was incubated with 50 μl of 10 μg/ml anti-c-Met mAbs (40,000 cells and 5 μg/ml final mAb concentration; in triplicate) for 10 min and then transferred to the wells of the CIM-16 plate. Cells were allowed to settle for 30 min at room temperature in the hood. The plate was then place in the RTCA-DP apparatus and readings were taken every 2 min for 24 hrs. As the cells are drawn to the chemoattractant (HGF), they pass through the pores of the membrane and attach to the underside of the membrane resulting in changes in electrical impedance which is converted to a cell index by the RTCA apparatus. The higher the cell index the greater the number of cells which migrated. As shown in FIG. 13, 5 ng/ml HGF induced cell migration and the described anti-c-Met mAbs inhibited this migration to varying degrees. Data are shown as the cell index normalized to the untreated control (+/−SD) at 8 hrs after the beginning of the experiment.

```
                              Sequence Listing

Heavy chain variable domain region      Light chain variable domain region

A1     QVQLQESGPGLVKPSQTLSLTCTVSGGSISSGGYYW    LPVLTQPASVSGSPGQSITISCTGTSSDVGGY
           SWIRQHPGKGLEWIGEINHSGSTNYNPSLKSRVTIS    NYVSWYQQHPGKAPKLMIYDVSDRPSGVS
           VDTSKNQFSLKLSSVTAADTAVYYCARGRDGYDFDP    TRFSGSKSGNTASLTISGLQAEDEADYYCSSY
           WGQGTLVTVSS                             RSSSALVVFGGGTKLTVL
           SEQ ID NO. 1                            SEQ ID NO. 2

A2     QVQLQESGPGLVKPSGTLSLTCAVSGGSISRSNWW     LPVLTQPASVSGSPGQSITISCTGTSSDVGGY
           SWVRQPPGKGLEWIGEVYHSGSTNYNPSLKSRVTIS    KYVSWYQQHPGKAPKLLIYDVTDRPSGVSN
           VDKSKNQFSLKVNSVTAADTAVYYCARDSDGGYYF     RFSGSQSGNTASLTISGLQTEDEADYYCSSYT
           DYWGQGTLVTVSS                           DNGALVVFGGGTKLTVL
           SEQ ID NO. 3                            SEQ ID NO. 4

A8     QITLKESGAEVKKPGSSVKVSCKASGGTFSSYGISWV   SYELMQPASVSGSPGQSITISCTGTSSDVGG
           RQAPGQGLEWMGGIIPMFGTANYAQKFQGRVTIT      YDHVSWYQQHPGKAPKLMIYAVRNRPSGV
           ADESTSTAYMELSSLRSEDTAVYYCARDEVAPDYYG    PDRFSGSKSGNTASLTISGLQAEDEADYYCS
           SGPSYGMDVWGQGTMVTVSS                    SYTSSLTYVFGTGTKVTVL
           SEQ ID NO. 5                            SEQ ID NO. 6
```

Sequence Listing

| | Heavy chain variable domain region | Light chain variable domain region |
|---|---|---|
| B12 | QVQLVESGAEVKKPGASVKVSCKASGYTFTGYYMH WVRQAPGQGLEWMGWINPNSGNTGYAQKFQGR VTMTRNTSISTAYMELSSLRSEDTAVYYCARRGTTVS FDYWGQGTTVTVSS<br>SEQ ID NO. 7 | QAVLTQPPSVSGSPGQSITISCTGTSSDVGT FNLVSWYQQHPGKAPKLIIYEVSKRPSDVSP RYSGSKSGTTASLTISVLQTEDEADYYCCSYT TSSSYVFGIGTKVTVL<br>SEQ ID NO. 8 |
| D6 | QVQLQQWGAGLLKPSETLSLTCAVYGGSFSGYYWS WIRQPPGKGLEWIGEINHSGSTNYNPSLKSRVTISV DTSKNQFSLKLSSVTAADTAVYYCARGRDGYDFDP WGQGTLVTVSS<br>SEQ ID NO. 9 | QSVLTQPPSASGSPGQSVTISCTGTSSDVGG YNYVSWYQQHPGKAPKLMIYEVSKRPSGV PDRFSGSKSGNTASLTVSGLQAEDEADYYCS SYAGSNNLVVFGGGTQLTVL<br>SEQ ID NO. 10 |
| E1 | QVQLVQSGAEVKKPGASVKVSCKTSGYTFSGDYMH WVRQAPGQGLEWMGWINPNSGGTNYAQKFQGR VTMTRDTSISTAYMELSRLRSDDTAVYYCAREPGRD YYYYDGMDVWGQGTTVTVSS<br>SEQ ID NO. 11 | QSVVTQPPSVSGAPGQRVTISCTGSSSNIGA GYDVHWYQQLPGTVPKLLIYGNSNRPSGVP DRFSGSKSGTSASLAITGLQAEDEADYYCQS YDSSLSAYVFGTGTKVTVL<br>SEQ ID NO. 12 |
| E6 | QVQLQQWGAGLLKPSETLSLTCAVYGGSFSGYYWS WIRQPPGKGLEWIGEINHSGSTNYNPSLKSRVTISV DTSKNQFSLKLSSVTAADTAVYYCARGGRVYSNYY MDVWGKGTTVTVSS<br>SEQ ID NO. 13 | QAVLTQPASVSGSPGQSITISCTGTRSDVGG YNYVSWYQQHPGKAPKLLVYDVSNRPSGV SNRFSGSQSGNTASLTISGLQTEDEADYYCS SYTDNSALVVFGGGTKVTVL<br>SEQ ID NO. 14 |
| F3 | QVQLVESGPGLVKPSGTLSLTCAVSGGSISSSNWWS WVRQPPGKGLEWIGEIYHSGSTNYNPSLKSRVTISV DKSKNQFSLKLSSVTAADTAVYYCARSAYGDYFLDY WGQGTLVTVSS<br>SEQ ID NO. 15 | QSVLTQPASVSGSPGQSITISCTGTSSDVGG YNYVSWYQQHPGKAPKLLIYDVDSRPSGVS NRFSGSKSGNTASLTISGLQAEDEADYYCSS FTSSSTLVVFGGGTKVTVL<br>SEQ ID NO. 16 |
| H6 | EVQLLESGGGLVQPGGSLRLSCAASGFTFSSYEMN WVRQAPGKGLEWVSYISSSGSTIYYADSVKGRFTISR DNAKNSLYLQMNSLRAEDTAVYYCARDGAATGDQI DYWGQGTLVTVSS<br>SEQ ID NO. 17 | AIRMTQSPAFMSATPGDKVNISYKASQDVD DDMTWCQEKPGEAAIFIFQEAATLVPGIPP RLSGSGNGTDFTLTINNMESEDAAYYFCLQ QDNFPLTFGQGTKVDIK<br>SEQ ID NO. 18 |
| H8 | EVQLVQSGAEVKKPGASVKVSCKASGYTFSSYYM WVRQAPGQGLEWMGWINPNSGNTGYAQKFQGRH VTMTRNTSISTAYMELSSLRSEDTAVYYCARRGTTVS FDYWGQGTLVTVSS<br>SEQ ID NO. 19 | QLVLTQSPSVSVAPGQRVTISCSGSNSNIGN NYVSWYHHLPGTAPKLLIYDNNKRPSGIPD RFSGSKSGTSATLGITGLQPGDEAHYYCGT WDSTLSAGVFGGGTKLTVL<br>SEQ ID NO. 20 |
| H8-9 | EVQLVQSGAEVKKPGASVKVSCKASGYTFYSYYMH WVRQAPGQGLEWMGWINPNSGNTGYAQKFQGR VTMTRNTSISTAYMELSSLRSEDTAVYYCARRGTTVS FDTWGQGTLVTVSS<br>SEQ ID NO. 21 | QLVLTQSPSVSVAPGQRVTISCSGSNSNIGN NYVSWYHHLPGTAPKLLIYDNNKRPSGIPD RFSGSKSGTSATLGITGLQPGDEAHYYCGT WDSTLSAWVFGGGTKLTVL<br>SEQ ID NO. 22 |
| H8-9EE8L3 | EVQLVQSGAEVKKPGASVKVSCKASGYTFYSYYMH WVRQAPGQGLEWMGWINPNSGNTGYAQKFQGR VTMTRNTSISTAYMELSSLRSEDTAVYYCARRGTTVS FDTWGQGTLVTVSS<br>SEQ ID NO. 21 | QLVLTQSPSVSVAPGQRVTISCSGSNSNIGN NYVSWYHHLPGTAPKLLIYDNNKRPSGIPD RFSGSKSGTSATLGITGLQPGDEAHYYCGT WDSTLSAWLFGGGTKLTVL<br>SEQ ID NO. 23 |
| H8-G3S | EVQLVQSGAEVKKPGASVKVSCKASGYTFYSEYMH WVRQAPGQGLEWMGWINPNSGNTGYAQKFQGR VTMTRNTSISTAYMELSSLRSEDTAVYYCARRGTTVS FDTWGQGTLVTVSS<br>SEQ ID NO. 24 | QLVLTQSPSVSVAPGQRVTISCSGSNSNIGN NYVSWYHHLPGTAPKLLIYDNNKRPSGIPD RFSGSKSGTSATLGITGLQPGDEAHYYCGT WDSTLSAWVFGGGTKLTVL<br>SEQ ID NO. 22 |
| H8-A2 | EVQLVQSGAEVKKPGASVKVSCKASGYTFYSEYMH WVRQAPGQGLEWMGWINPNSGNTGVAPKFQGR VTMTRNTSISTAYMELSSLRSEDTAVYYCARRGTTVS FDTWGQGTLVTVSS<br>SEQ ID NO. 25 | QLVLTQSPSVSVAPGQRVTISCSGSNSNIGN NYVSWYHHLPGTAPKLLIYDNNKRPSGIPD RFSGSKSGTSATLGITGLQPGDEAHYYCGT WDSTLSAWAFGGGTKLTVL<br>SEQ ID NO. 26 |
| H8-B6 | EVQLVQSGAEVKKPGASVKVSCKASGYTFYSEYMH WVRQAPGQGLEWMGWINPNSGNTGYAQKFQGR VTMTRNTSISTAYMELSSLRSEDTAVYYCARRGTTVS FDTWGQGTLVTVSS<br>SEQ ID NO. 27 | QLVLTQSPSVSVAPGQRVTISCSGSNSFTDN TYVSWYHHLPGTAPKLLIYDTNKRPSGIPDR FSGSKSGTSATLGITGLQPGDEAHYYCGTW DSTLSAWVFGGGTKLTVL<br>SEQ ID NO. 28 |

-continued

| | Heavy chain variable domain region | Light chain variable domain region |
|---|---|---|
| H8-C1 | EVQLVQSGAEVKKPGASVKVSCKASGYTFYSEYMH WVRQAPGQGLEWMGWINPNSGNTGLAPKFQGR VTMTRNTSISTAYMELSSLRSEDTAVYYCARRGTTVS FDTWGQGTLVTVSS<br>SEQ ID NO. 29 | QLVLTQSPSVSVAPGQRVTISCSGSNSNIGN NYVSWYHHLPGTAPKLLIYDNNKRPSGIPD RFSGSKSGTSATLGITGLQPGDEAHYYCGT WDSTLSAWLFGGGTKLTVL<br>SEQ ID NO. 23 |
| H8-D4 | EVQLVQSGAEVKKPGASVKVSCKASGYTFYSEYMH WVRQAPGQGLEWMGWINPNSGNTGYAQKFQGR VTMTRNTSISTAYMELSSLRSEDTAVYYCARRGTTVS FDTWGQGTLVTVSS<br>SEQ ID NO. 24 | QLVLTQSPSVSVAPGQRVTISCSGSNSNIGN NYVSWYHHLPGTAPKLLIYDNNKRQSGIPD RFSGSKSGTSATLGITGLQPGDEAHYYCGT WDSTLSAWVFGGGTKLTVL<br>SEQ ID NO. 30 |
| H8-D5 | EVQLVQSGAEVKKPGASVKVSCKASGYTFYSYYMH WVRQAPGQGLEWMGWINPNSGNTGVAQKFQGR VTMTRNTSISTAYMELSSLRSEDTAVYYCARRGTTVS FDTWGQGTLVTVSS<br>SEQ ID NO. 31 | QLVLTQSPSVSVAPGQRVTISCSGSNSNIGN NYVSWYHHLPGTAPKLLIYDNNKRPSGIPD RFSGSKSGTSATLGITGLQPGDEAHYYCGT WDSTLSAWLFGGGTKLTVL<br>SEQ ID NO. 23 |
| H8-D6 | EVQLVQSGAEVKKPGASVKVSCKASGYTFYSEYMH WVRQAPGQGLEWMGWINPNSGNTGYAQKFQGR VTMTRNTSISTAYMELSSLRSEDTAVYYCARRGTTVS FDTWGQGTLVTVSS<br>SEQ ID NO. 24 | QLVLTQSPSVSVAPGQRVTISCSGSNSNIGN NYVSWYHHLPGTAPKLLIYDNNKRPSGIPD RFSGSKSGTSATLGITGLQPGDEAHYYCGT WDSTLSAWLFGGGTKLTVL<br>SEQ ID NO. 23 |
| H8-D10 | EVQLVQSGAEVKKPGASVKVSCKASGYTFYSEYMH WVRQAPGQGLEWMGWINPNSGNTGLAQKFQGR VTMTRNTSISTAYMELSSLRSEDTAVYYCARRGTTVS FDTWGQGTLVTVSS<br>SEQ ID NO. 32 | QLVLTQSPSVSVAPGQRVTISCSGSNSNIGN NYVSWYHHLPGTAPKLLIYDNNKRPSGIPD RFSGSKSGTSATLGITGLQPGDEAHYYCGT WDSTLSAWLFGGGTKLTVL<br>SEQ ID NO. 23 |
| H8-E5 | EVQLVQSGAEVKKPGASVKVSCKASGYTFYSEYMH WVRQAPGQGLEWMGWINPNSGNTGYAPKFQGR VTMTRNTSISTAYMELSSLRSEDTAVYYCARRGTTVS FDTWGQGTLVTVSS<br>SEQ ID NO. 33 | QLVLTQSPSVSVAPGQRVTISCSGSNSNIGN NYVSWYHHLPGTAPKLLIYDNNKRPSGIPD RFSGSKSGTSATLGITGLQPGDEAHYYCGT WDSTLSAWVFGGGTKLTVL<br>SEQ ID NO. 22 |
| H8-G7 | EVQLVQSGAEVKKPGASVKVSCKASGYTFYSEYMH WVRQAPGQGLEWMGWINPNSGNTGVAQKFQGR VTMTRNTSISTAYMELSSLRSEDTAVYYCARRGTTVS FDTWGQGTLVTVSS<br>SEQ ID NO. 34 | QLVLTQSPSVSVAPGQRVTISCSGSNSNIGN NYVSWYHHLPGTAPKLLIYDNNKRPSGIPD RFSGSKSGTSATLGITGLQPGDEAHYYCGT WDSTLSAWVFGGGTKLTVL<br>SEQ ID NO. 22 |
| H8-G9 | EVQLVQSGAEVKKPGASVKVSCKASGYTFYSEYMH WVRQAPGQGLEWMGWINPNSGNTGYAQKFQGR VTMTRNTSISTAYMELSSLRSEDTAVYYCARRGTTVS FDTWGQGTLVTVSS<br>SEQ ID NO. 24 | QLVLTQSPSVSVAPGQRVTISCSGSNSFSSN NYVSWYHHLPGTAPKLLIYDNNKRPSGIPD RFSGSKSGTSATLGITGLQPGDEAHYYCGT WDSTLSAWVFGGGTKLTVL<br>SEQ ID NO. 35 |
| H8-H6 | EVQLVQSGAEVKKPGASVKVSCKASGYTFYSYYMH WVRQAPGQGLEWMGWINPNSGNTGLAQKFQGR VTMTRNTSISTAYMELSSLRSEDTAVYYCARRGTTVS FDTWGQGTLVTVSS<br>SEQ ID NO. 36 | QLVLTQSPSVSVAPGQRVTISCSGSNSNIGN NYVSWYHHLPGTAPKLLIYDNNKRPSGIPD RFSGSKSGTSATLGITGLQPGDEAHYYCGT WDSTLSAWAFGGGTKLTVL<br>SEQ ID NO. 26 |
| H8-2A2 | EVQLVQSGAEVKKPGASVKVSCKASGYTFYSEYMH WVRQAPGQGLEWMGWINPNSGNTGLAPKFQGR VTMTRNTSISTAYMELSSLRSEDTAVYYCARRGTTVS FDTWGQGTLVTVSS<br>SEQ ID NO. 29 | QLVLTQSPSVSVAPGQRVTISCSGSNSNIGN NYVSWYHHLPGTAPKLLIYDNNKRPSGIPD RFSGSKSGTSATLGITGLQPGDEAHYYCGT WDSTLSAWVFGGGTKLTVL<br>SEQ ID NO. 22 |
| H8-2B1 | EVQLVQSGAEVKKPGASVKVSCKASGYTFYSYYMH WVRQAPGQGLEWMGWINPNSGNTGLAPKFQGR VTMTRNTSISTAYMELSSLRSEDTAVYYCARRGTTVS FDTWGQGTLVTVSS<br>SEQ ID NO. 37 | QLVLTQSPSVSVAPGQRVTISCSGSNSNIGN NYVSWYHHLPGTAPKLLIYDNNKRPSGIPDR FSGSKSGTSATLGITGLQPGDEAHYYCGTW DSTLSAWAFGGGTKLTVL<br>SEQ ID NO. 38 |
| H8-2B2 | EVQLVQSGAEVKKPGASVKVSCKASGYTFYSEYMH WVRQAPGQGLEWMGWINPNSGNTGVAQKFQGR VTMTRNTSISTAYMELSSLRSEDTAVYYCARRGTTVS FDTWGQGTLVTVSS<br>SEQ ID NO. 34 | QLVLTQSPSVSVAPGQRVTISCSGSNSNIGN NYVSWYHHLPGTAPKLLIYDNNKRPSGIPD RFSGSKSGTSATLGITGLQPGDEAHYYCGT WDSTLSAWLFGGGTKLTVL<br>SEQ ID NO. 23 |

Sequence Listing

| | Heavy chain variable domain region | Light chain variable domain region |
|---|---|---|
| H8-2B4 | EVQLVQSGAEVKKPGASVKVSCKASGYTFYSYYMH<br>WVRQAPGQGLEWMGWINPNSGNTGLAPKFQGR<br>VTMTRNTSISTAYMELSSLRSEDTAVYYCARRGTTVS<br>FDTWGQGTLVTVSS<br>SEQ ID NO. 37 | QLVLTQSPSVSVAPGQRVTISCSGSNSNIGN<br>NYVSWYHHLPGTAPKLLIYDNNKRPSGIPD<br>RFSGSKSGTSATLGITGLQPGDEAHYYCGT<br>WDSTLSAWLFGGGTKLTVL<br>SEQ ID NO. 23 |
| H8-2B7 | EVQLVQSGAEVKKPGASVKVSCKASGYTFYSEYMH<br>WVRQAPGQGLEWMGWINPNSGNTGLAQKFQGR<br>VTMTRNTSISTAYMELSSLRSEDTAVYYCARRGTTVS<br>FDTWGQGTLVTVSS<br>SEQ ID NO. 32 | QLVLTQSPSVSVAPGQRVTISCSASNSNIGN<br>NYVSWYHHLPGTAPKLLIYDNNKRPSGIPD<br>RFSGSKSGTSATLGITGLQPGDEAHYYCGT<br>WDSTLSAWVFGGGTKLTVL<br>SEQ ID NO. 39 |
| H8-A7P | EVQLVQSGAEVKKPGASVKVSCKASGYTFYSEYMH<br>WVRQAPGQGLEWMGWINPNSGNTGLAQKFQGR<br>VTMTRNTSISTAYMELSSLRSEDTAVYYCARRGTTVS<br>FDTWGQGTLVTVSS<br>SEQ ID NO. 32 | QLVLTQSPSVSVAPGQRVTISCSGSNSNIGN<br>NYVSWYHHLPGTAPKLLIYDNNKRPSGIPD<br>RFSGSKSGTSATLGITGLQPGDEAHYYCGT<br>WDSTLSAWVFGGGTKLTVL<br>SEQ ID NO. 22 |
| GCE-A10 | QVQLVQSGAEVKKPGASVKVSCKASGYTFSGD<br>YMHWVRQAPGQGLEWMGWINPNSGGTNYA<br>QKFQGRVTMTRDTSISTAYMELSRLRSDDTAVY<br>YCAREPARDYYYYDGLDVWGQGTTVTVSS<br>SEQ ID NO. 40 | QSVVTQPPSVSGAPGQRVTISCLGSASN<br>IGAGHDVHWYQQLPGTAPKLLIYGNSN<br>RPSGVPDRFSGSKSGTSASLAITGLQAED<br>EADYYCQSYSSSLSAYVFGTGTKVTVL<br>SEQ ID NO. 41 |
| GCE-A11 | QVQLVQSGAEVKKPGASVKVSCKASGFTFSGD<br>YIHWVRQAPGQGLEWMGWINPNSGGTNYA<br>QKFQGRVTMTRDTSISTAYMELSRLRSDDTAVY<br>YCAREPARDYYYYDGLDVWGQGTTVTVSS<br>SEQ ID NO. 42 | QSVVTQPPSVSGAPGQRVTISCLGSSSNI<br>GAGHDVHWYQQLPGTAPKLLIYGNSN<br>RISGVPDRFSGSKSGTSASLAITGLQAED<br>EADYYCQSYSSSLSAYLFGTGTKVTVL<br>SEQ ID NO. 43 |
| GCE-A13 | QVQLVQSGAEVKKPGASVKVSCKASGYTFSGD<br>YLHWVRQAPGQGLEWMGWINPNSGGTNYA<br>QKFQGRVTMTRDTSISTAYMELSRLRSDDTAVY<br>YCAREPARDYYYYDGLDVWGQGTTVTVSS<br>SEQ ID NO. 44 | QSVVTQPPSVSGAPGQRVTISCLGSASN<br>IGAGHDVHWYQQLPGTAPKLLIYGNSN<br>RPSGVPDRFSGSKSGTSASLAITGLQAED<br>EADYYCQSYSSSLSAYVFGTGTKVTVL<br>SEQ ID NO. 41 |
| GCE-A14 | QVQLVQSGAEVKKPGASVKVSCKASGYTFSGD<br>YIHWVRQAPGQGLEWMGWINPNSGGTNYA<br>QKFQGRVTMTRDTSISTAYMELSRLRSDDTAVY<br>YCAREPARDYYYYDGLDVWGQGTTVTVSS<br>SEQ ID NO. 45 | QSVVTQPPSVSGAPGQRVTISCIGSSSNI<br>GAGHDVHWYQQLPGTAPKLLIYGNSN<br>RPSGVPDRFSGSKSGTSASLAITGLQAED<br>EADYYCQSYSSSLSAYVFGTGTKVTVL<br>SEQ ID NO. 46 |
| GCE-A16 | QVQLVQSGAEVKKPGASVKVSCKASGYTFSGD<br>YLHWVRQAPGQGLEWMGWINPNTGGTNYA<br>QKFQGRVTMTRDTSISTAYMELSRLRSDDTAVY<br>YCAREPARDYYYYDGLDVWGQGTTVTVSS<br>SEQ ID NO. 47 | QSVVTQPPSVSGAPGQRVTISCIGSSSNI<br>GAGYDVHWYQQLPGTAPKLLIYGNSNL<br>PSGVPDRFSGSKSGTSASLAITGLQAEDE<br>ADYYCQSYESSLSAYVFGTGTKVTVL<br>SEQ ID NO. 48 |
| GCE-A18 | QVQLVQSGAEVKKPGASVKVSCKASGYTFSGD<br>YMHWVRQAPGQGLEWMGWINPNSGGTNYA<br>QKFQGRVTMTRDTSISTAYMELSRLRSDDTAVY<br>YCAREPGRDYYYYDGLDVWGQGTTVTVSS<br>SEQ ID NO. 49 | QSVVTQPPSVSGAPGQRVTISCIGSASNI<br>GAGHDVHWYQQLPGTAPKLLIYGNSN<br>RPSGVPDRFSGSKSGTSASLAITGLQAED<br>EADYYCQSYSSSLSAYVFGTGTKVTVL<br>SEQ ID NO. 50 |
| GCE-B2 | QVQLVQSGAEVKKPGASVKVSCKASGYTFSGD<br>YMHWVRQAPGQGLEWMGWINPNTGGTNYA<br>QKFQGRVTMTRDTSISTAYMELSRLRSDDTAVY<br>YCAREPARDYYYYDGLDVWGQGTTVTVSS<br>SEQ ID NO. 51 | QSVVTQPPSVSGAPGQRVTISCLGSASN<br>IGAGHDVHWYQQLPGTAPKLLIYGNSN<br>RPSGVPDRFSGSKSGTSASLAITGLQAED<br>EADYYCQSYSSSLSAYVFGTGTKVTVL<br>SEQ ID NO. 52 |
| GCE-B9 | QVQLVQSGAEVKKPGASVKVSCKASGFTFSGD<br>YMHWVRQAPGQGLEWMGWINPNSGGTNYA<br>QKFQGRVTMTRDTSISTAYMELSRLRSDDTAVY<br>YCAREPARDYYYYDGLDVWGQGTTVTVSS<br>SEQ ID NO. 53 | QSVVTQPPSVSGAPGQRVTISCLGSSSNI<br>GAGHDVHWYQQLPGTAPKLLIYGNSNL<br>PSGVPDRFSGSKSGTSASLAITGLQAEDE<br>ADYYCQSYSSSLSAVLFGTGTKVTVL<br>SEQ ID NO. 54 |
| GCE-B11 | QVQLVQSGAEVKKPGASVKVSCKASGYTFSGD<br>YIHWVRQAPGQGLEWMGWINPNSGGTNYA<br>QKFQGRVTMTRDTSISTAYMELSRLRSDDTAVY<br>YCAREPARDYYYYDGLDVWGQGTTVTVSS<br>SEQ ID NO. 45 | QSVVTQPPSVSGAPGQRVTISCIGSSSNI<br>GAGYDVHWYQQLPGTAPKLLIYGNSNR<br>ISGVPDRFSGSKSGTSASLAITGLQAEDE<br>ADYYCQSYSSSLSAVLFGTGTKVTVL<br>SEQ ID NO. 55 |

Sequence Listing

| | Heavy chain variable domain region | Light chain variable domain region |
|---|---|---|
| GCE-B13 | QVQLVQSGAEVKKPGASVKVSCKASGSTFSGD<br>YIHWVRQAPGQGLEWMGWINPNSGGTNYA<br>QKFQGRVTMTRDTSISTAYMELSRLRSDDTAVY<br>YCAREPARDYYYYDGLDVWGQGTTVTVSS<br>SEQ ID NO. 56 | QSVVTQPPSVSGAPGQRVTISCLGSASN<br>IGAGHDVHWYQQLPGTAPKLLIYGNSN<br>RPSGVPDRFSGSKSGTSASLAITGLQAED<br>EADYYCQSYSSSLSAVLFGTGTKVTVL<br>SEQ ID NO. 57 |
| GCE-B19 | QVQLVQSGAEVKKPGASVKVSCKASGFTFSGD<br>YIHWVRQAPGQGLEWMGWINPNSGGTNYA<br>QKFQGRVTMTRDTSISTAYMELSRLRSDDTAVY<br>YCAREPGRDYYYYDGLDVWGQGTTVTVSS<br>SEQ ID NO. 58 | QSVVTQPPSVSGAPGQRVTISCLGSASN<br>IGAGHDVHWYQQLPGTAPKLLIYGNSN<br>RPSGVPDRFSGSKSGTSASLAITGLQAED<br>EADYYCQSYSSSLSAVLFGTGTKVTVL<br>SEQ ID NO. 57 |
| GCE-BR1 | QVQLVQSGAEVKKPGASVKVSCKASGSTFSGD<br>YLHWVRQAPGQGLEWMGWINPNSGGTNYA<br>QKFQGRVTMTRDTSISTAYMELSRLRSDDTAVY<br>YCAREPARDYYYYDGLDVWGQGTTVTVSS<br>SEQ ID NO. 59 | QSVVTQPPSVSGAPGQRVTISCLGSASN<br>IGAGYDVHWYQQLPGTAPKLLIYGNSN<br>RPSGVPDRFSGSKSGTSASLAITGLQAED<br>EADYYCQSYSSSLSAVLFGTGTKVTVL<br>SEQ ID NO. 60 |
| GCE-B20 | QVQLVQSGAEVKKPGASVKVSCKASGYTFSGD<br>YLHWVRQAPGQGLEWMGWINPNSGGTNYA<br>QKFQGRVTMTRDTSISTAYMELSRLRSDDTAVY<br>YCAREPARDYYYYDGMDVWGQGTTVTVSS<br>SEQ ID NO. 61 | QSVVTQPPSVSGAPGQRVTISCLGSASN<br>IGAGHDVHWYQQLPGTAPKLLIYGNSN<br>RISGVPDRFSGSKSGTSASLAITGLQAED<br>EADYYCQSYSSSLSAVLFGTGTKVTVL<br>SEQ ID NO. 62 |
| GCE-A19 | QVQLVQSGAEVKKPGASVKVSCKASGFTFSGD<br>YLHWVRQAPGQGLEWMGWINPNSGGTNYA<br>QKFQGRVTMTRDTSISTAYMELSRLRSDDTAVY<br>YCAREPARDYYYYYGLDVWGQGTTVTVSS<br>SEQ ID NO. 63 | QSVVTQPPSVSGAPGQRVTISCLGSSSNI<br>GAGHDVHWYQQLPGTAPKLLIYGNSN<br>RISGVPDRFSGSKSGTSASLAITGLQAED<br>EADYYCQSYSSSLSAYVFGTGTKVTVL<br>SEQ ID NO. 64 |
| GCE-B10 | QVQLVQSGAEVKKPGASVKVSCKASGFTFSGD<br>YLHWVRQAPGQGLEWMGWINPNTGGTNYA<br>QKFQGRVTMTRDTSISTAYMELSRLKSDDTAVY<br>YCAREPARDYYYYDGLDVWGQGTTVTVSS<br>SEQ ID NO. 65 | QSVVTQPPSVSGAPGQRVTISCLGSSSNI<br>GAGHDVHWYQQLPGTAPKLLIYGNSNL<br>PSGVPDRFSGSKSGTSASLAITGLQAEDE<br>ADYYCQSYSSSLSAYVFGTGTKVTVL<br>SEQ ID NO. 66 |
| GCE-B5 | QVQLVQSGAEVKKPGASVKVSCKASGFTFSGD<br>YIHWVRQAPGQGLEWMGWINPNSGGTNYA<br>QKFQGRVTMTRDTSISTAYMELSRLRSDDTAVY<br>YCAREPGRDYYYYDGLDVWGQGTTVTVSS<br>SEQ ID NO. 58 | QSVVTQPPSVSGAPGQRVTISCLGSASN<br>IGAGHDVHWYQQLPGTAPKLLIYGNSN<br>RPSGVPDRFSGSKSGTSASLAITGLQAED<br>EADYYCQSYSSSLSAVVFGTGTKVTVL<br>SEQ ID NO. 67 |
| GCE-B4 | QVQLVQSGAEVKKPGASVKVSCKASGYTFSGD<br>YLHWVRQAPGQGLEWMGWINPNSGGTNYA<br>QKFQGRVTMTRDTSISTAYMELSRLRSDDTAVY<br>YCAREPARDYYYYDGMDVWGQGTTVTVSS<br>SEQ ID NO. 61 | QSVVTQPPSVSGAPGQRVTISCIGSASNI<br>GAGHDVHWYQQLPGTAPKLLIYGNSN<br>RISGVPDRFSGSKSGTSASLAITGLQAED<br>EADYYCQSYSSSLSAVLFGTGTKVTVL<br>SEQ ID NO. 68 |
| GCE-A26 | QVQLVQSGAEVKKPGASVKVSCKASGFTFSGD<br>YLHWVRQAPGQGLEWMGWINPNSGGTNYA<br>QKFQGRVTMTRDTSISTAYMELSRLRSDDTAVY<br>YCAREPARDYYYYDGLDVWGQGTTVTVSS<br>SEQ ID NO. 69 | QSVVTQPPSVSGAPGQRVTISCLGSSSNI<br>GAGHDVHWYQQLPGTAPKLLIYGNSN<br>RPSGVPDRFSGSKSGTSASLAITGLQAED<br>EADYYCQSYSSSLSAYLFGTGTKVTVL<br>SEQ ID NO. 70 |
| GCE-L1A-9 | QVQLVQSGAEVKKPGASVKVSCKASGYTFSGD<br>YMHWVRQAPGQGLEWMGWINPNSGGTNYA<br>QKFQGRVTMTRDTSISTAYMELSRLRSDDTAVY<br>YCAREPGRDYYYYDGMDVWGQGTTVTVSS<br>SEQ ID NO. 71 | QSVVTQPPSVSGAPGQRVTISCLGSSSNI<br>GAGHDVHWYQQLPGTAPKLLIYGNSNR<br>PSGVPDRFSGSKSGTSASLAITGLQAEDE<br>ADYYCQSYSSSLSAYVFGTGTKVTVL<br>SEQ ID NO. 72 |
| GCE-H3B-36 | QVQLVQSGAEVKKPGASVKVSCKASGYTFSGD<br>YMHWVRQAPGQGLEWMGWINPNSGGTNYA<br>QKFQGRVTMTRDTSISTAYMELSRLRSDDTAVY<br>YCAREPGRDYYYYDGLDVWGQGTTVTVSS<br>SEQ ID NO. 49 | QSVVTQPPSVSGAPGQRVTISCTGSSSN<br>IGAGYDVHWYQQLPGTAPKLLIYGNSN<br>RPSGVPDRFSGSKSGTSASLAITGLQAED<br>EADYYCQSYSSSLSAYVFGTGTKVTVL<br>SEQ ID NO. 73 |
| GCE-H13-1 | QVQLVQSGAEVKKPGASVKVSCKASGSTFSGD<br>YLHWVRQAPGQGLEWMGWINPNSGGTNYA<br>QKFQGRVTMTRDTSISTAYMELSRLRSDDTAVY<br>YCAREPGRDYYYYDGLDVWGQGTTVTVSS<br>SEQ ID NO. 74 | QSVVTQPPSVSGAPGQRVTISCTGSSSN<br>IGAGYDVHWYQQLPGTAPKLLIYGNSN<br>RPSGVPDRFSGSKSGTSASLAITGLQAED<br>EADYYCQSYSSSLSAYVFGTGTKVTVL<br>SEQ ID NO. 73 |

Sequence Listing

| | Heavy chain variable domain region | Light chain variable domain region |
|---|---|---|
| GCE-H13-2 | QVQLVQSGAEVKKPGASVKVSCKASGYTFSGD YLHWVRQAPGQGLEWMGWINPNSGGTNYA QKFQGRVTMTRDTSISTAYMELSRLSDDTAVY YCAREPARDYYYYDGMDVWGQGTTVTVSS SEQ ID NO. 61 | QSVVTQPPSVSGAPGQRVTISCTGSSSN IGAGYDVHWYQQLPGTAPKLLIYGNSN RPSGVPDRFSGSKSGTSASLAITGLQAED EADYYCQSYSSSLSAYVFGTGTKVTVL SEQ ID NO. 73 |
| GCE-H13-3 | QVQLVQSGAEVKKPGASVKVSCKASGYTFSGD YLHWVRQAPGQGLEWMGWINPNSGGTNYA QKFQGRVTMTRDTSISTAYMELSRLSDDTAVY YCAREPARDYYYYDGLDVWGQGTTVTVSS SEQ ID NO. 44 | QSVVTQPPSVSGAPGQRVTISCTGSSSN IGAGYDVHWYQQLPGTAPKLLIYGNSN RPSGVPDRFSGSKSGTSASLAITGLQAED EADYYCQSYSSSLSAYVFGTGTKVTVL SEQ ID NO. 73 |
| GCE-H13-4 | QVQLVQSGAEVKKPGASVKVSCKASGYTFSGD YMHWVRQAPGQGLEWMGWINPNSGGTNYA QKFQGRVTMTRDTSISTAYMELSRLSDDTAVY YCAREPARDYYYYDGLDVWGQGTTVTVSS SEQ ID NO. 40 | QSVVTQPPSVSGAPGQRVTISCTGSSSN IGAGYDVHWYQQLPGTAPKLLIYGNSN RPSGVPDRFSGSKSGTSASLAITGLQAED EADYYCQSYSSSLSAYVFGTGTKVTVL SEQ ID NO. 73 |
| GCE-H13-5 | QVQLVQSGAEVKKPGASVKVSCKASGFTFSGD YLHWVRQAPGQGLEWMGWINPNSGGTNYA QKFQGRVTMTRDTSISTAYMELSRLSDDTAVY YCAREPARDYYYYDGMDVWGQGTTVTVSS SEQ ID NO. 75 | QSVVTQPPSVSGAPGQRVTISCTGSSSN IGAGYDVHWYQQLPGTAPKLLIYGNSN RPSGVPDRFSGSKSGTSASLAITGLQAED EADYYCQSYSSSLSAYVFGTGTKVTVL SEQ ID NO. 73 |
| GCE-H13-6 | QVQLVQSGAEVKKPGASVKVSCKASGFTFSGD YLHWVRQAPGQGLEWMGWINPNSGGTNYA QKFQGRVTMTRDTSISTAYMELSRLSDDTAVY YCAREPARDYYYYDGLDVWGQGTTVTVSS SEQ ID NO. 69 | QSVVTQPPSVSGAPGQRVTISCTGSSSN IGAGYDVHWYQQLPGTAPKLLIYGNSN RPSGVPDRFSGSKSGTSASLAITGLQAED EADYYCQSYSSSLSAYVFGTGTKVTVL SEQ ID NO. 73 |
| GCE-H13-8 | QVQLVQSGAEVKKPGASVKVSCKASGYTFSGD YLHWVRQAPGQGLEWMGWINPNSGGTNYA QKFQGRVTMTRDTSISTAYMELSRLSDDTAVY YCAREPGRDYYYYDGLDVWGQGTTVTVSS SEQ ID NO. 76 | QSVVTQPPSVSGAPGQRVTISCTGSSSN IGAGYDVHWYQQLPGTAPKLLIYGNSN RPSGVPDRFSGSKSGTSASLAITGLQAED EADYYCQSYSSSLSAYVFGTGTKVTVL SEQ ID NO. 73 |
| H8-9EH11L | EVQLVQSGAEVKKPGASVKVSCKASGYTFYSYY MHWVRQAPGQGLEWMGWINPNSGNTGYA QKFQGRVTMTRNTSISTAYMELSSLRSEDTAVY YCARRGTTVSFDTWGQGTLVTVSS SEQ ID NO. 21 | QLVLTQSPSVSVAPGQRVTISCSGSNSFI GNNYVSWYHHLPGTAPKLLIYDNNKRP SGIPDRFSGSKSGTSATLGITGLQPGDEA HYYCGTWDSTLSAWVFGGGTKLTVL SEQ ID NO. 77 |
| H8-9EG11L | EVQLVQSGAEVKKPGASVKVSCKASGYTFYSYY MHWVRQAPGQGLEWMGWINPNSGNTGYA QKFQGRVTMTRNTSISTAYMELSSLRSEDTAVY YCARRGTTVSFDTWGQGTLVTVSS SEQ ID NO. 21 | QLVLTQSPSVSVAPGQRVTISCSGSNSNI GNTYVSWYHHLPGTAPKLLIYDNNKRPS GIPDRFSGSKSGTSATLGITGLQPGDEA HYYCGTWDSTLSAWVFGGGTKLTVL SEQ ID NO. 78 |
| H8-6AG2H3 | EVQLVQSGAEVKKPGASVKVSCKASGYTFSDYY MHWVRQAPGQGLEWMGWINPNSGNTGYA QKFQGRVTMTRNTSISTAYMELSRSEDTAVY YCARRATTVSFDTWGQGTLVTVSS SEQ ID NO. 79 | QLVLTQSPSVSVAPGQRVTISCSGSNSNI GNNYVSWYHHLPGTAPKLLIYDNNKRP SGIPDRFSGSKSGTSATLGITGLQPGDEA HYYCGTWDSTLSAGVFGGGTKLTVL SEQ ID NO. 20 |
| A1-2 | QVQLQESGPGLVKPSQTLSLTCTVSGGSISSGG YYWSWIRQHPGKGLEWIGESTHSGSTNYNPSL KSRVTISVDTSKNQFSLKLSSVTAADTAVYYCAR GRDGYDFDAWGQGTLVTVSS SEQ ID NO. 80 | LPVLTQPASVSGSPGQSITISCTGTSFDV GGYNVSWYQQHPGKAPKLMIYDVS RPSGVSTRFSGSKSGNTASLTISGLQAED EADYYCSSFRSSSALVVFGGGTKLTVL SEQ ID NO. 81 |
| A1-4 | QVQLQESGPGLVKPSQTLSLTCTVSGGSISSGG YYWSWIRQHPGKGLEWIGESSHSGSTNYNPSL KSRVTISVDTSKNQFSLKLSSVTAADTAVYYCAR GRDGYYFDAWGQGTLVTVSS SEQ ID NO. 82 | LPVLTQPASVSGSPGQSITISCTGTSSDV GGYPYVSWYQQHPGKAPKLMIYVVSD RPSGVSTRFSGSKSGNTASLTISGLQAED EADYYCSSYRSSSALVVFGGGTQLTVL SEQ ID NO. 83 |
| A1-6 | QVQLQESGPGLVKPSQTLSLTCTVSGGSISSGGY YWSWIRQHPGKGLEWIGEITHSGSTNYNPSLKS RVTISVDTSKNQFSLKLSSVTAADTAVYYCARGR DGYDIDAWGQGTLVTVSS SEQ ID NO. 84 | LPVLTQPASVSGSPGQSITISCTGTSWD VGGYPYVSWYQQHPGKAPKLMIYDVS DRPSGVSTRFSGSKSGNTASLTISGLQAE DEADYYCSSYRSVSALVVFGGGTKLTVL SEQ ID NO. 85 |

Sequence Listing

| | Heavy chain variable domain region | Light chain variable domain region |
|---|---|---|
| A1-8 | QVQLQESGPGLVKPSQTLSLTCTVSGGSISSGG YYWSWIRQHPGKGLEWIGEISHSGSTNYNPSLE SRVTISVDTSKNQFSLKLSSVTAADTAVYYCARG RDGYDLDRWGQGTLVTVSS<br>SEQ ID NO. 86 | LPVLTQPASVSGSPGQSITISCTGTSSDV GGYPYVSWYQQHPGKAPKLMIYRVSDR PSGVSTRFSGSKSGNTASLTISGLQAEDE ADYYCSSYRSSAALVVFGGGTKLTVL<br>SEQ ID NO. 87 |
| A1-9 | QVQLQESGPGLVKPSQTLSLTCTVSGGSISSGG YYWSWIRQHPGKGLEWIGEISHSGSTNYNPSLK SRVTISVDTSKNQFSLKLSSVTAADTAVYYCARG RDGYYLDQWGQGTLVTVSS<br>SEQ ID NO. 88 | LPVLTQPASVSGSPGQSITISCTGTSSDV GGYNYVSWYQQHPGKAPKLMIYNVSD RPSGVSTRFSGSKSGNTASLTISGLQAED EADYYCSSFRSSALVVFGGGTKLTVL<br>SEQ ID NO. 89 |
| A1-24 | QVQLQESGPGLVKPSQTLSLTCTVSGGSISSGG YYWSWIRQHPGKGLEWIGESTHSGSTNYNPSL ESRVTISVDTSKNQFSLKLSSVTAADTAVYYCAR GRDSYDFDAWGQGTLVTVSS<br>SEQ ID NO. 90 | LPVLTQPASVSGSPGQSITISCTGTSFDV GGYNYVSWYQQHPGKAPKLMIYDVSD RPSGVSTRFSGSKSGNTASLTISGLQAED EADYYCSSFRSSAALVVFGGGTKLTVL<br>SEQ ID NO. 91 |
| A1-32 | QVQLQESGPGLVKPSQTLSLTCTVSGGSISSGG YYWSWIRQHPGKGLEWIGESTHSGSTNYNPSL DSRVTISVDTSKNQFSLKLSSVTAADTAVYYCAR GRDGYYLDQWGQGTLVTVSS<br>SEQ ID NO. 92 | LPVLTQPASVSGSPGQSITISCTGTSFDV GGYPYVSWYQQHPGKAPKLMIYDVSD RPSGVSTRFSGSKSGNTASLTISGLQAED EADYYCSSFRSSAALVVFGGGTKLTVL<br>SEQ ID NO. 93 |

We claim:

1. A fully human anti-c-Met antibody of an IgG class, comprising all of the complementarity determining regions (CDRs) as set forth in a heavy and light chain variable sequence of SEQ ID NO. 1 and SEQ ID NO. 2, respectively.

2. The fully human anti-c-Met antibody of claim 1, wherein the antibody has a heavy chain/light chain variable domain sequence of SEQ ID NO. 1/SEQ ID NO. 2.

3. A fully human anti-c-Met antibody Fab fragment, comprising all of the complementarity determining regions (CDRs) as set forth in a heavy and light chain variable sequence of SEQ ID NO. 1 and SEQ ID NO. 2, respectively.

4. The fully human anti-c-Met Fab fragment of claim 3, wherein the fragment has a heavy chain/light chain variable domain sequence of SEQ ID NO. 1/SEQ ID NO. 2.

5. A single chain anti-c-Met antibody, comprising all of the complementarity determining regions (CDRs) as set forth in a heavy and light chain variable sequence of SEQ ID NO. 1 and SEQ ID NO. 2, respectively, wherein a peptide linker connects the heavy and light chain variable domain sequences.

6. The single chain anti-c-Met antibody of claim 5, wherein the single chain antibody has a heavy chain/light chain variable domain sequence of SEQ ID NO. 1/SEQ ID NO. 2.

7. A method for treating cancer, comprising administering to a subject having a cancer expressing c-Met an effective amount of the anti-c-Met antibody of claim 1.

8. The method of claim 7, wherein the anti-c-Met antibody has a heavy chain/light chain variable domain sequence of SEQ ID NO. 1/SEQ ID NO. 2.

9. The method of claim 7, wherein the cancer is a HGF-dependent or HGF-independent c-Met-activation-related cancer.

10. The method of claim 7, wherein the cancer is a prostate cancer, osteosarcoma, lung cancer, breast cancer, endometrial cancer, glioblastoma, or colon cancer.

11. A method for treating cancer, comprising administering to a subject having a cancer expressing c-Met an effective amount of the anti-c-Met antibody Fab fragment of claim 3.

12. The method of claim 11, wherein anti-c-Met antibody Fab fragment has a heavy chain/light chain variable domain sequence of SEQ ID NO. 1/SEQ ID NO. 2.

13. The method of claim 11, wherein the cancer is a HGF-dependent or HGF-independent c-Met-activation-related cancer.

14. The method of claim 11, wherein the cancer is a prostate cancer, osteosarcoma, lung cancer, breast cancer, endometrial cancer, glioblastoma, or colon cancer.

15. A method for treating cancer, comprising administering to a subject having a cancer expressing c-Met an effective amount of the single chain anti-c-Met antibody of claim 5.

16. The method of claim 15, wherein single chain anti-c-Met antibody has a heavy chain/light chain variable domain sequence of SEQ ID NO. 1/SEQ ID NO. 2.

17. The method of claim 15, wherein the cancer is a HGF-dependent or HGF-independent c-Met-activation-related cancer.

18. The method of claim 15, wherein the cancer is a prostate cancer, osteosarcoma, lung cancer, breast cancer, endometrial cancer, glioblastoma, or colon cancer.

* * * * *

SEQUENCE LISTING

<160> NUMBER OF SEQ ID NOS: 93

<210> SEQ ID NO 1
<211> LENGTH: 119
<212> TYPE: PRT
<213> ORGANISM: Homo sapiens

<400> SEQUENCE: 1

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Gly Tyr Tyr Trp Ser Trp Ile Arg Gln His Pro Gly Lys Gly Leu Glu
        35                  40                  45

Trp Ile Gly Glu Ile Asn His Ser Gly Ser Thr Asn Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Gly Arg Asp Gly Tyr Asp Phe Asp Pro Trp Gly Gln Gly
            100                 105                 110

Thr Leu Val Thr Val Ser Ser
        115

<210> SEQ ID NO 2
<211> LENGTH: 111
<212> TYPE: PRT
<213> ORGANISM: Homo sapiens

<400> SEQUENCE: 2

Leu Pro Val Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr

```
            20                  25                  30
Asn Tyr Val Ser Trp Tyr Gln Gln His Pro Gly Lys Ala Pro Lys Leu
        35                  40                  45

Met Ile Tyr Asp Val Ser Asp Arg Pro Ser Gly Val Ser Thr Arg Phe
 50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Ser Ser Tyr Arg Ser Ser
                 85                  90                  95

Ser Ala Leu Val Val Phe Gly Gly Gly Thr Lys Leu Thr Val Leu
                100                 105                 110
```

<210> SEQ ID NO 3
<211> LENGTH: 119
<212> TYPE: PRT
<213> ORGANISM: Homo sapiens

<400> SEQUENCE: 3

```
Gln Val Gln Leu Gln Glu Ser Gly Pro Gly Leu Val Lys Pro Ser Gly
 1               5                  10                  15

Thr Leu Ser Leu Thr Cys Ala Val Ser Gly Gly Ser Ile Ser Arg Ser
        20                  25                  30

Asn Trp Trp Ser Trp Val Arg Gln Pro Pro Gly Lys Gly Leu Glu Trp
        35                  40                  45

Ile Gly Glu Val Tyr His Ser Gly Ser Thr Asn Tyr Asn Pro Ser Leu
 50                  55                  60

Lys Ser Arg Val Thr Ile Ser Val Asp Lys Ser Lys Asn Gln Phe Ser
 65                  70                  75                  80

Leu Lys Val Asn Ser Val Thr Ala Ala Asp Thr Ala Val Tyr Tyr Cys
                 85                  90                  95

Ala Arg Asp Ser Asp Gly Gly Tyr Tyr Phe Asp Tyr Trp Gly Gln Gly
                100                 105                 110

Thr Leu Val Thr Val Ser Ser
        115
```

<210> SEQ ID NO 4
<211> LENGTH: 111
<212> TYPE: PRT
<213> ORGANISM: Homo sapiens

<400> SEQUENCE: 4

```
Leu Pro Val Leu Thr Gln Pro Ala Ser Val Ser Gly Ser Pro Gly Gln
 1               5                  10                  15

Ser Ile Thr Ile Ser Cys Thr Gly Thr Ser Ser Asp Val Gly Gly Tyr
        20                  25                  30

Lys Tyr Val Ser Trp Tyr Gln Gln His Pro Gly Lys Ala Pro Lys Leu
        35                  40                  45

Leu Ile Tyr Asp Val Thr Asp Arg Pro Ser Gly Val Ser Asn Arg Phe
 50                  55                  60

Ser Gly Ser Gln Ser Gly Asn Thr Ala Ser Leu Thr Ile Ser Gly Leu
 65                  70                  75                  80

Gln Thr Glu Asp Glu Ala Asp Tyr Tyr Cys Ser Ser Tyr Thr Asp Asn
                 85                  90                  95

Gly Ala Leu Val Val Phe Gly Gly Gly Thr Lys Leu Thr Val Leu
                100                 105                 110
```

```
<210> SEQ ID NO 5
<211> LENGTH: 127
<212> TYPE: PRT
<213> ORGANISM: Homo sapiens

<400> SEQUENCE: 5

Gln Ile Thr Leu Lys Glu Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Gly Ile Ser Trp Val Arg Gln Ala Pro Gly Gln Gly Leu Glu Trp Met
        35                  40                  45

Gly Gly Ile Ile Pro Met Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Glu Val Ala Pro Asp Tyr Tyr Gly Ser Gly Pro Ser Tyr
            100                 105                 110

Gly Met Asp Val Trp Gly Gln Gly Thr Met Val Thr Val Ser Ser
        115                 120                 125

<210> SEQ ID NO 6
<211> LENGTH: 110
<212> TYPE: PRT
<213> ORGANISM: Homo sapiens

<400> SEQUENCE: 6

Ser Tyr Glu Leu Met Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asp His Val Ser Trp Tyr Gln Gln His Pro Gly Lys Ala Pro Lys Leu
        35                  40                  45

Met Ile Tyr Ala Val Arg Asn Arg Pro Ser Gly Val Pro Asp Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Leu Thr Tyr Val Phe Gly Thr Gly Thr Lys Val Thr Val Leu
            100                 105                 110

<210> SEQ ID NO 7
<211> LENGTH: 118
<212> TYPE: PRT
<213> ORGANISM: Homo sapiens

<400> SEQUENCE: 7

Gln Val Gln Leu Val Glu Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Asn Thr Gly Tyr Ala Gln Lys Phe
    50                  55                  60
```

Gln Gly Arg Val Thr Met Thr Arg Asn Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Gly Thr Thr Val Ser Phe Asp Tyr Trp Gly Gln Gly Thr
            100                 105                 110

Thr Val Thr Val Ser Ser
            115

<210> SEQ ID NO 8
<211> LENGTH: 110
<212> TYPE: PRT
<213> ORGANISM: Homo sapiens

<400> SEQUENCE: 8

Gln Ala Val Leu Thr Gln Pro Pro Ser Val Ser Gly Ser Pro Gly Gln
1               5                   10                  15

Ser Ile Thr Ile Ser Cys Thr Gly Thr Ser Ser Asp Val Gly Thr Phe
                20                  25                  30

Asn Leu Val Ser Trp Tyr Gln Gln His Pro Gly Lys Ala Pro Lys Leu
            35                  40                  45

Ile Ile Tyr Glu Val Ser Lys Arg Pro Ser Asp Val Ser Pro Arg Tyr
50                  55                  60

Ser Gly Ser Lys Ser Gly Thr Thr Ala Ser Leu Thr Ile Ser Val Leu
65                  70                  75                  80

Gln Thr Glu Asp Glu Ala Asp Tyr Tyr Cys Cys Ser Tyr Thr Thr Ser
                85                  90                  95

Ser Ser Tyr Val Phe Gly Ile Gly Thr Lys Val Thr Val Leu
            100                 105                 110

<210> SEQ ID NO 9
<211> LENGTH: 117
<212> TYPE: PRT
<213> ORGANISM: Homo sapiens

<400> SEQUENCE: 9

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
                20                  25                  30

Tyr Trp Ser Trp Ile Arg Gln Pro Pro Gly Lys Gly Leu Glu Trp Ile
            35                  40                  45

Gly Glu Ile Asn His Ser Gly Ser Thr Asn Tyr Asn Pro Ser Leu Lys
50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Gly Arg Asp Gly Tyr Asp Phe Asp Pro Trp Gly Gln Gly Thr Leu
            100                 105                 110

Val Thr Val Ser Ser
            115

<210> SEQ ID NO 10
<211> LENGTH: 111
<212> TYPE: PRT
<213> ORGANISM: Homo sapiens

<400> SEQUENCE: 10

| Gln | Ser | Val | Leu | Thr | Gln | Pro | Pro | Ser | Ala | Ser | Gly | Ser | Pro | Gly | Gln |
|---|---|---|---|---|---|---|---|---|---|---|---|---|---|---|---|
| 1 | | | | 5 | | | | | 10 | | | | | 15 | |

Ser Val Thr Ile Ser Cys Thr Gly Thr Ser Ser Asp Val Gly Gly Tyr
                20                  25                  30

Asn Tyr Val Ser Trp Tyr Gln Gln His Pro Gly Lys Ala Pro Lys Leu
                35                  40                  45

Met Ile Tyr Glu Val Ser Lys Arg Pro Ser Gly Val Pro Asp Arg Phe
 50                 55                  60

Ser Gly Ser Lys Ser Gly Asn Thr Ala Ser Leu Thr Val Ser Gly Leu
65                  70                  75                  80

Gln Ala Glu Asp Glu Ala Asp Tyr Tyr Cys Ser Ser Tyr Ala Gly Ser
                85                  90                  95

Asn Asn Leu Val Val Phe Gly Gly Gly Thr Gln Leu Thr Val Leu
            100                  105                110

<210> SEQ ID NO 11
<211> LENGTH: 123
<212> TYPE: PRT
<213> ORGANISM: Homo sapiens

<400> SEQUENCE: 11

Gln Val Gln Leu Val Gln Ser Gly Ala Glu Val Lys Lys Pro Gly Ala
1                  5                  10                15

Ser Val Lys Val Ser Cys Lys Thr Ser Gly Tyr Thr Phe Ser Gly Asp
                20                  25                  30

Tyr Met His Trp Val Arg Gln Ala Pro Gly Gln Gly Leu Glu Trp Met
                35                  40                  45

Gly Trp Ile Asn Pro Asn Ser Gly Gly Thr Asn Tyr Ala Gln Lys Phe
 50                 55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Glu Pro Gly Arg Asp Tyr Tyr Tyr Asp Gly Met Asp Val
            100                  105                110

Trp Gly Gln Gly Thr Thr Val Thr Val Ser Ser
            115                  120

<210> SEQ ID NO 12
<211> LENGTH: 111
<212> TYPE: PRT
<213> ORGANISM: Homo sapiens

<400> SEQUENCE: 12

Gln Ser Val Val Thr Gln Pro Pro Ser Val Ser Gly Ala Pro Gly Gln
1                  5                  10                15

Arg Val Thr Ile Ser Cys Thr Gly Ser Ser Ser Asn Ile Gly Ala Gly
                20                  25                  30

Tyr Asp Val His Trp Tyr Gln Gln Leu Pro Gly Thr Val Pro Lys Leu
                35                  40                  45

Leu Ile Tyr Gly Asn Ser Asn Arg Pro Ser Gly Val Pro Asp Arg Phe
 50                 55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

Leu Ser Ala Tyr Val Phe Gly Thr Gly Thr Lys Val Thr Val Leu
            100                 105                 110

<210> SEQ ID NO 13
<211> LENGTH: 120
<212> TYPE: PRT
<213> ORGANISM: Homo sapiens

<400> SEQUENCE: 13

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Gly Gly Arg Val Tyr Ser Asn Tyr Tyr Met Asp Val Trp Gly Lys
            100                 105                 110

Gly Thr Thr Val Thr Val Ser Ser
        115                 120

<210> SEQ ID NO 14
<211> LENGTH: 111
<212> TYPE: PRT
<213> ORGANISM: Homo sapiens

<400> SEQUENCE: 14

Gln Ala Val Leu Thr Gln Pro Ala Ser Val Ser Gly Ser Pro Gly Gln
1               5                   10                  15

Ser Ile Thr Ile Ser Cys Thr Gly Thr Arg Ser Asp Val Gly Gly Tyr
            20                  25                  30

Asn Tyr Val Ser Trp Tyr Gln Gln His Pro Gly Lys Ala Pro Lys Leu
        35                  40                  45

Leu Val Tyr Asp Val Ser Asn Arg Pro Ser Gly Val Ser Asn Arg Phe
    50                  55                  60

Ser Gly Ser Gln Ser Gly Asn Thr Ala Ser Leu Thr Ile Ser Gly Leu
65                  70                  75                  80

Gln Thr Glu Asp Glu Ala Asp Tyr Tyr Cys Ser Ser Tyr Thr Asp Asn
                85                  90                  95

Ser Ala Leu Val Val Phe Gly Gly Gly Thr Lys Val Thr Val Leu
            100                 105                 110

<210> SEQ ID NO 15
<211> LENGTH: 119
<212> TYPE: PRT
<213> ORGANISM: Homo sapiens

<400> SEQUENCE: 15

Gln Val Gln Leu Val Glu Ser Gly Pro Gly Leu Val Lys Pro Ser Gly
1               5                   10                  15

Thr Leu Ser Leu Thr Cys Ala Val Ser Gly Gly Ser Ile Ser Ser Ser

```
                    20                  25                  30

Asn Trp Trp Ser Trp Val Arg Gln Pro Pro Gly Lys Gly Leu Glu Trp
            35                  40                  45

Ile Gly Glu Ile Tyr His Ser Gly Ser Thr Asn Tyr Asn Pro Ser Leu
        50                  55                  60

Lys Ser Arg Val Thr Ile Ser Val Asp Lys Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Ser Ala Tyr Gly Asp Tyr Phe Leu Asp Tyr Trp Gly Gln Gly
            100                 105                 110

Thr Leu Val Thr Val Ser Ser
        115

<210> SEQ ID NO 16
<211> LENGTH: 111
<212> TYPE: PRT
<213> ORGANISM: Homo sapiens

<400> SEQUENCE: 16

Gln Ser Val Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Leu Ile Tyr Asp Val Asp Ser Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Phe Thr Ser Ser
                85                  90                  95

Ser Thr Leu Val Val Phe Gly Gly Gly Thr Lys Val Thr Val Leu
            100                 105                 110

<210> SEQ ID NO 17
<211> LENGTH: 120
<212> TYPE: PRT
<213> ORGANISM: Homo sapiens

<400> SEQUENCE: 17

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Glu Met Asn Trp Val Arg Gln Ala Pro Gly Lys Gly Leu Glu Trp Val
        35                  40                  45

Ser Tyr Ile Ser Ser Ser Gly Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Ala Ala Thr Gly Asp Gln Ile Asp Tyr Trp Gly Gln
            100                 105                 110

Gly Thr Leu Val Thr Val Ser Ser
```

-continued

```
            115                 120

<210> SEQ ID NO 18
<211> LENGTH: 107
<212> TYPE: PRT
<213> ORGANISM: Homo sapiens

<400> SEQUENCE: 18

Ala Ile Arg Met Thr Gln Ser Pro Ala Phe Met Ser Ala Thr Pro Gly
1               5                   10                  15

Asp Lys Val Asn Ile Ser Tyr Lys Ala Ser Gln Asp Val Asp Asp
            20                  25                  30

Met Thr Trp Cys Gln Glu Lys Pro Gly Glu Ala Ala Ile Phe Ile Phe
        35                  40                  45

Gln Glu Ala Ala Thr Leu Val Pro Gly Ile Pro Pro Arg Leu Ser Gly
    50                  55                  60

Ser Gly Asn Gly Thr Asp Phe Thr Leu Thr Ile Asn Asn Met Glu Ser
65                  70                  75                  80

Glu Asp Ala Ala Tyr Tyr Phe Cys Leu Gln Gln Asp Asn Phe Pro Leu
                85                  90                  95

Thr Phe Gly Gln Gly Thr Lys Val Asp Ile Lys
            100                 105

<210> SEQ ID NO 19
<211> LENGTH: 117
<212> TYPE: PRT
<213> ORGANISM: Homo sapiens

<400> SEQUENCE: 19

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ser Ser Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Asn Thr Gly Tyr Ala Gln Lys Phe
    50                  55                  60

Gln Gly Arg Val Thr Met Thr Arg Asn Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Gly Thr Thr Val Ser Phe Asp Tyr Trp Gly Gln Gly Thr
            100                 105                 110

Leu Val Thr Val Ser
        115

<210> SEQ ID NO 20
<211> LENGTH: 110
<212> TYPE: PRT
<213> ORGANISM: Homo sapiens

<400> SEQUENCE: 20

Gln Leu Val Leu Thr Gln Ser Pro Ser Val Ser Val Ala Pro Gly Gln
1               5                   10                  15

Arg Val Thr Ile Ser Cys Ser Gly Ser Asn Ser Asn Ile Gly Asn Asn
            20                  25                  30

Tyr Val Ser Trp Tyr His His Leu Pro Gly Thr Ala Pro Lys Leu Leu
        35                  40                  45
```

```
Ile Tyr Asp Asn Asn Lys Arg Pro Ser Gly Ile Pro Asp Arg Phe Ser
        50                  55                  60

Gly Ser Lys Ser Gly Thr Ser Ala Thr Leu Gly Ile Thr Gly Leu Gln
 65                  70                  75                  80

Pro Gly Asp Glu Ala His Tyr Tyr Cys Gly Thr Trp Asp Ser Thr Leu
                 85                  90                  95

Ser Ala Gly Val Phe Gly Gly Gly Thr Lys Leu Thr Val Leu
            100                 105                 110
```

<210> SEQ ID NO 21
<211> LENGTH: 118
<212> TYPE: PRT
<213> ORGANISM: Homo sapiens

<400> SEQUENCE: 21

```
Glu Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Tyr Ser Tyr
                 20                  25                  30

Tyr Met His Trp Val Arg Gln Ala Pro Gly Gln Gly Leu Glu Trp Met
             35                  40                  45

Gly Trp Ile Asn Pro Asn Ser Gly Asn Thr Gly Tyr Ala Gln Lys Phe
        50                  55                  60

Gln Gly Arg Val Thr Met Thr Arg Asn Thr Ser Ile Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Arg Gly Thr Thr Val Ser Phe Asp Thr Trp Gly Gln Gly Thr
                100                 105                 110

Leu Val Thr Val Ser Ser
            115
```

<210> SEQ ID NO 22
<211> LENGTH: 110
<212> TYPE: PRT
<213> ORGANISM: Homo sapiens

<400> SEQUENCE: 22

```
Gln Leu Val Leu Thr Gln Ser Pro Ser Val Ser Val Ala Pro Gly Gln
 1               5                  10                  15

Arg Val Thr Ile Ser Cys Ser Gly Ser Asn Ser Asn Ile Gly Asn Asn
                 20                  25                  30

Tyr Val Ser Trp Tyr His His Leu Pro Gly Thr Ala Pro Lys Leu Leu
             35                  40                  45

Ile Tyr Asp Asn Asn Lys Arg Pro Ser Gly Ile Pro Asp Arg Phe Ser
        50                  55                  60

Gly Ser Lys Ser Gly Thr Ser Ala Thr Leu Gly Ile Thr Gly Leu Gln
 65                  70                  75                  80

Pro Gly Asp Glu Ala His Tyr Tyr Cys Gly Thr Trp Asp Ser Thr Leu
                 85                  90                  95

Ser Ala Trp Val Phe Gly Gly Gly Thr Lys Leu Thr Val Leu
            100                 105                 110
```

<210> SEQ ID NO 23
<211> LENGTH: 110
<212> TYPE: PRT
<213> ORGANISM: Homo sapiens

<400> SEQUENCE: 23

Gln Leu Val Leu Thr Gln Ser Pro Ser Val Ser Ala Pro Gly Gln
1               5                   10                  15

Arg Val Thr Ile Ser Cys Ser Gly Ser Asn Ser Asn Ile Gly Asn Asn
            20                  25                  30

Tyr Val Ser Trp Tyr His His Leu Pro Gly Thr Ala Pro Lys Leu Leu
        35                  40                  45

Ile Tyr Asp Asn Asn Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Pro Gly Asp Glu Ala His Tyr Tyr Cys Gly Thr Trp Asp Ser Thr Leu
                85                  90                  95

Ser Ala Trp Leu Phe Gly Gly Gly Thr Lys Leu Thr Val Leu
            100                 105                 110

<210> SEQ ID NO 24
<211> LENGTH: 118
<212> TYPE: PRT
<213> ORGANISM: Homo sapiens

<400> SEQUENCE: 24

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Tyr Ser Glu
            20                  25                  30

Tyr Met His Trp Val Arg Gln Ala Pro Gly Gln Gly Leu Glu Trp Met
        35                  40                  45

Gly Trp Ile Asn Pro Asn Ser Gly Asn Thr Gly Tyr Ala Gln Lys Phe
    50                  55                  60

Gln Gly Arg Val Thr Met Thr Arg Asn Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Gly Thr Thr Val Ser Phe Asp Thr Trp Gly Gln Gly Thr
            100                 105                 110

Leu Val Thr Val Ser Ser
        115

<210> SEQ ID NO 25
<211> LENGTH: 118
<212> TYPE: PRT
<213> ORGANISM: Homo sapiens

<400> SEQUENCE: 25

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Tyr Ser Glu
            20                  25                  30

Tyr Met His Trp Val Arg Gln Ala Pro Gly Gln Gly Leu Glu Trp Met
        35                  40                  45

Gly Trp Ile Asn Pro Asn Ser Gly Asn Thr Gly Val Ala Pro Lys Phe
    50                  55                  60

Gln Gly Arg Val Thr Met Thr Arg Asn Thr Ser Ile Ser Thr Ala Tyr
65                  70                  75                  80

Met Glu Leu Ser Ser Leu Arg Ser Glu Asp Thr Ala Val Tyr Tyr Cys
                    85                  90                  95

Ala Arg Arg Gly Thr Thr Val Ser Phe Asp Thr Trp Gly Gln Gly Thr
            100                 105                 110

Leu Val Thr Val Ser Ser
            115

<210> SEQ ID NO 26
<211> LENGTH: 110
<212> TYPE: PRT
<213> ORGANISM: Homo sapiens

<400> SEQUENCE: 26

Gln Leu Val Leu Thr Gln Ser Pro Ser Val Ser Val Ala Pro Gly Gln
1               5                   10                  15

Arg Val Thr Ile Ser Cys Ser Gly Ser Asn Ser Asn Ile Gly Asn Asn
            20                  25                  30

Tyr Val Ser Trp Tyr His His Leu Pro Gly Thr Ala Pro Lys Leu Leu
        35                  40                  45

Ile Tyr Asp Asn Asn Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Pro Gly Asp Glu Ala His Tyr Tyr Cys Gly Thr Trp Asp Ser Thr Leu
                85                  90                  95

Ser Ala Trp Ala Phe Gly Gly Gly Thr Lys Leu Thr Val Leu
            100                 105                 110

<210> SEQ ID NO 27
<211> LENGTH: 118
<212> TYPE: PRT
<213> ORGANISM: Homo sapiens

<400> SEQUENCE: 27

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Tyr Ser Glu
            20                  25                  30

Tyr Met His Trp Val Arg Gln Ala Pro Gly Gln Gly Leu Glu Trp Met
        35                  40                  45

Gly Trp Ile Asn Pro Asn Ser Gly Asn Thr Gly Tyr Ala Gln Lys Phe
    50                  55                  60

Gln Gly Arg Val Thr Met Thr Arg Asn Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Gly Thr Thr Val Ser Phe Asp Thr Trp Gly Gln Gly Thr
            100                 105                 110

Leu Val Thr Val Ser Ser
            115

<210> SEQ ID NO 28
<211> LENGTH: 110
<212> TYPE: PRT
<213> ORGANISM: Homo sapiens

<400> SEQUENCE: 28

Gln Leu Val Leu Thr Gln Ser Pro Ser Val Ser Val Ala Pro Gly Gln

```
              1               5                  10                 15
            Arg Val Thr Ile Ser Cys Ser Gly Ser Asn Ser Phe Thr Asp Asn Thr
                            20                 25                 30

Tyr Val Ser Trp Tyr His His Leu Pro Gly Thr Ala Pro Lys Leu Leu
                        35                 40                 45

Ile Tyr Asp Thr Asn Lys Arg Pro Ser Gly Ile Pro Asp Arg Phe Ser
                    50                 55                 60

Gly Ser Lys Ser Gly Thr Ser Ala Thr Leu Gly Ile Thr Gly Leu Gln
            65                 70                 75                 80

Pro Gly Asp Glu Ala His Tyr Tyr Cys Gly Thr Trp Asp Ser Thr Leu
                            85                 90                 95

Ser Ala Trp Val Phe Gly Gly Gly Thr Lys Leu Thr Val Leu
                        100                105                110

<210> SEQ ID NO 29
<211> LENGTH: 118
<212> TYPE: PRT
<213> ORGANISM: Homo sapiens

<400> SEQUENCE: 29

Glu Val Gln Leu Val Gln Ser Gly Ala Glu Val Lys Lys Pro Gly Ala
            1               5                  10                 15

Ser Val Lys Val Ser Cys Lys Ala Ser Gly Tyr Thr Phe Tyr Ser Glu
                            20                 25                 30

Tyr Met His Trp Val Arg Gln Ala Pro Gly Gln Gly Leu Glu Trp Met
                        35                 40                 45

Gly Trp Ile Asn Pro Asn Ser Gly Asn Thr Gly Leu Ala Pro Lys Phe
                    50                 55                 60

Gln Gly Arg Val Thr Met Thr Arg Asn Thr Ser Ile Ser Thr Ala Tyr
            65                 70                 75                 80

Met Glu Leu Ser Ser Leu Arg Ser Glu Asp Thr Ala Val Tyr Tyr Cys
                            85                 90                 95

Ala Arg Arg Gly Thr Thr Val Ser Phe Asp Thr Trp Gly Gln Gly Thr
                        100                105                110

Leu Val Thr Val Ser Ser
                        115

<210> SEQ ID NO 30
<211> LENGTH: 110
<212> TYPE: PRT
<213> ORGANISM: Homo sapiens

<400> SEQUENCE: 30

Gln Leu Val Leu Thr Gln Ser Pro Ser Val Ser Val Ala Pro Gly Gln
            1               5                  10                 15

Arg Val Thr Ile Ser Cys Ser Gly Ser Asn Ser Asn Ile Gly Asn Asn
                            20                 25                 30

Tyr Val Ser Trp Tyr His His Leu Pro Gly Thr Ala Pro Lys Leu Leu
                        35                 40                 45

Ile Tyr Asp Asn Asn Lys Arg Gln Ser Gly Ile Pro Asp Arg Phe Ser
                    50                 55                 60

Gly Ser Lys Ser Gly Thr Ser Ala Thr Leu Gly Ile Thr Gly Leu Gln
            65                 70                 75                 80

Pro Gly Asp Glu Ala His Tyr Tyr Cys Gly Thr Trp Asp Ser Thr Leu
                            85                 90                 95

Ser Ala Trp Val Phe Gly Gly Gly Thr Lys Leu Thr Val Leu
```

<210> SEQ ID NO 31
<211> LENGTH: 118
<212> TYPE: PRT
<213> ORGANISM: Homo sapiens

<400> SEQUENCE: 31

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Tyr Ser Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Asn Thr Gly Val Ala Gln Lys Phe
    50                  55                  60

Gln Gly Arg Val Thr Met Thr Arg Asn Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Gly Thr Thr Val Ser Phe Asp Tyr Trp Gly Gln Gly Thr
            100                 105                 110

Leu Val Thr Val Ser Ser
        115

<210> SEQ ID NO 32
<211> LENGTH: 118
<212> TYPE: PRT
<213> ORGANISM: Homo sapiens

<400> SEQUENCE: 32

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Tyr Ser Glu
            20                  25                  30

Tyr Met His Trp Val Arg Gln Ala Pro Gly Gln Gly Leu Glu Trp Met
        35                  40                  45

Gly Trp Ile Asn Pro Asn Ser Gly Asn Thr Gly Leu Ala Gln Lys Phe
    50                  55                  60

Gln Gly Arg Val Thr Met Thr Arg Asn Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Gly Thr Thr Val Ser Phe Asp Tyr Trp Gly Gln Gly Thr
            100                 105                 110

Leu Val Thr Val Ser Ser
        115

<210> SEQ ID NO 33
<211> LENGTH: 118
<212> TYPE: PRT
<213> ORGANISM: Homo sapiens

<400> SEQUENCE: 33

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Tyr Ser Glu
            20                  25                  30

Tyr Met His Trp Val Arg Gln Ala Pro Gly Gln Gly Leu Glu Trp Met
            35                  40                  45

Gly Trp Ile Asn Pro Asn Ser Gly Asn Thr Gly Tyr Ala Pro Lys Phe
        50                  55                  60

Gln Gly Arg Val Thr Met Thr Arg Asn Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Gly Thr Thr Val Ser Phe Asp Tyr Trp Gly Gln Gly Thr
            100                 105                 110

Leu Val Thr Val Ser Ser
            115

<210> SEQ ID NO 34
<211> LENGTH: 118
<212> TYPE: PRT
<213> ORGANISM: Homo sapiens

<400> SEQUENCE: 34

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Tyr Ser Glu
            20                  25                  30

Tyr Met His Trp Val Arg Gln Ala Pro Gly Gln Gly Leu Glu Trp Met
            35                  40                  45

Gly Trp Ile Asn Pro Asn Ser Gly Asn Thr Gly Val Ala Gln Lys Phe
        50                  55                  60

Gln Gly Arg Val Thr Met Thr Arg Asn Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Gly Thr Thr Val Ser Phe Asp Tyr Trp Gly Gln Gly Thr
            100                 105                 110

Leu Val Thr Val Ser Ser
            115

<210> SEQ ID NO 35
<211> LENGTH: 110
<212> TYPE: PRT
<213> ORGANISM: Homo sapiens

<400> SEQUENCE: 35

Gln Leu Val Leu Thr Gln Ser Pro Ser Val Ser Val Ala Pro Gly Gln
1               5                   10                  15

Arg Val Thr Ile Ser Cys Ser Gly Ser Asn Ser Phe Ser Asn Asn
            20                  25                  30

Tyr Val Ser Trp Tyr His His Leu Pro Gly Thr Ala Pro Lys Leu Leu
            35                  40                  45

Ile Tyr Asp Asn Asn Lys Arg Pro Ser Gly Ile Pro Asp Arg Phe Ser
        50                  55                  60

Gly Ser Lys Ser Gly Thr Ser Ala Thr Leu Gly Ile Thr Gly Leu Gln
65                  70                  75                  80

Pro Gly Asp Glu Ala His Tyr Tyr Cys Gly Thr Trp Asp Ser Thr Leu
                85                  90                  95

Ser Ala Trp Val Phe Gly Gly Gly Thr Lys Leu Thr Val Leu
            100                 105                 110

<210> SEQ ID NO 36
<211> LENGTH: 118
<212> TYPE: PRT
<213> ORGANISM: Homo sapiens

<400> SEQUENCE: 36

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Tyr Ser Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Asn Thr Gly Leu Ala Gln Lys Phe
    50                  55                  60

Gln Gly Arg Val Thr Met Thr Arg Asn Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Gly Thr Thr Val Ser Phe Asp Tyr Trp Gly Gln Gly Thr
            100                 105                 110

Leu Val Thr Val Ser Ser
        115
```

<210> SEQ ID NO 37
<211> LENGTH: 118
<212> TYPE: PRT
<213> ORGANISM: Homo sapiens

<400> SEQUENCE: 37

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Tyr Ser Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Asn Thr Gly Leu Ala Pro Lys Phe
    50                  55                  60

Gln Gly Arg Val Thr Met Thr Arg Asn Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Gly Thr Thr Val Ser Phe Asp Tyr Trp Gly Gln Gly Thr
            100                 105                 110

Leu Val Thr Val Ser Ser
        115
```

<210> SEQ ID NO 38
<211> LENGTH: 110
<212> TYPE: PRT
<213> ORGANISM: Homo sapiens

<400> SEQUENCE: 38

```
Gln Leu Val Leu Thr Gln Ser Pro Ser Val Ser Val Ala Pro Gly Gln
1               5                   10                  15

Arg Val Thr Ile Ser Cys Ser Gly Ser Asn Ser Asn Ile Gly Asn Asn
            20                  25                  30
```

Tyr Val Ser Trp Tyr His His Leu Pro Gly Thr Ala Pro Lys Leu Leu
             35                  40                  45

Ile Tyr Asp Thr Asn Lys Arg Pro Ser Gly Ile Pro Asp Arg Phe Ser
 50                      55                  60

Gly Ser Lys Ser Gly Thr Ser Ala Thr Leu Gly Ile Thr Gly Leu Gln
 65                  70                  75                  80

Pro Gly Asp Glu Ala His Tyr Tyr Cys Gly Thr Trp Asp Ser Thr Leu
                 85                  90                  95

Ser Ala Trp Ala Phe Gly Gly Gly Thr Lys Leu Thr Val Leu
             100                 105                 110

<210> SEQ ID NO 39
<211> LENGTH: 110
<212> TYPE: PRT
<213> ORGANISM: Homo sapiens

<400> SEQUENCE: 39

Gln Leu Val Leu Thr Gln Ser Pro Ser Val Ser Val Ala Pro Gly Gln
 1               5                  10                  15

Arg Val Thr Ile Ser Cys Ser Ala Ser Asn Ser Asn Ile Gly Asn Asn
             20                  25                  30

Tyr Val Ser Trp Tyr His His Leu Pro Gly Thr Ala Pro Lys Leu Leu
             35                  40                  45

Ile Tyr Asp Asn Asn Lys Arg Pro Ser Gly Ile Pro Asp Arg Phe Ser
 50                      55                  60

Gly Ser Lys Ser Gly Thr Ser Ala Thr Leu Gly Ile Thr Gly Leu Gln
 65                  70                  75                  80

Pro Gly Asp Glu Ala His Tyr Tyr Cys Gly Thr Trp Asp Ser Thr Leu
                 85                  90                  95

Ser Ala Trp Val Phe Gly Gly Gly Thr Lys Leu Thr Val Leu
             100                 105                 110

<210> SEQ ID NO 40
<211> LENGTH: 123
<212> TYPE: PRT
<213> ORGANISM: Homo sapiens

<400> SEQUENCE: 40

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Ser Gly Asp
             20                  25                  30

Tyr Met His Trp Val Arg Gln Ala Pro Gly Gln Gly Leu Glu Trp Met
             35                  40                  45

Gly Trp Ile Asn Pro Asn Ser Gly Gly Thr Asn Tyr Ala Gln Lys Phe
 50                      55                  60

Gln Gly Arg Val Thr Met Thr Arg Asp Thr Ser Ile Ser Thr Ala Tyr
 65                  70                  75                  80

Met Glu Leu Ser Arg Leu Arg Ser Asp Asp Thr Ala Val Tyr Tyr Cys
                 85                  90                  95

Ala Arg Glu Pro Ala Arg Asp Tyr Tyr Tyr Asp Gly Leu Asp Val
             100                 105                 110

Trp Gly Gln Gly Thr Thr Val Thr Val Ser Ser
             115                 120

<210> SEQ ID NO 41
<211> LENGTH: 111

<212> TYPE: PRT
<213> ORGANISM: Homo sapiens

<400> SEQUENCE: 41

Gln Ser Val Val Thr Gln Pro Pro Ser Val Ser Gly Ala Pro Gly Gln
1               5                   10                  15

Arg Val Thr Ile Ser Cys Leu Gly Ser Ala Ser Asn Ile Gly Ala Gly
            20                  25                  30

His Asp Val His Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Ser Ser Ser
                85                  90                  95

Leu Ser Ala Tyr Val Phe Gly Thr Gly Thr Lys Val Thr Val Leu
            100                 105                 110

<210> SEQ ID NO 42
<211> LENGTH: 123
<212> TYPE: PRT
<213> ORGANISM: Homo sapiens

<400> SEQUENCE: 42

Gln Val Gln Leu Val Gln Ser Gly Ala Glu Val Lys Lys Pro Gly Ala
1               5                   10                  15

Ser Val Lys Val Ser Cys Lys Ala Ser Gly Phe Thr Phe Ser Gly Asp
            20                  25                  30

Tyr Ile His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Glu Pro Ala Arg Asp Tyr Tyr Tyr Asp Gly Leu Asp Val
            100                 105                 110

Trp Gly Gln Gly Thr Thr Val Thr Val Ser Ser
        115                 120

<210> SEQ ID NO 43
<211> LENGTH: 111
<212> TYPE: PRT
<213> ORGANISM: Homo sapiens

<400> SEQUENCE: 43

Gln Ser Val Val Thr Gln Pro Pro Ser Val Ser Gly Ala Pro Gly Gln
1               5                   10                  15

Arg Val Thr Ile Ser Cys Leu Gly Ser Ser Ser Asn Ile Gly Ala Gly
            20                  25                  30

His Asp Val His Trp Tyr Gln Gln Leu Pro Gly Thr Ala Pro Lys Leu
        35                  40                  45

Leu Ile Tyr Gly Asn Ser Asn Arg Ile Ser Gly Val Pro Asp Arg Phe
    50                  55                  60

Ser Gly Ser Lys Ser Gly Thr Ser Ala Ser Leu Ala Ile Thr Gly Leu 65                  70                  75                  80
Gln Ala Glu Asp Glu Ala Asp Tyr Tyr Cys Gln Ser Tyr Ser Ser Ser
                    85                  90                  95

Leu Ser Ala Tyr Leu Phe Gly Thr Gly Thr Lys Val Thr Val Leu
                100                 105                 110

<210> SEQ ID NO 44
<211> LENGTH: 123
<212> TYPE: PRT
<213> ORGANISM: Homo sapiens

<400> SEQUENCE: 44

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ser Gly Asp
                20                  25                  30

Tyr Leu His Trp Val Arg Gln Ala Pro Gly Gln Gly Leu Glu Trp Met
            35                  40                  45

Gly Trp Ile Asn Pro Asn Ser Gly Gly Thr Asn Tyr Ala Gln Lys Phe
        50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Glu Pro Ala Arg Asp Tyr Tyr Tyr Asp Gly Leu Asp Val
                100                 105                 110

Trp Gly Gln Gly Thr Thr Val Thr Val Ser Ser
            115                 120

<210> SEQ ID NO 45
<211> LENGTH: 123
<212> TYPE: PRT
<213> ORGANISM: Homo sapiens

<400> SEQUENCE: 45

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ser Gly Asp
                20                  25                  30

Tyr Ile His Trp Val Arg Gln Ala Pro Gly Gln Gly Leu Glu Trp Met
            35                  40                  45

Gly Trp Ile Asn Pro Asn Ser Gly Gly Thr Asn Tyr Ala Gln Lys Phe
        50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Glu Pro Ala Arg Asp Tyr Tyr Tyr Asp Gly Leu Asp Val
                100                 105                 110

Trp Gly Gln Gly Thr Thr Val Thr Val Ser Ser
            115                 120

<210> SEQ ID NO 46
<211> LENGTH: 111
<212> TYPE: PRT
<213> ORGANISM: Homo sapiens

<400> SEQUENCE: 46

Gln Ser Val Val Thr Gln Pro Pro Ser Val Ser Gly Ala Pro Gly Gln
1               5                   10                  15

Arg Val Thr Ile Ser Cys Ile Gly Ser Ser Asn Ile Gly Ala Gly
            20                  25                  30

His Asp Val His Trp Tyr Gln Gln Leu Pro Gly Thr Ala Pro Lys Leu
            35                  40                  45

Leu Ile Tyr Gly Asn Ser Asn Arg Pro Ser Gly Val Pro Asp Arg Phe
        50                  55                  60

Ser Gly Ser Lys Ser Gly Thr Ser Ala Ser Leu Ala Ile Thr Gly Leu
65              70                  75                  80

Gln Ala Glu Asp Glu Ala Asp Tyr Tyr Cys Gln Ser Tyr Ser Ser Ser
                85                  90                  95

Leu Ser Ala Tyr Val Phe Gly Thr Gly Thr Lys Val Thr Val Leu
            100                 105                 110

<210> SEQ ID NO 47
<211> LENGTH: 123
<212> TYPE: PRT
<213> ORGANISM: Homo sapiens

<400> SEQUENCE: 47

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ser Gly Asp
            20                  25                  30

Tyr Leu His Trp Val Arg Gln Ala Pro Gly Gln Gly Leu Glu Trp Met
            35                  40                  45

Gly Trp Ile Asn Pro Asn Thr Gly Gly Thr Asn Tyr Ala Gln Lys Phe
        50                  55                  60

Gln Gly Arg Val Thr Met Thr Arg Asp Thr Ser Ile Ser Thr Ala Tyr
65              70                  75                  80

Met Glu Leu Ser Arg Leu Arg Ser Asp Asp Thr Ala Val Tyr Tyr Cys
                85                  90                  95

Ala Arg Glu Pro Ala Arg Asp Tyr Tyr Tyr Asp Gly Leu Asp Val
            100                 105                 110

Trp Gly Gln Gly Thr Thr Val Thr Val Ser Ser
        115                 120

<210> SEQ ID NO 48
<211> LENGTH: 111
<212> TYPE: PRT
<213> ORGANISM: Homo sapiens

<400> SEQUENCE: 48

Gln Ser Val Val Thr Gln Pro Pro Ser Val Ser Gly Ala Pro Gly Gln
1               5                   10                  15

Arg Val Thr Ile Ser Cys Ile Gly Ser Ser Ser Asn Ile Gly Ala Gly
            20                  25                  30

Tyr Asp Val His Trp Tyr Gln Gln Leu Pro Gly Thr Ala Pro Lys Leu
            35                  40                  45

Leu Ile Tyr Gly Asn Ser Asn Leu Pro Ser Gly Val Pro Asp Arg Phe
        50                  55                  60

Ser Gly Ser Lys Ser Gly Thr Ser Ala Ser Leu Ala Ile Thr Gly Leu
65              70                  75                  80

Gln Ala Glu Asp Glu Ala Asp Tyr Tyr Cys Gln Ser Tyr Glu Ser Ser
                85                  90                  95

```
Leu Ser Ala Tyr Val Phe Gly Thr Gly Thr Lys Val Thr Val Leu
            100                 105                 110

<210> SEQ ID NO 49
<211> LENGTH: 123
<212> TYPE: PRT
<213> ORGANISM: Homo sapiens

<400> SEQUENCE: 49

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ser Gly Asp
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Glu Pro Gly Arg Asp Tyr Tyr Tyr Asp Gly Leu Asp Val
            100                 105                 110

Trp Gly Gln Gly Thr Thr Val Thr Val Ser Ser
            115                 120

<210> SEQ ID NO 50
<211> LENGTH: 111
<212> TYPE: PRT
<213> ORGANISM: Homo sapiens

<400> SEQUENCE: 50

Gln Ser Val Val Thr Gln Pro Pro Ser Val Ser Gly Ala Pro Gly Gln
1               5                   10                  15

Arg Val Thr Ile Ser Cys Ile Gly Ser Ala Ser Asn Ile Gly Ala Gly
            20                  25                  30

His Asp Val His Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Ser Ser Ser
                85                  90                  95

Leu Ser Ala Tyr Val Phe Gly Thr Gly Thr Lys Val Thr Val Leu
            100                 105                 110

<210> SEQ ID NO 51
<211> LENGTH: 123
<212> TYPE: PRT
<213> ORGANISM: Homo sapiens

<400> SEQUENCE: 51

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ser Gly Asp
            20                  25                  30
```

Tyr Met His Trp Val Arg Gln Ala Pro Gly Gln Gly Leu Glu Trp Met
            35                  40                  45

Gly Trp Ile Asn Pro Asn Thr Gly Gly Thr Asn Tyr Ala Gln Lys Phe
 50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Glu Pro Ala Arg Asp Tyr Tyr Tyr Asp Gly Leu Asp Val
            100                 105                 110

Trp Gly Gln Gly Thr Thr Val Thr Val Ser Ser
            115                 120

<210> SEQ ID NO 52
<211> LENGTH: 111
<212> TYPE: PRT
<213> ORGANISM: Homo sapiens

<400> SEQUENCE: 52

Gln Ser Val Val Thr Gln Pro Pro Ser Val Ser Gly Ala Pro Gly Gln
1               5                   10                  15

Arg Val Thr Ile Ser Cys Leu Gly Ser Ala Ser Asn Ile Gly Ala Gly
            20                  25                  30

Tyr Asp Val His Trp Tyr Gln Gln Leu Pro Gly Thr Ala Pro Lys Leu
            35                  40                  45

Leu Ile Tyr Gly Asn Ser Asn Arg Pro Ser Gly Val Pro Asp Arg Phe
 50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Ser Ser Ser
                85                  90                  95

Leu Ser Ala Tyr Val Phe Gly Thr Gly Thr Lys Val Thr Val Leu
            100                 105                 110

<210> SEQ ID NO 53
<211> LENGTH: 123
<212> TYPE: PRT
<213> ORGANISM: Homo sapiens

<400> SEQUENCE: 53

Gln Val Gln Leu Val Gln Ser Gly Ala Glu Val Lys Lys Pro Gly Ala
1               5                   10                  15

Ser Val Lys Val Ser Cys Lys Ala Ser Gly Phe Thr Phe Ser Gly Asp
            20                  25                  30

Tyr Met His Trp Val Arg Gln Ala Pro Gly Gln Gly Leu Glu Trp Met
            35                  40                  45

Gly Trp Ile Asn Pro Asn Ser Gly Gly Thr Asn Tyr Ala Gln Lys Phe
 50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Glu Pro Ala Arg Asp Tyr Tyr Tyr Asp Gly Leu Asp Val
            100                 105                 110

Trp Gly Gln Gly Thr Thr Val Thr Val Ser Ser
            115                 120

<210> SEQ ID NO 54
<211> LENGTH: 111
<212> TYPE: PRT
<213> ORGANISM: Homo sapiens

<400> SEQUENCE: 54

Gln Ser Val Val Thr Gln Pro Pro Ser Val Ser Gly Ala Pro Gly Gln
1               5                   10                  15

Arg Val Thr Ile Ser Cys Leu Gly Ser Ser Ser Asn Ile Gly Ala Gly
            20                  25                  30

His Asp Val His Trp Tyr Gln Gln Leu Pro Gly Thr Ala Pro Lys Leu
        35                  40                  45

Leu Ile Tyr Gly Asn Ser Asn Leu Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Ser Ser Ser
                85                  90                  95

Leu Ser Ala Val Leu Phe Gly Thr Gly Thr Lys Val Thr Val Leu
            100                 105                 110

<210> SEQ ID NO 55
<211> LENGTH: 111
<212> TYPE: PRT
<213> ORGANISM: Homo sapiens

<400> SEQUENCE: 55

Gln Ser Val Val Thr Gln Pro Pro Ser Val Ser Gly Ala Pro Gly Gln
1               5                   10                  15

Arg Val Thr Ile Ser Cys Ile Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Gly Asn Ser Asn Arg Ile Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Ser Ser Ser
                85                  90                  95

Leu Ser Ala Val Leu Phe Gly Thr Gly Thr Lys Val Thr Val Leu
            100                 105                 110

<210> SEQ ID NO 56
<211> LENGTH: 123
<212> TYPE: PRT
<213> ORGANISM: Homo sapiens

<400> SEQUENCE: 56

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ser Gly Asp
            20                  25                  30

Tyr Ile His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr

```
                65                  70                  75                  80
Met Glu Leu Ser Arg Leu Arg Ser Asp Asp Thr Ala Val Tyr Tyr Cys
                    85                  90                  95

Ala Arg Glu Pro Ala Arg Asp Tyr Tyr Tyr Asp Gly Leu Asp Val
                100                 105                 110

Trp Gly Gln Gly Thr Thr Val Thr Val Ser Ser
            115                 120
```

<210> SEQ ID NO 57
<211> LENGTH: 111
<212> TYPE: PRT
<213> ORGANISM: Homo sapiens

<400> SEQUENCE: 57

```
Gln Ser Val Val Thr Gln Pro Pro Ser Val Ser Gly Ala Pro Gly Gln
1               5                   10                  15

Arg Val Thr Ile Ser Cys Leu Gly Ser Ala Ser Asn Ile Gly Ala Gly
                20                  25                  30

His Asp Val His Trp Tyr Gln Gln Leu Pro Gly Thr Ala Pro Lys Leu
            35                  40                  45

Leu Ile Tyr Gly Asn Ser Asn Arg Pro Ser Gly Val Pro Asp Arg Phe
        50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Ser Ser Ser
                85                  90                  95

Leu Ser Ala Val Leu Phe Gly Thr Gly Thr Lys Val Thr Val Leu
            100                 105                 110
```

<210> SEQ ID NO 58
<211> LENGTH: 123
<212> TYPE: PRT
<213> ORGANISM: Homo sapiens

<400> SEQUENCE: 58

```
Gln Val Gln Leu Val Gln Ser Gly Ala Glu Val Lys Lys Pro Gly Ala
1               5                   10                  15

Ser Val Lys Val Ser Cys Lys Ala Ser Gly Phe Thr Phe Ser Gly Asp
                20                  25                  30

Tyr Ile His Trp Val Arg Gln Ala Pro Gly Gln Gly Leu Glu Trp Met
            35                  40                  45

Gly Trp Ile Asn Pro Asn Ser Gly Gly Thr Asn Tyr Ala Gln Lys Phe
        50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Glu Pro Gly Arg Asp Tyr Tyr Tyr Asp Gly Leu Asp Val
                100                 105                 110

Trp Gly Gln Gly Thr Thr Val Thr Val Ser Ser
            115                 120
```

<210> SEQ ID NO 59
<211> LENGTH: 123
<212> TYPE: PRT
<213> ORGANISM: Homo sapiens

<400> SEQUENCE: 59

-continued

Gln Val Gln Leu Val Gln Ser Gly Ala Glu Val Lys Lys Pro Gly Ala
1               5                   10                  15

Ser Val Lys Val Ser Cys Lys Ala Ser Gly Ser Thr Phe Ser Gly Asp
            20                  25                  30

Tyr Leu His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Glu Pro Ala Arg Asp Tyr Tyr Tyr Asp Gly Leu Asp Val
            100                 105                 110

Trp Gly Gln Gly Thr Thr Val Thr Val Ser Ser
            115                 120

<210> SEQ ID NO 60
<211> LENGTH: 111
<212> TYPE: PRT
<213> ORGANISM: Homo sapiens

<400> SEQUENCE: 60

Gln Ser Val Val Thr Gln Pro Pro Ser Val Ser Gly Ala Pro Gly Gln
1               5                   10                  15

Arg Val Thr Ile Ser Cys Leu Gly Ser Ala Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Ser Ser Ser
                85                  90                  95

Leu Ser Ala Val Leu Phe Gly Thr Gly Thr Lys Val Thr Val Leu
            100                 105                 110

<210> SEQ ID NO 61
<211> LENGTH: 123
<212> TYPE: PRT
<213> ORGANISM: Homo sapiens

<400> SEQUENCE: 61

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ser Gly Asp
            20                  25                  30

Tyr Leu His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

```
Ala Arg Glu Pro Ala Arg Asp Tyr Tyr Tyr Tyr Asp Gly Met Asp Val
            100                 105                 110

Trp Gly Gln Gly Thr Thr Val Thr Val Ser Ser
        115                 120

<210> SEQ ID NO 62
<211> LENGTH: 111
<212> TYPE: PRT
<213> ORGANISM: Homo sapiens

<400> SEQUENCE: 62

Gln Ser Val Val Thr Gln Pro Pro Ser Val Ser Gly Ala Pro Gly Gln
1               5                   10                  15

Arg Val Thr Ile Ser Cys Leu Gly Ser Ala Ser Asn Ile Gly Ala Gly
            20                  25                  30

His Asp Val His Trp Tyr Gln Gln Leu Pro Gly Thr Ala Pro Lys Leu
        35                  40                  45

Leu Ile Tyr Gly Asn Ser Asn Arg Ile Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Ser Ser Ser
                85                  90                  95

Leu Ser Ala Val Leu Phe Gly Thr Gly Thr Lys Val Thr Val Leu
            100                 105                 110

<210> SEQ ID NO 63
<211> LENGTH: 123
<212> TYPE: PRT
<213> ORGANISM: Homo sapiens

<400> SEQUENCE: 63

Gln Val Gln Leu Val Gln Ser Gly Ala Glu Val Lys Lys Pro Gly Ala
1               5                   10                  15

Ser Val Lys Val Ser Cys Lys Ala Ser Gly Phe Thr Phe Ser Gly Asp
            20                  25                  30

Tyr Leu His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Glu Pro Ala Arg Asp Tyr Tyr Tyr Tyr Gly Leu Asp Val
            100                 105                 110

Trp Gly Gln Gly Thr Thr Val Thr Val Ser Ser
        115                 120

<210> SEQ ID NO 64
<211> LENGTH: 111
<212> TYPE: PRT
<213> ORGANISM: Homo sapiens

<400> SEQUENCE: 64

Gln Ser Val Val Thr Gln Pro Pro Ser Val Ser Gly Ala Pro Gly Gln
1               5                   10                  15
```

Arg Val Thr Ile Ser Cys Leu Gly Ser Ser Asn Ile Gly Ala Gly
            20                  25                  30

His Asp Val His Trp Tyr Gln Gln Leu Pro Gly Thr Ala Pro Lys Leu
        35                  40                  45

Leu Ile Tyr Gly Asn Ser Asn Arg Ile Ser Gly Val Pro Asp Arg Phe
50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Ser Ser Ser
                85                  90                  95

Leu Ser Ala Tyr Val Phe Gly Thr Gly Thr Lys Val Thr Val Leu
            100                 105                 110

<210> SEQ ID NO 65
<211> LENGTH: 123
<212> TYPE: PRT
<213> ORGANISM: Homo sapiens

<400> SEQUENCE: 65

Gln Val Gln Leu Val Gln Ser Gly Ala Glu Val Lys Lys Pro Gly Ala
1               5                   10                  15

Ser Val Lys Val Ser Cys Lys Ala Ser Gly Phe Thr Phe Ser Gly Asp
            20                  25                  30

Tyr Leu His Trp Val Arg Gln Ala Pro Gly Gln Gly Leu Glu Trp Met
        35                  40                  45

Gly Trp Ile Asn Pro Asn Thr Gly Gly Thr Asn Tyr Ala Gln Lys Phe
50                  55                  60

Gln Gly Arg Val Thr Met Thr Arg Asp Thr Ser Ile Ser Thr Ala Tyr
65                  70                  75                  80

Met Glu Leu Ser Arg Leu Lys Ser Asp Asp Thr Ala Val Tyr Tyr Cys
                85                  90                  95

Ala Arg Glu Pro Ala Arg Asp Tyr Tyr Tyr Asp Gly Leu Asp Val
            100                 105                 110

Trp Gly Gln Gly Thr Thr Val Thr Val Ser Ser
        115                 120

<210> SEQ ID NO 66
<211> LENGTH: 111
<212> TYPE: PRT
<213> ORGANISM: Homo sapiens

<400> SEQUENCE: 66

Gln Ser Val Val Thr Gln Pro Pro Ser Val Ser Gly Ala Pro Gly Gln
1               5                   10                  15

Arg Val Thr Ile Ser Cys Leu Gly Ser Ser Asn Ile Gly Ala Gly
            20                  25                  30

His Asp Val His Trp Tyr Gln Gln Leu Pro Gly Thr Ala Pro Lys Leu
        35                  40                  45

Leu Ile Tyr Gly Asn Ser Asn Leu Pro Ser Gly Val Pro Asp Arg Phe
50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Ser Ser Ser
                85                  90                  95

Leu Ser Ala Tyr Val Phe Gly Thr Gly Thr Lys Val Thr Val Leu
            100                 105                 110

<210> SEQ ID NO 67
<211> LENGTH: 111
<212> TYPE: PRT
<213> ORGANISM: Homo sapiens

<400> SEQUENCE: 67

Gln Ser Val Val Thr Gln Pro Pro Ser Val Ser Gly Ala Pro Gly Gln
1               5                   10                  15

Arg Val Thr Ile Ser Cys Leu Gly Ser Ala Ser Asn Ile Gly Ala Gly
            20                  25                  30

His Asp Val His Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Ser Ser Ser
                85                  90                  95

Leu Ser Ala Val Val Phe Gly Thr Gly Thr Lys Val Thr Val Leu
            100                 105                 110

<210> SEQ ID NO 68
<211> LENGTH: 111
<212> TYPE: PRT
<213> ORGANISM: Homo sapiens

<400> SEQUENCE: 68

Gln Ser Val Val Thr Gln Pro Pro Ser Val Ser Gly Ala Pro Gly Gln
1               5                   10                  15

Arg Val Thr Ile Ser Cys Ile Gly Ser Ala Ser Asn Ile Gly Ala Gly
            20                  25                  30

His Asp Val His Trp Tyr Gln Gln Leu Pro Gly Thr Ala Pro Lys Leu
        35                  40                  45

Leu Ile Tyr Gly Asn Ser Asn Arg Ile Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Ser Ser Ser
                85                  90                  95

Leu Ser Ala Val Leu Phe Gly Thr Gly Thr Lys Val Thr Val Leu
            100                 105                 110

<210> SEQ ID NO 69
<211> LENGTH: 123
<212> TYPE: PRT
<213> ORGANISM: Homo sapiens

<400> SEQUENCE: 69

Gln Val Gln Leu Val Gln Ser Gly Ala Glu Val Lys Lys Pro Gly Ala
1               5                   10                  15

Ser Val Lys Val Ser Cys Lys Ala Ser Gly Phe Thr Phe Ser Gly Asp
            20                  25                  30

Tyr Leu His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr

```
                65                  70                  75                  80
Met Glu Leu Ser Arg Leu Arg Ser Asp Asp Thr Ala Val Tyr Tyr Cys
                    85                  90                  95

Ala Arg Glu Pro Ala Arg Asp Tyr Tyr Tyr Asp Gly Leu Asp Val
                100                 105                 110

Trp Gly Gln Gly Thr Thr Val Thr Val Ser Ser
            115                 120
```

<210> SEQ ID NO 70
<211> LENGTH: 111
<212> TYPE: PRT
<213> ORGANISM: Homo sapiens

<400> SEQUENCE: 70

```
Gln Ser Val Val Thr Gln Pro Pro Ser Val Ser Gly Ala Pro Gly Gln
1               5                   10                  15

Arg Val Thr Ile Ser Cys Leu Gly Ser Ser Ser Asn Ile Gly Ala Gly
                20                  25                  30

His Asp Val His Trp Tyr Gln Gln Leu Pro Gly Thr Ala Pro Lys Leu
            35                  40                  45

Leu Ile Tyr Gly Asn Ser Asn Arg Pro Ser Gly Val Pro Asp Arg Phe
        50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Ser Ser Ser
                85                  90                  95

Leu Ser Ala Tyr Leu Phe Gly Thr Gly Thr Lys Val Thr Val Leu
                100                 105                 110
```

<210> SEQ ID NO 71
<211> LENGTH: 123
<212> TYPE: PRT
<213> ORGANISM: Homo sapiens

<400> SEQUENCE: 71

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ser Gly Asp
                20                  25                  30

Tyr Met His Trp Val Arg Gln Ala Pro Gly Gln Gly Leu Glu Trp Met
            35                  40                  45

Gly Trp Ile Asn Pro Asn Ser Gly Gly Thr Asn Tyr Ala Gln Lys Phe
        50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Glu Pro Gly Arg Asp Tyr Tyr Tyr Asp Gly Met Asp Val
                100                 105                 110

Trp Gly Gln Gly Thr Thr Val Thr Val Ser Ser
            115                 120
```

<210> SEQ ID NO 72
<211> LENGTH: 111
<212> TYPE: PRT
<213> ORGANISM: Homo sapiens

<400> SEQUENCE: 72

Gln Ser Val Val Thr Gln Pro Pro Ser Val Ser Gly Ala Pro Gly Gln
1               5                   10                  15

Arg Val Thr Ile Ser Cys Leu Gly Ser Ser Asn Ile Gly Ala Gly
            20                  25                  30

Tyr Asp Val His Trp Tyr Gln Gln Leu Pro Gly Thr Ala Pro Lys Leu
            35                  40                  45

Leu Ile Tyr Gly Asn Ser Asn Arg Pro Ser Gly Val Pro Asp Arg Phe
50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Ser Ser Ser
                85                  90                  95

Leu Ser Ala Tyr Val Phe Gly Thr Gly Thr Lys Val Thr Val Leu
            100                 105                 110

<210> SEQ ID NO 73
<211> LENGTH: 111
<212> TYPE: PRT
<213> ORGANISM: Homo sapiens

<400> SEQUENCE: 73

Gln Ser Val Val Thr Gln Pro Pro Ser Val Ser Gly Ala Pro Gly Gln
1               5                   10                  15

Arg Val Thr Ile Ser Cys Thr Gly Ser Ser Asn Ile Gly Ala Gly
            20                  25                  30

Tyr Asp Val His Trp Tyr Gln Gln Leu Pro Gly Thr Ala Pro Lys Leu
            35                  40                  45

Leu Ile Tyr Gly Asn Ser Asn Arg Pro Ser Gly Val Pro Asp Arg Phe
50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Ser Ser Ser
                85                  90                  95

Leu Ser Ala Tyr Val Phe Gly Thr Gly Thr Lys Val Thr Val Leu
            100                 105                 110

<210> SEQ ID NO 74
<211> LENGTH: 123
<212> TYPE: PRT
<213> ORGANISM: Homo sapiens

<400> SEQUENCE: 74

Gln Val Gln Leu Val Gln Ser Gly Ala Glu Val Lys Lys Pro Gly Ala
1               5                   10                  15

Ser Val Lys Val Ser Cys Lys Ala Ser Gly Ser Thr Phe Ser Gly Asp
            20                  25                  30

Tyr Leu His Trp Val Arg Gln Ala Pro Gly Gln Gly Leu Glu Trp Met
            35                  40                  45

Gly Trp Ile Asn Pro Asn Ser Gly Gly Thr Asn Tyr Ala Gln Lys Phe
50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Glu Pro Gly Arg Asp Tyr Tyr Tyr Asp Gly Leu Asp Val
            100                 105                 110

```
Trp Gly Gln Gly Thr Thr Val Thr Val Ser Ser
        115                 120
```

<210> SEQ ID NO 75
<211> LENGTH: 123
<212> TYPE: PRT
<213> ORGANISM: Homo sapiens

<400> SEQUENCE: 75

```
Gln Val Gln Leu Val Gln Ser Gly Ala Glu Val Lys Lys Pro Gly Ala
1               5                   10                  15

Ser Val Lys Val Ser Cys Lys Ala Ser Gly Phe Thr Phe Ser Gly Asp
            20                  25                  30

Tyr Leu His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Glu Pro Ala Arg Asp Tyr Tyr Tyr Asp Gly Met Asp Val
            100                 105                 110

Trp Gly Gln Gly Thr Thr Val Thr Val Ser Ser
        115                 120
```

<210> SEQ ID NO 76
<211> LENGTH: 123
<212> TYPE: PRT
<213> ORGANISM: Homo sapiens

<400> SEQUENCE: 76

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ser Gly Asp
            20                  25                  30

Tyr Leu His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Glu Pro Gly Arg Asp Tyr Tyr Tyr Asp Gly Leu Asp Val
            100                 105                 110

Trp Gly Gln Gly Thr Thr Val Thr Val Ser Ser
        115                 120
```

<210> SEQ ID NO 77
<211> LENGTH: 110
<212> TYPE: PRT
<213> ORGANISM: Homo sapiens

<400> SEQUENCE: 77

```
Gln Leu Val Leu Thr Gln Ser Pro Ser Val Ser Val Ala Pro Gly Gln
1               5                   10                  15
```

Arg Val Thr Ile Ser Cys Ser Gly Ser Asn Ser Phe Ile Gly Asn Asn
            20                  25                  30

Tyr Val Ser Trp Tyr His His Leu Pro Gly Thr Ala Pro Lys Leu Leu
            35                  40                  45

Ile Tyr Asp Asn Asn Lys Arg Pro Ser Gly Ile Pro Asp Arg Phe Ser
        50                  55                  60

Gly Ser Lys Ser Gly Thr Ser Ala Thr Leu Gly Ile Thr Gly Leu Gln
65                  70                  75                  80

Pro Gly Asp Glu Ala His Tyr Tyr Cys Gly Thr Trp Asp Ser Thr Leu
                85                  90                  95

Ser Ala Trp Val Phe Gly Gly Gly Thr Lys Leu Thr Val Leu
            100                 105                 110

<210> SEQ ID NO 78
<211> LENGTH: 110
<212> TYPE: PRT
<213> ORGANISM: Homo sapiens

<400> SEQUENCE: 78

Gln Leu Val Leu Thr Gln Ser Pro Ser Val Ser Val Ala Pro Gly Gln
1               5                   10                  15

Arg Val Thr Ile Ser Cys Ser Gly Ser Asn Ser Asn Ile Gly Asn Thr
            20                  25                  30

Tyr Val Ser Trp Tyr His His Leu Pro Gly Thr Ala Pro Lys Leu Leu
            35                  40                  45

Ile Tyr Asp Asn Asn Lys Arg Pro Ser Gly Ile Pro Asp Arg Phe Ser
        50                  55                  60

Gly Ser Lys Ser Gly Thr Ser Ala Thr Leu Gly Ile Thr Gly Leu Gln
65                  70                  75                  80

Pro Gly Asp Glu Ala His Tyr Tyr Cys Gly Thr Trp Asp Ser Thr Leu
                85                  90                  95

Ser Ala Trp Val Phe Gly Gly Gly Thr Lys Leu Thr Val Leu
            100                 105                 110

<210> SEQ ID NO 79
<211> LENGTH: 118
<212> TYPE: PRT
<213> ORGANISM: Homo sapiens

<400> SEQUENCE: 79

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ser Asp Tyr
            20                  25                  30

Tyr Met His Trp Val Arg Gln Ala Pro Gly Gln Gly Leu Glu Trp Met
            35                  40                  45

Gly Trp Ile Asn Pro Asn Ser Gly Asn Thr Gly Tyr Ala Gln Lys Phe
        50                  55                  60

Gln Gly Arg Val Thr Met Thr Arg Asn Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Ala Thr Thr Val Ser Phe Asp Tyr Trp Gly Gln Gly Thr
            100                 105                 110

Leu Val Thr Val Ser Ser
            115

```
<210> SEQ ID NO 80
<211> LENGTH: 119
<212> TYPE: PRT
<213> ORGANISM: Homo sapiens

<400> SEQUENCE: 80

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Gly Tyr Tyr Trp Ser Trp Ile Arg Gln His Pro Gly Lys Gly Leu Glu
        35                  40                  45

Trp Ile Gly Glu Ser Thr His Ser Gly Ser Thr Asn Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
            85                  90                  95

Cys Ala Arg Gly Arg Asp Gly Tyr Asp Phe Asp Ala Trp Gly Gln Gly
        100                 105                 110

Thr Leu Val Thr Val Ser Ser
        115

<210> SEQ ID NO 81
<211> LENGTH: 111
<212> TYPE: PRT
<213> ORGANISM: Homo sapiens

<400> SEQUENCE: 81

Leu Pro Val Leu Thr Gln Pro Ala Ser Val Ser Gly Ser Pro Gly Gln
1               5                   10                  15

Ser Ile Thr Ile Ser Cys Thr Gly Thr Ser Phe Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Asp Arg Pro Ser Gly Val Ser Thr Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Phe Arg Ser Ser
            85                  90                  95

Ser Ala Leu Val Val Phe Gly Gly Gly Thr Lys Leu Thr Val Leu
        100                 105                 110

<210> SEQ ID NO 82
<211> LENGTH: 119
<212> TYPE: PRT
<213> ORGANISM: Homo sapiens

<400> SEQUENCE: 82

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Gly Tyr Tyr Trp Ser Trp Ile Arg Gln His Pro Gly Lys Gly Leu Glu
        35                  40                  45

Trp Ile Gly Glu Ser Ser His Ser Gly Ser Thr Asn Tyr Asn Pro Ser
```

```
                     50                  55                  60

Leu Lys Ser Arg Val Thr Ile Ser Val Asp Thr Ser Lys Asn Gln Phe
 65                  70                  75                  80

Ser Leu Lys Leu Ser Ser Val Thr Ala Ala Asp Thr Ala Val Tyr Tyr
                     85                  90                  95

Cys Ala Arg Gly Arg Asp Gly Tyr Tyr Phe Asp Ala Trp Gly Gln Gly
                100                 105                 110

Thr Leu Val Thr Val Ser Ser
            115
```

<210> SEQ ID NO 83
<211> LENGTH: 111
<212> TYPE: PRT
<213> ORGANISM: Homo sapiens

<400> SEQUENCE: 83

```
Leu Pro Val Leu Thr Gln Pro Ala Ser Val Ser Gly Ser Pro Gly Gln
 1               5                  10                  15

Ser Ile Thr Ile Ser Cys Thr Gly Thr Ser Ser Asp Val Gly Gly Tyr
                 20                  25                  30

Pro Tyr Val Ser Trp Tyr Gln Gln His Pro Gly Lys Ala Pro Lys Leu
             35                  40                  45

Met Ile Tyr Val Val Ser Asp Arg Pro Ser Gly Val Ser Thr Arg Phe
 50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Ser Ser Tyr Arg Ser Ser
                     85                  90                  95

Ser Ala Leu Val Val Phe Gly Gly Gly Thr Gln Leu Thr Val Leu
                100                 105                 110
```

<210> SEQ ID NO 84
<211> LENGTH: 119
<212> TYPE: PRT
<213> ORGANISM: Homo sapiens

<400> SEQUENCE: 84

```
Gln Val Gln Leu Gln Glu Ser Gly Pro Gly Leu Val Lys Pro Ser Gln
 1               5                  10                  15

Thr Leu Ser Leu Thr Cys Thr Val Ser Gly Gly Ser Ile Ser Ser Gly
                 20                  25                  30

Gly Tyr Tyr Trp Ser Trp Ile Arg Gln His Pro Gly Lys Gly Leu Glu
             35                  40                  45

Trp Ile Gly Glu Ile Thr His Ser Gly Ser Thr Asn Tyr Asn Pro Ser
 50                  55                  60

Leu Lys Ser Arg Val Thr Ile Ser Val Asp Thr Ser Lys Asn Gln Phe
 65                  70                  75                  80

Ser Leu Lys Leu Ser Ser Val Thr Ala Ala Asp Thr Ala Val Tyr Tyr
                     85                  90                  95

Cys Ala Arg Gly Arg Asp Gly Tyr Asp Ile Asp Ala Trp Gly Gln Gly
                100                 105                 110

Thr Leu Val Thr Val Ser Ser
            115
```

<210> SEQ ID NO 85
<211> LENGTH: 111
<212> TYPE: PRT

```
<213> ORGANISM: Homo sapiens

<400> SEQUENCE: 85

Leu Pro Val Leu Thr Gln Pro Ala Ser Val Ser Gly Ser Pro Gly Gln
1               5                   10                  15

Ser Ile Thr Ile Ser Cys Thr Gly Thr Ser Trp Asp Val Gly Gly Tyr
                20                  25                  30

Pro Tyr Val Ser Trp Tyr Gln Gln His Pro Gly Lys Ala Pro Lys Leu
            35                  40                  45

Met Ile Tyr Asp Val Ser Asp Arg Pro Ser Gly Val Ser Thr Arg Phe
        50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Arg Ser Val
                85                  90                  95

Ser Ala Leu Val Val Phe Gly Gly Gly Thr Lys Leu Thr Val Leu
            100                 105                 110

<210> SEQ ID NO 86
<211> LENGTH: 119
<212> TYPE: PRT
<213> ORGANISM: Homo sapiens

<400> SEQUENCE: 86

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
                20                  25                  30

Gly Tyr Tyr Trp Ser Trp Ile Arg Gln His Pro Gly Lys Gly Leu Glu
            35                  40                  45

Trp Ile Gly Glu Ile Ser His Ser Gly Ser Thr Asn Tyr Asn Pro Ser
        50                  55                  60

Leu Glu Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Gly Arg Asp Gly Tyr Asp Leu Asp Arg Trp Gly Gln Gly
            100                 105                 110

Thr Leu Val Thr Val Ser Ser
            115

<210> SEQ ID NO 87
<211> LENGTH: 111
<212> TYPE: PRT
<213> ORGANISM: Homo sapiens

<400> SEQUENCE: 87

Leu Pro Val Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
                20                  25                  30

Pro Tyr Val Ser Trp Tyr Gln Gln His Pro Gly Lys Ala Pro Lys Leu
            35                  40                  45

Met Ile Tyr Arg Val Ser Asp Arg Pro Ser Gly Val Ser Thr Arg Phe
        50                  55                  60

Ser Gly Ser Lys Ser Gly Asn Thr Ala Ser Leu Thr Ile Ser Gly Leu
65                  70                  75                  80
```

Gln Ala Glu Asp Glu Ala Asp Tyr Tyr Cys Ser Ser Tyr Arg Ser Ser
                85                  90                  95

Ala Ala Leu Val Val Phe Gly Gly Gly Thr Lys Leu Thr Val Leu
            100                 105                 110

<210> SEQ ID NO 88
<211> LENGTH: 119
<212> TYPE: PRT
<213> ORGANISM: Homo sapiens

<400> SEQUENCE: 88

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Gly Tyr Tyr Trp Ser Trp Ile Arg Gln His Pro Gly Lys Gly Leu Glu
        35                  40                  45

Trp Ile Gly Glu Ile Ser His Ser Gly Ser Thr Asn Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Gly Arg Asp Gly Tyr Tyr Leu Asp Gln Trp Gly Gln Gly
            100                 105                 110

Thr Leu Val Thr Val Ser Ser
        115

<210> SEQ ID NO 89
<211> LENGTH: 111
<212> TYPE: PRT
<213> ORGANISM: Homo sapiens

<400> SEQUENCE: 89

Leu Pro Val Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asn Val Ser Asp Arg Pro Ser Gly Val Ser Thr Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Phe Arg Ser Ser
                85                  90                  95

Ser Ala Leu Val Val Phe Gly Gly Gly Thr Lys Leu Thr Val Leu
            100                 105                 110

<210> SEQ ID NO 90
<211> LENGTH: 119
<212> TYPE: PRT
<213> ORGANISM: Homo sapiens

<400> SEQUENCE: 90

Gln Val Gln Leu Gln Glu Ser Gly Pro Gly Leu Val Lys Pro Ser Gln
1               5                   10                  15

```
Thr Leu Ser Leu Thr Cys Thr Val Ser Gly Gly Ser Ile Ser Ser Gly
            20                  25                  30

Gly Tyr Tyr Trp Ser Trp Ile Arg Gln His Pro Gly Lys Gly Leu Glu
        35                  40                  45

Trp Ile Gly Glu Ser Thr His Ser Gly Ser Thr Asn Tyr Asn Pro Ser
 50                  55                  60

Leu Glu Ser Arg Val Thr Ile Ser Val Asp Thr Ser Lys Asn Gln Phe
 65                  70                  75                  80

Ser Leu Lys Leu Ser Ser Val Thr Ala Ala Asp Thr Ala Val Tyr Tyr
                85                  90                  95

Cys Ala Arg Gly Arg Asp Ser Tyr Asp Phe Asp Ala Trp Gly Gln Gly
                100                 105                 110

Thr Leu Val Thr Val Ser Ser
            115

<210> SEQ ID NO 91
<211> LENGTH: 111
<212> TYPE: PRT
<213> ORGANISM: Homo sapiens

<400> SEQUENCE: 91

Leu Pro Val Leu Thr Gln Pro Ala Ser Val Ser Gly Ser Pro Gly Gln
 1               5                  10                  15

Ser Ile Thr Ile Ser Cys Thr Gly Thr Ser Phe Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Asp Arg Pro Ser Gly Val Ser Thr Arg Phe
 50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Ser Ser Phe Arg Ser Ser
                85                  90                  95

Ala Ala Leu Val Val Phe Gly Gly Gly Thr Lys Leu Thr Val Leu
                100                 105                 110

<210> SEQ ID NO 92
<211> LENGTH: 119
<212> TYPE: PRT
<213> ORGANISM: Homo sapiens

<400> SEQUENCE: 92

Gln Val Gln Leu Gln Glu Ser Gly Pro Gly Leu Val Lys Pro Ser Gln
 1               5                  10                  15

Thr Leu Ser Leu Thr Cys Thr Val Ser Gly Gly Ser Ile Ser Ser Gly
            20                  25                  30

Gly Tyr Tyr Trp Ser Trp Ile Arg Gln His Pro Gly Lys Gly Leu Glu
        35                  40                  45

Trp Ile Gly Glu Ser Thr His Ser Gly Ser Thr Asn Tyr Asn Pro Ser
 50                  55                  60

Leu Asp Ser Arg Val Thr Ile Ser Val Asp Thr Ser Lys Asn Gln Phe
 65                  70                  75                  80

Ser Leu Lys Leu Ser Ser Val Thr Ala Ala Asp Thr Ala Val Tyr Tyr
                85                  90                  95

Cys Ala Arg Gly Arg Asp Gly Tyr Tyr Leu Asp Gln Trp Gly Gln Gly
                100                 105                 110
```

```
Thr Leu Val Thr Val Ser Ser
        115

<210> SEQ ID NO 93
<211> LENGTH: 111
<212> TYPE: PRT
<213> ORGANISM: Homo sapiens

<400> SEQUENCE: 93

Leu Pro Val Leu Thr Gln Pro Ala Ser Val Ser Gly Ser Pro Gly Gln
1               5                   10                  15

Ser Ile Thr Ile Ser Cys Thr Gly Thr Ser Phe Asp Val Gly Gly Tyr
                20                  25                  30

Pro Tyr Val Ser Trp Tyr Gln Gln His Pro Gly Lys Ala Pro Lys Leu
            35                  40                  45

Met Ile Tyr Asp Val Ser Asp Arg Pro Ser Gly Val Ser Thr Arg Phe
        50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Phe Arg Ser Ser
                85                  90                  95

Ala Ala Leu Val Val Phe Gly Gly Gly Thr Lys Leu Thr Val Leu
            100                 105                 110
```